US009322037B2

(12) United States Patent
Liu et al.

(10) Patent No.: US 9,322,037 B2
(45) Date of Patent: Apr. 26, 2016

(54) CAS9-FOKI FUSION PROTEINS AND USES THEREOF

(71) Applicant: President and Fellows of Harvard College, Cambridge, MA (US)

(72) Inventors: David R. Liu, Lexington, MA (US); John Paul Guilinger, Ridgway, CO (US); David B. Thompson, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/320,498

(22) Filed: Jun. 30, 2014

(65) Prior Publication Data

US 2015/0071899 A1    Mar. 12, 2015

Related U.S. Application Data

(60) Provisional application No. 61/980,315, filed on Apr. 16, 2014, provisional application No. 61/915,414, filed on Dec. 12, 2013, provisional application No. 61/874,609, filed on Sep. 6, 2013.

(51) Int. Cl.

| C12N 9/12 | (2006.01) |
|---|---|
| C12N 9/22 | (2006.01) |
| C12N 15/90 | (2006.01) |
| A61K 47/00 | (2006.01) |
| A61K 38/00 | (2006.01) |

(52) U.S. Cl.
CPC ............ *C12N 15/907* (2013.01); *C12N 9/1241* (2013.01); *C12N 9/22* (2013.01); *A61K 38/00* (2013.01); *A61K 47/00* (2013.01); *C07K 2319/80* (2013.01)

(58) Field of Classification Search
None
See application file for complete search history.

(56) References Cited

U.S. PATENT DOCUMENTS

| 6,453,242 B1 | 9/2002 | Eisenberg et al. |
| 6,503,717 B2 | 1/2003 | Case et al. |
| 6,534,261 B1 | 3/2003 | Cox, III et al. |

(Continued)

FOREIGN PATENT DOCUMENTS

| AU | 2012244264 | 11/2012 |
| CN | 103233028 A | 8/2013 |

(Continued)

OTHER PUBLICATIONS

U.S. Appl. No. 14/234,031, filed Mar. 24, 2014, Liu et al.*

(Continued)

*Primary Examiner* — Robert Mondesi
*Assistant Examiner* — Richard Ekstrom
(74) *Attorney, Agent, or Firm* — Wolf, Greenfield & Sacks, P.C.

(57) ABSTRACT

Some aspects of this disclosure provide compositions, methods, and kits for improving the specificity of RNA-programmable endonucleases, such as Cas9. Also provided are variants of Cas9, e.g., Cas9 dimers and fusion proteins, engineered to have improved specificity for cleaving nucleic acid targets. Also provided are compositions, methods, and kits for site-specific nucleic acid modification using Cas9 fusion proteins (e.g., nuclease-inactivated Cas9 fused to a nuclease catalytic domain). Such Cas9 variants are useful in clinical and research settings involving site-specific modification of DNA, for example, genomic modifications.

10 Claims, 35 Drawing Sheets

(56) References Cited

U.S. PATENT DOCUMENTS

| | | |
|---|---|---|
| 6,599,692 B1 | 7/2003 | Case et al. |
| 6,607,882 B1 | 8/2003 | Cox, III et al. |
| 6,824,978 B1 | 11/2004 | Cox, III et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,163,824 B2 | 1/2007 | Cox, III et al. |
| 7,794,931 B2 | 9/2010 | Breaker et al. |
| 7,919,277 B2 | 4/2011 | Russell et al. |
| 8,361,725 B2 | 1/2013 | Russell et al. |
| 8,492,082 B2 | 7/2013 | De Franciscis et al. |
| 8,546,553 B2 | 10/2013 | Terns et al. |
| 8,680,069 B2 | 3/2014 | de Fougerolles et al. |
| 8,697,359 B1 | 4/2014 | Zhang |
| 8,846,578 B2 | 9/2014 | McCray et al. |
| 2006/0088864 A1 | 4/2006 | Smolke et al. |
| 2008/0124725 A1 | 5/2008 | Barrangou et al. |
| 2008/0182254 A1 | 7/2008 | Hall et al. |
| 2009/0130718 A1 | 5/2009 | Short |
| 2010/0076057 A1 | 3/2010 | Sontheimer et al. |
| 2010/0093617 A1 | 4/2010 | Barrangou et al. |
| 2010/0104690 A1 | 4/2010 | Barrangou et al. |
| 2010/0316643 A1* | 12/2010 | Eckert et al. ............... 424/134.1 |
| 2011/0059160 A1* | 3/2011 | Essner et al. ............... 424/450 |
| 2011/0104787 A1 | 5/2011 | Church et al. |
| 2011/0189776 A1 | 8/2011 | Terns et al. |
| 2011/0217739 A1 | 9/2011 | Terns et al. |
| 2012/0141523 A1* | 6/2012 | Castado et al. ............ 424/190.1 |
| 2012/0270273 A1 | 10/2012 | Zhang et al. |
| 2013/0130248 A1 | 5/2013 | Haurwitz et al. |
| 2013/0158245 A1 | 6/2013 | Russell et al. |
| 2013/0165389 A1* | 6/2013 | Schellenberger et al. ... 514/19.3 |
| 2014/0017214 A1 | 1/2014 | Cost |
| 2014/0065711 A1 | 3/2014 | Liu et al. |
| 2014/0068797 A1 | 3/2014 | Doudna et al. |
| 2014/0127752 A1 | 5/2014 | Zhou et al. |
| 2014/0186843 A1 | 7/2014 | Zhang et al. |
| 2014/0234289 A1 | 8/2014 | Liu et al. |
| 2014/0273037 A1 | 9/2014 | Wu |
| 2014/0273226 A1 | 9/2014 | Wu |
| 2014/0273230 A1* | 9/2014 | Chen et al. ................... 435/462 |
| 2014/0295556 A1* | 10/2014 | Joung et al. ................. 435/440 |
| 2014/0295557 A1 | 10/2014 | Joung et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0349400 A1 | 11/2014 | Jakimo et al. |
| 2014/0356867 A1 | 12/2014 | Peter et al. |
| 2014/0356956 A1 | 12/2014 | Church et al. |
| 2014/0356958 A1 | 12/2014 | Mali et al. |
| 2014/0356959 A1 | 12/2014 | Church et al. |
| 2014/0357523 A1 | 12/2014 | Zeiner et al. |
| 2014/0377868 A1 | 12/2014 | Joung et al. |
| 2015/0010526 A1 | 1/2015 | Liu et al. |
| 2015/0031089 A1 | 1/2015 | Lindstrom |
| 2015/0031132 A1 | 1/2015 | Church et al. |
| 2015/0031133 A1 | 1/2015 | Church et al. |
| 2015/0044191 A1 | 2/2015 | Liu et al. |
| 2015/0044192 A1 | 2/2015 | Liu et al. |
| 2015/0044772 A1* | 2/2015 | Zhao ........................... 435/462 |
| 2015/0056177 A1 | 2/2015 | Liu et al. |
| 2015/0056629 A1 | 2/2015 | Guthrie-Honea |
| 2015/0064789 A1* | 3/2015 | Paschon et al. ............. 435/462 |

FOREIGN PATENT DOCUMENTS

| | | |
|---|---|---|
| CN | 103388006 A | 11/2013 |
| CN | 103614415 A | 3/2014 |
| CN | 103642836 A | 3/2014 |
| CN | 103668472 A | 3/2014 |
| CN | 103820441 A | 5/2014 |
| CN | 103820454 A | 5/2014 |
| CN | 103911376 A | 7/2014 |
| CN | 103923911 A | 7/2014 |
| CN | 104004778 A | 8/2014 |
| CN | 104342457 | 2/2015 |
| EP | 2 734 621 A2 | 5/2014 |
| JP | 2014523747 A | 9/2014 |
| WO | WO 2007/025097 A2 | 3/2007 |
| WO | WO 2007/136815 A2 | 11/2007 |
| WO | WO 2010/054108 A2 | 5/2010 |
| WO | WO 2010/054154 A2 | 5/2010 |
| WO | WO 2010/075424 A2 | 7/2010 |
| WO | WO 2010/132092 A2 | 11/2010 |
| WO | WO 2011/017293 A2 | 2/2011 |
| WO | WO 2011/053982 A2 | 5/2011 |
| WO | WO 2012/054726 A1 | 4/2012 |
| WO | WO 2012/138927 A2 | 10/2012 |
| WO | WO 2012/158985 A2 | 11/2012 |
| WO | WO 2012/158986 A2 | 11/2012 |
| WO | WO 2012/164565 A1 | 12/2012 |
| WO | WO 2013/012674 A1 | 1/2013 |
| WO | WO 2013/066438 A2 | 5/2013 |
| WO | WO 2013/098244 A1 | 7/2013 |
| WO | WO 2013/126794 A1 | 8/2013 |
| WO | WO 2013/130824 A1 | 9/2013 |
| WO | WO 2013/141680 A1 | 9/2013 |
| WO | WO 2013/142378 A9 | 9/2013 |
| WO | WO 2013/142578 A2 | 9/2013 |
| WO | WO 2013/166315 A1 | 11/2013 |
| WO | WO 2013/169398 A2 | 11/2013 |
| WO | WO 2013/169802 A1 | 11/2013 |
| WO | WO 2013/176772 A2 | 11/2013 |
| WO | WO 2013/176915 A1 | 11/2013 |
| WO | WO 2013/176916 A1 | 11/2013 |
| WO | WO 2013/181440 A1 | 12/2013 |
| WO | WO 2013/186754 A2 | 12/2013 |
| WO | WO 2013/188037 A2 | 12/2013 |
| WO | WO 2013/188522 A2 | 12/2013 |
| WO | WO 2013/188638 A2 | 12/2013 |
| WO | WO 2014/011237 A1 | 1/2014 |
| WO | WO 2014/011901 A2 | 1/2014 |
| WO | WO 2014/018423 A2 | 1/2014 |
| WO | WO 2014/022120 A1 | 2/2014 |
| WO | WO 2014/022702 A2 | 2/2014 |
| WO | WO 2014/036219 A2 | 3/2014 |
| WO | WO 2014/039513 A2 | 3/2014 |
| WO | WO 2014/039523 A1 | 3/2014 |
| WO | WO 2014/039684 A1 | 3/2014 |
| WO | WO 2014/039692 A2 | 3/2014 |
| WO | WO 2014/039702 A2 | 3/2014 |
| WO | WO 2014/039872 A1 | 3/2014 |
| WO | WO 2014/039970 A1 | 3/2014 |
| WO | WO 2014/041327 A1 | 3/2014 |
| WO | WO 2014/043143 A1 | 3/2014 |
| WO | WO 2014/047103 A2 | 3/2014 |
| WO | WO 2014/059173 A2 | 4/2014 |
| WO | WO 2014/059255 A1 | 4/2014 |
| WO | WO 2014/065596 A1 | 5/2014 |
| WO | WO 2014/066505 A1 | 5/2014 |
| WO | WO 2014/068346 A2 | 5/2014 |
| WO | WO 2014/070887 A1 | 5/2014 |
| WO | WO 2014/071006 A1 | 5/2014 |
| WO | WO 2014/071219 A1 | 5/2014 |
| WO | WO 2014/071235 A1 | 5/2014 |
| WO | WO 2014/072941 A1 | 5/2014 |
| WO | WO 2014/081729 A1 | 5/2014 |
| WO | WO 2014/081730 A1 | 5/2014 |
| WO | WO 2014/081855 A1 | 5/2014 |
| WO | WO 2014/082644 A1 | 6/2014 |
| WO | WO 2014/085261 A1 | 6/2014 |
| WO | WO 2014/085593 A1 | 6/2014 |
| WO | WO 2014/085830 A2 | 6/2014 |
| WO | WO 2014/089212 A1 | 6/2014 |
| WO | WO 2014/089290 A1 | 6/2014 |
| WO | WO 2014/089348 A1 | 6/2014 |
| WO | WO 2014/089513 A1 | 6/2014 |
| WO | WO 2014/089533 A2 | 6/2014 |
| WO | WO 2014/089541 A2 | 6/2014 |
| WO | WO 2014/093479 A1 | 6/2014 |
| WO | WO 2014/093595 A1 | 6/2014 |
| WO | WO 2014/093622 A2 | 6/2014 |
| WO | WO 2014/093635 A1 | 6/2014 |

(56) References Cited

FOREIGN PATENT DOCUMENTS

| WO | WO 2014/093655 A2 | 6/2014 |
|---|---|---|
| WO | WO 2014/093661 A2 | 6/2014 |
| WO | WO 2014/093694 A1 | 6/2014 |
| WO | WO 2014/093701 A1 | 6/2014 |
| WO | WO 2014/093709 A1 | 6/2014 |
| WO | WO 2014/093712 A1 | 6/2014 |
| WO | WO 2014/093718 A1 | 6/2014 |
| WO | WO 2014/099744 A1 | 6/2014 |
| WO | WO 2014/099750 A2 | 6/2014 |
| WO | WO 2014/113493 A1 | 7/2014 |
| WO | WO 2014/124226 A1 | 8/2014 |
| WO | WO 2014/128659 A1 | 8/2014 |
| WO | WO 2014/130955 A1 | 8/2014 |
| WO | WO2014127287 A1 * | 8/2014 |
| WO | WO 2014/131833 A1 | 9/2014 |
| WO | WO 2014/143381 A1 | 9/2014 |
| WO | WO 2014/144094 A1 | 9/2014 |
| WO | WO 2014/144155 A1 | 9/2014 |
| WO | WO 2014/144288 A1 | 9/2014 |
| WO | WO 2014/144592 A2 | 9/2014 |
| WO | WO 2014/144761 A2 | 9/2014 |
| WO | WO 2014/145599 A2 | 9/2014 |
| WO | WO 2014/150624 A1 | 9/2014 |
| WO | WO 2014/152432 A2 | 9/2014 |
| WO | WO 2014/153470 A2 | 9/2014 |
| WO | WO 2014/164466 A1 | 10/2014 |
| WO | WO 2014/165177 A1 | 10/2014 |
| WO | WO 2014/165349 A1 | 10/2014 |
| WO | WO 2014/165825 A2 | 10/2014 |
| WO | WO 2014/172458 A1 | 10/2014 |
| WO | WO 2014/172470 A | 10/2014 |
| WO | WO 2014/182700 A1 | 11/2014 |
| WO | WO 2014/183071 A2 | 11/2014 |
| WO | WO 2014/184143 A1 | 11/2014 |
| WO | WO 2014/184741 A1 | 11/2014 |
| WO | WO 2014/184744 A1 | 11/2014 |
| WO | WO 2014/186585 A2 | 11/2014 |
| WO | WO 2014/186686 A2 | 11/2014 |
| WO | WO 2014/190181 A1 | 11/2014 |
| WO | WO 2014/191128 A1 | 12/2014 |
| WO | WO 2014/191518 A1 | 12/2014 |
| WO | WO 2014/191521 A2 | 12/2014 |
| WO | WO 2014/191525 A1 | 12/2014 |
| WO | WO 2014/191527 A1 | 12/2014 |
| WO | WO 2014/197568 A2 | 12/2014 |
| WO | WO 2014/197748 A2 | 12/2014 |
| WO | WO 2014/200659 A1 | 12/2014 |
| WO | WO 2014/201015 A2 | 12/2014 |
| WO | WO 2014/204578 A1 | 12/2014 |
| WO | WO 2014/204723 A1 | 12/2014 |
| WO | WO 2014/204724 A1 | 12/2014 |
| WO | WO 2014/204725 A1 | 12/2014 |
| WO | WO 2014/204726 A1 | 12/2014 |
| WO | WO 2014/204727 A1 | 12/2014 |
| WO | WO 2014/204728 A1 | 12/2014 |
| WO | WO 2014/204729 A1 | 12/2014 |
| WO | WO 2015/002780 A1 | 1/2015 |
| WO | WO 2015/004241 A2 | 1/2015 |
| WO | WO 2015/006290 A1 | 1/2015 |
| WO | WO 2015/006294 A2 | 1/2015 |
| WO | WO 2015/006498 A2 | 1/2015 |
| WO | WO 2015/006747 A2 | 1/2015 |
| WO | WO 2015/010114 A1 | 1/2015 |
| WO | WO 2015/013583 A2 | 1/2015 |
| WO | WO 2015/017866 A1 | 2/2015 |
| WO | WO2015/018503 A1 | 2/2015 |
| WO | WO 2015/021353 A1 | 2/2015 |
| WO | WO 2015/021426 A1 | 2/2015 |
| WO | WO 2015/021990 A1 | 2/2015 |
| WO | WO 2015/024017 A2 | 2/2015 |
| WO | WO 2015/026883 A1 | 2/2015 |
| WO | WO 2015/026885 A1 | 2/2015 |
| WO | WO 2015/026886 A1 | 2/2015 |
| WO | WO 2015/026887 A1 | 2/2015 |
| WO | WO 2015/027134 A1 | 2/2015 |

OTHER PUBLICATIONS

U.S. Appl. No. 14/320,071, filed Jun. 30, 2014, Liu et al.*
U.S. Appl. No. 14/320,519, filed Jun. 30, 2014, Liu et al.*
U.S. Appl. No. 14/320,370, filed Jun. 30, 2014, Liu et al.*
U.S. Appl. No. 14/320,413, filed Jun. 30, 2014, Liu et al.*
U.S. Appl. No. 14/462,163, filed Aug. 18, 2014, Liu et al.*
U.S. Appl. No. 14/462,189, filed Aug. 18, 2014, Liu et al.*
U.S. Appl. No. 14/320,467, filed Jun. 30, 2014, Liu et al.*
U.S. Appl. No. 14/326,329, filed Jul. 8, 2014, Liu et al.*
U.S. Appl. No. 14/326,340, filed Jul. 8, 2014, Liu et al.*
U.S. Appl. No. 14/326,361, filed Jul. 8, 2014, Liu et al.*
U.S. Appl. No. 14/325,815, filed Jul. 8, 2014, Liu et al.*
U.S. Appl. No. 14/326,109, filed Jul. 8, 2014, Liu et al.*
U.S. Appl. No. 14/326,140, filed Jul. 8, 2014, Liu et al.*
U.S. Appl. No. 14/326,269, filed Jul. 8, 2014, Liu et al.*
U.S. Appl. No. 14/326,290, filed Jul. 8, 2014, Liu et al.*
U.S. Appl. No. 14/326,318, filed Jul. 8, 2014, Liu et al.*
U.S. Appl. No. 14/326,303, filed Jul. 8, 2014, Liu et al.*
U.S. Appl. No. 61/716,256, filed Oct. 19, 2012, Jinek et al.
U.S. Appl. No. 61/717,324, filed Oct. 23, 2012, Cho et al.
U.S. Appl. No. 61/734,256, filed Dec. 6, 2012, Chen et al.
U.S. Appl. No. 61/758,624, filed Jan. 30, 2013, Chen et al.
U.S. Appl. No. 61/761,046, filed Feb. 5, 2013, Knight et al.
U.S. Appl. No. 61/794,422, filed Mar. 15, 2013, Knight et al.
U.S. Appl. No. 61/803,599, filed Mar. 20, 2013, Kim et al.
U.S. Appl. No. 61/837,481, filed Jun. 20, 2013, Cho et al.
U.S. Appl. No. 14/258,458, filed Apr. 22, 2014, Cong.
International Search Report and Written Opinion for PCT/US2012/047778, mailed May 30, 2013.
International Preliminary Report on Patentability for PCT/US2012/047778, mailed Feb. 6, 2014.
International Search Report for PCT/US2013/032589, mailed Jul. 26, 2013.
GENBANK Submission; NIH/NCBI, Accession No. J04623. Kita et al., Apr. 26, 1993. 2 pages.
GENBANK Submission; NIH/NCBI, Accession No. NC_002737.1. Ferretti et al., Jun. 27, 2013. 1 page.
GENBANK Submission; NIH/NCBI, Accession No. NC_015683.1. Trost et al., Jul. 6, 2013. 1 page.
GENBANK Submission; NIH/NCBI, Accession No. NC_016782.1. Trost et al., Jun. 11, 2013. 1 page.
GENBANK Submission; NIH/NCBI, Accession No. NC_016786.1. Trost et al., Aug. 28, 2013. 1 page.
GENBANK Submission; NIH/NCBI, Accession No. NC_017053.1. Fittipaldi et al., Jul. 6, 2013. 1 page.
GENBANK Submission; NIH/NCBI, Accession No. NC_017317.1. Trost et al., Jun. 11, 2013. 1 page.
GENBANK Submission; NIH/NCBI, Accession No. NC_017861.1. Heidelberg et al., Jun. 11, 2013. 1 page.
GENBANK Submission; NIH/NCBI, Accession No. NC_018010.1. Lucas et al., Jun. 11, 2013. 2 pages.
GENBANK Submission; NIH/NCBI, Accession No. NC_018721.1. Feng et al., Jun. 11, 2013. 1 pages.
GENBANK Submission; NIH/NCBI, Accession No. NC_021284.1. Ku et al., Jul. 12, 2013. 1 page.
GENBANK Submission; NIH/NCBI, Accession No. NC_021314.1. Zhang et al., Jul. 15, 2013. 1 page.
GENBANK Submission; NIH/NCBI, Accession No. NC_021846.1. Lo et al., Jul. 22, 2013. 1 page.
GENBANK Submission; NIH/NCBI, Accession No. NP_472073.1. Glaser et al., Jun. 27, 2013. 2 pages.
GENBANK Submission; NIH/NCBI, Accession No. P42212. Prasher et al., Mar. 19, 2014. 7 pages.
GENBANK Submission; NIH/NCBI, Accession No. YP_002342100.1. Bernardini et al., Jun. 10, 2013. 2 pages.
GENBANK Submission; NIH/NCBI, Accession No. YP_002344900.1. Gundogdu et al., Mar. 19, 2014. 2 pages.
GENBANK Submission; NIH/NCBI, Accession No. YP_820832.1. Makarova et al., Aug. 27, 2013. 2 pages.
UNIPROT Submission; UniProt, Accession No. P04275. Last modified Jul. 9, 2014, version 107. 29 pages.

(56) References Cited

OTHER PUBLICATIONS

UNIPROT Submission; UniProt, Accession No. P04264. Last modified Jun. 11, 2014, version 6. 15 pages.
UNIPROT Submission; UniProt, Accession No. P01011. Last modified Jun. 11, 2014, version 2. 15 pages.
Akopian et al., Chimeric recombinases with designed DNA sequence recognition. Proc Natl Acad Sci U S A. Jul. 22, 2003;100(15):8688-91. Epub Jul. 1, 2003.
Arnold et al., Mutants of Tn3 resolvase which do not require accessory binding sites for recombination activity. EMBO J. Mar. 1, 1999;18(5):1407-14.
Barrangou et al., CRISPR provides acquired resistance against viruses in prokaryotes. Science. Mar. 23, 2007;315(5819):1709-12.
Bhagwat, DNA-cytosine deaminases: from antibody maturation to antiviral defense. DNA Repair (Amst). Jan. 5, 2004;3(1):85-9.
Bibikova et al., Stimulation of homologous recombination through targeted cleavage by chimeric nucleases. Mol Cell Biol. Jan. 2001;21(1):289-97.
Brown et al., Serine recombinases as tools for genome engineering. Methods. Apr. 2011;53(4):372-9. doi: 10.1016/j.ymeth.2010.12.031. Epub Dec. 30, 2010.
Burke et al., Activating mutations of Tn3 resolvase marking interfaces important in recombination catalysis and its regulation. Mol Microbiol. Feb. 2004;51(4):937-48.
Carroll et al., Gene targeting in *Drosophila* and Caenorhabditis elegans with zinc-finger nucleases. Methods Mol Biol. 2008;435:63-77. doi: 10.1007/978-1-59745-232-8_5.
Chang et al., Modification of DNA ends can decrease end joining relative to homologous recombination in mammalian cells. Proc Natl Acad Sci U S A. Jul. 1987;84(14):4959-63.
Charpentier et al., Biotechnology: Rewriting a genome. Nature. Mar. 7, 2013;495(7439):50-1. doi: 10.1038/495050a.
Chavez et al., Therapeutic applications of the ΦC31 integrase system. Curr Gene Ther. Oct. 2011;11(5):375-81. Review.
Chelico et al., Biochemical basis of immunological and retroviral responses to DNA-targeted cytosine deamination by activation-induced cytidine deaminase and APOBEC3G. J Biol Chem. Oct. 9, 2009;284(41):27761-5. doi: 10.1074/jbc.R109.052449. Epub Aug. 13, 2009.
Cho et al., Analysis of off-target effects of CRISPR/Cas-derived RNA-guided endonucleases and nickases. Genome Res. Jan. 2014;24(1):132-41. doi: 10.1101/gr.162339.113. Epub Nov. 19, 2013.
Christian et al., Targeting DNA double-strand breaks with TAL effector nucleases. Genetics. Oct. 2010;186(2):757-61. Doi: 10.1534/genetics.110.120717. Epub Jul. 26, 2010.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Cong et al., Multiplex genome engineering using CRISPR/Cas systems. Science. Feb. 15, 2013;339(6121):819-23. doi: 10.1126/science.1231143. Epub Jan. 3, 2013.
Conticello, The AID/APOBEC family of nucleic acid mutators. Genome Biol. 2008;9(6):229. doi: 10.1186/gb-2008-9-6-229. Epub Jun. 17, 2008.
Cradick et al., CRISPR/Cas9 systems targeting β-globin and CCR5 genes have substantial off-target activity. Nucleic Acids Res. Nov. 1, 2013;41(20):9584-92. doi: 10.1093/nar/gkt714. Epub Aug. 11, 2013.
De Souza, Primer: genome editing with engineered nucleases. Nat Methods. Jan. 2012;9(1):27.
Deltcheva et al., CRISPR RNA maturation by trans-encoded small RNA and host factor RNase III. Nature. Mar. 31, 2011;471(7340):602-7. doi: 10.1038/nature09886.
Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.
Esvelt et al., Orthogonal Cas9 proteins for RNA-guided gene regulation and editing. Nat Methods. Nov. 2013;10(11):1116-21. doi: 10.1038/nmeth.2681. Epub Sep. 29, 2013.
Fu et al., Improving CRISPR-Cas nuclease specificity using truncated guide RNAs. Nat Biotechnol. Mar. 2014;32(3):279-84. doi: 10.1038/nbt.2808. Epub Jan. 26, 2014.
Fu et al., High-frequency off-target mutagenesis induced by CRISPR-Cas nucleases in human cells. Nat Biotechnol. Sep. 2013;31(9):822-6. doi: 10.1038/nbt.2623. Epub Jun. 23, 2013.
Gaj et al., ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012. Supplementary materials included.
Gasiunas et al., RNA-dependent DNA endonuclease Cas9 of the CRISPR system: Holy Grail of genome editing? Trends Microbiol. Nov. 2013;21(11):562-7. doi: 10.1016/j.tim.2013.09.001. Epub Oct. 1, 2013.
Gerber et al., RNA editing by base deamination: more enzymes, more targets, new mysteries. Trends Biochem Sci. Jun. 2001;26(6):376-84.
Gilbert et al., CRISPR-mediated modular RNA-guided regulation of transcription in eukaryotes. Cell. 2013 154(2):442-51.
Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.
Guilinger et al., Fusion of catalytically inactive Cas9 to FokI nuclease improves the specificity of genome modification. Nat Biotechnol. Jun. 2014;32(6):577-82. doi: 10.1038/nbt.2909. Epub Apr. 25, 2014.
Guo et al., Directed evolution of an enhanced and highly efficient FokI cleavage domain for zinc finger nucleases. J Mol Biol. Jul. 2, 2010;400(1):96-107. doi: 10.1016/j.jmb.2010.04.060. Epub May 4, 2010.
Hale et al., RNA-guided RNA cleavage by a CRISPR RNA-Cas protein complex. Cell. Nov. 25, 2009;139(5):945-56. doi: 10.1016/j.cell.2009.07.040.
Horvath et al., CRISPR/Cas, the immune system of bacteria and archaea. Science. Jan. 8, 2010;327(5962):167-70. doi: 10.1126/science.1179555.
Hsu et al., DNA targeting specificity of RNA-guided Cas9 nucleases. Nat Biotechnol. Sep. 2013;31(9):827-32. doi: 10.1038/nbt.2647. Epub Jul. 21, 2013.
Humbert et al., Targeted gene therapies: tools, applications, optimization. Crit Rev Biochem Mol Biol. May-Jun. 2012;47(3):264-81. doi: 10.3109/10409238.2012.658112.
Hurt et al., Highly specific zinc finger proteins obtained by directed domain shuffling and cell-based selection. Proc Natl Acad Sci U S A. Oct. 14, 2003;100(21):12271-6. Epub Oct. 3, 2003.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Jinek et al., RNA-programmed genome editing in human cells. Elife. Jan. 29, 2013;2:e00471. doi: 10.7554/eLife.00471.
Jinek et al., Structures of Cas9 endonucleases reveal RNA-mediated conformational activation. Science. Mar. 14, 2014;343(6176):1247997. doi: 10.1126/science.1247997. Epub Feb. 6, 2014.
Jore et al., Structural basis for CRISPR RNA-guided DNA recognition by Cascade. Nat Struct Mol Biol. May 2011;18(5):529-36. doi: 10.1038/nsmb.2019. Epub Apr. 3, 2011.
Kim et al., Highly efficient RNA-guided genome editing in human cells via delivery of purified Cas9 ribonucleoproteins. Genome Res. Jun. 2014;24(6):1012-9. doi: 10.1101/gr.171322.113. Epub Apr. 2, 2014.
Kim et al., Hybrid restriction enzymes: zinc finger fusions to Fok I cleavage domain. Proc Natl Acad Sci U S A. Feb. 6, 1996;93(3):1156-60.

(56) References Cited

OTHER PUBLICATIONS

Kim et al., TALENs and ZFNs are associated with different mutationsignatures. Nat Methods. Mar. 2013;10(3):185. doi: 10.1038/nmeth.2364. Epub Feb. 10, 2013.
Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.
Li et al., Tal nucleases (TALNs): hybrid proteins composed of TAL effectors and FokI DNA-cleavage domain. Nucleic Acids Res. Jan. 2011;39(1):359-72. doi: 10.1093/nar/gkq704. Epub Aug. 10, 2010.
Maeder et al., CRISPR RNA-guided activation of endogenous human genes. Nat Methods. Oct. 2013;10(10):977-9. doi: 10.1038/nmeth.2598. Epub Jul. 25, 2013.
Mali et al., Cas9 as a versatile tool for engineeringbiology. Nat Methods. Oct. 2013;10(10):957-63. doi: 10.1038/nmeth.2649.
Mali et al., CAS9 transcriptional activators for target specificity screening and paired nickases for cooperative genome engineering. Nat Biotechnol. Sep. 2013;31(9):833-8. doi: 10.1038/nbt.2675. Epub Aug. 1, 2013.
Mali et al., RNA-guided human genome engineering via Cas9. Science. Feb. 15, 2013;339(6121):823-6. doi: 10.1126/science.1232033. Epub Jan. 3, 2013.
Miller et al., A Tale nuclease architecture for efficient genome editing. Nat Biotechnol. Feb. 2011;29(2):143-8. doi:10.1038/nbt.1755. Epub Dec. 22, 2010.
Narayanan et al., Clamping down on weak terminal base pairs: oligonucleotides with molecular caps as fidelity-enhancing elements at the 5'- and 3'-terminal residues. Nucleic Acids Res. May 20, 2004;32(9):2901-11. Print 2004.
Navaratnam et al., An overview of cytidine deaminases. Int J Hematol. Apr. 2006;83(3):195-200.
Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.
O'Connell et al., Programmable RNA recognition and cleavage by CRISPR/Cas9. Nature. Sep. 28, 2014. doi: 10.1038/nature13769. [Epub ahead of print].
Pan et al., Biological and biomedical applications of engineered nucleases. Mol Biotechnol. Sep. 2013;55(1):54-62. doi: 10.1007/s12033-012-9613-9.
Pattanayak et al., High-throughput profiling of off-target DNA cleavage reveals RNA-programmed Cas9 nuclease specificity. Nat Biotechnol. Sep. 2013;31(9):839-43. doi: 10.1038/nbt.2673. Epub Aug. 11, 2013.
Pattanayak et al., Revealing off-target cleavage specificities of zinc-finger nucleases by in vitro selection. Nat Methods. Aug. 7, 2011;8(9):765-70. doi: 10.1038/nmeth.1670.
Pennisi et al., The CRISPR craze. Science. Aug. 23, 2013;341(6148):833-6. doi: 10.1126/science.341.6148.833.
Perez-Pinera et al., Advances in targeted genome editing. Curr Opin Chem Biol. Aug. 2012;16(3-4):268-77. doi: 10.1016/j.cbpa.2012.06.007. Epub Jul. 20, 2012.
Perez-Pinera et al., RNA-guided gene activation by CRISPR-Cas9-based transcription factors. Nat Methods. Oct. 2013;10(10):973-6. doi: 10.1038/nmeth.2600. Epub Jul. 25, 2013.
Pham et al., Reward versus risk: DNA cytidine deaminases triggering immunity and disease. Biochemistry. Mar. 1, 2005;44(8):2703-15.
Porteus, Design and testing of zinc finger nucleases for use in mammalian cells. Methods Mol Biol. 2008;435:47-61. doi: 10.1007/978-1-59745-232-8_4.
Qi et al., Repurposing CRISPR as an RNA-guided platform for sequence-specific control of gene expression. Cell. Feb. 28, 2013;152(5):1173-83. doi: 10.1016/j.cell.2013.02.022.
Ran et al., Double nicking by RNA-guided CRISPR Cas9 for enhanced genome editing specificity. Cell. Sep. 12, 2013;154(6):1380-9. doi: 10.1016/j.cell.2013.08.021. Epub Aug. 29, 2013.
Reynaud et al., What role for AID: mutator, or assembler of the immunoglobulin mutasome? Nat Immunol. Jul. 2003;4(7):631-8.
Reyon et al., FLASH assembly of TALENs for high-throughput genome editing. Nat Biotechnol. May 2012;30(5):460-5. doi: 10.1038/nbt.2170.
Sander et al., CRISPR-Cas systems for editing, regulating and targeting genomes. Nat Biotechnol. Apr. 2014;32(4):347-55. doi: 10.1038/nbt.2842. Epub Mar. 2, 2014.
Sapranauskas et al., The *Streptococcus thermophilus* CRISPR/Cas system provides immunity in *Escherichia coli*. Nucleic Acids Res. Nov. 2011;39(21):9275-82. doi: 10.1093/nar/gkr606. Epub Aug. 3, 2011.
Sashital et al., Mechanism of foreign DNA selection in a bacterial adaptive immune system. Mol Cell. Jun. 8, 2012;46(5):606-15. doi: 10.1016/j.molcel.2012.03.020. Epub Apr. 19, 2012.
Schriefer et al., Low pressure DNA shearing: a method for random DNA sequence analysis. Nucleic Acids Res. Dec. 25, 1990;18(24):7455-6.
Schwank et al., Functional repair of CFTR by CRISPR/Cas9 in intestinal stem cell organoids of cystic fibrosis patients. Cell Stem Cell. Dec. 5, 2013;13(6):653-8. doi:10.1016/j.stem.2013.11.002.
Semenova et al., Interference by clustered regularly interspaced short palindromic repeat(CRISPR) RNA is governed by a seed sequence. Proc Natl Acad Sci U S A. Jun. 21, 2011;108(25):10098-103. doi: 10.1073/pnas.1104144108. Epub Jun. 6, 2011.
Shalem et al., Genome-scale CRISPR-Cas9 knockout screening in human cells. Science. Jan. 3, 2014;343(6166):84-7. doi: 10.1126/science.1247005. Epub Dec. 12, 2013.
Sheridan, First CRISPR-Cas patent opens race to stake out intellectual property. Nat Biotechnol. 2014;32(7):599-601.
Siebert et al., An improved PCR method for walking in uncloned genomic DNA. Nucleic Acids Res. Mar. 25, 1995;23(6):1087-8.
Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014.
Vanamee et al., FokI requires two specific DNA sites for cleavage. J Mol Biol. May 25, 2001;309(1):69-78.
Wah et al., Structure of FokI has implications for DNA cleavage. Proc Natl Acad Sci U S A. Sep. 1, 1998;95(18):10564-9.
Wang et al., Genetic screens in human cells using the CRISPR-Cas9 system. Science. Jan. 3, 2014;343(6166):80-4. doi: 10.1126/science.1246981. Epub Dec. 12, 2013.
Wang et al., One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.
Wiedenheft et al., RNA-guided genetic silencing systems in bacteria and archaea. Nature. Feb. 15, 2012;482(7385):331-8. doi: 10.1038/nature10886. Review.
Wood et al., Targeted genome editing across species using ZFNs and TALENs. Science. Jul. 15, 2011;333(6040):307. doi: 10.1126/science.1207773. Epub Jun. 23, 2011.
Wu et al., Correction of a genetic disease in mouse via use of CRISPR-Cas9. Cell Stem Cell. Dec. 5, 2013;13(6):659-62. doi: 10.1016/j.stem.2013.10.016.
Yin et al., Genome editing with Cas9 in adult mice corrects a disease mutation and phenotype. Nat Biotechnol. Jun. 2014;32(6):551-3. doi: 10.1038/nbt.2884. Epub Mar. 30, 2014.
International Search Report and Written Opinion for PCT/US2014/054291, mailed Mar. 27, 2015.
Invitation to Pay Additional Fees for PCT/US2014/054291, mailed Dec. 18, 2014.
International Search Report and Written Opinion for PCT/US2014/052231, mailed Dec. 4, 2014.
International Search Report and Written Opinion for PCT/US2014/052231, mailed Jan. 30, 2015. (Corrected Version).
International Search Report and Written Opinion for PCT/US2014/050283, mailed Nov. 6, 2014.
NCBI Reference Sequence: NM_002427.3. Wu et al., May 3, 2014. 5 pages.
Barrangou, RNA-mediated programmable DNA cleavage. Nat Biotechnol. Sep. 2012;30(9):836-8. doi: 10.1038/nbt.2357.
Carroll, A CRISPR approach to gene targeting. Mol Ther. Sep. 2012;20(9):1658-60. doi: 10.1038/mt.2012.171.

(56) References Cited

OTHER PUBLICATIONS

Fuchs et al., Polyarginine as a multifunctional fusion tag. Protein Sci. Jun. 2005;14(6):1538-44.

Liu et al., Fast Colorimetric Sensing of Adenosine and Cocaine Based on a General Sensor Design Involving Aptamers and Nanoparticles. Angew Chem. 2006;118(1):96-100.

Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.

Pattanayak et al., Determining the specificities of TALENs, Cas9, and other genome-editing enzymes. Methods Enzymol. 2014;546:47-78. doi: 10.1016/B978-0-12-801185-0.00003-9.

Sang, Prospects for transgenesis in the chick. Mech Dev. Sep. 2004;121(9):1179-86.

Zhang et al., CRISPR/Cas9 for genome editing: progress, implications and challenges. Hum Mol Genet. Sep. 15, 2014;23(R1):R40-6. doi: 10.1093/hmg/ddu125. Epub Mar. 20, 2014.

* cited by examiner

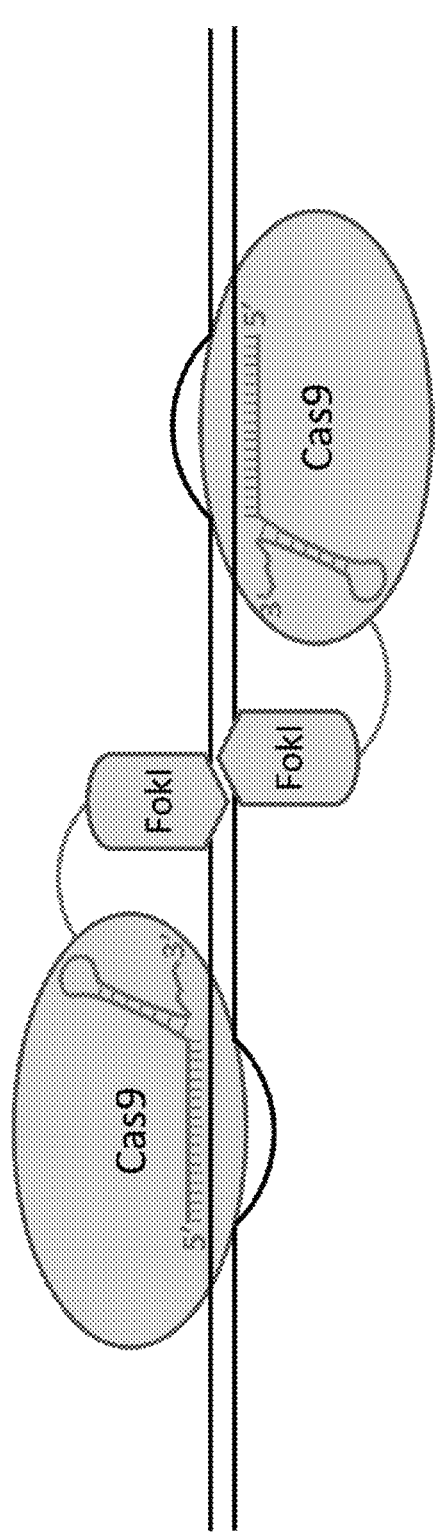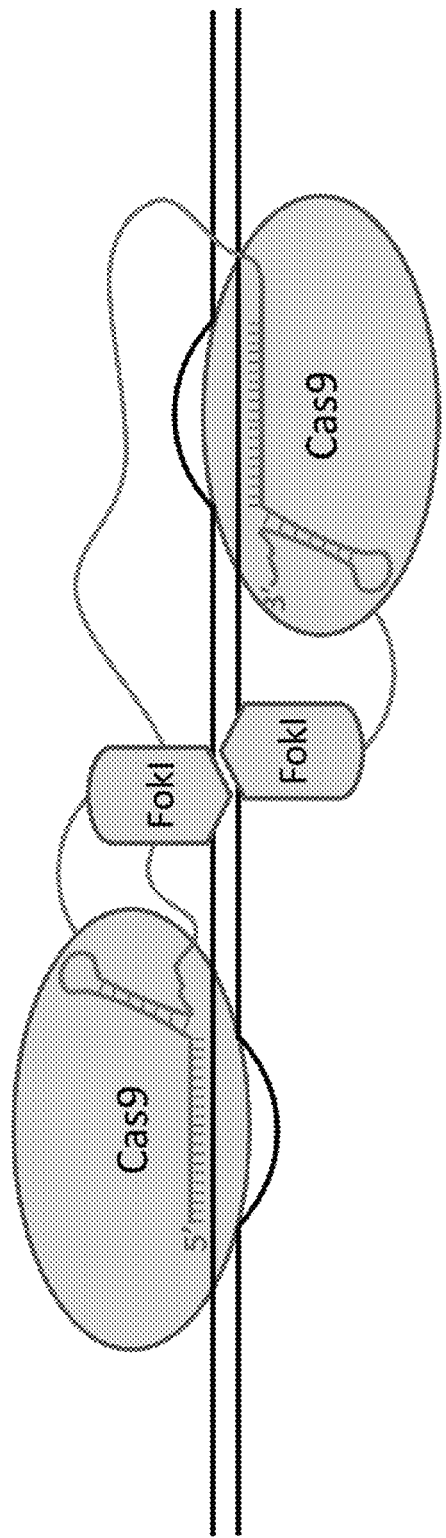
FIG. 1A
FIG. 1B

| name | NLS-linker-Fok1 | Fok1-linker-dCas9 |
|---|---|---|
| Fok1-(GGS)x3 | GGS | GGSGGSGGS |
| Fok1-(GGS)x6 | GGS | GGSGGSGGSGGSGGSGGS |
| Fok1-L0 | GGS | - |
| Fok1-L1 | GGS | MKIIEQLPSA |
| Fok1-L2 | GGS | VRHKLKRVGS |
| Fok1-L3 | GGS | VPFLLEPDNINGKTC |
| Fok1-L4 | GGS | GHGTGSTGSGSS |
| Fok1-L5 | GGS | MSRPDPA |
| Fok1-L6 | GGS | GSAGSAAGSGEF |
| Fok1-L7 | GGS | SGSETPGTSESA |
| Fok1-L8 | GGS | SGSETPGTSESATPES |
| Fok1-L9 | GGS | SGSETPGTSESATPEGGSGGS |
| NLS-(GGS) | GGS | GGSM |
| NLS-(GGS)x3 | GGSGGSGGS | GGSM |
| NLS-L1 | VPFLLEPDNINGKTC | GGSM |
| NLS-L2 | GSAGSAAGSGEF | GGSM |
| NLS-L3 | SIVAQLSRPDPA | GGSM |
| wild-type Cas9 | N/A | N/A |
| Cas9 nickase | N/A | N/A |

FIG. 12A

HBC
CCGTTACTGCCCTGTGGGGCAAGGTGAACGTGGATGAAGTTGGTGGTGAGGCCCTGGGCAGGTTGGTATCAAGGTTACAAGACAGGTTTAAGG
CCGTTACTGCCCTGTGGGGCAAG (H1)  CGTGGATGAAGTTGGTGGTGGG (H2)                                       5
                                   TGAAGTTGGTGGTGAGGCCCTGG (H3)                                 11
                                   TTGGTGGTGAGGCCCTGGGCAGG (H4)                                 16
                                       TGGTGAGGCCCTGGGCAGGTTGG (H5)                             20
                                           CCCTGGGCAGGTTGGTATCAAGG (H6)                         28
                                                   AAGGTTACAAGACAGGTTTAAGG (H7)                 47

EMX
CCCTTCTTCTTCTGCTCGGACTCAGGCCCTTCCTCCTCCAGCTTCTGCCGTTTGTACTTTGTCCTCGGTTCTGG
CCCTTCTTCTTCTGCTCGGACTC (E1)                                                                   23
                          GCCGTTTGTACTTTGTCCTCCGG (E2)                                          
                            TGTACTTTGTCCTCCGGTTCTGG (E3)                                        29

VEGF
CCAGGAGCAAACTCCCCCCACCCCCTTTCCAAAGCCCATTCCCTCTTTAGCCAGCCAGACGG
CCAGGAGCAAACTCCCCCCACCC (V1)                                                                   14
                        ATTCCCTCTTTAGCCAGCCAGACGG (V2)                                          16
                          TCCCTCTTTAGCCAGCCAGAGCGGG (V3)                                        
                              CCAGAGCCGGGGTGTGCAGACGG (V4)                                      27

FIG. 13 (continued)

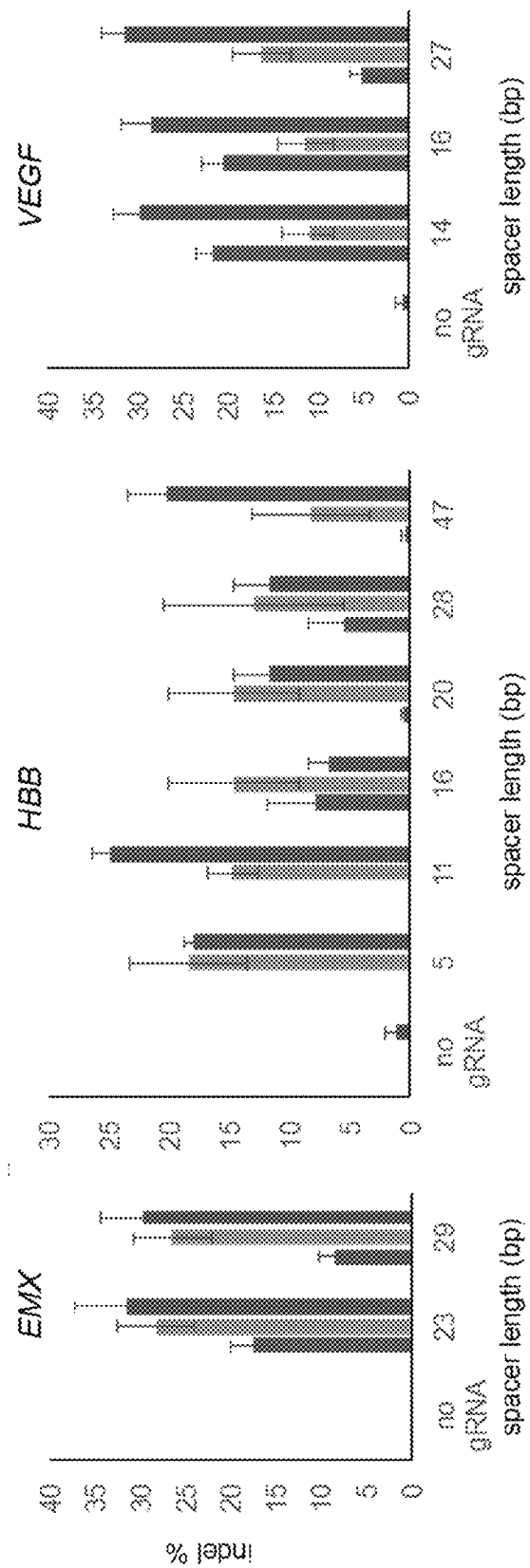

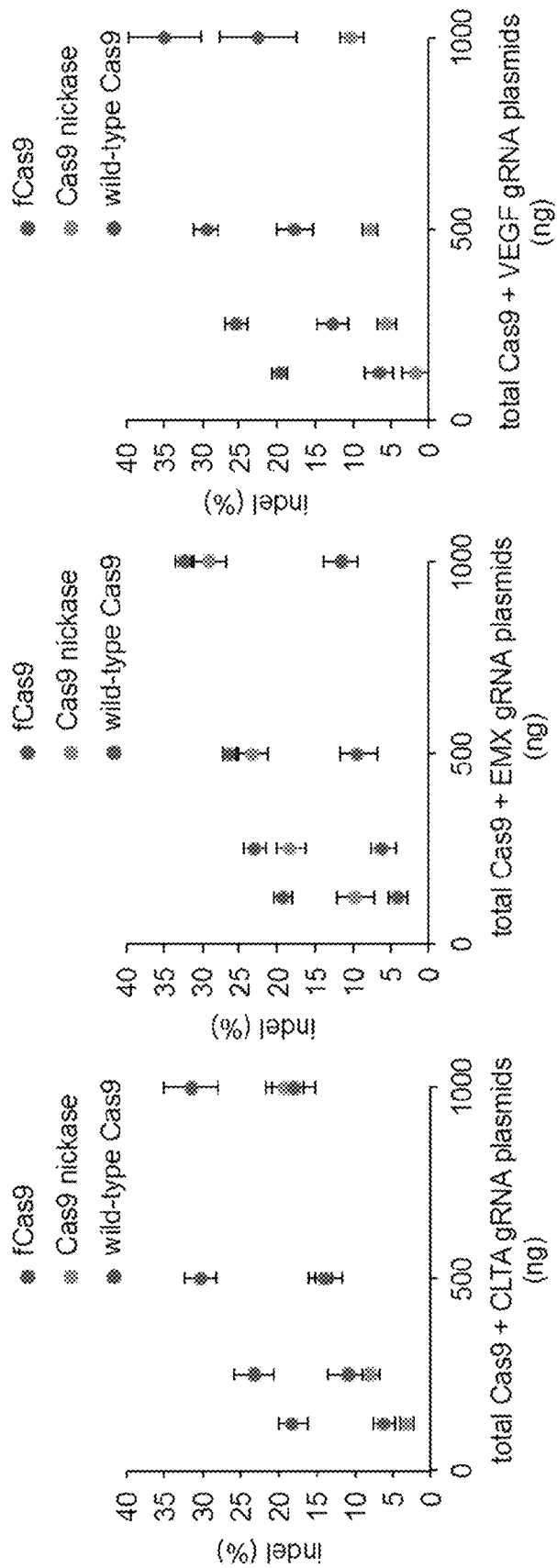

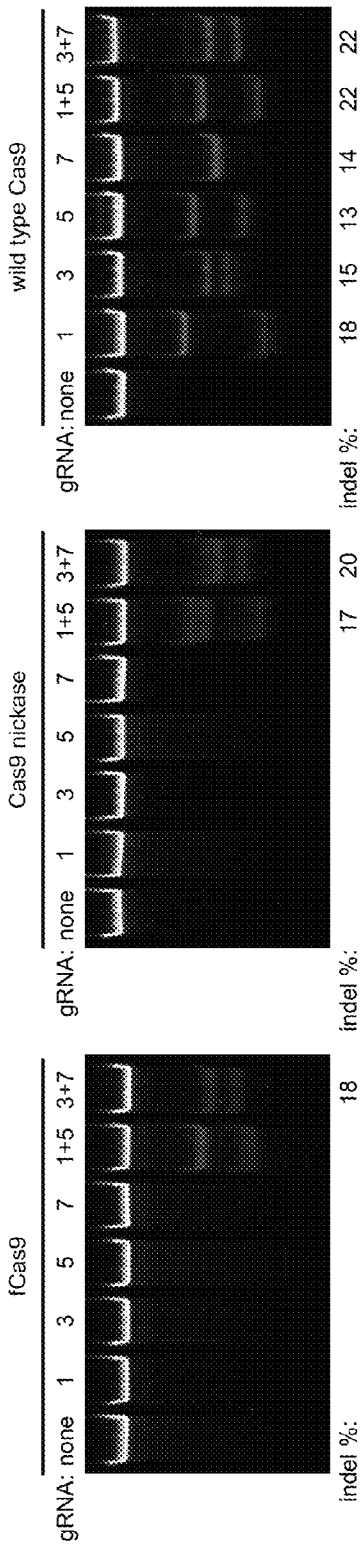
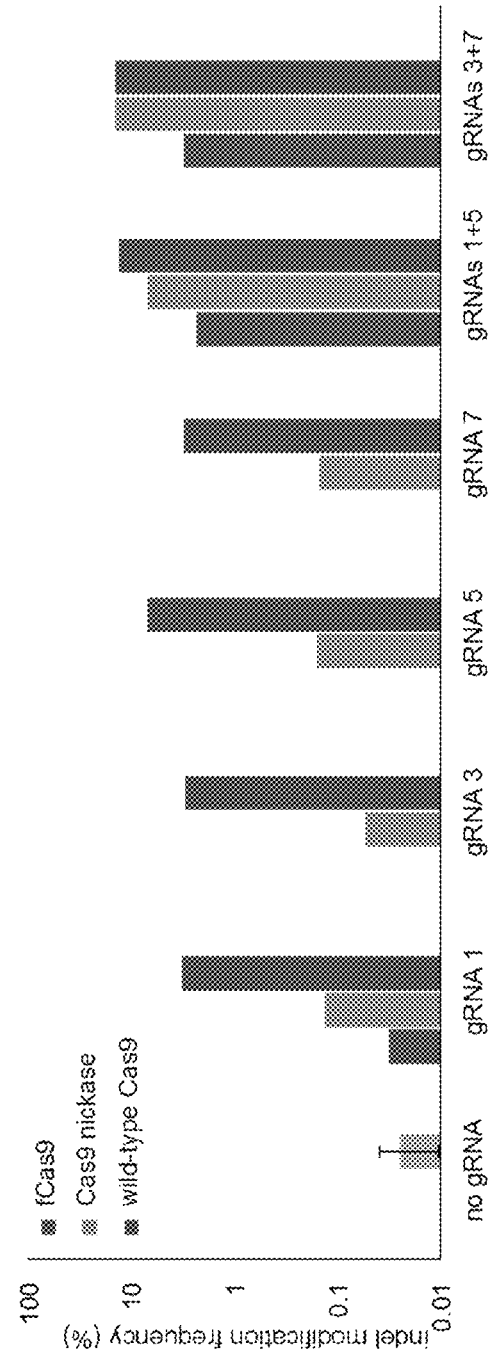
FIG. 16A
FIG. 16B

CRA
CCAGCAAGAGAGGCTCCCGAGCGAGCAAGCTCAGTTTACACCCGATCCACTGGGGAGCAGGAAATATCTGTGGGCTTGTGACACGGACTCAAGTGGGCTGG
CCAGCAAGAGAGGCTCCCGAGCGAG (CRA-1)
CCGAGCGAGCAAGCTCAGTTTA (CRA-2)
CCGATCCACTGGGGAGCAGGAA (CRA-3)
AGTTTACACCCGATCCACTGGGG (CRA-4)
TGGGGAGCAGGAAATATCTGTGG (CRA-5)
ATATCTGTGGGCTTGTGACACGG (CRA-6)
GCTTGTGACACGGACTCAAGTGG (CRA-6)
TGACACGGACTCAAGTGGGCTGG (CRA-7)

guide RNA spacer length (bp)

|  | CRA-4 | CRA-5 | CRA-6 | CRA-8 |
|---|---|---|---|---|
| CRA-1 | 7 | 25 | 38 | 48 |
| CRA-2 |  | 12 | 25 | 35 |
| CRA-3 |  |  | 0 | 10 |

FIG. 19A

CRB
CCTGGCCATCTCTGACCTGTTTTCCTTCTTACTGTCCCCTTCTGGGCTCACTATGCTGCCGCCCAGTGGGACTTTGGAAATACAATGTGTCAACTCTTGACAGGGC
TCTATTTTATAGG
CCTGGCCATCTCTGACCTGTTTT (CB-1)
CCCCTTCTGGGCTCACTATGCTG (CB-2)
CCGCCCAGTGGGACTTTGGAAAT (CB-3)
TCACTATGCTGCCGCCCAGTGGG (CB-4)
CAATGTGTCAACTCTTGACAGGG (CB-5)
TTGACAGGGCTCTATTTTATAGG (CB-6)

guide RNA spacer length (bp)

| | CB-4 | CB-5 | CB-6 |
|---|---|---|---|
| CB-1 | 25 | 60 | 74 |
| CB-2 | | 24 | 38 |
| CB-3 | | | 16 |

SEQUENCE LISTING

<160> NUMBER OF SEQ ID NOS: 328

<210> SEQ ID NO 1
<211> LENGTH: 4104
<212> TYPE: DNA

<213> ORGANISM: Streptococcus pyogenes

<400> SEQUENCE: 1

```
atggataaga aatactcaat aggcttagat atcggcacaa atagcgtcgg atgggcggtg      60
atcactgatg attataaggt tccgtctaaa aagttcaagg ttctgggaaa tacagaccgc     120
cacagtatca aaaaaatct tataggggct cttttatttg gcagtggaga gacagcggaa     180
gcgactcgtc tcaaacggac agctcgtaga aggtatacac gtcggaagaa tcgtatttgt     240
tatctacagg agattttttc aaatgagatg gcgaaagtag atgatagttt ctttcatcga     300
cttgaagagt cttttttggt ggaagaagac aagaagcatg aacgtcatcc tattttttgga    360
aatatagtag atgaagttgc ttatcatgag aaatatccaa ctatctatca tctgcgaaaa     420
aaattggcag attctactga taaagcggat ttgcgcttaa tctatttggc cttagcgcat     480
atgattaagt ttcgtggtca ttttttgatt gagggagatt aaatcctga taatagtgat      540
gtggacaaac tatttatcca gttggtacaa atctacaatc aattatttga agaaaaccct     600
attaacgcaa gtagagtaga tgctaaagcg attctttctg cacgattgag taaatcaaga     660
cgattagaaa atctcattgc tcagctcccc ggtgagaaga gaaatggctt gtttgggaat     720
ctcattgctt tgtcattggg attgaccct aattttaaat caaattttga tttggcagaa      780
gatgctaaat tacagctttc aaaagatact tacgatgatg atttagataa tttattggcg     840
caaattggag atcaatatgc tgatttgttt ttggcagcta gaattttatc agatgctatt     900
ttactttcag atatcctaag agtaaatagt gaaataacta aggctcccct atcagcttca     960
atgattaagc gctacgatga acatcatcaa gacttgactc ttttaaaagc tttagttcga    1020
caacaacttc cagaaaagta taaagaaatc tttttgatc aatcaaaaaa cggatatgca     1080
ggttatattg atggggagc tagccaagaa gaattttata aatttatcaa accaattta      1140
gaaaaaatgg atggtactga ggaattattg gtgaaactaa atcgtgaaga tttgctgcgc     1200
aagcaacgga cctttgacaa cggctctatt ccccatcaaa ttcacttggg tgagctgcat    1260
gctatttga gaagacaaga agacttttat ccattttttaa aagacaatcg tgagaagatt    1320
gaaaaaatct tgactttttcg aattccttat tatgttggtc cattggcgcg tggcaatagt    1380
cgttttgcat ggatgactcg gaagtctgaa gaaacaatta ccccatggaa ttttgaagaa    1440
gttgtcgata aggtgcttc agctcaatca tttattgaac gcatgacaaa ctttgataaa    1500
aatcttccaa atgaaaagt actaccaaaa catagtttgc tttatgagta ttttacggtt     1560
tataacgaat tgacaaaggt caaatatgtt actgagggaa tgcgaaaacc agcattctt     1620
tcaggtgaac agaagaaagc cattgttgat ttactcttca aaacaaatcg aaaagtaacc    1680
gttaagcaat aaaagaaga ttatttcaaa aaaatagaat gttttgatag tgttgaaatt    1740
tcaggagttg aagatagatt taatgcttca ttaggcgcct accatgattt gctaaaaatt    1800
attaaagata aagatttttt ggataatgaa gaaatgaag atatcttaga ggatattgtt    1860
ttaacattga ccttatttga agataggggg atgattgagg aaagacttaa aacatatgct    1920
caccttcttgg atgataaggt gatgaaacag cttaaacgtc gccgttatac tggttgggga    1980
cgttgtctc gaaaattgat taatggtatt agggataagc aatctggcaa acaatatta     2040
gatttttga aatcagatgg ttttgccaat cgcaatttta tgcagctgat ccatgatgat     2100
agtttgacat ttaaagaaga tattcaaaaa gcacaggtgt ctggacaagg ccatagttta    2160
catgaacaga ttgctaactt agctggcagt cctgctatta aaaaaggtat tttacagact    2220
gtaaaaattg ttgatgaact ggtcaaagta atggggcata agccagaaaa tatcgttatt    2280
```

```
gaaatggcac gtgaaaatca gacaactcaa aagggccaga aaaattcgcg agagcgtatg    2340
aaacgaatcg aagaaggtat caagaattta ggaagtcaga ttcttaaaga gcatcctgtt    2400
gaaaatactc aattgcaaaa tgaaaagctc tatctctatt atctacaaaa tggaagagac    2460
atgtatgtgg accaagaatt agatattaat cgtttaagtg attatgatgt cgatcacatt    2520
gttccacaaa gtttcattaa agacgattca atagacaata aggtactaac gcgttctgat    2580
aaaaatcgtg gtaaatcgga taacgttcca agtgaagaag tagtcaaaaa gatgaaaaac    2640
tattggagac aacttctaaa cgccaagtta atcactcaac gtaagtttga taattttaacg    2700 aaagctgaac gtggaggttt gagtgaactt gataaagctg gtttatcaa acgccaattg    2760 gttgaaactc gccaaatcac taagcatgtg gcacaaattt tggatagtcg catgaatact    2820
aaatacgatg aaaatgataa acttattcga gaggttaaag tgattacctt aaaatctaaa    2880
ttagtttctg acttccgaaa agatttccaa ttctataaag tacgtgagat taacaattac    2940
catcatgccc atgatgcgta tctaaatgcc gtcgttggaa ctgctttgat taagaaatat    3000
ccaaaacttg aatcggagtt tgtctatggt gattataaag tttatgatgt tcgtaaaatg    3060
attgctaagt ctgagcaaga aataggcaaa gcaaccgcaa atatttctt ttactctaat    3120 atcatgaact tcttcaaaac agaaattaca cttgcaaatg gagagattcg caaacgccct    3180
ctaatcgaaa ctaatgggga aactggagaa attgtctggg ataaagggcg agattttgcc    3240
acagtgcgca agtattgtc catgccccaa gtcaatattg tcaagaaaac agaagtacag    3300
acaggcggat tctccaagga gtcaatttta ccaaaaagaa attcggacaa gcttattgct    3360
cgtaaaaaag actgggatcc aaaaaaatat ggtggttttg atagtccaac ggtagcttat    3420
tcagtcctag tggttgctaa ggtggaaaaa gggaaatcga agaagttaaa atccgttaaa    3480
gagttactag ggatcacaat tatggaaaga agttccttttg aaaaaaatcc gattgacttt    3540
ttagaagcta aaggatataa ggaagttaaa aaagacttaa tcattaaact acctaaatat    3600 agtcttttttg agttagaaaa cggtcgtaaa cggatgctgg ctagtgccgg agaattacaa    3660
aaaggaaatg agctggctct gccaagcaaa tatgtgaatt ttttatattt agctagtcat    3720
tatgaaaagt tgaagggtag tccagaagat aacgaacaaa aacaattgtt tgtggagcag    3780
cataagcatt atttagatga gattattgag caaatcagtg aattttctaa gcgtgttatt    3840
ttagcagatg ccaatttaga taaagttctt agtgcatata caaacatag agacaaacca    3900 atacgtgaac aagcagaaaa tattattcat ttatttacgt tgacgaatct tggagctccc    3960 gctgcttttta aatattttga tacaacaatt gatcgtaaac gatatacgtc tacaaaagaa    4020
gttttagatg ccactcttat ccatcaatcc atcactggtc tttatgaaac acgcattgat    4080
ttgagtcagc taggaggtga ctga                                            4104
```

<210> SEQ ID NO 2
<211> LENGTH: 1367
<212> TYPE: PRT
<213> ORGANISM: Streptococcus pyogenes

<400> SEQUENCE: 2

Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Phe
            20                  25                  30

Lys Val Leu Gly Asn Thr Asp Arg His Ser Ile Lys Lys Asn Leu Ile
        35                  40                  45

```
Gly Ala Leu Leu Phe Gly Ser Gly Glu Thr Ala Glu Ala Thr Arg Leu
         50                  55                  60

Lys Arg Thr Ala Arg Arg Tyr Thr Arg Arg Lys Asn Arg Ile Cys
 65                  70                  75                  80

Tyr Leu Gln Glu Ile Phe Ser Asn Glu Met Ala Lys Val Asp Asp Ser
                     85                  90                  95

Phe Phe His Arg Leu Glu Glu Ser Phe Leu Val Glu Glu Asp Lys Lys
                 100                 105                 110

His Glu Arg His Pro Ile Phe Gly Asn Ile Val Asp Glu Val Ala Tyr
             115                 120                 125

His Glu Lys Tyr Pro Thr Ile Tyr His Leu Arg Lys Lys Leu Ala Asp
         130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                 165                 170                 175

Asp Asn Ser Asp Val Asp Lys Leu Phe Ile Gln Leu Val Gln Ile Tyr
             180                 185                 190

Asn Gln Leu Phe Glu Glu Asn Pro Ile Asn Ala Ser Arg Val Asp Ala
         195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Arg Asn Gly Leu Phe Gly Asn
225                 230                 235                 240

Leu Ile Ala Leu Ser Leu Gly Leu Thr Pro Asn Phe Lys Ser Asn Phe
                 245                 250                 255

Asp Leu Ala Glu Asp Ala Lys Leu Gln Leu Ser Lys Asp Thr Tyr Asp
             260                 265                 270

Asp Asp Leu Asp Asn Leu Leu Ala Gln Ile Gly Asp Gln Tyr Ala Asp
         275                 280                 285

Leu Phe Leu Ala Ala Lys Asn Leu Ser Asp Ala Ile Leu Leu Ser Asp
290                 295                 300

Ile Leu Arg Val Asn Ser Glu Ile Thr Lys Ala Pro Leu Ser Ala Ser
305                 310                 315                 320

Met Ile Lys Arg Tyr Asp Glu His His Gln Asp Leu Thr Leu Leu Lys
                 325                 330                 335

Ala Leu Val Arg Gln Gln Leu Pro Glu Lys Tyr Lys Glu Ile Phe Phe
             340                 345                 350

Asp Gln Ser Lys Asn Gly Tyr Ala Gly Tyr Ile Asp Gly Gly Ala Ser
         355                 360                 365

Gln Glu Glu Phe Tyr Lys Phe Ile Lys Pro Ile Leu Glu Lys Met Asp
         370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                 405                 410                 415

Gly Glu Leu His Ala Ile Leu Arg Arg Gln Glu Asp Phe Tyr Pro Phe
             420                 425                 430

Leu Lys Asp Asn Arg Glu Lys Ile Glu Lys Ile Leu Thr Phe Arg Ile
         435                 440                 445

Pro Tyr Tyr Val Gly Pro Leu Ala Arg Gly Asn Ser Arg Phe Ala Trp
450                 455                 460
```

```
Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Ala Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
610                 615                 620

Leu Phe Glu Asp Arg Gly Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly His Ser Leu
705                 710                 715                 720

His Glu Gln Ile Ala Asn Leu Ala Gly Ser Pro Ala Ile Lys Lys Gly
                725                 730                 735

Ile Leu Gln Thr Val Lys Ile Val Asp Glu Leu Val Lys Val Met Gly
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Ile Lys Asp
        835                 840                 845

Asp Ser Ile Asp Asn Lys Val Leu Thr Arg Ser Asp Lys Asn Arg Gly
850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
```

-continued

```
                885                 890                 895
Asp Asn Leu Thr Lys Ala Glu Arg Gly Gly Leu Ser Glu Leu Asp Lys
                    900                 905                 910
Ala Gly Phe Ile Lys Arg Gln Leu Val Glu Thr Arg Gln Ile Thr Lys
            915                 920                 925
His Val Ala Gln Ile Leu Asp Ser Arg Met Asn Thr Lys Tyr Asp Glu
        930                 935                 940
Asn Asp Lys Leu Ile Arg Glu Val Lys Val Ile Thr Leu Lys Ser Lys
945                 950                 955                 960
Leu Val Ser Asp Phe Arg Lys Asp Phe Gln Phe Tyr Lys Val Arg Glu
                965                 970                 975
Ile Asn Asn Tyr His His Ala His Asp Ala Tyr Leu Asn Ala Val Val
                    980                 985                 990
Gly Thr Ala Leu Ile Lys Lys Tyr Pro Lys Leu Glu Ser Glu Phe Val
            995                 1000                1005
Tyr Gly Asp Tyr Lys Val Tyr Asp Val Arg Lys Met Ile Ala Lys
        1010                1015                1020
Ser Glu Gln Glu Ile Gly Lys Ala Thr Ala Lys Tyr Phe Phe Tyr
    1025                1030                1035
Ser Asn Ile Met Asn Phe Phe Lys Thr Glu Ile Thr Leu Ala Asn
    1040                1045                1050
Gly Glu Ile Arg Lys Arg Pro Leu Ile Glu Thr Asn Gly Glu Thr
    1055                1060                1065
Gly Glu Ile Val Trp Asp Lys Gly Arg Asp Phe Ala Thr Val Arg
    1070                1075                1080
Lys Val Leu Ser Met Pro Gln Val Asn Ile Val Lys Lys Thr Glu
    1085                1090                1095
Val Gln Thr Gly Gly Phe Ser Lys Glu Ser Ile Leu Pro Lys Arg
    1100                1105                1110
Asn Ser Asp Lys Leu Ile Ala Arg Lys Lys Asp Trp Asp Pro Lys
    1115                1120                1125
Lys Tyr Gly Gly Phe Asp Ser Pro Thr Val Ala Tyr Ser Val Leu
    1130                1135                1140
Val Val Ala Lys Val Glu Lys Gly Lys Ser Lys Lys Leu Lys Ser
    1145                1150                1155
Val Lys Glu Leu Leu Gly Ile Thr Ile Met Glu Arg Ser Ser Phe
    1160                1165                1170
Glu Lys Asn Pro Ile Asp Phe Leu Glu Ala Lys Gly Tyr Lys Glu
    1175                1180                1185
Val Lys Lys Asp Leu Ile Ile Lys Leu Pro Lys Tyr Ser Leu Phe
    1190                1195                1200
Glu Leu Glu Asn Gly Arg Lys Arg Met Leu Ala Ser Ala Gly Glu
    1205                1210                1215
Leu Gln Lys Gly Asn Glu Leu Ala Leu Pro Ser Lys Tyr Val Asn
    1220                1225                1230
Phe Leu Tyr Leu Ala Ser His Tyr Glu Lys Leu Lys Gly Ser Pro
    1235                1240                1245
Glu Asp Asn Glu Gln Lys Gln Leu Phe Val Glu Gln His Lys His
    1250                1255                1260
Tyr Leu Asp Glu Ile Ile Glu Gln Ile Ser Glu Phe Ser Lys Arg
    1265                1270                1275
Val Ile Leu Ala Asp Ala Asn Leu Asp Lys Val Leu Ser Ala Tyr
    1280                1285                1290
```

| Asn | Lys | His | Arg | Asp | Lys | Pro | Ile | Arg | Glu | Gln | Ala | Glu | Asn | Ile |
|---|---|---|---|---|---|---|---|---|---|---|---|---|---|---|
| | 1295 | | | | 1300 | | | | 1305 | | | | | |

| Ile | His | Leu | Phe | Thr | Leu | Thr | Asn | Leu | Gly | Ala | Pro | Ala | Ala | Phe |
|---|---|---|---|---|---|---|---|---|---|---|---|---|---|---|
| 1310 | | | | | 1315 | | | | | 1320 | | | | |

| Lys | Tyr | Phe | Asp | Thr | Thr | Ile | Asp | Arg | Lys | Arg | Tyr | Thr | Ser | Thr |
|---|---|---|---|---|---|---|---|---|---|---|---|---|---|---|
| 1325 | | | | | 1330 | | | | | 1335 | | | | |

| Lys | Glu | Val | Leu | Asp | Ala | Thr | Leu | Ile | His | Gln | Ser | Ile | Thr | Gly |
|---|---|---|---|---|---|---|---|---|---|---|---|---|---|---|
| 1340 | | | | | 1345 | | | | | 1350 | | | | |

| Leu | Tyr | Glu | Thr | Arg | Ile | Asp | Leu | Ser | Gln | Leu | Gly | Gly | Asp |
|---|---|---|---|---|---|---|---|---|---|---|---|---|---|
| 1355 | | | | | 1360 | | | | | 1365 | | | |

<210> SEQ ID NO 3
<211> LENGTH: 4212
<212> TYPE: DNA
<213> ORGANISM: Artificial Sequence
<220> FEATURE:
<223> OTHER INFORMATION: Synthetic Polynucleotide

<400> SEQUENCE: 3

```
atggataaaa agtattctat tggtttagac atcggcacta attccgttgg atgggctgtc      60
ataaccgatg aatacaaagt accttcaaag aaatttaagg tgttgggaa cacagaccgt     120
cattcgatta aaaagaatct tatcggtgcc tcctattcg atagtggcga acggcagag       180
gcgactcgcc tgaaacgaac cgctcggaga aggtatacac gtcgcaagaa ccgaatatgt     240
tacttacaag aaattttag caatgagatg gccaaagttg acgattcttt ctttcaccgt     300
ttggaagagt ccttccttgt cgaagaggac aagaaacatg aacggcaccc catctttgga    360
aacatagtag atgaggtggc atatcatgaa aagtacccaa cgatttatca cctcagaaaa    420
aagctagttg actcaactga taaagcggac ctgaggttaa tctacttggc tcttgcccat    480
atgataaagt tccgtgggca ctttctcatt gagggtgatc taaatccgga caactcggat    540
gtcgacaaac tgttcatcca gttagtacaa acctataatc agttgtttga agagaaccct    600
ataaatgcaa gtggcgtgga tgcgaaggct attcttagcg cccgcctctc taaatcccga    660
cggctagaaa acctgatcgc acaattaccc ggagagaaga aaaatgggtt gttcggtaac    720
cttatagcgc tctcactagg cctgacacca aattttaagt cgaacttcga cttagctgaa    780
gatgccaaat tgcagcttag taaggacacg tacgatgacg atctcgacaa tctactggca    840
caaattggag atcagtatgc ggacttattt ttggctgcca aaaaccttag cgatgcaatc    900
ctcctatctg acatactgag agttaatact gagattacca aggcgccgtt atccgcttca    960
atgatcaaaa ggtacgatga acatcaccaa gacttgacac ttctcaaggc cctagtccgt   1020
cagcaactgc ctgagaaata taaggaaata ttctttgatc agtcgaaaaa cgggtacgca   1080
ggttatattg acggcggagc gagtcaagag gaattctaca gtttatcaa acccatatta    1140
gagaagatgg atgggacgga agagttgctt gtaaaactca atcgcgaaga tctactgcga   1200
aagcagcgga ctttcgacaa cggtagcatt ccacatcaaa tccacttagg cgaattgcat   1260
gctatactta aaggcagga ggattttat ccgttcctca aagacaatcg tgaaaagatt   1320
gagaaaatcc taacctttcg catccttac tatgtgggac ccctggcccg agggaactct   1380
cggttcgcat ggatgacaag aaagtccgaa gaaacgatta ctccatggaa ttttgaggaa   1440
gttgtcgata aggtgcgtc agctcaatcg ttcatcgaga ggatgaccaa ctttgacaag   1500
aatttaccga acgaaaaagt attgcctaag cacagtttac tttacgagta tttcacagtg   1560
tacaatgaac tcacgaaagt taagtatgtc actgagggca tgcgtaaacc cgcctttcta   1620
```

```
agcggagaac agaagaaagc aatagtagat ctgttattca agaccaaccg caaagtgaca    1680
gttaagcaat tgaaagagga ctactttaag aaaattgaat gcttcgattc tgtcgagatc    1740
tccggggtag aagatcgatt taatgcgtca cttggtacgt atcatgacct cctaaagata    1800
attaaagata aggacttcct ggataacgaa gagaatgaag atatcttaga agatatagtg    1860
ttgactctta ccctctttga agatcgggaa atgattgagg aaagactaaa aacatacgct    1920
cacctgttcg acgataaggt tatgaaacag ttaaagaggc gtcgctatac gggctgggga    1980
cgattgtcgc ggaaacttat caacgggata agagacaagc aaagtggtaa aactattctc    2040
gattttctaa agagcgacgg cttcgccaat aggaacttta tgcagctgat ccatgatgac    2100
tctttaacct tcaaagagga tatacaaaag gcacaggttt ccggacaagg ggactcattg    2160
cacgaacata ttgcgaatct tgctggttcg ccagccatca aaagggcat actccagaca    2220 gtcaaagtag tggatgagct agttaaggtc atgggacgtc acaaaccgga aacattgta    2280 atcgagatgg cacgcgaaaa tcaaacgact cagaaggggc aaaaaaacag tcgagagcgg    2340
atgaagagaa tagaagaggg tattaaagaa ctgggcagcc agatcttaaa ggagcatcct    2400
gtggaaaata cccaattgca gaacgagaaa ctttacctct attacctaca aaatggaagg    2460
gacatgtatg ttgatcagga actggacata aaccgtttat ctgattacga cgtcgatcac    2520
attgtacccc aatccttttt gaaggacgat tcaatcgaca ataaagtgct tacacgctcg    2580
gataagaacc gagggaaaag tgacaatgtt ccaagcgagg aagtcgtaaa gaaaatgaag    2640
aactattggc ggcagctcct aaatgcgaaa ctgataacgc aaagaaagtt cgataactta    2700
actaaagctg agaggggtgg cttgtctgaa cttgacaagg ccggatttat taaacgtcag    2760
ctcgtggaaa cccgccaaat cacaaagcat gttgcacaga tactagattc ccgaatgaat    2820
acgaaatacg acgagaacga taagctgatt cgggaagtca agtaatcac tttaaagtca    2880 aaattggtgt cggacttcag aaaggatttt caattctata agttaggga gataaataac    2940 taccaccatg cgcacgacgc ttatcttaat gccgtcgtag ggaccgcact cattaagaaa    3000
tacccgaagc tagaaagtga gtttgtgtat ggtgattaca agtttatga cgtccgtaag    3060 atgatcgcga aaagcgaaca ggagataggc aaggctacag ccaaatactt ctttttattct    3120 aacattatga atttctttaa gacggaaatc actctggcaa acggagagat acgcaaacga    3180
cctttaattg aaaccaatgg ggagacaggt gaaatcgtat gggataaggg ccggacttc    3240 gcgacggtga gaaaagtttt gtccatgccc caagtcaaca tagtaaagaa aactgaggtg    3300
cagaccggag ggttttcaaa ggaatcgatt cttccaaaaa ggaatagtga taagctcatc    3360
gctcgtaaaa aggactggga cccgaaaaag tacggtggct tcgatagccc tacagttgcc    3420
tattctgtcc tagtagtggc aaaagttgag aagggaaaat ccaagaaact gaagtcagtc    3480
aaagaattat tggggataac gattatggag cgctcgtctt ttgaaaagaa ccccatcgac    3540
ttccttgagg cgaaaggtta caggaagta aaaaaggatc tcataattaa actaccaaag    3600
tatagtctgt ttgagttaga aaatggccga aaacggatgt tggctagcgc cggagagctt    3660
caaaagggga cgaactcgc actaccgtct aaatacgtga atttcctgta tttagcgtcc    3720
cattacgaga agttgaaagg ttcacctgaa gataacgaac agaagcaact ttttgttgag    3780
cagcacaaac attatctcga cgaaatcata gagcaaattt cggaattcag taagagagtc    3840
atcctagctg atgccaatct ggacaaagta ttaagcgcat acaacaagca cagggataaa    3900
cccatacgtg agcaggcgga aaatattatc catttgttta ctcttaccaa cctcggcgct    3960
```

-continued

```
ccagccgcat tcaagtattt tgacacaacg atagatcgca aacgatacac ttctaccaag    4020
gaggtgctag acgcgacact gattcaccaa tccatcacgg gattatatga aactcggata    4080
gatttgtcac agcttggggg tgacggatcc cccaagaaga agaggaaagt ctcgagcgac    4140
tacaaagacc atgacggtga ttataaagat catgacatcg attacaagga tgacgatgac    4200
aaggctgcag ga                                                        4212
```

<210> SEQ ID NO 4
<211> LENGTH: 1368
<212> TYPE: PRT
<213> ORGANISM: Artificial Sequence
<220> FEATURE:
<223> OTHER INFORMATION: Synthetic Polypeptide

<400> SEQUENCE: 4

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320
```

-continued

```
Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735
```

-continued

```
Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
```

```
               1145                1150                1155

Ser Val Lys Glu Leu Leu Gly Ile Thr Ile Met Glu Arg Ser Ser
       1160                1165                1170

Phe Glu Lys Asn Pro Ile Asp Phe Leu Glu Ala Lys Gly Tyr Lys
       1175                1180                1185

Glu Val Lys Lys Asp Leu Ile Ile Lys Leu Pro Lys Tyr Ser Leu
       1190                1195                1200

Phe Glu Leu Glu Asn Gly Arg Lys Arg Met Leu Ala Ser Ala Gly
       1205                1210                1215

Glu Leu Gln Lys Gly Asn Glu Leu Ala Leu Pro Ser Lys Tyr Val
       1220                1225                1230

Asn Phe Leu Tyr Leu Ala Ser His Tyr Glu Lys Leu Lys Gly Ser
       1235                1240                1245

Pro Glu Asp Asn Glu Gln Lys Gln Leu Phe Val Glu Gln His Lys
       1250                1255                1260

His Tyr Leu Asp Glu Ile Ile Glu Gln Ile Ser Glu Phe Ser Lys
       1265                1270                1275

Arg Val Ile Leu Ala Asp Ala Asn Leu Asp Lys Val Leu Ser Ala
       1280                1285                1290

Tyr Asn Lys His Arg Asp Lys Pro Ile Arg Glu Gln Ala Glu Asn
       1295                1300                1305

Ile Ile His Leu Phe Thr Leu Thr Asn Leu Gly Ala Pro Ala Ala
       1310                1315                1320

Phe Lys Tyr Phe Asp Thr Thr Ile Asp Arg Lys Arg Tyr Thr Ser
       1325                1330                1335

Thr Lys Glu Val Leu Asp Ala Thr Leu Ile His Gln Ser Ile Thr
       1340                1345                1350

Gly Leu Tyr Glu Thr Arg Ile Asp Leu Ser Gln Leu Gly Gly Asp
       1355                1360                1365

<210> SEQ ID NO 5
<211> LENGTH: 1368
<212> TYPE: PRT
<213> ORGANISM: Artificial Sequence
<220> FEATURE:
<223> OTHER INFORMATION: Synthetic Polypeptide

<400> SEQUENCE: 5

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
```

```
            130                 135                 140
Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
        210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560
```

-continued

```
Val Lys Gln Leu Lys Glu Asp Tyr Phe Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975
```

-continued

```
Glu Ile Asn Asn Tyr His His Ala His Asp Ala Tyr Leu Asn Ala Val
            980                 985                 990
Val Gly Thr Ala Leu Ile Lys Lys Tyr Pro Lys Leu Glu Ser Glu Phe
        995                1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Gly
    1205                1210                1215
Glu Leu Gln Lys Gly Asn Glu Leu Ala Leu Pro Ser Lys Tyr Val
    1220                1225                1230
Asn Phe Leu Tyr Leu Ala Ser His Tyr Glu Lys Leu Lys Gly Ser
    1235                1240                1245
Pro Glu Asp Asn Glu Gln Lys Gln Leu Phe Val Glu Gln His Lys
    1250                1255                1260
His Tyr Leu Asp Glu Ile Ile Glu Gln Ile Ser Glu Phe Ser Lys
    1265                1270                1275
Arg Val Ile Leu Ala Asp Ala Asn Leu Asp Lys Val Leu Ser Ala
    1280                1285                1290
Tyr Asn Lys His Arg Asp Lys Pro Ile Arg Glu Gln Ala Glu Asn
    1295                1300                1305
Ile Ile His Leu Phe Thr Leu Thr Asn Leu Gly Ala Pro Ala Ala
    1310                1315                1320
Phe Lys Tyr Phe Asp Thr Thr Ile Asp Arg Lys Arg Tyr Thr Ser
    1325                1330                1335
Thr Lys Glu Val Leu Asp Ala Thr Leu Ile His Gln Ser Ile Thr
    1340                1345                1350
Gly Leu Tyr Glu Thr Arg Ile Asp Leu Ser Gln Leu Gly Gly Asp
    1355                1360                1365
```

-continued

<210> SEQ ID NO 6
<211> LENGTH: 198
<212> TYPE: PRT
<213> ORGANISM: Artificial Sequence
<220> FEATURE:
<223> OTHER INFORMATION: Synthetic Polypeptide

<400> SEQUENCE: 6

```
Gly Ser Gln Leu Val Lys Ser Glu Leu Glu Glu Lys Ser Glu Leu
1               5                   10                  15

Arg His Lys Leu Lys Tyr Val Pro His Glu Tyr Ile Glu Leu Ile Glu
            20                  25                  30

Ile Ala Arg Asn Ser Thr Gln Asp Arg Ile Leu Glu Met Lys Val Met
        35                  40                  45

Glu Phe Phe Met Lys Val Tyr Gly Tyr Arg Gly Lys His Leu Gly Gly
    50                  55                  60

Ser Arg Lys Pro Asp Gly Ala Ile Tyr Thr Val Gly Ser Pro Ile Asp
65                  70                  75                  80

Tyr Gly Val Ile Val Asp Thr Lys Ala Tyr Ser Gly Gly Tyr Asn Leu
                85                  90                  95

Pro Ile Gly Gln Ala Asp Glu Met Gln Arg Tyr Val Glu Glu Asn Gln
            100                 105                 110

Thr Arg Asn Lys His Ile Asn Pro Asn Glu Trp Trp Lys Val Tyr Pro
        115                 120                 125

Ser Ser Val Thr Glu Phe Lys Phe Leu Phe Val Ser Gly His Phe Lys
    130                 135                 140

Gly Asn Tyr Lys Ala Gln Leu Thr Arg Leu Asn His Ile Thr Asn Cys
145                 150                 155                 160

Asn Gly Ala Val Leu Ser Val Glu Glu Leu Leu Ile Gly Gly Glu Met
                165                 170                 175

Ile Lys Ala Gly Thr Leu Thr Leu Glu Glu Val Arg Arg Lys Phe Asn
            180                 185                 190

Asn Gly Glu Ile Asn Phe
        195
```

<210> SEQ ID NO 7
<211> LENGTH: 4221
<212> TYPE: DNA
<213> ORGANISM: Artificial Sequence
<220> FEATURE:
<223> OTHER INFORMATION: Synthetic Polynucleotide

<400> SEQUENCE: 7

| | | |
|---|---|---|
| atggactata aggaccacga cggagactac aaggatcatg atattgatta caaagacgat | | 60 |
| gacgataaga tggcccccaaa gaagaagcgg aaggtcggta tccacggagt cccagcagcc | | 120 |
| gataaaaagt attctattgg tttagctatc ggcactaatt ccgttggatg ggctgtcata | | 180 |
| accgatgaat acaaagtacc ttcaaagaaa tttaaggtgt tggggaacac agaccgtcat | | 240 |
| tcgattaaaa agaatcttat cggtgccctc ctattcgata gtggcgaaac ggcagaggcg | | 300 |
| actcgcctga acgaaccgc tcggagaagg tatacacgtc gcaagaaccg aatatgttac | | 360 |
| ttacaagaaa ttttttagcaa tgagatggcc aaagttgacg attctttctt tcaccgtttg | | 420 |
| gaagagtcct tccttgtcga agaggacaag aaacatgaac ggcaccccat ctttggaaac | | 480 |
| atagtagatg aggtggcata tcatgaaaag tacccaacga tttatcacct cagaaaaaag | | 540 |
| ctagttgact caactgataa agcggacctg aggttaatct acttggctct tgcccatatg | | 600 |
| ataaagttcc gtgggcactt tctcattgag ggtgatctaa atccggacaa ctcggatgtc | | 660 |

```
gacaaactgt tcatccagtt agtacaaacc tataatcagt tgtttgaaga gaaccctata    720
aatgcaagtg gcgtggatgc gaaggctatt cttagcgccc gcctctctaa atcccgacgg    780
ctagaaaacc tgatcgcaca attacccgga gagaagaaaa atgggttgtt cggtaacctt    840
atagcgctct cactaggcct gacaccaaat tttaagtcga acttcgactt agctgaagat    900
gccaaattgc agcttagtaa ggacacgtac gatgacgatc tcgacaatct actggcacaa    960
attggagatc agtatgcgga cttatttttg gctgccaaaa accttagcga tgcaatcctc   1020
ctatctgaca tactgagagt taatactgag attaccaagg cgccgttatc cgcttcaatg   1080
atcaaaaggt acgatgaaca tcaccaagac ttgacacttc tcaaggccct agtccgtcag   1140
caactgcctg agaaatataa ggaaatattc tttgatcagt cgaaaaacgg gtacgcaggt   1200
tatattgacg gcggagcgag tcaagaggaa ttctacaagt ttatcaaacc catattagag   1260
aagatggatg ggacggaaga gttgcttgta aaactcaatc gcgaagatct actgcgaaag   1320
cagcggactt cgacaacgg tagcattcca catcaaatcc acttaggcga attgcatgct   1380
atacttagaa ggcaggagga ttttttatccg ttcctcaaag acaatcgtga aaagattgag   1440
aaaatcctaa cctttcgcat accttactat gtgggacccc tggcccgagg gaactctcgg   1500
ttcgcatgga tgacaagaaa gtccgaagaa acgattactc catggaattt tgaggaagtt   1560
gtcgataaag gtgcgtcagc tcaatcgttc atcgagagga tgaccaactt tgacaagaat   1620
ttaccgaacg aaaaagtatt gcctaagcac agtttacttt acgagtattt cacagtgtac   1680
aatgaactca cgaaagttaa gtatgtcact gagggcatgc gtaaacccgc ctttctaagc   1740
ggagaacaga agaaagcaat agtagatctg ttattcaaga ccaaccgcaa agtgacagtt   1800
aagcaattga agaggacta ctttaagaaa attgaatgct tcgattctgt cgagatctcc    1860
ggggtagaag atcgatttaa tgcgtcactt ggtacgtatc atgacctcct aaagataatt   1920
aaagataagg acttcctgga taacgaagag aatgaagata tcttagaaga tatagtgttg   1980
actcttaccc tctttgaaga tcgggaaatg attgaggaaa gactaaaaac atacgctcac   2040
ctgttcgacg ataaggttat gaaacagtta aagaggcgtc gctatacggg ctggggacga   2100
ttgtcgcgga aacttatcaa cgggataaga gacaagcaaa gtggtaaaac tattctcgat   2160
tttctaaaga gcgacggctt cgccaatagg aactttatgc agctgatcca tgatgactct   2220
ttaaccttca aagaggatat acaaaaggca caggtttccg gacaagggga ctcattgcac   2280
gaacatattg cgaatcttgc tggttcgcca gccatcaaaa agggcatact ccagacagtc   2340
aaagtagtgg atgagctagt taaggtcatg ggacgtcaca accggaaaaa cattgtaatc   2400
gagatggcac gcgaaaatca aacgactcag aagggcaaa aaacagtcg agagcggatg   2460
aagagaatag aagagggtat taagaactg ggcagccaga tcttaaagga gcatcctgtg   2520
gaaaatacccc aattgcagaa cgagaaactt tacctctatt acctacaaaa tggaagggac   2580
atgtatgttg atcaggaact ggacataaac cgtttatctg attacgacgt cgatcacatt   2640
gtaccccaat cctttttgaa ggacgattca atcgacaata agtgcttac acgctcggat   2700
aagaaccgag ggaaaagtga caatgttcca agcgaggaag tcgtaaagaa atgaagaac   2760
tattggcggc agctcctaaa tgcgaaactg ataacgcaaa gaaagttcga taacttaact   2820
aaagctgaga ggggtggctt gtctgaactt gacaaggccg gatttattaa acgtcagctc   2880
gtggaaaccc gccaaatcac aaagcatgtt gcacagatac tagattcccg aatgaatacg   2940
aaatacgacg agaacgataa gctgattcgg gaagtcaaag taatcactt aaagtcaaaa   3000
```

```
ttggtgtcgg acttcagaaa ggattttcaa ttctataaag ttagggagat aaataactac    3060
caccatgcgc acgacgctta tcttaatgcc gtcgtaggga ccgcactcat taagaaatac    3120
ccgaagctag aaagtgagtt tgtgtatggt gattacaaag tttatgacgt ccgtaagatg    3180
atcgcgaaaa gcgaacagga gataggcaag gctacagcca aatacttctt ttattctaac    3240
attatgaatt tctttaagac ggaaatcact ctggcaaacg gagagatacg caaacgacct    3300
ttaattgaaa ccaatgggga gacaggtgaa atcgtatggg ataagggccg ggacttcgcg    3360
acggtgagaa aagttttgtc catgccccaa gtcaacatag taaagaaaac tgaggtgcag    3420
accggagggt tttcaaagga atcgattctt ccaaaaagga atagtgataa gctcatcgct    3480
cgtaaaaagg actgggaccc gaaaaagtac ggtggcttcg atagccctac agttgcctat    3540
tctgtcctag tagtggcaaa agttgagaag ggaaaatcca agaaactgaa gtcagtcaaa    3600
gaattattgg ggataacgat tatggagcgc tcgtcttttg aaaagaaccc catcgacttc    3660
cttgaggcga aaggttacaa ggaagtaaaa aaggatctca taattaaaact accaaagtat    3720
agtctgtttg agttagaaaa tggccgaaaa cggatgttgg ctagcgccgg agagcttcaa    3780
aaggggaacg aactcgcact accgtctaaa tacgtgaatt tcctgtattt agcgtcccat    3840
tacgagaagt tgaaaggttc acctgaagat aacgaacaga agcaacttttt tgttgagcag    3900
cacaaacatt atctcgacga aatcatagag caaatttcgg aattcagtaa gagagtcatc    3960
ctagctgatg ccaatctgga caaagtatta agcgcataca acaagcacag ggataaaccc    4020
atacgtgagc aggcggaaaa tattatccat ttgtttactc ttaccaacct cggcgctcca    4080
gccgcattca gtattttga cacaacgata gatcgcaaac gatacacttc taccaaggag    4140
gtgctagacg cgacactgat tcaccaatcc atcacgggat tatatgaaac tcggatagat    4200
ttgtcacagc ttgggggtga c                                              4221
```

<210> SEQ ID NO 8
<211> LENGTH: 1368
<212> TYPE: PRT
<213> ORGANISM: Artificial Sequence
<220> FEATURE:
<223> OTHER INFORMATION: Synthetic Polypeptide

<400> SEQUENCE: 8

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

```
Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
            165                 170                 175

Asp Asn Ser Asp Val Asp Lys Leu Phe Ile Gln Leu Val Gln Thr Tyr
        180                 185                 190

Asn Gln Leu Phe Glu Glu Asn Pro Ile Asn Ala Ser Gly Val Asp Ala
    195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
```

```
                565                 570                 575
Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Asn Glu Asp Ile Leu Glu Asp Ile Val Leu Thr Leu Thr
610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990
```

```
Val Gly Thr Ala Leu Ile Lys Lys Tyr Pro Lys Leu Glu Ser Glu Phe
        995                 1000                    1005

Val Tyr Gly Asp Tyr Lys Val Tyr Asp Val Arg Lys Met Ile Ala
   1010                 1015                 1020

Lys Ser Glu Gln Glu Ile Gly Lys Ala Thr Ala Lys Tyr Phe Phe
   1025                 1030                 1035

Tyr Ser Asn Ile Met Asn Phe Phe Lys Thr Glu Ile Thr Leu Ala
   1040                 1045                 1050

Asn Gly Glu Ile Arg Lys Arg Pro Leu Ile Glu Thr Asn Gly Glu
   1055                 1060                 1065

Thr Gly Glu Ile Val Trp Asp Lys Gly Arg Asp Phe Ala Thr Val
   1070                 1075                 1080

Arg Lys Val Leu Ser Met Pro Gln Val Asn Ile Val Lys Lys Thr
   1085                 1090                 1095

Glu Val Gln Thr Gly Gly Phe Ser Lys Glu Ser Ile Leu Pro Lys
   1100                 1105                 1110

Arg Asn Ser Asp Lys Leu Ile Ala Arg Lys Lys Asp Trp Asp Pro
   1115                 1120                 1125

Lys Lys Tyr Gly Gly Phe Asp Ser Pro Thr Val Ala Tyr Ser Val
   1130                 1135                 1140

Leu Val Val Ala Lys Val Glu Lys Gly Lys Ser Lys Lys Leu Lys
   1145                 1150                 1155

Ser Val Lys Glu Leu Leu Gly Ile Thr Ile Met Glu Arg Ser Ser
   1160                 1165                 1170

Phe Glu Lys Asn Pro Ile Asp Phe Leu Glu Ala Lys Gly Tyr Lys
   1175                 1180                 1185

Glu Val Lys Lys Asp Leu Ile Ile Lys Leu Pro Lys Tyr Ser Leu
   1190                 1195                 1200

Phe Glu Leu Glu Asn Gly Arg Lys Arg Met Leu Ala Ser Ala Gly
   1205                 1210                 1215

Glu Leu Gln Lys Gly Asn Glu Leu Ala Leu Pro Ser Lys Tyr Val
   1220                 1225                 1230

Asn Phe Leu Tyr Leu Ala Ser His Tyr Glu Lys Leu Lys Gly Ser
   1235                 1240                 1245

Pro Glu Asp Asn Glu Gln Lys Gln Leu Phe Val Glu Gln His Lys
   1250                 1255                 1260

His Tyr Leu Asp Glu Ile Ile Glu Gln Ile Ser Glu Phe Ser Lys
   1265                 1270                 1275

Arg Val Ile Leu Ala Asp Ala Asn Leu Asp Lys Val Leu Ser Ala
   1280                 1285                 1290

Tyr Asn Lys His Arg Asp Lys Pro Ile Arg Glu Gln Ala Glu Asn
   1295                 1300                 1305

Ile Ile His Leu Phe Thr Leu Thr Asn Leu Gly Ala Pro Ala Ala
   1310                 1315                 1320

Phe Lys Tyr Phe Asp Thr Thr Ile Asp Arg Lys Arg Tyr Thr Ser
   1325                 1330                 1335

Thr Lys Glu Val Leu Asp Ala Thr Leu Ile His Gln Ser Ile Thr
   1340                 1345                 1350

Gly Leu Tyr Glu Thr Arg Ile Asp Leu Ser Gln Leu Gly Gly Asp
   1355                 1360                 1365
```

<210> SEQ ID NO 9
<211> LENGTH: 4836

<212> TYPE: DNA
<213> ORGANISM: Artificial Sequence
<220> FEATURE:
<223> OTHER INFORMATION: Synthetic Polynucleotide

<400> SEQUENCE: 9

| | | | | | |
|---|---|---|---|---|---|
| atggataaaa | agtattctat | tggtttagct | atcggcacta | attccgttgg | atgggctgtc | 60 |
| ataaccgatg | aatacaaagt | accttcaaag | aaatttaagg | tgttggggaa | cacagaccgt | 120 |
| cattcgatta | aaaagaatct | tatcggtgcc | ctcctattcg | atagtggcga | aacggcagag | 180 |
| gcgactcgcc | tgaaacgaac | cgctcggaga | aggtatacac | gtcgcaagaa | ccgaatatgt | 240 |
| tacttacaag | aaattttttag | caatgagatg | gccaaagttg | acgattcttt | ctttcaccgt | 300 |
| ttggaagagt | ccttccttgt | cgaagaggac | aagaaacatg | aacggcaccc | catctttgga | 360 |
| aacatagtag | atgaggtggc | atatcatgaa | agtacccaa | cgatttatca | cctcagaaaa | 420 |
| aagctagttg | actcaactga | taaagcggac | ctgaggttaa | tctacttggc | tcttgcccat | 480 |
| atgataaagt | tccgtgggca | ctttctcatt | gagggtgatc | taaatccgga | caactcggat | 540 |
| gtcgacaaac | tgttcatcca | gttagtacaa | acctataatc | agttgtttga | agagaaccct | 600 |
| ataaatgcaa | gtggcgtgga | tgcgaaggct | attcttagcg | cccgcctctc | taaatcccga | 660 |
| cggctagaaa | acctgatcgc | acaattaccc | ggagagaaga | aaaatgggtt | gttcggtaac | 720 |
| cttatagcgc | tctcactagg | cctgacacca | aattttaagt | cgaacttcga | cttagctgaa | 780 |
| gatgccaaat | tgcagcttag | taaggacacg | tacgatgacg | atctcgacaa | tctactggca | 840 |
| caaattggag | atcagtatgc | ggacttattt | ttggctgcca | aaaaccttag | cgatgcaatc | 900 |
| ctcctatctg | acatactgag | agttaatact | gagattacca | aggcgccgtt | atccgcttca | 960 |
| atgatcaaaa | ggtacgatga | acatcaccaa | gacttgacac | ttctcaaggc | cctagtccgt | 1020 |
| cagcaactgc | ctgagaaata | taaggaaata | ttctttgatc | agtcgaaaaa | cgggtacgca | 1080 |
| ggttatattg | acggcggagc | gagtcaagag | gaattctaca | agtttatcaa | acccatatta | 1140 |
| gagaagatgg | atgggacgga | agagttgctt | gtaaaactca | atcgcgaaga | tctactgcga | 1200 |
| aagcagcgga | ctttcgacaa | cggtagcatt | ccacatcaaa | tccacttagg | cgaattgcat | 1260 |
| gctatactta | gaaggcagga | ggattttttat | ccgttcctca | agacaatcg | tgaaaagatt | 1320 |
| gagaaaatcc | taaccttttcg | cataccttac | tatgtgggac | ccctggcccg | agggaactct | 1380 |
| cggttcgcat | ggatgacaag | aaagtccgaa | gaaacgatta | ctccatggaa | ttttgaggaa | 1440 |
| gttgtcgata | aggtgcgtc | agctcaatcg | ttcatcgaga | ggatgaccaa | ctttgacaag | 1500 |
| aatttaccga | acgaaaaagt | attgcctaag | cacagtttac | tttacgagta | tttcacagtg | 1560 |
| tacaatgaac | tcacgaaagt | taagtatgtc | actgagggca | tgcgtaaacc | cgcctttcta | 1620 |
| agcggagaac | agaagaaagc | aatagtagat | ctgttattca | agaccaaccg | caaagtgaca | 1680 |
| gttaagcaat | tgaaagagga | ctactttaag | aaaattgaat | gcttcgattc | tgtcgagatc | 1740 |
| tccggggtag | aagatcgatt | taatgcgtca | cttggtacgt | atcatgacct | cctaaagata | 1800 |
| attaaagata | aggacttcct | ggataacgaa | gagaatgaag | atatcttaga | agatatagtg | 1860 |
| ttgactctta | ccctctttga | agatcgggaa | atgattgagg | aaagactaaa | aacatacgct | 1920 |
| cacctgttcg | acgataaggt | tatgaaacag | ttaaagaggc | gtcgctatac | gggctgggga | 1980 |
| cgattgtcgc | ggaaacttat | caacgggata | agagacaagc | aaagtggtaa | aactattctc | 2040 |
| gattttctaa | agagcgacgg | cttcgccaat | aggaacttta | tgcagctgat | ccatgatgac | 2100 |
| tctttaacct | tcaaagagga | tatacaaaag | gcacaggttt | ccggacaagg | ggactcattg | 2160 |

```
cacgaacata ttgcgaatct tgctggttcg ccagccatca aaaagggcat actccagaca   2220
gtcaaagtag tggatgagct agttaaggtc atgggacgtc acaaaccgga aaacattgta   2280
atcgagatgg cacgcgaaaa tcaaacgact cagaaggggc aaaaaaacag tcgagagcgg   2340
atgaagagaa tagaagaggg tattaaagaa ctgggcagcc agatcttaaa ggagcatcct   2400
gtggaaaata cccaattgca gaacgagaaa ctttacctct attacctaca aaatggaagg   2460
gacatgtatg ttgatcagga actggacata aaccgtttat ctgattacga cgtcgatgcc   2520
attgtacccc aatcctttt gaaggacgat tcaatcgaca ataaagtgct tacacgctcg    2580
gataagaacc gagggaaaag tgacaatgtt ccagcgagg aagtcgtaaa gaaaatgaag    2640
aactattggc ggcagctcct aaatgcgaaa ctgataacgc aaagaaagtt cgataactta   2700
actaaagctg agaggggtgg cttgtctgaa cttgacaagg ccggatttat taaacgtcag   2760
ctcgtggaaa cccgccaaat cacaaagcat gttgcacaga tactagattc ccgaatgaat   2820
acgaaatacg acgagaacga taagctgatt cgggaagtca agtaatcac tttaaagtca    2880 aaattggtgt cggacttcag aaaggatttt caattctata agttaggga gataaataac    2940 taccaccatg cgcacgacgc ttatcttaat gccgtcgtag ggaccgcact cattaagaaa   3000
tacccgaagc tagaaagtga gtttgtgtat ggtgattaca agtttatga cgtccgtaag    3060 atgatcgcga aaagcgaaca ggagataggc aaggctacag ccaaatactt cttttattct   3120
aacattatga atttctttaa gacgaaaatc actctggcaa acgagagat acgcaaacga    3180 cctttaattg aaaccaatgg ggagacaggt gaaatcgtat gggataaggg ccgggacttc   3240
gcgacggtga gaaaagtttt gtccatgccc caagtcaaca tagtaaagaa aactgaggtg   3300
cagaccggag ggttttcaaa ggaatcgatt cttccaaaaa ggaatagtga taagctcatc   3360
gctcgtaaaa aggactggga cccgaaaaag tacggtggct tcgatagccc tacagttgcc   3420
tattctgtcc tagtagtggc aaaagttgag aagggaaaat ccaagaaact gaagtcagtc   3480
aaagaattat tggggataac gattatggag cgctcgtctt ttgaaaagaa ccccatcgac   3540
ttccttgagg cgaaaggtta caaggaagta aaaaggatc tcataattaa actaccaaag    3600
tatagtctgt ttgagttaga aaatggccga aaacggatgt tggctagcgc cggagagctt   3660
caaaagggga acgaactcgc actaccgtct aaatacgtga atttcctgta tttagcgtcc   3720
cattacgaga agttgaaagg ttcacctgaa gataacgaac agaagcaact tttgttgag    3780 cagcacaaac attatctcga cgaaatcata gagcaaattt cggaattcag taagagagtc   3840
atcctagctg atgccaatct ggacaaagta ttaagcgcat acaacaagca cagggataaa   3900
cccatacgtg agcaggcgga aaatattatc catttgttta ctcttaccaa cctcggcgct   3960
ccagccgcat tcaagtattt tgacacaacg atagatcgca aacgatacac ttctaccaag   4020
gaggtgctag acgcgacact gattcaccaa tccatcacgg gattatatga aactcggata   4080
gatttgtcac agcttggggg tgacggatcc cccaagaaga agaggaaagt ctcgagcgac   4140
tacaaagacc atgacggtga ttataaagat catgacatcg attacaagga tgacgatgac   4200
aaggctgcag gatcaggtgg aagtggcggc agcggaggtt ctggatccca actagtcaaa   4260
agtgaactgg aggagaagaa atctgaactt cgtcataaat tgaaatatgt gcctcatgaa   4320
tatattgaat taattgaaat tgccagaaat tccactcagg atagaattct tgaaatgaag   4380
gtaatggaat ttttatgaa agtttatgga tatagaggta acatttggg tggatcaagg     4440 aaaccggacg gagcaattta tactgtcgga tctcctattg attacggtgt gatcgtggat   4500
actaaagctt atagcggagg ttataatctg ccaattggcc aagcagatga aatgcaacga   4560
```

-continued

```
tatgtcgaag aaaatcaaac acgaaacaaa catatcaacc ctaatgaatg gtggaaagtc    4620
tatccatctt ctgtaacgga atttaagttt ttatttgtga gtggtcactt taaaggaaac    4680
tacaaagctc agcttacacg attaaatcat atcactaatt gtaatggagc tgttcttagt    4740
gtagaagagc ttttaattgg tggagaaatg attaaagccg gcacattaac cttagaggaa    4800
gtcagacgga aatttaataa cggcgagata aacttt                              4836
```

<210> SEQ ID NO 10
<211> LENGTH: 4845
<212> TYPE: DNA
<213> ORGANISM: Artificial Sequence
<220> FEATURE:
<223> OTHER INFORMATION: Synthetic Polynucleotide

<400> SEQUENCE: 10

```
atggactaca aagaccatga cggtgattat aaagatcatg acatcgatta caaggatgac      60
gatgacaaga tggcccccaa gaagaagagg aaggtgggca ttcaccgcgg ggtacctatg     120
gataaaaagt attctattgg tttagctatc ggcactaatt ccgttggatg ggctgtcata     180
accgatgaat acaaagtacc ttcaaagaaa tttaaggtgt tggggaacac agaccgtcat     240
tcgattaaaa agaatcttat cggtgccctc ctattcgata gtggcgaaac ggcagaggcg     300
actcgcctga acgaaccgcg tcggagaagg tatacacgtc gcaagaaccg aatatgttac     360
ttacaagaaa tttttagcaa tgagatggcc aaagttgacg attctttctt tcaccgtttg     420
gaagagtcct tccttgtcga gaggacaag aaacatgaac ggcacccat ctttggaaac      480 atagtagatg aggtggcata tcatgaaaag tacccaacga tttatcacct cagaaaaaag     540
ctagttgact caactgataa agcggacctg aggttaatct acttggctct tgcccatatg     600
ataaagttcc gtgggcactt tctcattgag ggtgatctaa atccggacaa ctcggatgtc     660
gacaaactgt tcatccagtt agtacaaacc tataatcagt tgtttgaaga aacccctata     720
aatgcaagtg gcgtggatgc gaaggctatt cttagcgccc gcctctctaa atcccgacgg     780
ctagaaaacc tgatcgcaca attacccgga gagaagaaaa atgggttgtt cggtaacctt     840
atagcgctct cactaggcct gacaccaaat tttaagtcga acttcgactt agctgaagat     900
gccaaattgc agcttagtaa ggacacgtac gatgacgatc tcgacaatct actggcacaa     960
attggagatc agtatgcgga cttattttg gctgccaaaa accttagcga tgcaatcctc    1020
ctatctgaca tactgagagt taatactgag attaccaagg cgccgttatc cgcttcaatg    1080
atcaaaaggt acgatgaaca tcaccaagac ttgacacttc tcaaggccct agtccgtcag    1140
caactgcctg agaaatataa ggaaatattc tttgatcagt cgaaaaacgg gtacgcaggt    1200
tatattgacg gcggagcgag tcaagaggaa ttctacaagt ttatcaaacc catattagag    1260
aagatggatg gacggaaga gttgcttgta aaactcaatc gcgaagatct actgcgaaag    1320
cagcggactt tcgacaacgg tagcattcca catcaaatcc acttaggcga attgcatgct    1380
atacttagaa ggcaggagga ttttttatccg ttcctcaaag acaatcgtga aaagattgag    1440
aaaatcctaa cctttcgcat accttactat gtgggacccc tggcccgagg gaactctcgg    1500
ttcgcatgga tgacaagaaa gtccgaagaa acgattactc catggaattt tgaggaagtt    1560
gtcgataaag gtgcgtcagc tcaatcgttc atcgagagga tgaccaactt gacaagaat     1620 ttaccgaacg aaaagtatt gcctaagcac agtttacttt acgagtattt cacagtgtac    1680
aatgaactca cgaaagttaa gtatgtcact gagggcatgc gtaaaccgc ctttctaagc    1740
```

```
ggagaacaga agaaagcaat agtagatctg ttattcaaga ccaaccgcaa agtgacagtt    1800
aagcaattga agaggacta ctttaagaaa attgaatgct tcgattctgt cgagatctcc    1860
ggggtagaag atcgatttaa tgcgtcactt ggtacgtatc atgacctcct aaagataatt    1920
aaagataagg acttcctgga taacgaagag aatgaagata tcttagaaga tatagtgttg    1980
actcttaccc tctttgaaga tcgggaaatg attgaggaaa gactaaaaac atacgctcac    2040
ctgttcgacg ataaggttat gaaacagtta agaggcgtc gctatacggg ctggggacga    2100
ttgtcgcgga aacttatcaa cgggataaga gacaagcaaa gtggtaaaac tattctcgat    2160
tttctaaaga gcgacggctt cgccaatagg aactttatgc agctgatcca tgatgactct    2220
ttaaccttca aagaggatat acaaaaggca caggtttccg gacaagggga ctcattgcac    2280
gaacatattg cgaatcttgc tggttcgcca gccatcaaaa agggcatact ccagacagtc    2340
aaagtagtgg atgagctagt taaggtcatg ggacgtcaca aaccggaaaa cattgtaatc    2400
gagatggcac gcgaaaatca aacgactcag aaggggcaaa aaacagtcg agagcggatg    2460 aagagaatag aagagggtat taaagaactg ggcagcagaa tcttaaagga gcatcctgtg    2520
gaaaataccc aattgcagaa cgagaaactt tacctctatt acctacaaaa tggaagggac    2580
atgtatgttg atcaggaact ggacataaac cgtttatctg attacgacgt cgatgccatt    2640 gtacccaat cctttttgaa ggacgattca atcgacaata agtgcttac acgctcggat    2700 aagaaccgag ggaaaagtga caatgttcca agcgaggaag tcgtaaagaa aatgaagaac    2760
tattggcggc agctcctaaa tgcgaaactg ataacgcaaa gaaagttcga taacttaact    2820
aaagctgaga ggggtggctt gtctgaactt gacaaggccg gatttattaa acgtcagctc    2880
gtggaaaccc gccaaatcac aaagcatgtt gcacagatac tagattcccg aatgaatacg    2940
aaatacgacg agaacgataa gctgattcgg gaagtcaaag taatcacttt aaagtcaaaa    3000
ttggtgtcgg acttcagaaa ggattttcaa ttctataaag ttagggagat aaataactac    3060
caccatgcgc acgacgctta tcttaatgcc gtcgtaggga ccgcactcat taagaaatac    3120
ccgaagctag aaagtgagtt tgtgtatggt gattacaaag tttatgacgt ccgtaagatg    3180
atcgcgaaaa gcgaacagga gataggcaag gctacagcca atacttctt ttattctaac    3240 attatgaatt tctttaagac ggaaatcact ctggcaaacg gagagatacg caaacgacct    3300
ttaattgaaa ccaatgggga gacaggtgaa atcgtatggg ataagggccg ggacttcgcg    3360
acggtgagaa aagttttgtc catgccccaa gtcaacatag taaagaaaac tgaggtgcag    3420 accgagggt tttcaaagga atcgattctt ccaaaaagga atagtgataa gctcatcgct    3480
cgtaaaaagg actgggaccc gaaaaagtac ggtggcttcg atagccctac agttgcctat    3540
tctgtcctag tagtggcaaa agttgagaag ggaaaatcca agaaactgaa gtcagtcaaa    3600
gaattattgg ggataacgat tatggagcgc tcgtcttttg aaaagaaccc catcgacttc    3660
cttgaggcga aaggttacaa ggaagtaaaa aaggatctca taattaaact accaaagtat    3720
agtctgtttg agttagaaaa tggccgaaaa cggatgttgg ctagcgccgg agagcttcaa    3780
aaggggaacg aactcgcact accgtctaaa tacgtgaatt tcctgtattt agcgtcccat    3840
tacgagaagt tgaaaggttc acctgaagat aacgaacaga agcaacttttt tgttgagcag    3900 cacaaacatt atctcgacga aatcatagag caaatttcgg aattcagtaa gagagtcatc    3960
ctagctgatg ccaatctgga caaagtatta agcgcataca acaagcacag ggataaaccc    4020
atacgtgagc aggcggaaaa tattatccat ttgtttactc ttaccaacct cggcgctcca    4080
gccgcattca agtattttga cacaacgata gatcgcaaac gatacacttc taccaaggag    4140
```

```
gtgctagacg cgacactgat tcaccaatcc atcacgggat tatatgaaac tcggatagat    4200
ttgtcacagc ttgggggtga ctcaggtgga agtggcggca gcggaggttc tggatcccaa    4260
ctagtcaaaa gtgaactgga ggagaagaaa tctgaacttc gtcataaatt gaaatatgtg    4320
cctcatgaat atattgaatt aattgaaatt gccagaaatt ccactcagga tagaattctt    4380
gaaatgaagg taatggaatt ttttatgaaa gtttatggat atagaggtaa acatttgggt    4440
ggatcaagga aaccgacgg agcaatttat actgtcggat ctcctattga ttacggtgtg    4500
atcgtggata ctaaagctta tagcggaggt tataatctgc caattggcca agcagatgaa    4560
atgcaacgat atgtcgaaga aaatcaaaca cgaaacaaac atatcaaccc taatgaatgg    4620
tggaaagtct atccatcttc tgtaacggaa tttaagtttt tatttgtgag tggtcacttt    4680
aaaggaaact acaaagctca gcttacacga ttaaatcata tcactaattg taatggagct    4740
gttcttagtg tagaagagct tttaattggt ggagaaatga ttaaagccgg cacattaacc    4800
ttagaggaag tcagacggaa atttaataac ggcgagataa acttt               4845
```

<210> SEQ ID NO 11
<211> LENGTH: 4836
<212> TYPE: DNA
<213> ORGANISM: Artificial Sequence
<220> FEATURE:
<223> OTHER INFORMATION: Synthetic Polynucleotide

<400> SEQUENCE: 11

```
atgggatccc aactagtcaa aagtgaactg gaggagaaga atctgaact tcgtcataaa      60 ttgaaatatg tgcctcatga atatattgaa ttaattgaaa ttgccagaaa ttccactcag     120
gatagaattc ttgaaatgaa ggtaatgaa ttttttatga agtttatgg atatagaggt       180 aaacatttgg gtggatcaag gaaaccggac ggagcaattt atactgtcgg atctcctatt     240
gattacggtg tgatcgtgga tactaaagct tatagcggag gttataatct gccaattggc     300
caagcagatg aaatgcaacg atatgtcgaa gaaaatcaaa cacgaaacaa acatatcaac     360
cctaatgaat ggtggaaagt ctatccatct tctgtaacgg aatttaagtt tttatttgtg     420
agtggtcact ttaaaggaaa ctacaaagct cagcttacac gattaaatca tatcactaat     480
tgtaatggag ctgttcttag tgtagaagag ctttttaattg gtggagaaat gattaaagcc     540
ggcacattaa cttagagga agtcagacga aatttaata acggcgagat aaactttggc      600
ggtagtgggg gatctggggg aagtatggat aaaaagtatt ctattggttt agctatcggc     660
actaattccg ttgatggggc tgtcataacc gatgaataca agtaccttc aaagaaattt      720 aaggtgttgg ggaacacaga ccgtcattcg attaaaaaga atcttatcgg tgccctccta     780
ttcgatagtg gcgaaacggc agaggcgact cgcctgaaac gaaccgctcg gagaaggtat     840
acacgtcgca agaaccgaat atgttactta caagaaattt ttagcaatga gatggccaaa     900
gttgacgatt ctttctttca ccgtttggaa gagtccttcc ttgtcgaaga ggacaagaaa     960
catgaacggc accccatctt tggaaacata gtagatgagg tggcatatca tgaaaagtac    1020
ccaacgattt atcacctcag aaaaaagcta gttgactcaa ctgataaagc ggacctgagg    1080
ttaatctact ggctcttgc ccatatgata agttccgtg gcactttct cattgaggt      1140 gatctaaatc cggacaactc ggatgtcgac aaactgttca tccagttagt acaaacctat     1200
aatcagttgt tgaagagaa ccctataaat gcagtggcg tggatgcgaa ggctattctt       1260
agcgcccgcc tctctaaatc ccgacggcta gaaaacctga tcgcacaatt acccggagag    1320
```

```
aagaaaaatg ggttgttcgg taaccttata gcgctctcac taggcctgac accaaatttt    1380
aagtcgaact tcgacttagc tgaagatgcc aaattgcagc ttagtaagga cacgtacgat    1440
gacgatctcg acaatctact ggcacaaatt ggagatcagt atgcggactt attttttggct   1500
gccaaaaacc ttagcgatgc aatcctccta tctgacatac tgagagttaa tactgagatt    1560
accaaggcgc cgttatccgc ttcaatgatc aaaaggtacg atgaacatca ccaagacttg    1620
acacttctca aggccctagt ccgtcagcaa ctgcctgaga aatataagga aatattcttt    1680
gatcagtcga aaacgggta cgcaggttat attgacggcg gagcgagtca agaggaattc     1740
tacaagttta tcaaacccat attagagaag atggatggga cggaagagtt gcttgtaaaa    1800
ctcaatcgcg aagatctact gcgaaagcag cggactttcg acaacggtag cattccacat    1860
caaatccact taggcgaatt gcatgctata cttagaaggc aggaggattt ttatccgttc    1920
ctcaaagaca atcgtgaaaa gattgagaaa atcctaacct ttcgcatacc ttactatgtg    1980
ggacccctgg cccgagggaa ctctcggttc gcatggatga caagaaagtc cgaagaaacg    2040
attactccat ggaattttga ggaagttgtc gataaaggtg cgtcagctca atcgttcatc    2100
gagaggatga ccaactttga caagaattta ccgaacgaaa aagtattgcc taagcacagt    2160
ttactttacg agtatttcac agtgtacaat gaactcacga aagttaagta tgtcactgag    2220
ggcatgcgta aacccgcctt tctaagcgga gaacagaaga agcaatagt agatctgtta     2280
ttcaagacca accgcaaagt gacagttaag caattgaaag aggactactt taagaaaatt    2340
gaatgcttcg attctgtcga gatctccggg gtagaagatc gatttaatgc gtcacttggt    2400
acgtatcatg acctcctaaa gataattaaa gataaggact tcctggataa cgaagagaat    2460
gaagatatct tagaagatat agtgttgact cttaccctct ttgaagatcg ggaaatgatt    2520
gaggaaagac taaaaacata cgctcacctg ttcgacgata aggttatgaa acagttaaag    2580
aggcgtcgct atacgggctg gggacgattg tcgcggaaac ttatcaacgg gataagagac    2640
aagcaaagtg gtaaaactat tctcgattt ctaaagagcg acggcttcgc caataggaac    2700
tttatgcagc tgatccatga tgactcttta accttcaaag aggatataca aaaggcacag    2760
gtttccggac aaggggactc attgcacgaa catattgcga atcttgctgg ttcgccagcc    2820
atcaaaaagg gcatactcca gacagtcaaa gtagtggatg agctagttaa ggtcatggga    2880
cgtcacaaac cggaaaacat tgtaatcgag atggcacgcg aaaatcaaac gactcagaag    2940
gggcaaaaaa acagtcgaga gcggatgaag agaatagaag agggtattaa agaactgggc    3000
agccagatct taaaggagca tcctgtggaa aatacccaat tgcagaacga gaaactttac    3060
ctctattacc tacaaaatgg aagggacatg tatgttgatc aggaactgga cataaaccgt    3120
ttatctgatt acgacgtcga tgccattgta ccccaatcct ttttgaagga cgattcaatc    3180
gacaataaag tgcttacacg ctcggataag aaccgaggga aaagtgacaa tgttccaagc    3240
gaggaagtcg taaagaaaat gaagaactat tggcggcagc tcctaaatgc gaaactgata    3300
acgcaaagaa agttcgataa cttaactaaa gctgagaggg tggcttgtc tgaacttgac    3360
aaggccggat ttattaaacg tcagctcgtg gaaacccgcc aaatcacaaa gcatgttgca    3420
cagatactag attcccgaat gaatacgaaa tacgacgaga acgataagct gattcgggaa    3480
gtcaaagtaa tcactttaaa gtcaaaattg gtgtcggact tcagaaagga ttttcaattc    3540
tataaagtta gggagataaa taactaccac catgcgcacg acgcttatct taatgccgtc    3600
gtagggaccc cactcattaa gaaatacccg aagctagaaa gtgagtttgt gtatggtgat    3660
tacaaagttt atgacgtccg taagatgatc gcgaaaagcg aacaggagat aggcaaggct    3720
```

```
acagccaaat acttctttta ttctaacatt atgaatttct ttaagacgga aatcactctg    3780
gcaaacggag agatacgcaa acgaccttta attgaaacca atggggagac aggtgaaatc    3840
gtatgggata agggccggga cttcgcgacg gtgagaaaag ttttgtccat gccccaagtc    3900
aacatagtaa agaaaactga ggtgcagacc ggagggtttt caaaggaatc gattcttcca    3960
aaaaggaata gtgataagct catcgctcgt aaaaggact  gggacccgaa aaagtacggt    4020
ggcttcgata gccctacagt tgcctattct gtcctagtag tggcaaaagt tgagaaggga    4080
aaatccaaga aactgaagtc agtcaaagaa ttattgggga taacgattat ggagcgctcg    4140
tcttttgaaa agaaccccat cgacttcctt gaggcgaaag gttacaagga agtaaaaaag    4200
gatctcataa ttaaactacc aaagtatagt ctgtttgagt tagaaaatgg ccgaaaacgg    4260
atgttggcta gcgccggaga gcttcaaaag gggaacgaac tcgcactacc gtctaaatac    4320
gtgaatttcc tgtatttagc gtcccattac gagaagttga aaggttcacc tgaagataac    4380
gaacagaagc aacttttgt  tgagcagcac aaacattatc tcgacgaaat catagagcaa    4440
atttcggaat tcagtaagag agtcatccta gctgatgcca atctggacaa agtattaagc    4500
gcatacaaca agcacaggga taaacccata cgtgagcagg cggaaaatat tatccatttg    4560
tttactctta ccaacctcgg cgctccagcc gcattcaagt attttgacac aacgatagat    4620
cgcaaacgat acacttctac caaggaggtg ctagacgcga cactgattca ccaatccatc    4680
acgggattat atgaaactcg gatagatttg tcacagcttg ggggtgacgg atcccccaag    4740
aagaagagga agtctcgag  cgactacaaa gaccatgacg gtgattataa agatcatgac    4800
atcgattaca aggatgacga tgacaaggct gcagga                              4836
```

<210> SEQ ID NO 12
<211> LENGTH: 4854
<212> TYPE: DNA
<213> ORGANISM: Artificial Sequence
<220> FEATURE:
<223> OTHER INFORMATION: Synthetic Polynucleotide

<400> SEQUENCE: 12

```
atggactaca aagaccatga cggtgattat aaagatcatg acatcgatta caaggatgac      60
gatgacaaga tggccccaa  gaagaagagg aaggtgggca ttcaccgcgg ggtacctgga     120
ggttctatgg gatcccaact agtcaaaagt gaactggagg agaagaaatc tgaacttcgt     180
cataaattga aatatgtgcc tcatgaatat attgaattaa ttgaaattgc agaaattcc      240 actcaggata gaattcttga atgaaggta  atggaatttt ttatgaaagt ttatggatat     300
agaggtaaac atttgggtgg atcaaggaaa ccggacggag caatttatac tgtcggatct     360
cctattgatt acggtgtgat cgtggatact aaagcttata gcggaggtta taatctgcca     420
attggccaag cagatgaaat gcaacgatat gtcgaagaaa atcaaacacg aaacaaacat     480 atcaaccta  atgaatggtg gaaagtctat ccatcttctg taacgaatt  taagttttta     540 tttgtgagtg gtcactttaa aggaaactac aaagctcagc ttacacgatt aaatcatatc     600
actaattgta atggagctgt tcttagtgta gaagagcttt taattggtgg agaaatgatt     660
aaagccggca cattaacctt agaggaagtc agacggaaat ttaataacgg cgagataaac     720
tttggcggta gtggggatc  tgggggaagt atggataaaa agtattctat tggtttagct     780
atcggcacta ttccgttgg  atgggctgtc ataaccgatg aatacaaagt accttcaaag     840
aaatttaagg tgttggggaa cacagaccgt cattcgatta aaaagaatct tatcggtgcc     900
```

```
ctcctattcg atagtggcga aacggcagag gcgactcgcc tgaaacgaac cgctcggaga    960
aggtatacac gtcgcaagaa ccgaatatgt tacttacaag aaatttttag caatgagatg   1020
gccaaagttg acgattcttt cttttcaccgt ttggaagagt ccttccttgt cgaagaggac  1080
aagaaacatg aacggcaccc catctttgga aacatagtag atgaggtggc atatcatgaa   1140
aagtacccaa cgatttatca cctcagaaaa aagctagttg actcaactga taaagcggac   1200
ctgaggttaa tctacttggc tcttgcccat atgataaagt tccgtgggca ctttctcatt   1260
gagggtgatc taaatccgga caactcggat gtcgacaaac tgttcatcca gttagtacaa   1320
acctataatc agttgtttga agagaaccct ataaatgcaa gtggcgtgga tgcgaaggct   1380
attcttagcg cccgcctctc taaatcccga cggctagaaa acctgatcgc acaattaccc   1440
ggagagaaga aaaatgggtt gttcggtaac cttatagcgc tctcactagg cctgacacca   1500
aattttaagt cgaacttcga cttagctgaa gatgccaaat tgcagcttag taaggacacg   1560
tacgatgacg atctcgacaa tctactggca caaattggag atcagtatgc ggacttattt   1620
ttggctgcca aaaaccttag cgatgcaatc ctcctatctg acatactgag agttaatact   1680
gagattacca aggcgccgtt atccgcttca atgatcaaaa ggtacgatga acatcaccaa   1740
gacttgacac ttctcaaggc cctagtccgt cagcaactgc ctgagaaata taggaaata   1800
ttctttgatc agtcgaaaaa cgggtacgca ggttatattg acggcggagc gagtcaagag   1860
gaattctaca gtttatcaa acccatatta gagaagatgg atgggacgga agagttgctt   1920
gtaaaactca atcgcgaaga tctactgcga aagcagcgga cttttcgacaa cggtagcatt   1980
ccacatcaaa tccacttagg cgaattgcat gctatactta aaggcagga ggattttat    2040
ccgttcctca aagacaatcg tgaaaagatt gagaaaatcc taacctttcg cataccttac   2100
tatgtgggac ccctggcccg agggaactct cggttcgcat ggatgacaag aaagtccgaa   2160
gaaacgatta ctccatggaa ttttgaggaa gttgtcgata aggtgcgtc agctcaatcg   2220
ttcatcgaga ggatgaccaa cttttgacaag aatttaccga acgaaaaagt attgcctaag   2280
cacagtttac tttacgagta tttcacagtg tacaatgaac tcacgaaagt taagtatgtc    2340
actgagggca tgcgtaaacc cgccttctca agcggagaac agaagaaagc aatagtagat   2400
ctgttattca agaccaaccg caaagtgaca gttaagcaat tgaaagagga ctactttaag   2460
aaaattgaat gcttcgattc tgtcgagatc tccggggtag aagatcgatt taatgcgtca   2520
cttggtacgt atcatgacct cctaaagata attaaagata aggacttcct ggataacgaa   2580
gagaatgaag atatcttaga agatatagtg ttgactctta ccctctttga agatcggaa    2640
atgattgagg aaagactaaa aacatacgct cacctgttcg acgataaggt tatgaaacag   2700
ttaaagaggc gtcgctatac gggctgggga cgattgtcgc ggaaacttat caacgggata   2760
agagacaagc aaagtggtaa aactattctc gattttctaa agagcgacgg cttcgccaat   2820
aggaacttta tgcagctgat ccatgatgac tctttaacct tcaaagagga tataaaag    2880
gcacaggttt ccgacaagg ggactcattg cacgaacata ttgcgaatct tgctggttcg    2940
ccagccatca aaagggcat actccagaca gtcaaagtag tggatgagct agttaaggtc   3000
atgggacgtc acaaaccgga aaacattgta atcgagatgg cacgcgaaaa tcaaacgact   3060
cagaagggc aaaaaaacag tcgagagcgg atgaagagaa tagaagaggg tattaaagaa    3120
ctgggcagcc agatcttaaa ggagcatcct gtgaaaaata cccaattgca gaacgagaaa   3180
ctttacctct attacctaca aaatggaagg gacatgtatg ttgatcagga actggacata   3240
aaccgtttat ctgattacga cgtcgatgcc attgtacccc aatcctttt gaaggacgat   3300
```

-continued

```
tcaatcgaca ataaagtgct tacacgctcg gataagaacc gagggaaaag tgacaatgtt      3360
ccaagcgagg aagtcgtaaa gaaaatgaag aactattggc ggcagctcct aaatgcgaaa      3420
ctgataacgc aaagaaagtt cgataactta actaaagctg agagggtgg cttgtctgaa      3480 cttgacaagg ccggatttat taaacgtcag ctcgtggaaa cccgccaaat cacaaagcat      3540
gttgcacaga tactagattc ccgaatgaat acgaaatacg acgagaacga taagctgatt      3600
cgggaagtca aagtaatcac tttaaagtca aaattggtgt cggacttcag aaaggatttt      3660
caattctata aagttaggga gataaataac taccaccatg cgcacgacgc ttatcttaat      3720
gccgtcgtag ggaccgcact cattaagaaa tacccgaagc tagaaagtga gtttgtgtat      3780
ggtgattaca aagtttatga cgtccgtaag atgatcgcga aaagcgaaca ggagataggc      3840
aaggctacag ccaaatactt ctttattct aacattatga atttcttaa gacgaaatc       3900 actctggcaa acggagagat acgcaaacga cctttaattg aaaccaatgg ggagacaggt      3960
gaaatcgtat gggataaggg ccgggacttc gcgacggtga aaaagttttt gtccatgccc      4020
caagtcaaca tagtaaagaa aactgaggtg cagaccggag ggttttcaaa ggaatcgatt      4080
cttccaaaaa ggaatagtga taagctcatc gctcgtaaaa aggactggga cccgaaaaag      4140
tacggtggct tcgatagccc tacagttgcc tattctgtcc tagtagtggc aaaagttgag      4200
aagggaaaat ccaagaaact gaagtcagtc aaagaattat tggggataac gattatggag      4260
cgctcgtctt ttgaaaagaa ccccatcgac ttccttgagg cgaaaggtta caaggaagta      4320
aaaaaggatc tcataattaa actaccaaag tatagtctgt ttgagttaga aaatggccga      4380
aaacggatgt tggctagcgc cggagagctt caaaagggga acgaactcgc actaccgtct      4440
aaatacgtga atttcctgta tttagcgtcc cattacgaga agttgaaagg ttcacctgaa      4500
gataacgaac agaagcaact ttttgttgag cagcacaaac attatctcga cgaaatcata      4560
gagcaaattt cggaattcag taagagagtc atcctagctg atgccaatct ggacaaagta      4620
ttaagcgcat acaacaagca cagggataaa cccatacgtg agcaggcgga aaatattatc      4680
catttgttta ctcttaccaa cctcggcgct ccagccgcat tcaagtattt tgacacaacg      4740
atagatcgca acgatacac ttctaccaag gaggtgctag acgcgacact gattcaccaa      4800
tccatcacgg gattatatga aactcggata gatttgtcac agcttggggg tgac            4854
```

<210> SEQ ID NO 13
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 13
aaaaaaaaaa                                                              10

<210> SEQ ID NO 14
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 14

Gly Gly Ser Gly Gly Ser Gly Gly Ser
1               5

-continued

```
<210> SEQ ID NO 15
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 15

Gly Gly Ser Gly Gly Ser Gly Gly Ser Gly Gly Ser Gly Gly Ser Gly
1               5                   10                  15

Gly Ser

<210> SEQ ID NO 16
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 16

Ser Gly Ser Glu Thr Pro Gly Thr Ser Glu Ser Ala Thr Pro Glu Ser
1               5                   10                  15

<210> SEQ ID NO 17
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 17

Ser Gly Ser Glu Thr Pro Gly Thr Ser Glu Ser Ala
1               5                   10

<210> SEQ ID NO 18
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 18

Ser Gly Ser Glu Thr Pro Gly Thr Ser Glu Ser Ala Thr Pro Glu Gly
1               5                   10                  15

Gly Ser Gly Gly Ser
                20

<210> SEQ ID NO 19
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 19

Val Pro Phe Leu Leu Glu Pro Asp Asn Ile Asn Gly Lys Thr Cys
1               5                   10                  15

<210> SEQ ID NO 20
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 20
```

```
Gly Ser Ala Gly Ser Ala Ala Gly Ser Gly Glu Phe
1               5                   10
```

<210> SEQ ID NO 21
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 21

```
Ser Ile Val Ala Gln Leu Ser Arg Pro Asp Pro Ala
1               5                   10
```

<210> SEQ ID NO 22
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 22

```
Met Lys Ile Ile Glu Gln Leu Pro Ser Ala
1               5                   10
```

<210> SEQ ID NO 23
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 23

```
Val Arg His Lys Leu Lys Arg Val Gly Ser
1               5                   10
```

<210> SEQ ID NO 24
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 24

```
Gly His Gly Thr Gly Ser Thr Gly Ser Gly Ser Ser
1               5                   10
```

<210> SEQ ID NO 25
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 25

```
Met Ser Arg Pro Asp Pro Ala
1               5
```

<210> SEQ ID NO 26
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 26
cggcgagata aactttaat gaccggtcat catcacca                    38

<210> SEQ ID NO 27
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 27
ccaacggaat tagtgccgat agctaaacca atagaatact ttttatc                47

<210> SEQ ID NO 28
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 28
gataaaaagt attctattgg tttagctatc ggcactaatt ccgttgg                47

<210> SEQ ID NO 29
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 29
ttcaaaaagg attggggtac aatggcatcg acgtcgtaat cagataaac              49

<210> SEQ ID NO 30
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 30
gtttatctga ttacgacgtc gatgccattg taccccaatc cttttgaa               49

<210> SEQ ID NO 31
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 31
ttgggatcca gaacctcctc ctgcagcctt gtcatcg                           37

<210> SEQ ID NO 32
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 32
ttgggatcca gaacctccgc tgccgccact tccacctgat cctgcagcct tgtcatcg    58

<210> SEQ ID NO 33
<211> LENGTH: 37
<212> TYPE: DNA
<213> ORGANISM: Artificial Sequence
<220> FEATURE:

<223> OTHER INFORMATION: Synthetic Polynucleotide

<400> SEQUENCE: 33
cgatgacaag gctgcaggag gaggttctgg atcccaa                              37

<210> SEQ ID NO 34
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 34
cgatgacaag gctgcaggat caggtggaag tggcggcagc ggaggttctg gatcccaa      58

<210> SEQ ID NO 35
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 35
tggtgatgat gaccggtcat taaaagttta tctcgccg                             38

<210> SEQ ID NO 36
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 36
cggcgagata aacttttaat gaccggtcat catcacca                             38

<210> SEQ ID NO 37
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 37
tagggagagc cgccaccatg gactacaaag accatgacgg                           40

<210> SEQ ID NO 38
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 38
taaaccaata gaatactttt tatccatagg taccccgcgg tgaatg                    46

<210> SEQ ID NO 39
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 39
gataaaaagt attctattgg tttagctatc ggcactaatt ccgttgg                   47

```
<210> SEQ ID NO 40
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 40
ttcaaaaagg attggggtac aatggcatcg acgtcgtaat cagataaac                    49

<210> SEQ ID NO 41
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 41
gtttatctga ttacgacgtc gatgccattg taccccaatc cttttgaa                     49

<210> SEQ ID NO 42
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 42
ttgggatcca gaacctccgt caccccaag ctgtg                                    35

<210> SEQ ID NO 43
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 43
ttgggatcca gaacctccgc tgccgccact tccacctgag tcaccccaa gctgtg             56

<210> SEQ ID NO 44
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 44
cacagcttgg gggtgacgga ggttctggat cccaa                                   35

<210> SEQ ID NO 45
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 45
cacagcttgg gggtgactca ggtggaagtg gcggcagcgg aggttctgga tcccaa            56

<210> SEQ ID NO 46
<211> LENGTH: 38
<212> TYPE: DNA
<213> ORGANISM: Artificial Sequence
<220> FEATURE:
<223> OTHER INFORMATION: Synthetic Polynucleotide
```

<400> SEQUENCE: 46
tggtgatgat gaccggtcat taaaagttta tctcgccg                          38

<210> SEQ ID NO 47
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 47
tagggagagc cgccaccatg ggatcccaac tagtcaaaag                        40

<210> SEQ ID NO 48
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 48
accaatagaa tacttttat ccatgctgcc accaaagttt atctc                   45

<210> SEQ ID NO 49
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 49
accaatagaa tacttttat ccatgctgcc gccacttcca cctg                    44

<210> SEQ ID NO 50
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 50
gataaaaagt attctattgg tttagctatc ggcactaatt ccgttgg                47

<210> SEQ ID NO 51
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 51
ccaacggaat tagtgccgat agctaaacca atagaatact ttttatc                47

<210> SEQ ID NO 52
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 52
gtttatctga ttacgacgtc gatgccattg taccccaatc cttttgaa               49

<210> SEQ ID NO 53
<211> LENGTH: 36

```
<212> TYPE: DNA
<213> ORGANISM: Artificial Sequence
<220> FEATURE:
<223> OTHER INFORMATION: Synthetic Polynucleotide

<400> SEQUENCE: 53
tggtgatgat gaccggtcag tcaccccaa gctgtg                             36

<210> SEQ ID NO 54
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 54
cacagcttgg gggtgactga ccggtcatca tcacca                            36

<210> SEQ ID NO 55
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 55
cttttgacta gttgggatcc catggtggcg gctctcccta                        40

<210> SEQ ID NO 56
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 56
acacccctcg aacttcacct cggcgg                                       26

<210> SEQ ID NO 57
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 57
acaccgtcgc cctcgaactt cacctg                                       26

<210> SEQ ID NO 58
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 58
acacccagct cgatgcggtt caccag                                       26

<210> SEQ ID NO 59
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 59
```
acaccggtga accgcatcga gctgag                                    26

<210> SEQ ID NO 60
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 60
acaccgctga agggcatcga cttcag                                    26

<210> SEQ ID NO 61
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 61
acaccggcat cgacttcaag gaggag                                    26

<210> SEQ ID NO 62
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 62
acacccaagg aggacggcaa catccg                                    26

<210> SEQ ID NO 63
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 63
acaccaccat cttcttcaag gacgag                                    26

<210> SEQ ID NO 64
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 64
acacccaact acaagacccg cgccgg                                    26

<210> SEQ ID NO 65
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 65
acaccccgcg ccgaggtgaa gttcgg                                    26

<210> SEQ ID NO 66
<211> LENGTH: 26
<212> TYPE: DNA
<213> ORGANISM: Artificial Sequence

```
<220> FEATURE:
<223> OTHER INFORMATION: Synthetic Polynucleotide

<400> SEQUENCE: 66
acaccgaagt tcgagggcga cacccg                                    26

<210> SEQ ID NO 67
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 67
acaccttcga acttcacctc ggcgcg                                    26

<210> SEQ ID NO 68
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 68
acacctcagc tcgatgcggt tcaccg                                    26

<210> SEQ ID NO 69
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 69
acacccgatg cccttcagct cgatgg                                    26

<210> SEQ ID NO 70
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 70
aaaaccgccg aggtgaagtt cgaggg                                    26

<210> SEQ ID NO 71
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 71
aaaacaggtg aagttcgagg gcgacg                                    26

<210> SEQ ID NO 72
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 72
aaaactggtg aaccgcatcg agctgg                                    26
```

<210> SEQ ID NO 73
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 73
aaaactcagc tcgatgcggt tcaccg                                        26

<210> SEQ ID NO 74
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 74
aaaactgaag tcgatgccct tcagcg                                        26

<210> SEQ ID NO 75
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 75
aaaactcctc cttgaagtcg atgccg                                        26

<210> SEQ ID NO 76
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 76
aaaacggatg ttgccgtcct ccttgg                                        26

<210> SEQ ID NO 77
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 77
aaaactcgtc cttgaagaag atggtg                                        26

<210> SEQ ID NO 78
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 78
aaaaccggcg cgggtcttgt agttgg                                        26

<210> SEQ ID NO 79
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 79
aaaaccgaac ttcacctcgg cgcggg                                          26

<210> SEQ ID NO 80
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 80
aaaacgggtg tcgccctcga acttcg                                          26

<210> SEQ ID NO 81
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 81
aaaacgcgcc gaggtgaagt tcgaag                                          26

<210> SEQ ID NO 82
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 82
aaaacggtga accgcatcga gctgag                                          26

<210> SEQ ID NO 83
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 83
aaaaccatcg agctgaaggg catcgg                                          26

<210> SEQ ID NO 84
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 84
acacctggcc tgcttgctag acttgg                                          26

<210> SEQ ID NO 85
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 85
acaccgcaga tgtagtgttt ccacag                                          26

<210> SEQ ID NO 86

```
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 86 acaccottgc cccacagggc agtaag                                          26

<210> SEQ ID NO 87
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 87
acaccgagtc cgagcagaag aagaag                                          26

<210> SEQ ID NO 88
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 88
acaccgggtg gggggagttt gctccg                                          26

<210> SEQ ID NO 89
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 89
aaaaccaagt ctagcaagca ggccag                                          26

<210> SEQ ID NO 90
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 90
aaaactgtgg aaacactaca tctgcg                                          26

<210> SEQ ID NO 91
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 91
aaaacttctt cttctgctcg gactcg                                          26

<210> SEQ ID NO 92
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 92
```
aaaacttact gccctgtggg gcaagg                                              26

<210> SEQ ID NO 93
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 93
aaaacggagc aaactccccc cacccg                                              26

<210> SEQ ID NO 94
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 94
aggaaagaac atgtgagcaa aag                                                 23

<210> SEQ ID NO 95
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 95
cagcgagtca gtgagcga                                                       18

<210> SEQ ID NO 96
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 96
ctgtacaaaa aagcaggctt ta                                                  22

<210> SEQ ID NO 97
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 97
aacgtaggtc tctaccgctg tacaaaaaag caggcttta                                39

<210> SEQ ID NO 98
<211> LENGTH: 83
<212> TYPE: DNA
<213> ORGANISM: Artificial Sequence
<220> FEATURE:
<223> OTHER INFORMATION: Synthetic Polynucleotide

<400> SEQUENCE: 98
aaaaaaagca ccgactcggt gccactttt caagttgata acggactagc cttatttta           60 cttgctattt ctagctctaa aac                                                 83

<210> SEQ ID NO 99

<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 99
ttgctatttc tagctctaaa accgccgagg tgaagttcga ggggtgtttc gtcctttcca    60

<210> SEQ ID NO 100
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 100
ttgctatttc tagctctaaa acaggtgaag ttcgagggcg acggtgtttc gtcctttcca    60

<210> SEQ ID NO 101
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 101
ttgctatttc tagctctaaa actggtgaac cgcatcgagc tgggtgtttc gtcctttcca    60

<210> SEQ ID NO 102
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 102
ttgctatttc tagctctaaa actcagctcg atgcggttca ccggtgtttc gtcctttcca    60

<210> SEQ ID NO 103
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 103
ttgctatttc tagctctaaa actgaagtcg atgcccttca gcggtgtttc gtcctttcca    60

<210> SEQ ID NO 104
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 104
ttgctatttc tagctctaaa actcctcctt gaagtcgatg ccggtgtttc gtcctttcca    60

<210> SEQ ID NO 105
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 105
ttgctatttc tagctctaaa acggatgttg ccgtcctcct tgggtgtttc gtcctttcca    60

<210> SEQ ID NO 106
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 106
ttgctatttc tagctctaaa acgcttgagg gagatgagga ctggtgtttc gtcctttcca    60

<210> SEQ ID NO 107
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 107
ttgctatttc tagctctaaa acatgactgt gaagagcttc acggtgtttc gtcctttcca    60

<210> SEQ ID NO 108
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 108
ttgctatttc tagctctaaa acgaggacaa agtacaaacg gcggtgtttc gtcctttcca    60

<210> SEQ ID NO 109
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 109
ttgctatttc tagctctaaa acgaaccgga ggacaaagta caggtgtttc gtcctttcca    60

<210> SEQ ID NO 110
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 110
ttgctatttc tagctctaaa accaccacca acttcatcca cgggtgtttc gtcctttcca    60

<210> SEQ ID NO 111
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 111
ttgctatttc tagctctaaa acgggcctca ccaccaactt caggtgtttc gtcctttcca    60

<210> SEQ ID NO 112
<211> LENGTH: 60
<212> TYPE: DNA

<213> ORGANISM: Artificial Sequence
<220> FEATURE:
<223> OTHER INFORMATION: Synthetic Polynucleotide

<400> SEQUENCE: 112
ttgctatttc tagctctaaa acgcccaggg cctcaccacc aaggtgtttc gtcctttcca    60

<210> SEQ ID NO 113
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 113
ttgctatttc tagctctaaa acacctgccc agggcctcac caggtgtttc gtcctttcca    60

<210> SEQ ID NO 114
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 114
ttgctatttc tagctctaaa actgatacca acctgcccag ggggtgtttc gtcctttcca    60

<210> SEQ ID NO 115
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 115
ttgctatttc tagctctaaa actaaacctg tcttgtaacc ttggtgtttc gtcctttcca    60

<210> SEQ ID NO 116
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 116
ttgctatttc tagctctaaa acgctctggc taaagaggga atggtgtttc gtcctttcca    60

<210> SEQ ID NO 117
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 117
ttgctatttc tagctctaaa accggctctg gctaaagagg gaggtgtttc gtcctttcca    60

<210> SEQ ID NO 118
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 118
ttgctatttc tagctctaaa actctgcaca ccccggctct ggggtgtttc gtcctttcca    60

<210> SEQ ID NO 119
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 119
tacggcaagc tgaccctgaa                                           20

<210> SEQ ID NO 120
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 120
gtccatgccg agagtgatcc                                           20

<210> SEQ ID NO 121
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 121
gccaggggct gttatcttgg                                           20

<210> SEQ ID NO 122
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 122
atgcacagaa gcacaggttg a                                         21

<210> SEQ ID NO 123
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 123
ctgtgtcctc ttcctgccct                                           20

<210> SEQ ID NO 124
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 124
ctctccgagg agaaggccaa                                           20

<210> SEQ ID NO 125
<211> LENGTH: 20
<212> TYPE: DNA
<213> ORGANISM: Artificial Sequence
<220> FEATURE:

<223> OTHER INFORMATION: Synthetic Polynucleotide

<400> SEQUENCE: 125
ggtagaccac cagcagccta                                        20

<210> SEQ ID NO 126
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 126
cagtgccaga agagccaagg                                        20

<210> SEQ ID NO 127
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 127
ccacacagct tcccgttctc                                        20

<210> SEQ ID NO 128
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 128
gagagccgtt ccctctttgc                                        20

<210> SEQ ID NO 129
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 129
cctccccatt ggcctgcttc                                        20

<210> SEQ ID NO 130
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 130
tcgtcctgct ctcacttaga c                                      21

<210> SEQ ID NO 131
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 131
ttttgtggct tggccccagt                                        20

```
<210> SEQ ID NO 132
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 132
tgcagtctca tgacttggcc t                                              21

<210> SEQ ID NO 133
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 133
ttctgagggc tgctacctgt                                                20

<210> SEQ ID NO 134
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 134
acatgaagca actccagtcc ca                                             22

<210> SEQ ID NO 135
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 135
agcagaccca ctgagtcaac tg                                             22

<210> SEQ ID NO 136
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 136
cccgccacag tcgtgtcat                                                 19

<210> SEQ ID NO 137
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 137
cgccccggta caaggtga                                                  18

<210> SEQ ID NO 138
<211> LENGTH: 23
<212> TYPE: DNA
<213> ORGANISM: Artificial Sequence
<220> FEATURE:
<223> OTHER INFORMATION: Synthetic Polynucleotide
```

```
<400> SEQUENCE: 138
gtaccgtaca ttgtaggatg ttt                                              23

<210> SEQ ID NO 139
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 139
cctcatctcc ctcaagcagg c                                                21

<210> SEQ ID NO 140
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 140
attctgctct tgaggttatt tgt                                              23

<210> SEQ ID NO 141
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 141
cacctctgcc tcaagagcag aaaa                                             24

<210> SEQ ID NO 142
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 142
tgtgtgtgtg tgtgtgtagg act                                              23

<210> SEQ ID NO 143
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 143
tcatctgtgc ccctccctcc                                                  20

<210> SEQ ID NO 144
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 144
cgagaaggag gtgcaggag                                                   19

<210> SEQ ID NO 145
<211> LENGTH: 20
```

```
<212> TYPE: DNA
<213> ORGANISM: Artificial Sequence
<220> FEATURE:
<223> OTHER INFORMATION: Synthetic Polynucleotide

<400> SEQUENCE: 145
cgggagctgt tcagaggctg                                               20

<210> SEQ ID NO 146
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 146
ctcacctggg cgagaaaggt                                               20

<210> SEQ ID NO 147
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 147
aaaactcaaa gaaatgccca atca                                          24

<210> SEQ ID NO 148
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 148
agacgctgct cgctccattc                                               20

<210> SEQ ID NO 149
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 149
acaggcatga atcactgcac ct                                            22

<210> SEQ ID NO 150
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 150
gcggcaactt cagacaaccg a                                             21

<210> SEQ ID NO 151
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 151
```
gacccagggg caccagtt                                                     18

<210> SEQ ID NO 152
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 152
ctgccttcat tgcttaaaag tggat                                             25

<210> SEQ ID NO 153
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 153
acagttgaag gaaggaaaca tgc                                               23

<210> SEQ ID NO 154
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 154
gctgcatttg cccatttcca                                                   20

<210> SEQ ID NO 155
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 155
gttgggggag gaggagctta t                                                 21

<210> SEQ ID NO 156
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 156
ctaagagcta taagggcaaa tgact                                             25

<210> SEQ ID NO 157
<211> LENGTH: 152
<212> TYPE: DNA
<213> ORGANISM: Artificial Sequence
<220> FEATURE:
<223> OTHER INFORMATION: Synthetic Polynucleotide

<400> SEQUENCE: 157
ttctgagggc tgctacctgt acatctgcac aagattgcct ttactccatg cctttcttct       60
tctgctctaa ctctgacaat ctgtcttgcc atgccataag ccctattct ttctgtaacc      120 ccaagatggt ataaaagcat caatgattgg gc                                    152

```
<210> SEQ ID NO 158
<211> LENGTH: 155
<212> TYPE: DNA
<213> ORGANISM: Artificial Sequence
<220> FEATURE:
<223> OTHER INFORMATION: Synthetic Polynucleotide

<400> SEQUENCE: 158
aaaactcaaa gaaatgccca atcattgatg cttttatacc atcttggggt tacagaaaga      60 atagggctt atggcatggc aagacagatt gtcagagtta gagcagaaga agaaaggcat     120
ggagtaaagg caatcttgtg cagatgtaca ggtaa                                155

<210> SEQ ID NO 159
<211> LENGTH: 155
<212> TYPE: DNA
<213> ORGANISM: Artificial Sequence
<220> FEATURE:
<223> OTHER INFORMATION: Synthetic Polynucleotide

<400> SEQUENCE: 159
ttacctgtac atctgcacaa gattgccttt actccatgcc tttcttcttc tgctctaact      60
ctgacaatct gtcttgccat gccataagcc cctattcttt ctgtaacccc aagatggtat    120
aaaagcatca atgatgggc atttctttga gtttt                                 155

<210> SEQ ID NO 160
<211> LENGTH: 152
<212> TYPE: DNA
<213> ORGANISM: Artificial Sequence
<220> FEATURE:
<223> OTHER INFORMATION: Synthetic Polynucleotide

<400> SEQUENCE: 160
ttctgagggc tgctacctgt acatctgcac aagattgcct ttactccatg cctttcttct      60
tctgctctaa ctctgacaat ctgtcttgcc atgccataag cccctattct ttctgtaacc    120
ccaagatggt ataaaagcat caatgattgg gc                                   152

<210> SEQ ID NO 161
<211> LENGTH: 167
<212> TYPE: DNA
<213> ORGANISM: Artificial Sequence
<220> FEATURE:
<223> OTHER INFORMATION: Synthetic Polynucleotide

<400> SEQUENCE: 161
ttctgagggc tgctacctgt acatctgcac aagattgcct ttactccatg cctttcttct      60
tctgctctaa ctctgacaat ctgtcttgcc atgccataag cccctattct ttctgtaacc    120
ccaagatggt ataaaagcat caatgattgg gcatttcttt gagtttt                   167

<210> SEQ ID NO 162
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 162
ggcctgcttc gtggcaatgc                                                   20

<210> SEQ ID NO 163
<211> LENGTH: 20
<212> TYPE: DNA
```

```
<213> ORGANISM: Artificial Sequence
<220> FEATURE:
<223> OTHER INFORMATION: Synthetic Polynucleotide

<400> SEQUENCE: 163
acctgggcca gggagggagg                                               20

<210> SEQ ID NO 164
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 164
ctcacttaga ctttctctcc                                               20

<210> SEQ ID NO 165
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 165
ctcggagtct agctcctgca                                               20

<210> SEQ ID NO 166
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 166
tggccccagt ctctcttcta                                               20

<210> SEQ ID NO 167
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 167
cagcctctga acagctcccg                                               20

<210> SEQ ID NO 168
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 168
tgacttggcc tttgtaggaa                                               20

<210> SEQ ID NO 169
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 169
gaggctactg aaacataagt                                               20
```

```
<210> SEQ ID NO 170
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 170
tgctacctgt acatctgcac                                                 20

<210> SEQ ID NO 171
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 171
catcaatgat tgggcatttc                                                 20

<210> SEQ ID NO 172
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 172
actccagtcc caaatatgta                                                 20

<210> SEQ ID NO 173
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 173 actaggggggc gctcggccac                                                20

<210> SEQ ID NO 174
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 174
ctgagtcaac tgtaagcatt                                                 20

<210> SEQ ID NO 175
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 175
ggccaggtgc agtgattcat                                                 20

<210> SEQ ID NO 176
<211> LENGTH: 20
<212> TYPE: DNA
<213> ORGANISM: Artificial Sequence
<220> FEATURE:
```

<223> OTHER INFORMATION: Synthetic Polynucleotide

<400> SEQUENCE: 176
tcgtgtcatc ttgtttgtgc                                           20

<210> SEQ ID NO 177
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 177
ggcagagccc agcggacact                                           20

<210> SEQ ID NO 178
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 178
caaggtgagc ctgggtctgt                                           20

<210> SEQ ID NO 179
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 179
atcactgccc aagaagtgca                                           20

<210> SEQ ID NO 180
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 180
ttgtaggatg tttagcagca                                           20

<210> SEQ ID NO 181
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 181
acttgctctc tttagagaac                                           20

<210> SEQ ID NO 182
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 182
ctcaagcagg ccccgctggt                                           20

<210> SEQ ID NO 183
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 183
ttttggacca aaccttttg                                                  20

<210> SEQ ID NO 184
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 184
tgaggttatt tgtccattgt                                                 20

<210> SEQ ID NO 185
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 185 taagggagt atttacacca                                                  20

<210> SEQ ID NO 186
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 186
tcaagagcag aaaatgtgac                                                 20

<210> SEQ ID NO 187
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 187
cttgcaggga ccttctgatt                                                 20

<210> SEQ ID NO 188
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 188
tgtgtgtagg actaaactct                                                 20

<210> SEQ ID NO 189
<211> LENGTH: 20
<212> TYPE: DNA
<213> ORGANISM: Artificial Sequence
<220> FEATURE:
<223> OTHER INFORMATION: Synthetic Polynucleotide

```
<400> SEQUENCE: 189
gatagcagta tgaccttggg                                                    20

<210> SEQ ID NO 190
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 190
gagtccgagc agaagaagaa ggg                                                23

<210> SEQ ID NO 191
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 191
gaggccgagc agaagaaaga cgg                                                23

<210> SEQ ID NO 192
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 192
gagtcctagc aggagaagaa gag                                                23

<210> SEQ ID NO 193
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 193
gagtctaagc agaagaagaa gag                                                23

<210> SEQ ID NO 194
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 194
gagttagagc agaagaagaa agg                                                23

<210> SEQ ID NO 195
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 195
gggtgggggg agtttgctcc tgg                                                23

<210> SEQ ID NO 196
<211> LENGTH: 23
```

```
<212> TYPE: DNA
<213> ORGANISM: Artificial Sequence
<220> FEATURE:
<223> OTHER INFORMATION: Synthetic Polynucleotide

<400> SEQUENCE: 196
ggatggaggg agtttgctcc tgg                                              23

<210> SEQ ID NO 197
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 197
gggagggtgg agtttgctcc tgg                                              23

<210> SEQ ID NO 198
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 198
cgggggaggg agtttgctcc tgg                                              23

<210> SEQ ID NO 199
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 199 ggggaggga agtttgctcc tgg                                               23

<210> SEQ ID NO 200
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 200
gcagatgtag tgtttccaca ggg                                              23

<210> SEQ ID NO 201
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 201
acaaatgtag tatttccaca ggg                                              23

<210> SEQ ID NO 202
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 202
```

```
ccagatgtag tattcccaca ggg                                              23

<210> SEQ ID NO 203
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 203
ctagatgaag tgcttccaca tgg                                              23

<210> SEQ ID NO 204
<211> LENGTH: 89
<212> TYPE: DNA
<213> ORGANISM: Homo sapiens

<400> SEQUENCE: 204
ccgcgccgag gtgaagttcg agggcgacac cctggtgaac cgcatcgagc tgaagggcat      60
cgacttcaag gaggacggca acatcctgg                                        89

<210> SEQ ID NO 205
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 205
ccgcgccgag gtgaagttcg agg                                              23

<210> SEQ ID NO 206
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 206
ccgaggtgaa gttcgagggc gac                                              23

<210> SEQ ID NO 207
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 207
ccctggtgaa ccgcatcgag ctg                                              23

<210> SEQ ID NO 208
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 208
ggtgaaccgc atcgagctga agg                                              23

<210> SEQ ID NO 209
<211> LENGTH: 23
<212> TYPE: DNA
<213> ORGANISM: Artificial Sequence
```

```
<220> FEATURE:
<223> OTHER INFORMATION: Synthetic Polynucleotide

<400> SEQUENCE: 209
gctgaagggc atcgacttca agg                                              23

<210> SEQ ID NO 210
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 210
ggcatcgact tcaaggagga cgg                                              23

<210> SEQ ID NO 211
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 211
caaggaggac ggcaacatcc tgg                                              23

<210> SEQ ID NO 212
<211> LENGTH: 104
<212> TYPE: DNA
<213> ORGANISM: Homo sapiens

<400> SEQUENCE: 212
ggagcgcacc atcttcttca aggacgacgg caactacaag acccgcgccg aggtgaagtt      60
cgagggcgac accctggtga accgcatcga gctgaagggc atcg                      104

<210> SEQ ID NO 213
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 213
accatcttct tcaaggacga cgg                                              23

<210> SEQ ID NO 214
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 214
caactacaag acccgcgccg agg                                              23

<210> SEQ ID NO 215
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 215
ccgcgccgag gtgaagttcg agg                                              23
```

```
<210> SEQ ID NO 216
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 216
gaagttcgag ggcgacaccc tgg                                              23

<210> SEQ ID NO 217
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 217
cccgcgccga ggtgaagttc gag                                              23

<210> SEQ ID NO 218
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 218
cctggtgaac cgcatcgagc tga                                              23

<210> SEQ ID NO 219
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 219
ccgcatcgag ctgaagggca tcg                                              23

<210> SEQ ID NO 220
<211> LENGTH: 68
<212> TYPE: DNA
<213> ORGANISM: Homo sapiens

<400> SEQUENCE: 220
ccccaagtct agcaagcagg ccaaagatgt ctcccgcatg cgctcagtcc tcatctccct      60
caagcagg                                                              68

<210> SEQ ID NO 221
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 221
ccccaagtct agcaagcagg cca                                              23

<210> SEQ ID NO 222
<211> LENGTH: 23
<212> TYPE: DNA
<213> ORGANISM: Artificial Sequence
<220> FEATURE:
<223> OTHER INFORMATION: Synthetic Polynucleotide
```

<400> SEQUENCE: 222
agtcctcatc tccctcaagc agg							23

<210> SEQ ID NO 223
<211> LENGTH: 65
<212> TYPE: DNA
<213> ORGANISM: Homo sapiens

<400> SEQUENCE: 223
ccctgtggaa acactacatc tgcaatatct taatcctact cagtgaagct cttcacagtc			60 attgg									65

<210> SEQ ID NO 224
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 224
ccctgtggaa acactacatc tgc							23

<210> SEQ ID NO 225
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 225
gtgaagctct tcacagtcat tgg							23

<210> SEQ ID NO 226
<211> LENGTH: 93
<212> TYPE: DNA
<213> ORGANISM: Artificial Sequence
<220> FEATURE:
<223> OTHER INFORMATION: Synthetic Polynucleotide

<400> SEQUENCE: 226
ccgttactgc cctgtggggc aaggtgaacg tggatgaagt tggtggtgag gccctgggca			60 ggttggtatc aaggttacaa gacaggttta agg					93

<210> SEQ ID NO 227
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 227
ccgttactgc cctgtggggc aag							23

<210> SEQ ID NO 228
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 228
cgtggatgaa gttggtggtg gg							22

```
<210> SEQ ID NO 229
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 229
tgaagttggt ggtgaggccc tgg                                                23

<210> SEQ ID NO 230
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 230
ttggtggtga ggccctgggc agg                                                23

<210> SEQ ID NO 231
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 231
tggtgaggcc ctgggcaggt tgg                                                23

<210> SEQ ID NO 232
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 232
ccctgggcag gttggtatca agg                                                23

<210> SEQ ID NO 233
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 233
aaggttacaa gacaggttta agg                                                23

<210> SEQ ID NO 234
<211> LENGTH: 75
<212> TYPE: DNA
<213> ORGANISM: Artificial Sequence
<220> FEATURE:
<223> OTHER INFORMATION: Synthetic Polynucleotide

<400> SEQUENCE: 234
cccttcttct tctgctcgga ctcaggccct tcctcctcca gcttctgccg tttgtacttt         60
gtcctccggt tctgg                                                         75

<210> SEQ ID NO 235
<211> LENGTH: 23
<212> TYPE: DNA
<213> ORGANISM: Artificial Sequence
```

```
<220> FEATURE:
<223> OTHER INFORMATION: Synthetic Polynucleotide

<400> SEQUENCE: 235
cccttcttct tctgctcgga ctc                                              23

<210> SEQ ID NO 236
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 236
gccgtttgta ctttgtcctc cgg                                              23

<210> SEQ ID NO 237
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 237
tgtactttgt cctccggttc tgg                                              23

<210> SEQ ID NO 238
<211> LENGTH: 73
<212> TYPE: DNA
<213> ORGANISM: Artificial Sequence
<220> FEATURE:
<223> OTHER INFORMATION: Synthetic Polynucleotide

<400> SEQUENCE: 238
ccaggagcaa actcccccca cccccttttcc aaagcccatt ccctctttag ccagagccgg      60
ggtgtgcaga cgg                                                         73

<210> SEQ ID NO 239
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 239
ccaggagcaa actcccccca ccc                                              23

<210> SEQ ID NO 240
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 240
attccctctt tagccagagc cgg                                              23

<210> SEQ ID NO 241
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 241
```

```
tccctctttta gccagagccg ggg                                            23

<210> SEQ ID NO 242
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 242
ccagagccgg ggtgtgcaga cgg                                             23

<210> SEQ ID NO 243
<211> LENGTH: 106
<212> TYPE: DNA
<213> ORGANISM: Artificial Sequence
<220> FEATURE:
<223> OTHER INFORMATION: Synthetic Polynucleotide

<400> SEQUENCE: 243
gctgtttggg aggtcagaaa taggggtcc aggagcaaac tccccccacc cctttccaa       60 agcccattcc ctctttagcc agagccgggg tgtgcagacg gcagtc                    106

<210> SEQ ID NO 244
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 244
gctgtttggg aggtcagaaa taggggtcc aggaagccgg ggtgtgcaga cggcagtc        58

<210> SEQ ID NO 245
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 245
gctgtttggg aggtcagaaa taggggtcc aggagcaaac tccccccacc cctttccaa       60 agcccattcc ctctttagcc ggggtgtgca dacggcagtc                           100

<210> SEQ ID NO 246
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 246
gctgtttggg aggtcagaaa taggggtcc aggagagccg ggtgtgcag acggcagtc        59

<210> SEQ ID NO 247
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 247
gctgtttggg aggtcagaaa tagccggggt gtgcagacgg cagtc                     45
```

<210> SEQ ID NO 248
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 248
gctgtttggg aggtcagaaa tagggggtcc aggagccggg gtgtgcagac ggcagtc        57

<210> SEQ ID NO 249
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 249
gctgtttggg aggtcagaaa tagggggtcc agccggggtg tgcagacggc agtc        54

<210> SEQ ID NO 250
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 250
gctgtttggg aggtcagaaa tagggggtcc aggagcaaac tccccccacc cccttttccaa        60 agcccattcc ctctttagcc agggtgtgca gacggcagtc        100

<210> SEQ ID NO 251
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 251
gctgtttggg aggtcagaaa tagggggtcc aggatagccg gggtgtgcag acggcagtc        59

<210> SEQ ID NO 252
<211> LENGTH: 106
<212> TYPE: DNA
<213> ORGANISM: Artificial Sequence
<220> FEATURE:
<223> OTHER INFORMATION: Synthetic Polynucleotide

<400> SEQUENCE: 252
gctgtttggg aggtcagaaa tagggggtcc aggagcaaac tccccccacc cccttttccaa        60 agcccattcc ctctttagcc agagccgggg tgtgcagacg gcagtc        106

<210> SEQ ID NO 253
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 253
gctgtttggg aggtcagaaa tagggggtcc agacggcagt c        41

<210> SEQ ID NO 254
<211> LENGTH: 84
<212> TYPE: DNA

```
<213> ORGANISM: Artificial Sequence
<220> FEATURE:
<223> OTHER INFORMATION: Synthetic Polynucleotide

<400> SEQUENCE: 254
gctgtttggg aggtcagaaa tagggggtcc aggagcaaac tcccccacc  cctttccaa     60 agccggggtg tgcagacggc agtc                                           84

<210> SEQ ID NO 255
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 255
gctgtttggg aggtcagaaa tagggggtcc aaagcccatt ccctctttag ccagagccgg    60
ggtggcagac ggcagtc                                                   77

<210> SEQ ID NO 256
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 256
gctgtttggg aggtcagaaa tagggggtgt gcagacggca gtc                      43

<210> SEQ ID NO 257
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 257
gctgtttggg aggtcagaaa tagggggtcc agccggggtg tgcagacggc agtc          54

<210> SEQ ID NO 258
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 258
gctgtttggg aggtcagaaa tagggggtcc agggtgtgca gacggcagtc               50

<210> SEQ ID NO 259
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 259
gctgtttggg aggtcagaaa gagggggtcc aggagccggg gtgtgcagac ggcagtc       57

<210> SEQ ID NO 260
<211> LENGTH: 45
<212> TYPE: DNA
<213> ORGANISM: Artificial Sequence
<220> FEATURE:
<223> OTHER INFORMATION: Synthetic Polynucleotide
```

```
<400> SEQUENCE: 260
gctgtttggg aggtcagaaa tagccggggt gtgcagacgg cagtc              45

<210> SEQ ID NO 261
<211> LENGTH: 106
<212> TYPE: DNA
<213> ORGANISM: Artificial Sequence
<220> FEATURE:
<223> OTHER INFORMATION: Synthetic Polynucleotide

<400> SEQUENCE: 261
gctgtttggg aggtcagaaa taggggtcc aggagcaaac tccccccacc cccttttccaa    60 agcccattcc ctctttagcc agagccgggg tgtgcagacg gcagtc                 106

<210> SEQ ID NO 262
<211> LENGTH: 94
<212> TYPE: DNA
<213> ORGANISM: Artificial Sequence
<220> FEATURE:
<223> OTHER INFORMATION: Synthetic Polynucleotide

<400> SEQUENCE: 262
gctgtttggg aggtcagaaa taggggtcc aggagcaaac tccccccaag cccattccct    60
ctttagccag agccggggtg tgcagacggc agtc                              94

<210> SEQ ID NO 263
<211> LENGTH: 95
<212> TYPE: DNA
<213> ORGANISM: Artificial Sequence
<220> FEATURE:
<223> OTHER INFORMATION: Synthetic Polynucleotide

<400> SEQUENCE: 263
gctgtttggg aggtcagaaa taggggtcc aggagcaaac tccccccacc cccttttccc    60
tctttagcca gagccggggt gtgcagacgg cagtc                             95

<210> SEQ ID NO 264
<211> LENGTH: 94
<212> TYPE: DNA
<213> ORGANISM: Artificial Sequence
<220> FEATURE:
<223> OTHER INFORMATION: Synthetic Polynucleotide

<400> SEQUENCE: 264
gctgtttggg aggtcagaaa taggggtcc aggagcaaac tccccccacc cccttttccct   60 ctttagccag agccggggtg tgcagacggc agtc                              94

<210> SEQ ID NO 265
<211> LENGTH: 93
<212> TYPE: DNA
<213> ORGANISM: Artificial Sequence
<220> FEATURE:
<223> OTHER INFORMATION: Synthetic Polynucleotide

<400> SEQUENCE: 265
gctgtttggg aggtcagaaa taggggtcc aggagcaaac tccccccagc ccattccctc    60
tttagccaga gccggggtgt gcagacggca gtc                               93

<210> SEQ ID NO 266
<211> LENGTH: 94
<212> TYPE: DNA
```

```
<213> ORGANISM: Artificial Sequence
<220> FEATURE:
<223> OTHER INFORMATION: Synthetic Polynucleotide

<400> SEQUENCE: 266
gctgtttggg aggtcagaaa tagggggtcc aggagcaaac tcccccacc cccattccct      60 ctttagccag agccggggtg tgcagacggc agtc                                 94

<210> SEQ ID NO 267
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 267
gctgtttggg aggtcagaaa tagggggtcc aggagcaaac tcccccacc ccctttagcc      60 agagccgggg tgtgcagacg gcagtc                                          86

<210> SEQ ID NO 268
<211> LENGTH: 103
<212> TYPE: DNA
<213> ORGANISM: Artificial Sequence
<220> FEATURE:
<223> OTHER INFORMATION: Synthetic Polynucleotide

<400> SEQUENCE: 268
gctgtttggg aggtcagaaa tagggggtcc aggagcaaac tcccccacc cccttaaagc      60 ccattccctc tttagccaga gccggggtgt gcagacggca gtc                      103

<210> SEQ ID NO 269
<211> LENGTH: 93
<212> TYPE: DNA
<213> ORGANISM: Artificial Sequence
<220> FEATURE:
<223> OTHER INFORMATION: Synthetic Polynucleotide

<400> SEQUENCE: 269
gctgtttggg aggtcagaaa tagggggtcc aggagcaaac tcccccaagc ccattccctc      60
tttagccaga gccggggtgt gcagacggca gtc                                  93

<210> SEQ ID NO 270
<211> LENGTH: 132
<212> TYPE: DNA
<213> ORGANISM: Artificial Sequence
<220> FEATURE:
<223> OTHER INFORMATION: Synthetic Polynucleotide

<400> SEQUENCE: 270
cattcaacag atacttactg aatgctaatg tctcagacag gacattctga cacccccagga     60 gcaaactccc tccatcccac aaatccgtcc ttagatgtgc acacccaacc tcctaagaaa    120
tagaaggatg at                                                        132

<210> SEQ ID NO 271
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 271
cattcaacag atacttactg aatgctaatg tctcagacag gacattctga cacccccaggc     60
```

```
aaactccctc atcccacaa atccgtcctt agatgtgcac acccaacctc ctaagaaata    120
gaaggatgat                                                          130

<210> SEQ ID NO 272
<211> LENGTH: 123
<212> TYPE: DNA
<213> ORGANISM: Artificial Sequence
<220> FEATURE:
<223> OTHER INFORMATION: Synthetic Polynucleotide

<400> SEQUENCE: 272
cattcaacag atacttactg aatgctaatg tctcagacag gacattctga caccccatcc    60
ctccatccca caaatccgtc cttagatgtg cacacccaac ctcctaagaa atagaaggat   120
gat                                                                 123

<210> SEQ ID NO 273
<211> LENGTH: 129
<212> TYPE: DNA
<213> ORGANISM: Artificial Sequence
<220> FEATURE:
<223> OTHER INFORMATION: Synthetic Polynucleotide

<400> SEQUENCE: 273
cattcaacag atacttactg aatgctaatg tctcagacag gacattctga caccccagca    60
aactccctcc atcccacaaa tccgtcctta gatgtgcaca cccaacctcc taagaaatag   120
aaggatgat                                                           129

<210> SEQ ID NO 274
<211> LENGTH: 110
<212> TYPE: DNA
<213> ORGANISM: Artificial Sequence
<220> FEATURE:
<223> OTHER INFORMATION: Synthetic Polynucleotide

<400> SEQUENCE: 274
cattcaacag atacttactg aatgctaatg tctcagacag gacattctga caccccacaa    60
atccgtcctt agatgtgcac acccaacctc ctaagaaata gaaggatgat              110

<210> SEQ ID NO 275
<211> LENGTH: 119
<212> TYPE: DNA
<213> ORGANISM: Artificial Sequence
<220> FEATURE:
<223> OTHER INFORMATION: Synthetic Polynucleotide

<400> SEQUENCE: 275
cattcaacag atacttactg aatgctaatg tctcagacag gacattctga cactccctcc    60
atcccacaaa tccgtcctta gatgtgcaca cccaacctcc taagaaatag aaggatgat   119

<210> SEQ ID NO 276
<211> LENGTH: 118
<212> TYPE: DNA
<213> ORGANISM: Artificial Sequence
<220> FEATURE:
<223> OTHER INFORMATION: Synthetic Polynucleotide

<400> SEQUENCE: 276
cattcaacag atacttactg aatgctaatg tctcagacag gacattctga caccctcca     60 tcccacaaat ccgtccttag atgtgcacac ccaacctcct aagaaataga aggatgat    118
```

<210> SEQ ID NO 277
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 277
cattcaacag atacttactg aatgctaatg tctcagacag gacattctga caccccagga     60
tgat                                                                  64

<210> SEQ ID NO 278
<211> LENGTH: 117
<212> TYPE: DNA
<213> ORGANISM: Artificial Sequence
<220> FEATURE:
<223> OTHER INFORMATION: Synthetic Polynucleotide

<400> SEQUENCE: 278
cattcaacag atacttactg aatgctaatg tctcagacag gacattctga ctccctccat     60
cccacaaatc cgtccttaga tgtgcacacc caacctccta agaaatagaa ggatgat      117

<210> SEQ ID NO 279
<211> LENGTH: 132
<212> TYPE: DNA
<213> ORGANISM: Homo sapiens

<400> SEQUENCE: 279
cattcaacag atacttactg aatgctaatg tctcagacag gacattctga caccccagga     60
gcaaactccc tccatcccac aaatccgtcc ttagatgtgc acacccaacc tcctaagaaa   120
tagaaggatg at                                                       132

<210> SEQ ID NO 280
<211> LENGTH: 111
<212> TYPE: DNA
<213> ORGANISM: Artificial Sequence
<220> FEATURE:
<223> OTHER INFORMATION: Synthetic Polynucleotide

<400> SEQUENCE: 280
cattcaacag atacttactg aatgctaatg tctcagacag gacattctga caccccagga     60
catccgtcct tagatgtgca cacccaacct cctaagaaat agaaggatga t             111

<210> SEQ ID NO 281
<211> LENGTH: 117
<212> TYPE: DNA
<213> ORGANISM: Artificial Sequence
<220> FEATURE:
<223> OTHER INFORMATION: Synthetic Polynucleotide

<400> SEQUENCE: 281
cattcaacag atacttactg aatgctaatg tctcagacag gacattctga ctccctccat     60
cccacaaatc cgtccttaga tgtgcacacc caacctccta agaaatagaa ggatgat      117

<210> SEQ ID NO 282
<211> LENGTH: 99
<212> TYPE: DNA
<213> ORGANISM: Artificial Sequence
<220> FEATURE:
<223> OTHER INFORMATION: Synthetic Polynucleotide

<400> SEQUENCE: 282

```
cattcaacag atacttactg aatgctaatg tctcagacag gacattctga tccgtcctta      60
gatgtgcaca cccaacctcc taagaaatag aaggatgat                             99
```

<210> SEQ ID NO 283
<211> LENGTH: 121
<212> TYPE: DNA
<213> ORGANISM: Artificial Sequence
<220> FEATURE:
<223> OTHER INFORMATION: Synthetic Polynucleotide

<400> SEQUENCE: 283

```
cattcaacag atacttactg aatgctaatg tctcagacag gacattctga cacccagca      60 tctgatgaca aatccgtcct tagatgtgca cacccaacct cctaagaaat agaaggatga    120
t                                                                    121
```

<210> SEQ ID NO 284
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 284

```
cattcaacag atacttactg aatgctaatg tctcagacag gacattctga cacccagga      60 gcaaactccc tccatcccac aaatccgtcc ttagatgtgc acccaacctc ctaagaaata    120
gaaggatgat                                                            130
```

<210> SEQ ID NO 285
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 285

```
cattcaacag atacttactg aatgctaatg tctcagacag gacattctga cacccagga      60 gcaaactccc tccatcccac aaatccgtcc ttatgtgcac acccaacctc ctaagaaata    120
gaaggatgat                                                            130
```

<210> SEQ ID NO 286
<211> LENGTH: 132
<212> TYPE: DNA
<213> ORGANISM: Artificial Sequence
<220> FEATURE:
<223> OTHER INFORMATION: Synthetic Polynucleotide

<400> SEQUENCE: 286

```
cattcaacag atacttactg aatgctaatg tctcagacag gacattctga cacccagga      60 gcaaactccc tccatcccac aaatccgtcc ttagatgtgc acacccaacc tcctaagaaa    120
tagaaggatg at                                                         132
```

<210> SEQ ID NO 287
<211> LENGTH: 101
<212> TYPE: DNA
<213> ORGANISM: Artificial Sequence
<220> FEATURE:
<223> OTHER INFORMATION: Synthetic Polynucleotide

<400> SEQUENCE: 287

```
cattcaacag atacttactg aatgctaatg tctcagacag gacattctga aatccgtcct    60
tagatgtgca cacccaacct cctaagaaat agaaggatga t                       101
```

<210> SEQ ID NO 288
<211> LENGTH: 132
<212> TYPE: DNA
<213> ORGANISM: Artificial Sequence
<220> FEATURE:
<223> OTHER INFORMATION: Synthetic Polynucleotide

<400> SEQUENCE: 288

```
cattcaacag atacttactg aatgctaatg tctcagacag gacattctga caccccagga    60
gcaaactccc tccatcccac aaatccgtcc ttagatgtgc acacccaacc tcctaagaaa   120
tagaaggatg at                                                      132
```

<210> SEQ ID NO 289
<211> LENGTH: 119
<212> TYPE: DNA
<213> ORGANISM: Artificial Sequence
<220> FEATURE:
<223> OTHER INFORMATION: Synthetic Polynucleotide

<400> SEQUENCE: 289

```
cattcaacag atacttactg aatgctaatg tctcagacag gacattctga caccccagga    60
gcaaactccc tccgtcctta gatgtgcaca cccaacctcc taagaaatag aaggatgat    119
```

<210> SEQ ID NO 290
<211> LENGTH: 121
<212> TYPE: DNA
<213> ORGANISM: Artificial Sequence
<220> FEATURE:
<223> OTHER INFORMATION: Synthetic Polynucleotide

<400> SEQUENCE: 290

```
cattcaacag atacttactg aatgctaatg tctcagacag gacattctga caccccagga    60
gcaaactccc tctccgtcct tagatgtgca cacccaacct cctaagaaat agaaggatga   120
t                                                                  121
```

<210> SEQ ID NO 291
<211> LENGTH: 124
<212> TYPE: DNA
<213> ORGANISM: Artificial Sequence
<220> FEATURE:
<223> OTHER INFORMATION: Synthetic Polynucleotide

<400> SEQUENCE: 291

```
cattcaacag atacttactg aatgctaatg tctcagacag gacattctga caccccagga    60
gcaaactccc tccattccgt ccttagatgt gcacacccaa cctcctaaga aatagaagga   120
tgat                                                               124
```

<210> SEQ ID NO 292
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 292

```
cattcaacag atacttactg aatgctaatg tctcagacag gacattctga caccccagga    60
gcaaactccc tccatcccac aaatccgtcc ttagatgtgc acccaacctc ctaagaaata   120
```

```
gaaggatgat                                                                    130

<210> SEQ ID NO 293
<211> LENGTH: 122
<212> TYPE: DNA
<213> ORGANISM: Artificial Sequence
<220> FEATURE:
<223> OTHER INFORMATION: Synthetic Polynucleotide

<400> SEQUENCE: 293
cattcaacag atacttactg aatgctaatg tctcagacag gacattctga caccccagga    60
gcaaactccc tcctccgtcc ttagatgtgc acacccaacc tcctaagaaa tagaaggatg   120
at                                                                  122

<210> SEQ ID NO 294
<211> LENGTH: 123
<212> TYPE: DNA
<213> ORGANISM: Artificial Sequence
<220> FEATURE:
<223> OTHER INFORMATION: Synthetic Polynucleotide

<400> SEQUENCE: 294
cattcaacag atacttactg aatgctaatg tctcagacag gacattctga caccccagga    60
gcaaactccc tccatccgtc cttagatgtg cacacccaac ctcctaagaa atagaaggat   120
gat                                                                 123

<210> SEQ ID NO 295
<211> LENGTH: 128
<212> TYPE: DNA
<213> ORGANISM: Artificial Sequence
<220> FEATURE:
<223> OTHER INFORMATION: Synthetic Polynucleotide

<400> SEQUENCE: 295
cattcaacag atacttactg aatgctaatg tctcagacag gacattctga caccccagga    60
gcaaactccc tccatcccac aaatccgtcc ttagatgtgc acaccctcct aagaaataga   120
aggatgat                                                            128

<210> SEQ ID NO 296
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 296
cattcaacag atacttactg aatgctaatg tctcagacag gacattctga caccccagga    60
gcaaactccc tccatcccac aaatccgtcc agatgtgcac acccaacctc ctaagaaata   120
gaaggatgat                                                          130

<210> SEQ ID NO 297
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 297
ggggtggggg gagtttgctc c                                              21
```

<210> SEQ ID NO 298
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 298
aggagcaaac tccctccatc cc					22

<210> SEQ ID NO 299
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 299
gggatggagg gagtttgctc ct					22

<210> SEQ ID NO 300
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 300
auucccucuu uagccagagc					20

<210> SEQ ID NO 301
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 301

Gly Gly Ser Met
1

<210> SEQ ID NO 302
<211> LENGTH: 99
<212> TYPE: DNA
<213> ORGANISM: Artificial Sequence
<220> FEATURE:
<223> OTHER INFORMATION: Synthetic Polynucleotide

<400> SEQUENCE: 302
ccagcaagag gctcccgagc gagcaagctc agtttacacc cgatccactg gggagcagga		60 aatatctgtg ggcttgtgac acggactcaa gtgggctgg				99

<210> SEQ ID NO 303
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 303
ccagcaagag gctcccgagc gag					23

<210> SEQ ID NO 304
<211> LENGTH: 23
<212> TYPE: DNA

```
<213> ORGANISM: Artificial Sequence
<220> FEATURE:
<223> OTHER INFORMATION: Synthetic Polynucleotide

<400> SEQUENCE: 304
cccgagcgag caagctcagt tta                                              23

<210> SEQ ID NO 305
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 305
cccgatccac tggggagcag gaa                                              23

<210> SEQ ID NO 306
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 306
agtttacacc cgatccactg ggg                                              23

<210> SEQ ID NO 307
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 307
tggggagcag gaaatatctg tggg                                             24

<210> SEQ ID NO 308
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 308
atatctgtgg gcttgtgaca cgg                                              23

<210> SEQ ID NO 309
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 309
gcttgtgaca cggactcaag tgg                                              23

<210> SEQ ID NO 310
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 310
tgacacggac tcaagtgggc tgg                                              23
```

<210> SEQ ID NO 311
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 311
cctggccatc tctgacctgt ttttccttct tactgtcccc ttctgggctc actatgctgc    60
cgcccagtgg gactttggaa atacaatgtg tcaactcttg acagggctct attttatagg   120

<210> SEQ ID NO 312
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 312
cctggccatc tctgacctgt ttt                                             23

<210> SEQ ID NO 313
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 313
ccccttctgg gctcactatg ctg                                             23

<210> SEQ ID NO 314
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 314
ccgcccagtg ggactttgga aat                                             23

<210> SEQ ID NO 315
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 315
tcactatgct gccgcccagt ggg                                             23

<210> SEQ ID NO 316
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 316
caatgtgtca actcttgaca ggg                                             23

<210> SEQ ID NO 317
<211> LENGTH: 23
<212> TYPE: DNA

```
<213> ORGANISM: Artificial Sequence
<220> FEATURE:
<223> OTHER INFORMATION: Synthetic Polynucleotide

<400> SEQUENCE: 317
ttgacagggc tctattttat agg                                                23

<210> SEQ ID NO 318
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 318

Met Ala Pro Lys Lys Lys Arg Lys Val Gly Ile His Arg Gly Val Pro
1               5                   10                  15

<210> SEQ ID NO 319
<211> LENGTH: 4869
<212> TYPE: DNA
<213> ORGANISM: Artificial Sequence
<220> FEATURE:
<223> OTHER INFORMATION: Synthetic Polynucleotide

<400> SEQUENCE: 319
atggactaca aagaccatga cggtgattat aaagatcatg acatcgatta caaggatgac      60
gatgacaaga tggcccccaa gaagaagagg aaggtgggca ttcaccgcgg ggtacctgga     120
ggttctggat cccaactagt caaaagtgaa ctggaggaga gaaatctga acttcgtcat      180 aaattgaaat atgtgcctca tgaatatatt gaattaattg aaattgccag aaattccact     240
caggatagaa ttcttgaaat gaaggtaatg gaatttttta tgaaagtttta tggatataga     300 ggtaaacatt tgggtggatc aaggaaaccg gacggagcaa tttatactgt cggatctcct     360
attgattacg gtgtgatcgt ggatactaaa gcttatagcg gaggttataa tctgccaatt     420
ggccaagcag atgaaatgca acgatatgtc gaagaaaatc aaacacgaaa caaacatatc     480
aaccctaatg aatggtggaa agtctatcca tcttctgtaa cggaatttaa gtttttattt     540
gtgagtggtc acttaaaggg aaactacaaa gctcagctta cacgattaaa tcatatcact     600
aattgtaatg gagctgttct tagtgtagaa gagcttttaa ttggtggaga atgattaaa     660 gccggcacat taaccttaga ggaagtcaga cggaaattta taacggcga gataaacttt     720 agcggcagcg agactcccgg gacctcagag tccgccacac ccgaaagtga taaaaagtat     780
tctattggtt tagctatcgg cactaattcc gttggatggg ctgtcataac cgatgaatac     840
aaagtacctt caaagaaatt taaggtgttg gggaacacag accgtcattc gattaaaaag     900
aatcttatcg gtgccctcct attcgatagt ggcgaaacgg cagaggcgac tcgcctgaaa     960
cgaaccgctc ggagaaggta tacacgtcgc aagaaccgaa tatgttactt acaagaaatt    1020
tttagcaatg agatggccaa agttgacgat tctttctttc accgtttgga agagtccttc    1080
cttgtcgaag aggacaagaa acatgaacgg caccccatct ttggaaacat agtagatgag    1140
gtggcatatc atgaaaagta cccaacgatt tatcacctca gaaaaagct agttgactca    1200 actgataaag cggacctgag gttaatctac ttggctcttg cccatatgat aaagttccgt    1260
gggcactttc tcattgaggg tgatctaaat ccggacaact cggatgtcga caactgttc    1320 atccagttag tacaaaccta taatcagttg tttgaagaga acctataaa tgcaagtggc    1380 gtggatgcga aggctattct tagcgcccgc ctctctaaat cccgacggct agaaaacctg    1440
```

```
atcgcacaat tacccggaga gaagaaaaat gggttgttcg gtaaccttat agcgctctca   1500
ctaggcctga caccaaattt taagtcgaac ttcgacttag ctgaagatgc caaattgcag   1560
cttagtaagg acacgtacga tgacgatctc gacaatctac tggcacaaat tggagatcag   1620
tatgcggact tattttggc tgccaaaaac cttagcgatg caatcctcct atctgacata    1680
ctgagagtta atactgagat taccaaggcg ccgttatccg cttcaatgat caaaaggtac   1740
gatgaacatc accaagactt gacacttctc aaggccctag tccgtcagca actgcctgag   1800
aaatataagg aaatattctt tgatcagtcg aaaaacgggt acgcaggtta tattgacggc   1860
ggagcgagtc aagaggaatt ctacaagttt atcaaaccca tattagagaa gatggatggg   1920
acggaagagt tgcttgtaaa actcaatcgc gaagatctac tgcgaaagca gcggactttc   1980
gacaacggta gcattccaca tcaaatccac ttaggcgaat tgcatgctat acttagaagg   2040
caggaggatt tttatccgtt cctcaaagac aatcgtgaaa agattgagaa atcctaacc    2100
tttcgcatac cttactatgt gggacccctg gcccgaggga actctcggtt cgcatggatg   2160
acaagaaagt ccgaagaaac gattactcca tggaattttg aggaagttgt cgataaaggt   2220
gcgtcagctc aatcgttcat cgagaggatg accaactttg acaagaattt accgaacgaa   2280
aaagtattgc ctaagcacag tttactttac gagtatttca cagtgtacaa tgaactcacg   2340
aaagttaagt atgtcactga gggcatgcgt aaacccgcct ttctaagcgg agaacagaag   2400
aaagcaatag tagatctgtt attcaagacc aaccgcaaag tgacagttaa gcaattgaaa   2460
gaggactact ttaagaaaat tgaatgcttc gattctgtcg agatctccgg ggtagaagat   2520
cgatttaatg cgtcacttgg tacgtatcat gacctcctaa agataattaa agataaggac   2580
ttcctggata acgaagagaa tgaagatatc ttagaagata tagtgttgac tcttaccctc   2640
tttgaagatc gggaaatgat tgaggaaaga ctaaaaacat acgctcacct gttcgacgat   2700
aaggttatga acagttaaa gaggcgtcgc tatacgggct ggggacgatt gtcgcggaaa    2760
cttatcaacg ggataagaga caagcaaagt ggtaaaacta ttctcgattt tctaaagagc   2820
gacggcttcg ccaataggaa ctttatgcag ctgatccatg atgactcttt aaccttcaaa   2880
gaggatatac aaaaggcaca ggtttccgga caagggact cattgcacga acatattgcg     2940
aatcttgctg gttcgccagc catcaaaaag ggcatactcc agacagtcaa agtagtggat   3000
gagctagtta aggtcatggg acgtcacaaa ccggaaaaca ttgtaatcga gatggcacgc   3060
gaaaatcaaa cgactcagaa ggggcaaaaa aacagtcgag agcggatgaa gagaatagaa   3120
gagggtatta agaactggg cagccagatc ttaaaggagc atcctgtgga aaatacccaa    3180
ttgcagaacg agaaacttta cctctattac ctacaaaatg gaagggacat gtatgttgat   3240
caggaactgg acataaaccg tttatctgat tacgacgtcg atgccattgt acccccaatcc  3300
tttttgaagg acgattcaat cgacaataaa gtgcttacac gctcggataa gaaccgaggg   3360
aaaagtgaca atgttccaag cgaggaagtc gtaaagaaaa tgaagaacta ttggcggcag   3420
ctcctaaatg cgaaactgat aacgcaaaga aagttcgata acttaactaa agctgagagg   3480
ggtggcttgt ctgaacttga caaggccgga tttattaaac gtcagctcgt ggaaacccgc   3540
caaatcacaa agcatgttgc acagatacta gattcccgaa tgaatacgaa atacgacgag   3600
aacgataagc tgattcggga agtcaaagta atcactttaa agtcaaaatt ggtgtcggac   3660
ttcagaaagg attttcaatt ctataaagtt agggagataa ataactacca ccatgcgcac   3720
gacgcttatc ttaatgccgt cgtagggacc gcactcatta gaaatacccc gaagctagaa   3780
agtgagtttg tgtatggtga ttacaaagtt tatgacgtcc gtaagatgat cgcgaaaagc   3840
```

```
gaacaggaga taggcaaggc tacagccaaa tacttctttt attctaacat tatgaatttc    3900
tttaagacgg aaatcactct ggcaaacgga gagatacgca aacgaccttt aattgaaacc    3960 aatgggaga caggtgaaat cgtatgggat aagggccggg acttcgcgac ggtgagaaaa     4020
gttttgtcca tgccccaagt caacatagta aagaaaactg aggtgcagac cggagggttt    4080
tcaaaggaat cgattcttcc aaaaaggaat agtgataagc tcatcgctcg taaaaaggac    4140
tgggacccga aaaagtacgg tggcttcgat agccctacag ttgcctattc tgtcctagta    4200
gtggcaaaag ttgagaaggg aaaatccaag aaactgaagt cagtcaaaga attattgggg    4260
ataacgatta tggagcgctc gtcttttgaa aagaacccca tcgacttcct tgaggcgaaa    4320
ggttacaagg aagtaaaaaa ggatctcata attaaactac aaagtatag tctgtttgag     4380 ttagaaaatg gccgaaaacg gatgttggct agcgccggag agcttcaaaa ggggaacgaa    4440
ctcgcactac cgtctaaata cgtgaatttc ctgtatttag cgtcccatta cgagaagttg    4500
aaaggttcac ctgaagataa cgaacagaag caacttttg ttgagcagca caaacattat     4560
ctcgacgaaa tcatagagca aatttcggaa ttcagtaaga gagtcatcct agctgatgcc    4620
aatctggaca agtattaag cgcatacaac aagcacaggg ataaacccat acgtgagcag     4680
gcggaaaata ttatccattt gtttactctt accaacctcg gcgctccagc cgcattcaag    4740
tattttgaca caacgataga tcgcaaacga tacacttcta ccaaggaggt gctagacgcg    4800
acactgattc accaatccat cacgggatta tatgaaactc ggatagattt gtcacagctt    4860
gggggtgac                                                            4869
```

<210> SEQ ID NO 320
<211> LENGTH: 1367
<212> TYPE: PRT
<213> ORGANISM: Artificial Sequence
<220> FEATURE:
<223> OTHER INFORMATION: Synthetic Polypeptide

<400> SEQUENCE: 320

```
Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
                20                  25                  30

Val Leu Gly Asn Thr Asp Arg His Ser Ile Lys Lys Asn Leu Ile Gly
            35                  40                  45

Ala Leu Leu Phe Asp Ser Gly Glu Thr Ala Glu Ala Thr Arg Leu Lys
        50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175
```

```
Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
            195                 200                 205

Ala Ile Leu Ser Ala Arg Leu Ser Lys Ser Arg Arg Leu Glu Asn Leu
210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
            245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
            275                 280                 285

Phe Leu Ala Ala Lys Asn Leu Ser Asp Ala Ile Leu Leu Ser Asp Ile
            290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
            325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
            355                 360                 365

Glu Glu Phe Tyr Lys Phe Ile Lys Pro Ile Leu Glu Lys Met Asp Gly
            370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
            405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
            435                 440                 445

Tyr Tyr Val Gly Pro Leu Ala Arg Gly Asn Ser Arg Phe Ala Trp Met
450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
            485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
            515                 520                 525

Val Thr Glu Gly Met Arg Lys Pro Ala Phe Leu Ser Gly Glu Gln Lys
            530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
            565                 570                 575

Val Glu Ile Ser Gly Val Glu Asp Arg Phe Asn Ala Ser Leu Gly Thr
            580                 585                 590
```

```
Tyr His Asp Leu Leu Lys Ile Ile Lys Asp Lys Asp Phe Leu Asp Asn
            595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Tyr Thr
            645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
            675                 680                 685

Asn Arg Asn Phe Met Gln Leu Ile His Asp Asp Ser Leu Thr Phe Lys
            690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
            725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
            755                 760                 765

Thr Gln Lys Gly Gln Lys Asn Ser Arg Glu Arg Met Lys Arg Ile Glu
            770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
            805                 810                 815

Asn Gly Arg Asp Met Tyr Val Asp Gln Glu Leu Asp Ile Asn Arg Leu
            820                 825                 830

Ser Asp Tyr Asp Val Asp Ala Ile Val Pro Gln Ser Phe Leu Lys Asp
            835                 840                 845

Asp Ser Ile Asp Asn Lys Val Leu Thr Arg Ser Asp Lys Asn Arg Gly
            850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
            885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
            930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
            965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
```

1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
    1175                1180                1185

Val Lys Lys Asp Leu Ile Ile Lys Leu Pro Lys Tyr Ser Leu Phe
    1190                1195                1200

Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Arg Tyr Thr Ser Thr
    1325                1330                1335

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp
    1355                1360                1365

<210> SEQ ID NO 321
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 321

Met Asp Tyr Lys Asp His Asp Gly Asp Tyr Lys Asp His Asp Ile Asp
1               5                   10                  15
Tyr Lys Asp Asp Asp Asp Lys
            20

<210> SEQ ID NO 322
<211> LENGTH: 432
<212> TYPE: DNA
<213> ORGANISM: Artificial Sequence
<220> FEATURE:
<223> OTHER INFORMATION: Synthetic Polynucleotide

<400> SEQUENCE: 322

```
atggccctgt tggctacgc acgcgtgtct accagtcaac agtcactcga tttgcaagtg      60
agggctctta aagatgccgg agtgaaggca acagaattt ttactgataa ggccagcgga     120
agcagcacag acagagggg gctggatctc ctgagaatga aggtaaagga gggtgatgtg     180
atcttggtca aaaaattgga tcgactgggg agagacacac tgatatgct tcagcttatt     240
aaagagtttg acgctcaggg tgttgccgtg aggtttatcg atgacggcat ctcaaccgac    300
tcctacattg gtcttatgtt tgtgacaatt ttgtccgctg tggctcaggc tgagcggaga    360
aggattctcg aaaggacgaa tgagggacgg caagcagcta agttgaaagg tatcaaattt    420
ggcagacgaa gg                                                        432
```

<210> SEQ ID NO 323
<211> LENGTH: 414
<212> TYPE: DNA
<213> ORGANISM: Artificial Sequence
<220> FEATURE:
<223> OTHER INFORMATION: Synthetic Polynucleotide

<400> SEQUENCE: 323

```
atggcaacca ttggctacat aagggtgtct accatcgacc aaaatatcga cctgcagcgc     60
aacgctctga catccgccaa ctgcgatcgg atcttcgagg ataggatcag tggcaagatc    120
gccaaccggc ccggtctgaa gcgggctctg aagtacgtga ataagggcga tactctggtt    180
gtgtggaagt tggatcgctt gggtagatca gtgaagaatc tcgtagccct gataagcgag    240
ctgcacgaga ggggtgcaca tttccattct ctgaccgatt ccatcgatac gtctagcgcc    300
atgggccgat tcttcttta cgtcatgtcc gccctcgctg aaatggagcg cgaacttatt    360
gttgaacgga ctttggctgg actggcagcg gctagagcac agggccgact tgga          414
```

<210> SEQ ID NO 324
<211> LENGTH: 432
<212> TYPE: DNA
<213> ORGANISM: Artificial Sequence
<220> FEATURE:
<223> OTHER INFORMATION: Synthetic Polynucleotide

<400> SEQUENCE: 324

```
atgctcattg gctatgtaag ggtcagcacc aatgaccaaa acacagactt gcaacgcaat     60
gctttggttt gcgccggatg tgaacagata tttgaagata aactgagcgg cactcggaca    120
gacagacctg gcttaagag agcactgaaa agactgcaga aggggacac cctggtcgtc     180
tggaaactgg atcgcctcgg acgcagcatg aaacatctga ttagcctggt tggtgagctt    240
agggagagag gaatcaactt cagaagcctg accgactcca tcgacaccag tagccccatg    300
ggacgattct tcttctatgt gatgggagca cttgctgaga tggaaagaga gcttattatc    360
```

```
gaaagaacta tggctggtat cgctgctgcc cggaacaaag gcagacggtt cggcagaccg    420
ccgaagagcg gc                                                        432
```

<210> SEQ ID NO 325
<211> LENGTH: 144
<212> TYPE: PRT
<213> ORGANISM: Artificial Sequence
<220> FEATURE:
<223> OTHER INFORMATION: Synthetic Polypeptide

<400> SEQUENCE: 325

```
Met Ala Leu Phe Gly Tyr Ala Arg Val Ser Thr Ser Gln Gln Ser Leu
1               5                   10                  15

Asp Leu Gln Val Arg Ala Leu Lys Asp Ala Gly Val Lys Ala Asn Arg
            20                  25                  30

Ile Phe Thr Asp Lys Ala Ser Gly Ser Ser Thr Asp Arg Glu Gly Leu
        35                  40                  45

Asp Leu Leu Arg Met Lys Val Lys Glu Gly Asp Val Ile Leu Val Lys
    50                  55                  60

Lys Leu Asp Arg Leu Gly Arg Asp Thr Ala Asp Met Leu Gln Leu Ile
65                  70                  75                  80

Lys Glu Phe Asp Ala Gln Gly Val Ala Val Arg Phe Ile Asp Asp Gly
                85                  90                  95

Ile Ser Thr Asp Ser Tyr Ile Gly Leu Met Phe Val Thr Ile Leu Ser
            100                 105                 110

Ala Val Ala Gln Ala Glu Arg Arg Ile Leu Glu Arg Thr Asn Glu
        115                 120                 125

Gly Arg Gln Ala Ala Lys Leu Lys Gly Ile Lys Phe Gly Arg Arg Arg
    130                 135                 140
```

<210> SEQ ID NO 326
<211> LENGTH: 138
<212> TYPE: PRT
<213> ORGANISM: Artificial Sequence
<220> FEATURE:
<223> OTHER INFORMATION: Synthetic Polypeptide

<400> SEQUENCE: 326

```
Met Ala Thr Ile Gly Tyr Ile Arg Val Ser Thr Ile Asp Gln Asn Ile
1               5                   10                  15

Asp Leu Gln Arg Asn Ala Leu Thr Ser Ala Asn Cys Asp Arg Ile Phe
            20                  25                  30

Glu Asp Arg Ile Ser Gly Lys Ile Ala Asn Arg Pro Gly Leu Lys Arg
        35                  40                  45

Ala Leu Lys Tyr Val Asn Lys Gly Asp Thr Leu Val Val Trp Lys Leu
    50                  55                  60

Asp Arg Leu Gly Arg Ser Val Lys Asn Leu Val Ala Leu Ile Ser Glu
65                  70                  75                  80

Leu His Glu Arg Gly Ala His Phe His Ser Leu Thr Asp Ser Ile Asp
                85                  90                  95

Thr Ser Ser Ala Met Gly Arg Phe Phe Phe Tyr Val Met Ser Ala Leu
            100                 105                 110

Ala Glu Met Glu Arg Glu Leu Ile Val Glu Arg Thr Leu Ala Gly Leu
        115                 120                 125

Ala Ala Ala Arg Ala Gln Gly Arg Leu Gly
    130                 135
```

<210> SEQ ID NO 327
<211> LENGTH: 144
<212> TYPE: PRT
<213> ORGANISM: Artificial Sequence
<220> FEATURE:
<223> OTHER INFORMATION: Synthetic Polypeptide

<400> SEQUENCE: 327

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Tyr Val Met Gly Ala Leu Ala
            100                 105                 110

Glu Met Glu Arg Glu Leu Ile Ile Glu Arg Thr Met Ala Gly Ile Ala
        115                 120                 125

Ala Ala Arg Asn Lys Gly Arg Arg Phe Gly Arg Pro Pro Lys Ser Gly
    130                 135                 140

<210> SEQ ID NO 328
<211> LENGTH: 583
<212> TYPE: PRT
<213> ORGANISM: Flavobacterium okeanokoites

<400> SEQUENCE: 328

Met Phe Leu Ser Met Val Ser Lys Ile Arg Thr Phe Gly Trp Val Gln
1               5                   10                  15

Asn Pro Gly Lys Phe Glu Asn Leu Lys Arg Val Val Gln Val Phe Asp
            20                  25                  30

Arg Asn Ser Lys Val His Asn Glu Val Lys Asn Ile Lys Ile Pro Thr
        35                  40                  45

Leu Val Lys Glu Ser Lys Ile Gln Lys Glu Leu Val Ala Ile Met Asn
    50                  55                  60

Gln His Asp Leu Ile Tyr Thr Tyr Lys Glu Leu Val Gly Thr Gly Thr
65                  70                  75                  80

Ser Ile Arg Ser Glu Ala Pro Cys Asp Ala Ile Ile Gln Ala Thr Ile
                85                  90                  95

Ala Asp Gln Gly Asn Lys Lys Gly Tyr Ile Asp Asn Trp Ser Ser Asp
            100                 105                 110

Gly Phe Leu Arg Trp Ala His Ala Leu Gly Phe Ile Glu Tyr Ile Asn
        115                 120                 125

Lys Ser Asp Ser Phe Val Ile Thr Asp Val Gly Leu Ala Tyr Ser Lys
    130                 135                 140

Ser Ala Asp Gly Ser Ala Ile Glu Lys Glu Ile Leu Ile Glu Ala Ile
145                 150                 155                 160

Ser Ser Tyr Pro Pro Ala Ile Arg Ile Leu Thr Leu Leu Glu Asp Gly
                165                 170                 175

Gln His Leu Thr Lys Phe Asp Leu Gly Lys Asn Leu Gly Phe Ser Gly

```
                180             185             190
Glu Ser Gly Phe Thr Ser Leu Pro Glu Gly Ile Leu Leu Asp Thr Leu
            195             200             205
Ala Asn Ala Met Pro Lys Asp Lys Gly Glu Ile Arg Asn Asn Trp Glu
            210             215             220
Gly Ser Ser Asp Lys Tyr Ala Arg Met Ile Gly Gly Trp Leu Asp Lys
225             230             235             240
Leu Gly Leu Val Lys Gln Gly Lys Glu Phe Ile Ile Pro Thr Leu
            245             250             255
Gly Lys Pro Asp Asn Lys Glu Phe Ile Ser His Ala Phe Lys Ile Thr
            260             265             270
Gly Glu Gly Leu Lys Val Leu Arg Arg Ala Lys Gly Ser Thr Lys Phe
            275             280             285
Thr Arg Val Pro Lys Arg Val Tyr Trp Glu Met Leu Ala Thr Asn Leu
            290             295             300
Thr Asp Lys Glu Tyr Val Arg Thr Arg Ala Leu Ile Leu Glu Ile
305             310             315             320
Leu Ile Lys Ala Gly Ser Leu Lys Ile Glu Gln Ile Gln Asp Asn Leu
            325             330             335
Lys Lys Leu Gly Phe Asp Glu Val Ile Glu Thr Ile Glu Asn Asp Ile
            340             345             350
Lys Gly Leu Ile Asn Thr Gly Ile Phe Ile Glu Ile Lys Gly Arg Phe
            355             360             365
Tyr Gln Leu Lys Asp His Ile Leu Gln Phe Val Ile Pro Asn Arg Gly
            370             375             380
Val Thr Lys Gln Leu Val Lys Ser Glu Leu Glu Glu Lys Lys Ser Glu
385             390             395             400
Leu Arg His Lys Leu Lys Tyr Val Pro His Glu Tyr Ile Glu Leu Ile
            405             410             415
Glu Ile Ala Arg Asn Ser Thr Gln Asp Arg Ile Leu Glu Met Lys Val
            420             425             430
Met Glu Phe Phe Met Lys Val Tyr Gly Tyr Arg Gly Lys His Leu Gly
            435             440             445
Gly Ser Arg Lys Pro Asp Gly Ala Ile Tyr Thr Val Gly Ser Pro Ile
            450             455             460
Asp Tyr Gly Val Ile Val Asp Thr Lys Ala Tyr Ser Gly Gly Tyr Asn
465             470             475             480
Leu Pro Ile Gly Gln Ala Asp Glu Met Gln Arg Tyr Val Glu Glu Asn
            485             490             495
Gln Thr Arg Asn Lys His Ile Asn Pro Asn Glu Trp Trp Lys Val Tyr
            500             505             510
Pro Ser Ser Val Thr Glu Phe Lys Phe Leu Phe Val Ser Gly His Phe
            515             520             525
Lys Gly Asn Tyr Lys Ala Gln Leu Thr Arg Leu Asn His Ile Thr Asn
            530             535             540
Cys Asn Gly Ala Val Leu Ser Val Glu Glu Leu Leu Ile Gly Gly Glu
545             550             555             560
Met Ile Lys Ala Gly Thr Leu Thr Leu Glu Glu Val Arg Arg Lys Phe
            565             570             575
Asn Asn Gly Glu Ile Asn Phe
            580
```

CAS9-FOKI FUSION PROTEINS AND USES THEREOF

RELATED APPLICATION

This application claims the benefit of the filing date of U.S. provisional applications 61/874,609, filed Sep. 6, 2013; 61/915,414, filed Dec. 12, 2013; and and 61/980,315, filed Apr. 16, 2014; all entitled Cas9 Variants and Uses Thereof, the entire contents of each of which are incorporated herein by reference.

BACKGROUND OF THE INVENTION

Site-specific endonucleases theoretically allow for the targeted manipulation of a single site within a genome and are useful in the context of gene targeting for therapeutic and research applications. In a variety of organisms, including mammals, site-specific endonucleases have been used for genome engineering by stimulating either non-homologous end joining or homologous recombination. In addition to providing powerful research tools, site-specific nucleases also have potential as gene therapy agents, and two site-specific endonucleases have recently entered clinical trials: (1) CCR5-2246, targeting a human CCR-5 allele as part of an anti-HIV therapeutic approach (NCT00842634, NCT01044654, NCT01252641); and (2) VF24684, targeting the human VEGF-A promoter as part of an anti-cancer therapeutic approach (NCT01082926).

Specific cleavage of the intended nuclease target site without or with only minimal off-target activity is a prerequisite for clinical applications of site-specific endonuclease, and also for high-efficiency genomic manipulations in basic research applications. For example, imperfect specificity of engineered site-specific binding domains has been linked to cellular toxicity and undesired alterations of genomic loci other than the intended target. Most nucleases available today, however, exhibit significant off-target activity, and thus may not be suitable for clinical applications. An emerging nuclease platform for use in clinical and research settings are the RNA-guided nucleases, such as Cas9. While these nucleases are able to bind guide RNAs (gRNAs) that direct cleavage of specific target sites, off-target activity is still observed for certain Cas9:gRNA complexes (Pattanayak et al., "High-throughput profiling of off-target DNA cleavage reveals RNA-programmed Cas9 nuclease specificity." *Nat Biotechnol.* 2013; doi:10.1038/nbt.2673). Technology for engineering nucleases with improved specificity is therefore needed.

Another class of enzymes useful for targeted genetic manipulations are site-specific recombinases (SSRs). These enzymes perform rearrangements of DNA segments by recognizing and binding to short DNA sequences, at which they cleave the DNA backbone, exchange the two DNA helices involved and rejoin the DNA strands. Such rearrangements allow for the targeted insertion, inversion, excision, or translocation of DNA segments. However, like site-specific endonucleases, naturally-occurring SSRs typically recognize and bind specific consensus sequences, and are thus limited in this respect. Technology for engineering recombinases with altered and/or improved specificity is also needed.

SUMMARY OF THE INVENTION

Some aspects of this disclosure are based on the recognition that the reported toxicity of some engineered site-specific endonucleases is based on off-target DNA cleavage. Thus certain aspects described herein relate to the discovery that increasing the number of sequences (e.g., having a nuclease bind at more than one site at a desired target), and/or splitting the activities (e.g., target binding and target cleaving) of a nuclease between two or more proteins, will increase the specificity of a nuclease and thereby decrease the likelihood of off-target effects. Accordingly, some aspects of this disclosure provide strategies, compositions, systems, and methods to improve the specificity of site-specific nucleases, in particular, RNA-programmable endonucleases, such as Cas9 endonuclease. Certain aspects of this disclosure provide variants of Cas9 endonuclease engineered to have improved specificity.

Other aspects of this disclosure are based on the recognition that site-specific recombinases (SSRs) available today are typically limited to recognizing and binding distinct consensus sequences. Thus certain aspects described herein relate to the discovery that fusions between RNA-programmable (nuclease-inactivated) nucleases (or RNA-binding domains thereof), and a recombinase domain, provide novel recombinases theoretically capable of binding and recombining DNA at any site chosen, e.g., by a practitioner (e.g., sites specified by guide RNAs (gRNAs) that are engineered or selected according the sequence of the area to be recombined). Such novel recombinases are therefore useful, inter alia, for the targeted insertion, deletion, inversion, translocation or other genomic modifications. Thus, also provided are methods of using these inventive recombinase fusion proteins, e.g., for such targeted genomic manipulations.

Accordingly, one embodiment of the disclosure provides fusion proteins and dimers thereof, for example, fusion proteins comprising two domains: (i) a nuclease-inactivated Cas9 domain; and (ii) a nuclease domain (e.g., a monomer of the FokI DNA cleavage domain). See e.g., FIGS. 1A, 6D. The fusion protein may further comprise a nuclear localization signal (NLS) domain, which signals for the fusion proteins to be transported into the nucleus of a cell. In some embodiments, one or more domains of the fusion proteins are separated by a linker. In certain embodiments, the linker is a non-peptidic linker. In certain embodiments, the linker is a peptide linker. In the case of peptide linkers, the peptide linker may comprise an XTEN linker, an amino acid sequence comprising one or more repeats of the tri-peptide GGS, or any sequence as provided in FIG. 12A. In some embodiments, the fusion protein is encoded by a nucleotide sequence set forth as SEQ ID NO:9, SEQ ID NO:10, SEQ ID NO:11, or SEQ ID NO:12, or a variant or fragment of any one of SEQ ID NO:9, SEQ ID NO:10, SEQ ID NO:11, or SEQ ID NO:12. The nuclease-inactivated Cas9 domain is capable of binding a guide RNA (gRNA). In certain embodiments, having dimers of such fusion protein each comprising a gRNA binding two distinct regions of a target nucleic acid provides for improved specificity, for example as compared to monomeric RNA-guided nucleases comprising a single gRNA to direct binding to the target nucleic acid.

According to another aspect of the invention, methods for site-specific DNA cleavage using the inventive Cas9 variants are provided. The methods typically comprise (a) contacting DNA with a fusion protein of the invention (e.g., a fusion protein comprising a nuclease-inactivated Cas9 domain and a FokI DNA cleavage domain), wherein the inactive Cas9 domain binds a gRNA that hybridizes to a region of the DNA; (b) contacting the DNA with a second fusion protein (e.g., a fusion protein comprising a nuclease-inactivated Cas9 and FokI DNA cleavage domain), wherein the inactive Cas9 domain of the second fusion protein binds a second gRNA that hybridizes to a second region of DNA; wherein the binding of the fusion proteins in steps (a) and (b) results in the dimerization of the nuclease domains of the fusion proteins, such that the DNA is cleaved in a region between the bound fusion proteins. In some embodiments, the gRNAs of steps (a) and (b) hybridize to the same strand of the DNA, or the gRNAs of steps (a) and (b) hybridize to opposite strands of the DNA. In some embodiments, the gRNAs of steps (a) and (b) hybridize to regions of the DNA that are no more than 10, no more than 15, no more than 20, no more than 25, no more than 30, no more than 40, no more than 50, no more than 60, no more than 70, no more than 80, no more than 90, or no more than 100 base pairs apart. In some embodiments, the DNA is in a cell, for example, a eukaryotic cell or a prokaryotic cell, which may be in an individual, such as a human. In some embodiments, the DNA comprises a EMX gene. In some embodiments, the DNA comprises a HBB gene. In some embodiments, the DNA comprises a VEGF gene. In some embodiments, the DNA comprises a CLTA gene. In some embodiments, the DNA comprises a CCR5 gene.

According to another embodiments, a complex comprising a dimer of fusion proteins of the invention (e.g., a dimer of a fusion protein comprising a nuclease-inactivated Cas9 and a FokI DNA cleavage domain) are provided. In some embodiments, the nuclease-inactivated Cas9 domain of each fusion protein of the dimer binds a single extended gRNA, such that one fusion protein of the dimer binds a portion of the gRNA, and the other fusion protein of the dimer binds another portion of the gRNA. See e.g., FIG. 1B. In some embodiments, the gRNA is at least 50, at least 75, at least 100, at least 150, at least 200, at least 250, or at least 300 nucleotides in length. In some embodiments, the regions of the extended gRNA that hybridize to a target nucleic acid comprise 15-25, 19-21, or 20 nucleotides.

In another embodiment, methods for site-specific DNA cleavage are provided comprising contacting a DNA with a complex of two inventive fusion proteins bound to a single extended gRNA. In some embodiments, the gRNA contains two portions that hybridize to two separate regions of the DNA to be cleaved; the complex binds the DNA as a result of the portions of the gRNA hybridizing to the two regions; and binding of the complex results in dimerization of the nuclease domains of the fusion proteins, such that the domains cleave the DNA in a region between the bound fusion proteins. In some embodiments, the two portions of the gRNA hybridize to the same strand of the DNA. In other embodiments, the two portions of the gRNA hybridize to opposing strands of the DNA. In some embodiments, the two portions of the gRNA hybridize to regions of the DNA that are no more 10, no more than 15, no more than 20, no more than 25, no more than 30, no more than 40, no more than 50, no more than 60, no more than 70, no more than 80, no more than 90, or no more than 100 base pairs apart. In some embodiments, the DNA is in a cell, for example, a eukaryotic cell or a prokaryotic cell, which may be in an individual, such as a human.

According to another embodiment of the invention, split Cas9 proteins (including fusion proteins comprising a split Cas9 protein) comprising fragments of a Cas9 protein are provided. In some embodiments, a protein is provided that includes a gRNA binding domain of Cas9 but does not include a DNA cleavage domain. In other embodiments, proteins comprising a DNA cleavage domain of Cas9, but not a gRNA binding domain, are provided. In some embodiments, a fusion protein comprising two domains: (i) a nuclease-inactivated Cas9 domain, and (ii) a gRNA binding domain of Cas9 are provided, for example, wherein domain (ii) does not include a DNA cleavage domain. See e.g., FIG. 2B. In some embodiments, fusion proteins comprising two domains: (i) a nuclease-inactivated Cas9 domain, and (ii) a DNA cleavage domain are provided, for example, wherein domain (ii) does not include a gRNA binding domain. See e.g., FIG. 2C (fusion protein on right side, comprising a "B" domain). In some embodiments, protein dimers of any of the proteins described herein are provided. For example, in some embodiments, a dimer comprises two halves of a split Cas9 protein, for example, (i) a protein comprising a gRNA binding domain of Cas9, but not a DNA cleavage domain, and (ii) a protein comprising a DNA cleavage domain of Cas9, but not a gRNA binding domain. See e.g., FIG. 2A. In some embodiments, a dimer comprises one half of a split Cas9 protein, and a fusion protein comprising the other half of the split Cas9 protein. See e.g., FIG. 2B. For example, in certain embodiments such a dimer comprises (i) a protein comprising a gRNA binding domain of Cas9, but not a DNA cleavage domain, and (ii) a fusion protein comprising a nuclease-inactivated Cas9 and a DNA cleavage domain. In other embodiments, the dimer comprises (i) a protein comprising a DNA cleavage domain of Cas9, but not a gRNA binding domain, and (ii) a fusion protein comprising a nuclease-inactivated Cas9 and a gRNA binding domain of Cas9. In some embodiments, a dimer is provided that comprises two fusion proteins, each fusion protein comprising a nuclease-inactivated Cas9 and one half of a split Cas9. See e.g., FIG. 2C. For example, in certain embodiments, such a dimer comprises: (i) a fusion protein comprising a nuclease-inactivated Cas9 and a gRNA binding domain of Cas9, and (ii) a fusion protein comprising a nuclease-inactivated Cas9 and a DNA cleavage domain. In some embodiments, any of the provided protein dimers is associated with one or more gRNA(s).

In some embodiments, methods for site-specific DNA cleavage utilizing the inventive protein dimers are provided. For example, in some embodiments, such a method comprises contacting DNA with a protein dimer that comprises (i) a protein comprising a gRNA binding domain of Cas9, but not a DNA cleavage domain, and (ii) a protein comprising a DNA cleavage domain of Cas9, but not a gRNA binding domain, wherein the dimer binds a gRNA that hybridizes to a region of the DNA, and cleavage of the DNA occurs. See e.g., FIG. 2A. In some embodiments, the protein dimer used for site-specific DNA cleavage comprises (i) a protein comprising a gRNA binding domain of Cas9, but not a DNA cleavage domain, and (ii) a fusion protein comprising a nuclease-inactivated Cas9 and a DNA cleavage. See e.g., FIG. 2B. In some embodiments, the dimer used for site-specific DNA cleavage comprises (i) a protein comprising a DNA cleavage domain of Cas9, but not a gRNA binding domain, and (ii) a fusion protein comprising a nuclease-inactivated Cas9 and a gRNA binding domain of Cas9. In some embodiments, the protein dimer binds two gRNAs that hybridize to two regions of the DNA, and cleavage of the DNA occurs. See e.g., FIG. 2B. In some embodiments, the two gRNAs hybridize to regions of the DNA that are no more than 10, no more than 15, no more than 20, no more than 25, no more than 30, no more than 40, no more than 50, no more than 60, no more than 70, no more than 80, no more than 90, or no more than 100 base pairs apart. In some embodiments, the dimer used for site-specific DNA cleavage comprises two fusion proteins: (i) a fusion protein comprising a nuclease-inactivated Cas9 and a gRNA binding domain of Cas9, and (ii) a fusion protein comprising a nuclease-inactivated Cas9 and a DNA cleavage domain. In some embodiments, the protein dimer binds three gRNAs that hybridize to three regions of the DNA, and cleavage of the DNA occurs. Having such an arrangement, e.g., targeting more than one region of a target nucleic acid, for example using dimers associated with more than one gRNA (or a gRNA comprising more than one region that hybridizes to the target) increases the specificity of cleavage as compared to a nuclease binding a single region of a target nucleic acid. In some embodiments, the three gRNAs hybridize to regions of the DNA that are no more than 10, no more than 15, no more than 20, no more than 25, no more than 30, no more than 40, no more than 50, no more than 60, no more than 70, no more than 80, no more than 90, or no more than 100 base pairs apart between the first and second, and the second and third regions. In some embodiments, the DNA is in a cell, for example, a eukaryotic cell or a prokaryotic cell, which may be in an individual, such as a human.

According to another embodiment, minimal Cas9 proteins are provided, for example, wherein the protein comprises N- and/or C-terminal truncations and retains RNA binding and DNA cleavage activity. In some embodiments, the N-terminal truncation removes at least 5, at least 10, at least 15, at least 20, at least 25, at least 40, at least 40, at least 50, at least 75, at least 100, or at least 150 amino acids. In some embodiments, the C-terminal truncation removes at least 5, at least 10, at least 15, at least 20, at least 25, at least 40, at least 40, at least 50, at least 75, at least 100, or at least 150 amino acids. In some embodiments, the minimized Cas9 protein further comprises a bound gRNA.

In some embodiments, methods for site-specific DNA cleavage are provided comprising contacting a DNA with minimized Cas9 protein:gRNA complex.

According to another embodiment, dimers of Cas9 (or fragments thereof) wherein the dimer is coordinated through a single gRNA are provided. In some embodiments, the single gRNA comprises at least two portions that (i) are each able to bind a Cas9 protein and (ii) each hybridize to a target nucleic acid sequence (e.g., DNA sequence). In some embodiments, the portions of the gRNA that hybridize to the target nucleic acid each comprise no more than 5, no more than 10, or no more than 15 nucleotides complementary to the target nucleic acid sequence. In some embodiments, the portions of the gRNA that hybridize to the target nucleic acid are separated by a linker sequence. In some embodiments, the linker sequence hybridizes to the target nucleic acid. See e.g., FIG. 4. In some embodiments, methods for site-specific DNA cleavage are provided comprising contacting DNA with a dimer of Cas9 proteins coordinated through a single gRNA.

According to another embodiment, the disclosure provides fusion proteins and dimers and tetramers thereof, for example, fusion proteins comprising two domains: (i) a nuclease-inactivated Cas9 domain; and (ii) a recombinase catalytic domain. See, e.g., FIG. 5. The recombinase catalytic domain, in some embodiments, is derived from the recombinase catalytic domain of Hin recombinase, Gin recombinase, or Tn3 resolvase. The nuclease-inactivated Cas9 domain is capable of binding a gRNA, e.g., to target the fusion protein to a target nucleic acid sequence. The fusion proteins may further comprise a nuclear localization signal (NLS) domain, which signals for the fusion proteins to be transported into the nucleus of a cell. In some embodiments, one or more domains of the fusion proteins are separated by a linker. In certain embodiments, the linker is a non-peptidic linker. In certain embodiments, the linker is a peptide linker. In the case of peptide linkers, the peptide linker may comprise an XTEN linker, an amino acid sequence comprising one or more repeats of the tri-peptide GGS, or any sequence as provided in FIG. 12A.

In another embodiment, methods for site-specific recombination are provided, which utilize the inventive RNA-guided recombinase fusion proteins described herein. In some embodiments, the method is useful for recombining two separate DNA molecules, and comprises (a) contacting a first DNA with a first RNA-guided recombinase fusion protein, wherein the nuclease-inactivated Cas9 domain of the first fusion protein binds a first gRNA that hybridizes to a region of the first DNA; (b) contacting the first DNA with a second RNA-guided recombinase fusion protein, wherein the nuclease-inactivated Cas9 domain of the second fusion protein binds a second gRNA that hybridizes to a second region of the first DNA; (c) contacting a second DNA with a third RNA-guided recombinase fusion protein, wherein the nuclease-inactivated Cas9 domain of the third fusion protein binds a third gRNA that hybridizes to a region of the second DNA; and (d) contacting the second DNA with a fourth RNA-guided recombinase fusion protein, wherein the nuclease-inactivated Cas9 domain of the fourth fusion protein binds a fourth gRNA that hybridizes to a second region of the second DNA, wherein the binding of the fusion proteins in steps (a)-(d) results in the tetramerization of the recombinase catalytic domains of the fusion proteins, under conditions such that the DNAs are recombined. In some embodiments, methods for site-specific recombination between two regions of a single DNA molecule are provided. In some embodiments, the method comprises (a) contacting a DNA with a first RNA-guided recombinase fusion protein, wherein the nuclease-inactivated Cas9 domain binds a first gRNA that hybridizes to a region of the DNA; (b) contacting the DNA with a second RNA-guided recombinase fusion protein, wherein the nuclease-inactivated Cas9 domain of the second fusion protein binds a second gRNA that hybridizes to a second region of the DNA; (c) contacting the DNA with a third RNA-guided recombinase fusion protein, wherein the nuclease-inactivated Cas9 domain of the third fusion protein binds a third gRNA that hybridizes to a third region of the DNA; (d) contacting the DNA with a fourth RNA-guided recombinase fusion protein, wherein the nuclease-inactivated Cas9 domain of the fourth fusion protein binds a fourth gRNA that hybridizes to a fourth region of the DNA; wherein the binding of the fusion proteins in steps (a)-(d) results in the tetramerization of the recombinase catalytic domains of the fusion proteins, under conditions such that the DNA is recombined. In some embodiments involving methods for site-specific recombination, gRNAs hybridizing to the same DNA molecule hybridize to opposing strands of the DNA molecule. In some embodiments, e.g., involving site-specific recombination of a single DNA molecule, two gRNAs hybridize to one strand of the DNA, and the other two gRNAs hybridize to the opposing strand. In some embodiments, the gRNAs hybridize to regions of their respective DNAs (e.g., on the same strand) that are no more than 10, no more than 15, no more than 20, no more than 25, no more than 30, no more than 40, no more than 50, no more than 60, no more than 70, no more than 80, no more than 90, or no more than 100 base pairs apart. In some embodiments, the DNA is in a cell, for example, a eukaryotic cell or a prokaryotic cell, which may be in or obtained from an individual, such as a human.

According to another embodiment, polynucleotides are provided, for example, that encode any of the Cas9 proteins described herein (e.g., Cas9 variants, Cas9 dimers, Cas9 fusion proteins, Cas9 fragments, minimized Cas9 proteins, Cas9 variants without a cleavage domain, Cas9 variants without a gRNA domain, Cas9-recombinase fusions, etc.). In some embodiments, polynucleotides encoding any of the gRNAs described herein are provided. In some embodiments, polynucleotides encoding any inventive Cas9 protein described herein and any combination of gRNA(s) as described herein are provided. In some embodiments, vectors that comprise a polynucleotide described herein are provided.

In some embodiments, vectors for recombinant protein expression comprising a polynucleotide encoding any of the Cas9 proteins and/or gRNAs described herein are provided. In some embodiments, cells comprising genetic constructs for expressing any of the Cas9 proteins and/or gRNAs described herein are provided.

In some embodiments, kits are provided. For example, kits comprising any of the Cas9 proteins and/or gRNAs described herein are provided. In some embodiments, kits comprising any of the polynucleotides described herein, e.g., those encoding a Cas9 protein and/or gRNA, are provided. In some embodiments, kits comprising a vector for recombinant protein expression, wherein the vectors comprise a polynucleotide encoding any of the Cas9 proteins and/or gRNAs described herein, are provided. In some embodiments, kits comprising a cell comprising genetic constructs for expressing any of the Cas9 proteins and/or gRNAs described herein are provided.

Other advantages, features, and uses of the invention will be apparent from the Detailed Description of Certain Non-Limiting Embodiments of the Invention; the Drawings, which are schematic and not intended to be drawn to scale; and the Claims.

BRIEF DESCRIPTION OF THE DRAWINGS

FIG. 1 is a schematic detailing certain embodiments of the invention. (A) In this embodiment, nuclease-inactivated Cas9 protein is fused to a monomer of the FokI nuclease domain. Double-strand DNA-cleavage is achieved through dimerization of FokI monomers at the target site and is dependent on the simultaneous binding of two distinct Cas9:gRNA complexes. (B) In this embodiment, an alternate configuration is provided, wherein two Cas9-FokI fusions are coordinated through the action of a single extended gRNA containing two distinct gRNA motifs. The gRNA motifs comprise regions that hybridize the target in distinct regions, as well as regions that bind each fusion protein. The extended gRNA may enhance cooperative binding and alter the specificity profile of the fusions.

FIG. 15 shows graphs depicting the efficiency of genomic DNA modification by fCas9, Cas9 nickase, and wild-type Cas9 with varying amounts of Cas9 and gRNA expression plasmids. Indel modification efficiency from a Surveyor assay of renatured target-site DNA amplified from a population of cells treated with fCas9, Cas9 nickase, or wild-type Cas9 and two target site gRNAs. Either 700 ng of Cas9 expression plasmid with 250 ng of gRNA expression plasmid (950 ng total), 350 ng of Cas9 expression plasmid with 125 ng of gRNA expression plasmid (475 ng in total), 175 ng of Cas9 expression plasmid with 62.5 ng of gRNA expression plasmid (238 ng in total) or 88 ng of Cas9 expression plasmid with 31 ng of gRNA expression plasmid (119 ng in total) were transfected with an appropriate amount of inert, carrier plasmid to ensure uniform transfection of 950 ng of plasmid across all treatments. Indel modification efficiency for (A) gRNAs spaced 19-bp apart targeting the CLTA site, (B) gRNAs spaced 23 bp apart targeting the EMX site, and (C) gRNAs spaced 14 bp apart targeting the VEGF site. Error bars represent the standard error of the mean from three biological replicates performed on separate days.

FIG. 16 shows the ability of fCas9, Cas9 nickase, and wild-type Cas9 to modify genomic DNA in the presence of a single gRNA. (A) shows images of gels depicting Surveyor assay of a genomic GFP target from DNA of cells treated with the indicated combination of Cas9 protein and gRNA(s). Single gRNAs do not induce genome modification at a detectable level (<2% modification) for both fCas9 and Cas9 nickase. Wild-type Cas9 effectively modifies the GFP target for all tested single and paired gRNAs. For both fCas9 and Cas9 nickase, appropriately paired gRNAs induce genome modification at levels comparable to those of wild-type Cas9. (B) shows a graph depicting the results from sequencing GFP on-target sites amplified from 150 ng genomic DNA isolated from human cells treated with a plasmid expressing either wild-type Cas9, Cas9 nickase, or fCas9 and either a single plasmid expressing a single gRNAs (G1, G3, G5 or G7), or two plasmids each expressing a different gRNA (G1+G5, or G3+G7). As a negative control, transfection and sequencing were performed in triplicate as above without any gRNA expression plasmids. Error bars represent s.d. Sequences with more than one insertion or deletion at the GFP target site (the start of the G1 binding site to the end of the G7 binding site) were considered indels. Indel percentages were calculated by dividing the number of indels by total number of sequences. While wild-type Cas9 produced indels across all gRNA treatments, fCas9 and Cas9 nickase produced indels efficiently (>1%) only when paired gRNAs were present. Indels induced by fCas9 and single gRNAs were not detected above the no-gRNA control, while Cas9 nickase and single gRNAs modified the target GFP sequence at an average rate of 0.12%.

FIG. 19 shows the target DNA sequences in a genomic CCR5 gene. (A) Eight gRNA target sites were identified for testing Cas9 variant (e.g., FokI-dCas9) activity in an orientation in which the PAM is adjacent to the cleaved spacer sequence (orientation A). (B) Six gRNA target sites were identified for testing Cas9 variant (e.g., FokI-dCas9) activity in an orientation in which the PAM is adjacent to the cleaved spacer sequence (orientation B). Together, these fourteen gRNAs enable testing of Cas9 fusion variants across spacer lengths ranging from 0 to 74 bp. The sequences shown in (A) are identified as follows: "CRA" corresponds to SEQ ID NO:302; "CRA-1" corresponds to SEQ ID NO:303; "CRA-2" corresponds to SEQ ID NO:304; "CRA-3" corresponds to SEQ ID NO:305; "CRA-4" corresponds to SEQ ID NO:306; "CRA-5" corresponds to SEQ ID NO:307; "CRA-6" corresponds to SEQ ID NO:308; "CRA-7" corresponds to SEQ ID NO:309; and "CRA-8" corresponds to SEQ ID NO:310. The sequences shown in (B) are identified as follows: "CRB" corresponds to SEQ ID NO:311; "CB-1" corresponds to SEQ ID NO:312; "CB-2" corresponds to SEQ ID NO:313; "CB-3" corresponds to SEQ ID NO:314; "CB-4" corresponds to SEQ ID NO:315; "CB-5" corresponds to SEQ ID NO:316; and "CB-6" corresponds to SEQ ID NO:317.

DEFINITIONS

Figure 2A:
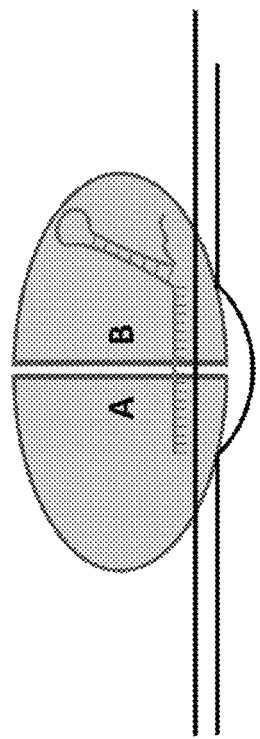
FIG. 2 is a schematic detailing certain embodiments of the invention. (A) In this embodiment, dimeric split Cas9 separates A) gRNA-binding ability from B) dsDNA cleavage. DNA cleavage occurs when both halves of the protein are co-localized to associate and refold into a nuclease-active state. (B) In this embodiment, nuclease-inactivated Cas9 mutant is fused to the A-half (or in some embodiments, the B-half) of the split Cas9 nuclease. Upon binding of both the Cas9-A-half (or Cas9-B-half) fusion and the inactive gRNA-binding Cas9 B-half (or A-half, respectively) at the target site, dsDNA is enabled following split protein reassembly. This split Cas9-pairing can use two distinct gRNA-binding Cas9 proteins to ensure the split nuclease-active Cas9 reassembles only on the correct target sequence. (C) In this embodiment, nuclease-inactivated Cas9 mutant is fused to the A-half of the split Cas9 nuclease. A separate nuclease-inactivated Cas9 mutant is fused to the B-half of the split Cas9 nuclease. Upon binding of one nuclease-inactivated Cas9 mutant to a gRNA target site and binding of the other nuclease-inactivated Cas9 mutant to a second gRNA target site, the split Cas9 halves can dimerize and bind a third gRNA target to become a fully active Cas9 nuclease that can cleave dsDNA. This split Cas9-pairing uses three distinct gRNA-binding Cas9 proteins to ensure the split nuclease-active Cas9 reassembles only on the correct target sequence. Any other DNA-binding domain in place of the inactive Cas9 (zinc fingers, TALE proteins, etc.) can be used to complete the reassembly of the split Cas9 nuclease.

As used herein and in the claims, the singular forms "a," "an," and "the" include the singular and the plural reference unless the context clearly indicates otherwise. Thus, for example, a reference to "an agent" includes a single agent and a plurality of such agents.

The term "Cas9" or "Cas9 nuclease" refers to an RNA-guided nuclease comprising a Cas9 protein, or a fragment thereof (e.g., a protein comprising an active or inactive DNA cleavage domain of Cas9, and/or the gRNA binding domain of Cas9). A Cas9 nuclease is also referred to sometimes as a casn1 nuclease or a CRISPR (clustered regularly interspaced short palindromic repeat)-associated nuclease. CRISPR is an adaptive immune system that provides protection against mobile genetic elements (viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (rnc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNA. However, single guide RNAs ("sgRNA", or simply "gNRA") can be engineered so as to incorporate aspects of both the crRNA and tracrRNA into a single RNA species. See e.g., Jinek M., Chylinski K., Fonfara I., Hauer M., Doudna J. A., Charpentier E. Science 337:816-821(2012), the entire contents of which is hereby incorporated by reference. Cas9 recognizes a short motif in the CRISPR repeat sequences (the PAM or protospacer adjacent motif) to help distinguish self versus non-self. Cas9 nuclease sequences and structures are well known to those of skill in the art (see, e.g., "Complete genome sequence of an M1 strain of Streptococcus pyogenes." Ferretti et al., J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. Science 337:816-821 (2012), the entire contents of each of which are incorporated herein by reference). Cas9 orthologs have been described in various species, including, but not limited to, S. pyogenes and S. thermophilus. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) RNA Biology 10:5, 726-737; the entire contents of which are incorporated herein by reference. In some embodiments, a Cas9 nuclease has an inactive (e.g., an inactivated) DNA cleavage domain. A nuclease-inactivated Cas9 protein may interchangeably be referred to as a "dCas9" protein (for nuclease "dead" Cas9). In some embodiments, dCas9 corresponds to, or comprises in part or in whole, the amino acid set forth as SEQ ID NO:5, below. In some embodiments, variants of dCas9 (e.g., variants of SEQ ID NO:5) are provided. For example, in some embodiments, variants having mutations other than D10A and H840A are provided, which e.g., result in nuclease inactivated Cas9 (dCas9). Such mutations, by way of example, include other amino acid substitutions at D10 and H840, or other substitutions within the nuclease domains of Cas9 (e.g., substitutions in the HNH nuclease subdomain and/or the RuvC1 subdomain). In some embodiments, variants or homologues of dCas9 (e.g., variants of SEQ ID NO:5) are provided which are at least about 70% identical, at least about 80% identical, at least about 90% identical, at least about 95% identical, at least about 98% identical, at least about 99% identical, at least about 99.5% identical, or at least about 99.9% to SEQ ID NO:5. In some embodiments, variants of dCas9 (e.g., variants of SEQ ID NO:5) are provided having amino acid sequences which are shorter, or longer than SEQ ID NO:5, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids or more.

dCas9 (D10A and H840A):

```
                                          (SEQ ID NO: 5)
MDKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP
```

-continued

```
INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDAIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD
```

Methods for generating a Cas9 protein (or a fragment thereof) having an inactive DNA cleavage domain are known (See, e.g., the Examples; and Jinek et al., *Science*. 337:816-821(2012); Qi et al., "Repurposing CRISPR as an RNA-Guided Platform for Sequence-Specific Control of Gene Expression" (2013) *Cell*. 28; 152(5):1173-83, the entire contents of each of which are incorporated herein by reference). For example, the DNA cleavage domain of Cas9 is known to include two subdomains, the HNH nuclease subdomain and the RuvC1 subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A and H840A completely inactivate the nuclease activity of *S. pyogenes* Cas9 (See e.g., the Examples; and Jinek et al., *Science*. 337:816-821(2012); Qi et al., *Cell*. 28; 152(5):1173-83 (2013)). In some embodiments, proteins comprising fragments of Cas9 are provided. For example, in some embodiments, a protein comprises one of two Cas9 domains: (1) the gRNA binding domain of Cas9; or (2) the DNA cleavage domain of Cas9. In some embodiments, proteins comprising Cas9 or fragments thereof are referred to as "Cas9 variants." A Cas9 variant shares homology to Cas9, or a fragment thereof. For example a Cas9 variant is at least about 70% identical, at least about 80% identical, at least about 90% identical, at least about 95% identical, at least about 98% identical, at least about 99% identical, at least about 99.5% identical, or at least about 99.9% to wild type Cas9. In some embodiments, the Cas9 variant comprises a fragment of Cas9 (e.g., a gRNA binding domain or a DNA-cleavage domain), such that the fragment is at least about 70% identical, at least about 80% identical, at least about 90% identical, at least about 95% identical, at least about 98% identical, at least about 99% identical, at least about 99.5% identical, or at least about 99.9% to the corresponding fragment of wild type Cas9. In some embodiments, wild type Cas9 corresponds to Cas9 from *Streptococcus pyogenes* (NCBI Reference Sequence: NC_017053.1, SEQ ID NO:1 (nucleotide); SEQ ID NO:2 (amino acid)).

```
                                            (SEQ ID NO: 1)
ATGGATAAGAAATACTCAATAGGCTTAGATATCGGCACAAATAGCGTCGG
ATGGGCGGTGATCACTGATGATTATAAGGTTCCGTCTAAAAAGTTCAAGG
TTCTGGGAAATACAGACCGCCACAGTATCAAAAAAAATCTTATAGGGGCT
CTTTTATTTGGCAGTGGAGAGACAGCGGAAGCGACTCGTCTCAAACGGAC
AGCTCGTAGAAGGTATACACGTCGGAAGAATCGTATTTGTTATCTACAGG
AGATTTTTTCAAATGAGATGGCGAAAGTAGATGATAGTTTCTTTCATCGA
CTTGAAGAGTCTTTTTTGGTGGAAGAAGACAAGAAGCATGAACGTCATCC
TATTTTTGGAAATATAGTAGATGAAGTTGCTTATCATGAGAAATATCCAA
CTATCTATCATCTGCGAAAAAATTGGCAGATTCTACTGATAAAGCGGAT
TTGCGCTTAATCTATTTGGCCTTAGCGCATATGATTAAGTTTCGTGGTCA
TTTTTTGATTGAGGGAGATTTAAATCCTGATAATAGTGATGTGGACAAAC
TATTTATCCAGTTGGTACAAATCTACAATCAATTATTTGAAGAAAACCCT
ATTAACGCAAGTAGAGTAGATGCTAAAGCGATTCTTTCTGCACGATTGAG
TAAATCAAGACGATTAGAAATCTCATTGCTCAGCTCCCCGGTGAGAAGA
GAAATGGCTTGTTTGGGAATCTCATTGCTTTGTCATTGGGATTGACCCCT
AATTTTAAATCAAATTTTGATTTGGCAGAAGATGCTAAATTACAGCTTTC
AAAAGATACTTACGATGATGATTTAGATAATTTATTGGCGCAAATTGGAG
ATCAATATGCTGATTTGTTTTTGGCAGCTAAGAATTTATCAGATGCTATT
TTACTTTCAGATATCCTAAGAGTAAATAGTGAAATAACTAAGGCTCCCCT
ATCAGCTTCAATGATTAAGCGCTACGATGAACATCATCAAGACTTGACTC
TTTTAAAAGCTTTAGTTCGACAACAACTTCCAGAAAAGTATAAAGAAATC
TTTTTTTGATCAATCAAAAAACGGATATGCAGGTTATATTGATGGGGGAGC
TAGCCAAGAAGAATTTTATAAATTTATCAAACCAATTTTAGAAAAAATGG
ATGGTACTGAGGAATTATTGGTGAAACTAAATCGTGAAGATTTGCTGCGC
AAGCAACGGACCTTTGACAACGGCTCTATTCCCCATCAAATTCACTTGGG
TGAGCTGCATGCTATTTTGAGAAGACAAGAAGACTTTTATCCATTTTTAA
AAGACAATCGTGAGAAGATTGAAAAAATCTTGACTTTTCGAATTCCTTAT
TATGTTGGTCCATTGGCGCGTGGCAATAGTCGTTTTGCATGGATGACTCG
GAAGTCTGAAGAAACAATTACCCCATGGAATTTTGAAGAAGTTGTCGATA
AAGGTGCTTCAGCTCAATCATTTATTGAACGCATGACAAACTTTGATAAA
AATCTTCCAAATGAAAAAGTACTACCAAAACATAGTTTGCTTTATGAGTA
TTTTACGGTTTATAACGAATTGACAAAGGTCAAATATGTTACTGAGGGAA
TGCGAAAACCAGCATTTCTTTCAGGTGAACAGAAGAAAGCCATTGTTGAT
TTACTCTTCAAAACAAATCGAAAAGTAACCGTTAAGCAATTAAAAGAAGA
TTATTTCAAAAAAATAGAATGTTTTGATAGTGTTGAAATTTCAGGAGTTG
AAGATAGATTTAATGCTTCATTAGGCGCCTACCATGATTTGCTAAAAATT
ATTAAAGATAAAGATTTTTTGGATAATGAAGAAAATGAAGATACTTAGA
GGATATTGTTTTAACATTGACCTTATTTGAAGATAGGGGGATGATTGAGG
AAAGACTTAAAACATATGCTCACCTCTTTGATGATAAGGTGATGAAACAG
CTTAAACGTCGCCGTTATACTGGTTGGGGACGTTTGTCTCGAAAATTGAT
TAATGGTATTAGGGATAAGCAATCTGGCAAAACAATATTAGATTTTTTGA
AATCAGATGGTTTTGCCAATCGCAATTTTATGCAGCTGATCCATGATGAT
AGTTTGACATTTAAAGAAGATATTCAAAAAGCACAGGTGTCTGGACAAGG
CCATAGTTTACATGAACAGATTGCTAACTTAGCTGGCAGTCCTGCTATTA
AAAAAGGTATTTTACAGACTGTAAAAATTGTTGATGAACTGGTCAAAGTA
ATGGGGCATAAGCCAGAAAATATCGTTATTGAAATGGCACGTGAAAATCA
GACAACTCAAAAGGGCCAGAAAAATTCGCGAGAGCGTATGAAACGAATCG
AAGAAGGTATCAAAGAATTAGGAAGTCAGATTCTTAAAGAGCATCCTGTT
GAAAATACTCAATTGCAAAATGAAAAGCTCTATCTCTATTATCTACAAAA
TGGAAGAGACATGTATGTGGACCAAGAATTAGATATTAATCGTTTAAGTG
ATTATGATGTCGATCACATTGTTCCACAAAGTTTCATTAAAGACGATTCA
ATAGACAATAAGGTACTAACGCGTTCTGATAAAAATCGTGGTAAATCGGA
TAACGTTCCAAGTGAAGAAGTAGTCAAAAAGATGAAAAACTATTGGAGAC
AACTTCTAAACGCCAAGTTAATCACTCAACGTAAGTTTGATAATTTAACG
AAAGCTGAACGTGGAGGTTTGAGTGAACTTGATAAAGCTGGTTTTATCAA
ACGCCAATTGGTTGAAACTCGCCAAATCACTAAGCATGTGGCACAAATTT
TGGATAGTCGCATGAATACTAAATACGATGAAAATGATAAACTTATTCGA
GAGGTTAAAGTGATTACCTTAAAATCTAAATTAGTTTCTGACTTCCGAAA
AGATTTCCAATTCTATAAAGTACGTGAGATTAACAATTACCATCATGCCC
ATGATGCGTATCTAAATGCCGTCGTTGGAACTGCTTTGATTAAGAAATAT
CCAAAACTTGAATCGGAGTTTGTCTATGGTGATTATAAAGTTTATGATGT
TCGTAAAATGATTGCTAAGTCTGAGCAAGAAATAGGCAAAGCAACCGCAA
```

-continued

```
AATATTTCTTTTACTCTAATATCATGAACTTCTTCAAAACAGAAATTACA
CTTGCAAATGGAGAGATTCGCAAACGCCCTCTAATCGAAACTAATGGGGA
AACTGGAGAAATTGTCTGGGATAAAGGGCGAGATTTTGCCACAGTGCGCA
AAGTATTGTCCATGCCCCAAGTCAATATTGTCAAGAAAACAGAAGTACAG
ACAGGCGGATTCTCCAAGGAGTCAATTTTACCAAAAAGAAATTCGGACAA
GCTTATTGCTCGTAAAAAAGACTGGGATCCAAAAAAATATGGTGGTTTTG
ATAGTCCAACGGTAGCTTATTCAGTCCTAGTGGTTGCTAAGGTGGAAAAA
GGGAAATCGAAGAAGTTAAAATCCGTTAAAGAGTTACTAGGGATCACAAT
TATGGAAAGAAGTTCCTTTGAAAAAAATCCGATTGACTTTTTAGAAGCTA
AAGGATATAAGGAAGTTAAAAAAGACTTAATCATTAAACTACCTAAATAT
AGTCTTTTTGAGTTAGAAAACGGTCGTAAACGGATGCTGGCTAGTGCCGG
AGAATTACAAAAGGAAATGAGCTGGCTCTGCCAAGCAAATATGTGAATT
TTTTATATTTAGCTAGTCATTATGAAAAGTTGAAGGGTAGTCCAGAAGAT
AACGAACAAAAACAATTGTTTGTGGAGCAGCATAAGCATTATTTAGATGA
GATTATTGAGCAAATCAGTGAATTTTCTAAGCGTGTTATTTAGCAGATG
CCAATTTAGATAAAGTTCTTAGTGCATATAACAAACATAGAGACAAACCA
ATACGTGAACAAGCAGAAAATATTATTCATTTATTTACGTTGACGAATCT
TGGAGCTCCCGCTGCTTTTTAAATATTTTGATACAACAATTGATCGTAAC
GATATACGTCTACAAAAGAAGTTTTAGATGCCACTCTTATCCATCAATCC
ATCACTGGTCTTTATGAAACACGCATTGATTTGAGTCAGCTAGGAGGTGA
CTGA
```

(SEQ ID NO: 2)
MDKKYSIGLDIGTNSVGWAVITDDYKVPSKKFKVLGNTDRHSIKKNLIGA
LLFGSGETAEATRLKRTARRRYTRRKNRICYLQEIFSNEMAKVDDSFFHR
LEESFLVEEDKKHERHPIFGNIVDEVAYHEKYPTIYHLRKKLADSTDKAD
LRLIYLALAHMIKFRGHFLIEGDLNPDNSDVDKLFIQLVQIYNQLFEENP
INASRVDAKAILSARLSKSRRLENLIAQLPGEKRNGLFGNLIALSLGLTP
NFKSNFDLAEDAKLQLSKDTYDDDLDNLLAQIGDQYADLFLAAKNLSDAI
LLSDILRVNSEITKAPLSASMIKRYDEHHQDLTLLKALVRQQLPEKYKEI
FFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVD
LLFKTNRKVTVKQLKEDYFKKIECFDSVEISGVEDRFNASLGAYHDLLKI
IKDKDFLDNEENEDILEDIVLTLTLFEDRGMIEERLKTYAHLFDDKVMKQ
LKRRRYTGWGRLSRKLINGIRDKQSGKTILDFLKSDGFANRNFMQLIHDD
SLTFKEDIQKAQVSGQHSLHEQIANLAGSPAIKKGILQTVKIVDELVKV
MGHKPENIVIEMARENQTTQKGQKNSRERMKRIEEGIKELGSQILKEHPV
ENTQLQNEKLYYLQNGRDMYVDQELDINRLSDYDVDHIVPQSFIKDDS
IDNKVLTRSDKNRGKSDNVPSEEVVKKMKNYWRQLLNAKLITQRKFDNLT
KAERGGLSELDKAGFIKRQLVETRQITKHVAQILDSRMNTKYDENDKLIR
EVKVITLKSKLVSDFRKDFQFYKVREINNYHHAHDAYLNAVVGTALIKKY
PKLESEFVYGDYKVYDVRKMIAKSEQEIGKATAKYFFYSNIMNFFKTEIT
LANGEIRKRPLIETNGETGEIVWDKGRDFATVRKVLSMPQVNIVKKTEVQ
TGGFSKESILPKRNSDKLIARKKDWDPKKYGGFDSPTVAYSVLVVAKVEK
GKSKKLKSVKELLGITIMERSSFEKNPIDFLEAKGYKEVKKDLIIKLPKY
SLFELENGRKRMLASAGELQKGNELALPSKYVNFLYLASHYEKLKGSPED
NEQKQLFVEQHKHYLDEIIEQISEFSKRVILADANLDKVLSAYNKHRDKP
IREQAENIIHLFTLTNLGAPAAFKYFDTTIDRKRYTSTKEVLDATLIHQS
ITGLYETRIDLSQLGGD

In some embodiments, wild type Cas9 corresponds to, or comprises, SEQ ID NO:3 (nucleotide) and/or SEQ ID NO:4 (amino acid).

(SEQ ID NO: 3)
```
ATGGATAAAAAGTATTCTATTGGTTTAGACATCGGCACTAATTCCGTTGG
ATGGGCTGTCATAACCGATGAATACAAAGTACCTTCAAAGAAATTTAAGG
TGTTGGGGAACACAGACCGTCATTCGATTAAAAAGAATCTTATCGGTGCC
CTCCTATTCGATAGTGGCGAAACGGCAGAGGCGACTCGCCTGAAACGAAC
CGCTCGGAGAAGGTATACACGTCGCAAGAACCGAATATGTTACTTACAAG
AAATTTTTAGCAATGAGATGGCCAAAGTTGACGATTCTTTCTTTCACCGT
TTGGAAGAGTCCTTCCTTGTCGAAGAGGACAAGAAACATGAACGGCACCC
CATCTTTGGAAACATAGTAGATGAGGTGGCATATCATGAAAAGTACCCAA
CGATTTATCACCTCAGAAAAAAGCTAGTTGACTGAACTGATAAAGCGAC
CTGAGGTTAATCTACTTGGCTCTTGCCCATATGATAAAGTTCCGTGGCA
CTTTCTCATTGAGGGTGATCTAAATCCGGACAACTCGGATGTCGACAAAC
TGTTCATCCAGTTAGTACAAACCTATAATCAGTTGTTTGAAGAGAACCCT
ATAAATGCAAGTGGCGTGGATGCGAAGGCTATTCTTAGCGCCCGCCTCTC
TAAATCCCGACGGCTAGAAAACTCGATCGCACAATTACCCGGAGAGAAGA
AAAATGGGTTGTTCGGTAACCTTATAGCGCTCTCACTAGGCGTGACACCA
ATTTTTAAGTCGAACTTCGACTTAGCTGAAGATGCCAAATTGCAGCTTAG
TAAGGACACGTACGATGACGATCTCGACAATCTACTGGCACAAATTGGAG
ATCAGTATGCGGACTTATTTTTGGCTGCCAAAAACCTTAGCGATGCAATC
CTCCTATCTGACATACTGAGAGTTAATACTGAGATTACCAAGCGCCGTT
ATCCGCTTCAATGATCAAAAGGTACGATGAACATCACCAAGACTTGACAC
TTCTCAAGGCCCTAGTCCGTCAGCAACTGCCTGAGAAATATAAGGAAATA
TTCTTTGATCAGTCGAAAAACGGGTACGCAGGTTATATTGACGGCGGAGC
```

(SEQ ID NO: 3) -continued
```
GAGTCAAGAGGAATTCTACAAGTTTATCAAACCCATATTAGAGAAGATGG
ATGGGACGGAAGAGTTGCTTGTAAAACTCAATCGCGAAGATCTACTGCGA
AAGCAGCGGACTTTCGACAACGGTAGCATTCCACATCAAATCCACTTAGG
CGAATTGCATGCTATACTTAGAAGGCAGGAGGATTTTTATCCGTTCCTCA
AAGACAATCGTGAAAAGATTGAGAAAATCCTAACCTTTCGCATACCTTAC
TATGTGGGACCCCTGGCCCGAGGGAACTCTCGGTTCGCATGGATGACAAG
AAAGTCCGAAGAAACGATTACTCCATGGAATTTTGAGGAAGTTGTCGATA
AAGGTGCGTCAGCTCAATCGTTCATCGAGAGGATGACCAACTTTGACAAG
AATTTACCGAACGAAAAAGTATTGCCTAAGCACAGTTTACTTTACGAGTA
TTTCACAGTGTACAATGAACTCACGAAAGTTAAGTATGTCACTGAGGGCA
TGCCTAAACCCGCCTTTCTAAGCGGAGAACAGAAGAAAGCAATAGTAGAT
CTGTTATTCAAGACCAACCGCAAAGTGACAGTTAAGCAATTGAAAGAGGA
CTACTTTAAGAAAATTGAATGCTTCGATTCTGTCGAGATCTCCGGGGTAG
AAGATCGATTTAATGCGTCACTTGGTACGTATCATGACCTCCTAAAGATA
ATTAAAGATAAGGACTTCCTGGATAACGAAGAGAATGAAGATATCTTAGA
AGATATAGTGTTGACTCTTACCCTCTTTGAAGATCGGGAAATGATTGAGG
AAAGACTAAAAACATACGCTCACCTGTTCGACGATAAGGTTATGAAACAG
TTAAAGAGGCGTCGCTATACGGGCTGGGGACGATTGTCGCGGAAACTTAT
CAACGGGATAAGACAAGCAAAGTGGTAAAACTATTCTCGATTTTCTAA
AGAGCGACGGCTTCGCCAATAGGAACTTTATGCAGCTGATCCATGATGAC
TCTTTAACCTTCAAAGAGGATATACAAAAGGCACAGGTTTCCGGACAAGG
GGACTCATTGCACGAACATATTGCGAATCTTGCTGGTTCGCCAGCCATCA
AAAAGGGCATACTCCAGACAGTCAAAGTAGTGGATGAGCTAGTTAAGGTC
ATGGGACGTCACAAACCGGAAAACATTGTAATCGAGATGGCACGCGAAAA
TCAAACGACTCAGAAGGGGCAAAAAAACAGTCGAGAGCGGATGAAGAGAA
TAGAGAGGGTATTAAAGAACTGGGCAGCCAGATCTTAAAGGAGCATCCT
GTGGAAAATACCCAATTGCAGAACGAGAAACTTTACCTCTATTACCTACA
AAATGAAGGGACATGTATGTTGATCAGGAACTGGACATAAACCGTTTAT
CTGATTACGACGTCGATCACATTGTACCCCAATCCTTTTTGAAGGACGAT
TCAATCGACAATAAAGTGCTTACACGCTCGGATAAGAACCGAGGGAAAA
TGACAATGTTCCAAGCGAGGAAGTCGTAAAGAAAATGAAGAACTATTGGC
GGCAGCTCCTAAATGCGAAACTGATAACGCAAAGAAGTTCGATAACTTA
ACTAAAGCTGAGAGGGGTGGCTTGTCTGAACTTGACAAGGCCGGATTTAT
TAAACGTCAGCTCGTGGAAACCCGCCAAATCACAAAGCATGTTGCACAGA
TACTAGATTCCCGAATGAATACGAAATACGACAAGAACGATAAGCTGATT
CGGGAAGTCAAAGTAATCACTTTAAAGTCAAAATTGGTGTCGGACTTCAG
AAAGGATTTTCAATTCTATAAAGTTAGGGAGATAAATAACTACCACCATG
CGCACGACGCTTATCTTAATGCCGTCGTAGGGACCGCACTCATTAAGAAA
TACCCGAAGCTAGAAAGTGAGTTTGTGATGGTGATTACAAAGTTATGA
CGTCCGTAAGATGATCGCGAAAAGCGAACAGGAGATAGGCAAGGCTACAG
CCAAATACTTCTTTTATTCTAACATTATGAATTTCTTTAAGACGGAAATC
ACTCTGGCAAACGGAGAGATACGCAAACGACCTTTAATTGAAACCAATGG
GGAGACAGGTGAAATCGTATGGGATAAGGGCCGGGACTTTGCCACGGTGA
GAAAAGTTTTGTCCATGCCCCAAGTCAACATAGTAAAGAAAACTGAGGTG
CAGACCGGAGGGTTTTCAAAGGAATCGATTCTTCCAAAAAGGAATAGTGA
TAAGCTCATCGCTCGTAAAAAGGACTGGGACCCGAAAAAGTACGGTGGCT
TCGATAGCCCTACAGTTGCCTATTCTGTCCTAGTAGTGGCAAAAGTTGAG
AAGGGAAAATCCAAGAAACTGAAGTCAGTCAAAGAATTATTGGGGATAAC
GATTATGGAGCGCTCGTCTTTTGAAAAGAACCCCATCGACTTCCTTGAGG
CGAAAGGTTACAAGGAAGTAAAAAAGGATCTCATAATTAAACTACCAAAG
TATAGTCTGTTTGAGTTAGAAAATGGCCGAAAACGGATGTTGGCTAGCGC
CGGAGAGCTTCAAAAGGGGAACGAACTCGCACTACCGTCTAAATACGTGA
ATTTCCTGTATTTAGCGTCCCATTACGAGAAGTTGAAAGGTTCACCTGAA
GATAACGAACAGAAGCAACTTTTTGTTGAGCAGCACAAACATTATCTCGA
CGAAATCATAGAGCAAATTTCGGAATTCAGTAAGAGAGTCATCCTAGCTG
ATGCCAATCTGGACAAAGTATTAAGCGCATACAACAAGCACAGGGATAAA
CCCATACGTGAGCAGGCGGAAAATATTATCCATTTGTTTACTCTTACCAA
CCTCGGCGCTCCAGCCGCATTCAAGTATTTTGACACAACGATAGATCGCA
AACGATACACTTCTACCAAGGAGGTGCTAGACGCGACACTGATTCACCAA
TCCATCACGGGATTATATGAAACTCGGATAGATTTGTCACAGCTTGGGGG
TGACGGGATCCCCCAAGAAGAAGAGGAAAGTCTCGAGCGACTACAAAGACC
ATGACGGTGATTATAAAGATCATGACATCGATTACAAGGATGACGATGAC
AAGGCTGCAGGA
```

(SEQ ID NO: 4)
MDKKYSIGLAIGTNSVGWAVITDEYKVPSKKFKVLGNTDRHSIKKNLIGA
LLFDSGETAEATRLKRTARRRYTRRKNRICYLQEIFSNEMAKVDDSFFHR
LEESFLVEEDKKHERHPIFGNIVDEVAYHEKYPTIYHLRKKLVDSTDKAD
LRLIYLALAHMIKFRGHFLIEGDLNPDNSDVDKLFIQLVQTYNQLFEENP
INASGVDAKAILSARLSKSRRLENLIAQLPGEKKNGLFGNLIALSLGLTP
NFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEI
FFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVD
LLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQ
LKRRRYTGWGRLSRKLINGIRDKQSGKTILDFLKSDGFANRNFMQLIHDD
SLTFKEDIQKAQVSGQGDSLHEHIANLAGSPAIKKGILQTVKVVDELVKV
MGRHKPENIVIEMARENQTTQKGQKNSRERMKRIEEGIKELGSQILKEHP

-continued

```
VENTQLQNEKLYLYYLQNGRDMYVDQELDINRLSDYDVDHIVPQSFLKDD
SIDNKVLTRSDKNRGKSDNVPSEEVVKKMKNYWRQLLNAKLITQRKFDNL
TKAERGGLSELDKAGFIKRQLVETRQITKHVAQILDSRMNTKYDENDKLI
REVKVITLKSKLVSDFRKDFQFYKVREINNYHHAHDAYLNAVVGTALIKK
YPKLESEFVYGDYKVYDVRKMIAKSEQEIGKATAKYFFYSNIMNFPKTEI
TLANGEIRKRPLIETNGETGEIVWDKGRDFATVRKVLSMPQVNIVKKTEV
QTGGFSKESILPKRNSDKLIARKKDWDPKKYGGFDSPTVAYSVLVVAKVE
KGKSKKLKSVKELLGITIMERSSFEKNPIDFLEAKGYKEVKKDLIIKLPK
YSLFELENGRKRMLASAGELQKGNELALPSKYVNFLYLASHYEKLKGSPE
DNEQKQLFVEQHKHYLDEIIEQISEFSKRVILADANLDKVLSAYNKHRDK
PIREQAENIIHLFTLTNLGAPAAFKYFDTTIDRKRYTSTKEVLDATLIHQ
SITGLYETRIDLSQLGGD
```

In some embodiments, Cas9 refers to Cas9 from: *Corynebacterium ulcerans* (NCBI Refs: NC_015683.1, NC_017317.1); *Corynebacterium diphtheria* (NCBI Refs: NC_016782.1, NC_016786.1); *Spiroplasma syrphidicola* (NCBI Ref: NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref: NC_018010.1); *Psychroflexus torquisI* (NCBI Ref: NC_018721.1); *Streptococcus thermophilus* (NCBI Ref: YP_820832.1), *Listeria innocua* (NCBI Ref: NP_472073.1), *Campylobacter jejuni* (NCBI Ref: YP_002344900.1) or *Neisseria. meningitidis* (NCBI Ref: YP_002342100.1).

The terms "conjugating," "conjugated," and "conjugation" refer to an association of two entities, for example, of two molecules such as two proteins, two domains (e.g., a binding domain and a cleavage domain), or a protein and an agent, e.g., a protein binding domain and a small molecule. In some aspects, the association is between a protein (e.g., RNA-programmable nuclease) and a nucleic acid (e.g., a guide RNA). The association can be, for example, via a direct or indirect (e.g., via a linker) covalent linkage. In some embodiments, the association is covalent. In some embodiments, two molecules are conjugated via a linker connecting both molecules. For example, in some embodiments where two proteins are conjugated to each other, e.g., a binding domain and a cleavage domain of an engineered nuclease, to form a protein fusion, the two proteins may be conjugated via a polypeptide linker, e.g., an amino acid sequence connecting the C-terminus of one protein to the N-terminus of the other protein.

The term "consensus sequence," as used herein in the context of nucleic acid sequences, refers to a calculated sequence representing the most frequent nucleotide residues found at each position in a plurality of similar sequences. Typically, a consensus sequence is determined by sequence alignment in which similar sequences are compared to each other and similar sequence motifs are calculated. In the context of nuclease target site sequences, a consensus sequence of a nuclease target site may, in some embodiments, be the sequence most frequently bound, or bound with the highest affinity, by a given nuclease. In the context of recombinase target site sequences, a consensus sequence of a recombinase target site may, in some embodiments, be the sequence most frequently bound, or bound with the highest affinity, by a given recombinase.

The term "engineered," as used herein refers to a protein molecule, a nucleic acid, complex, substance, or entity that has been designed, produced, prepared, synthesized, and/or manufactured by a human. Accordingly, an engineered product is a product that does not occur in nature.

The term "effective amount," as used herein, refers to an amount of a biologically active agent that is sufficient to elicit a desired biological response. For example, in some embodiments, an effective amount of a nuclease may refer to the amount of the nuclease that is sufficient to induce cleavage of a target site specifically bound and cleaved by the nuclease. In some embodiments, an effective amount of a recombinase may refer to the amount of the recombinase that is sufficient to induce recombination at a target site specifically bound and recombined by the recombinase. As will be appreciated by the skilled artisan, the effective amount of an agent, e.g., a nuclease, a recombinase, a hybrid protein, a fusion protein, a protein dimer, a complex of a protein (or protein dimer) and a polynucleotide, or a polynucleotide, may vary depending on various factors as, for example, on the desired biological response, the specific allele, genome, target site, cell, or tissue being targeted, and the agent being used.

The term "homologous," as used herein is an art-understood term that refers to nucleic acids or polypeptides that are highly related at the level of nucleotide and/or amino acid sequence. Nucleic acids or polypeptides that are homologous to each other are termed "homologues." Homology between two sequences can be determined by sequence alignment methods known to those of skill in the art. In accordance with the invention, two sequences are considered to be homologous if they are at least about 50-60% identical, e.g., share identical residues (e.g., amino acid residues) in at least about 50-60% of all residues comprised in one or the other sequence, at least about 70% identical, at least about 80% identical, at least about 90% identical, at least about 95% identical, at least about 98% identical, at least about 99% identical, at least about 99.5% identical, or at least about 99.9% identical, for at least one stretch of at least 20, at least 30, at least 40, at least 50, at least 60, at least 70, at least 80, at least 90, at least 100, at least 120, at least 150, or at least 200 amino acids.

The term "linker," as used herein, refers to a chemical group or a molecule linking two adjacent molecules or moieties, e.g., a binding domain (e.g., dCas9) and a cleavage domain of a nuclease (e.g., FokI). In some embodiments, a linker joins a nuclear localization signal (NLS) domain to another protein (e.g., a Cas9 protein or a nuclease or recombinase or a fusion thereof). In some embodiments, a linker joins a gRNA binding domain of an RNA-programmable nuclease and the catalytic domain of a recombinase. In some embodiments, a linker joins a dCas9 and a recombinase. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is a peptide linker. In some embodiments, the peptide linker is any stretch of amino acids having at least 1, at least 2, at least 3, at least 4, at least 5, at least 6, at least 7, at least 8, at least 9, at least 10, at least 15, at least 20, at least 25, at least 30, at least 40, at least 50, or more amino acids. In some embodiments, the peptide linker comprises repeats of the tri-peptide Gly-Gly-Ser, e.g., comprising the sequence $(GGS)_n$, wherein n represents at least 1, 2, 3, 4, 5, 6, 7, 8, 9, 10, or more repeats. In some embodiments, the linker comprises the sequence $(GGS)_6$ (SEQ ID NO:15). In some embodiments, the peptide linker is the 16 residue "XTEN" linker, or a variant thereof (See, e.g., the Examples; and Schellenberger et al. A recombinant polypeptide extends the in vivo half-life of peptides and proteins in a tunable manner. *Nat. Biotechnol.* 27, 1186-1190 (2009)). In some embodiments, the XTEN linker comprises the sequence SGSETPGTSESATPES (SEQ ID NO:16), SGSETPGTSESA (SEQ ID NO:17), or SGSETPGTSESATPEGGSGGS (SEQ ID NO:18). In some embodiments, the peptide linker is any linker as provided in FIG.

12A, for example, one or more selected from VPFLLEPDN-INGKTC (SEQ ID NO:19), GSAGSAAGSGEF (SEQ ID NO:20), SIVAQLSRPDPA (SEQ ID NO:21), MKIIEQLPSA (SEQ ID NO:22), VRHKLKRVGS (SEQ ID NO:23), GHGTGSTGSGSS (SEQ ID NO:24), MSRPDPA (SEQ ID NO:25); or GGSM (SEQ ID NO:301).

The term "mutation," as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. Various methods for making the amino acid substitutions (mutations) provided herein are well known in the art, and are provided by, for example, Green and Sambrook, *Molecular Cloning: A Laboratory Manual* (4$^{th}$ ed., Cold Spring Harbor Laboratory Press, Cold Spring Harbor, N.Y. (2012)).

The term "nuclease," as used herein, refers to an agent, for example, a protein, capable of cleaving a phosphodiester bond connecting two nucleotide residues in a nucleic acid molecule. In some embodiments, "nuclease" refers to a protein having an inactive DNA cleavage domain, such that the nuclease is incapable of cleaving a phosphodiester bond. In some embodiments, a nuclease is a protein, e.g., an enzyme that can bind a nucleic acid molecule and cleave a phosphodiester bond connecting nucleotide residues within the nucleic acid molecule. A nuclease may be an endonuclease, cleaving a phosphodiester bonds within a polynucleotide chain, or an exonuclease, cleaving a phosphodiester bond at the end of the polynucleotide chain. In some embodiments, a nuclease is a site-specific nuclease, binding and/or cleaving a specific phosphodiester bond within a specific nucleotide sequence, which is also referred to herein as the "recognition sequence," the "nuclease target site," or the "target site." In some embodiments, a nuclease is a RNA-guided (i.e., RNA-programmable) nuclease, which is associated with (e.g., binds to) an RNA (e.g., a guide RNA, "gRNA") having a sequence that complements a target site, thereby providing the sequence specificity of the nuclease. In some embodiments, a nuclease recognizes a single stranded target site, while in other embodiments, a nuclease recognizes a double-stranded target site, for example, a double-stranded DNA target site. The target sites of many naturally occurring nucleases, for example, many naturally occurring DNA restriction nucleases, are well known to those of skill in the art. In many cases, a DNA nuclease, such as EcoRI, HindIII, or BamHI, recognize a palindromic, double-stranded DNA target site of 4 to 10 base pairs in length, and cut each of the two DNA strands at a specific position within the target site. Some endonucleases cut a double-stranded nucleic acid target site symmetrically, i.e., cutting both strands at the same position so that the ends comprise base-paired nucleotides, also referred to herein as blunt ends. Other endonucleases cut a double-stranded nucleic acid target sites asymmetrically, i.e., cutting each strand at a different position so that the ends comprise unpaired nucleotides. Unpaired nucleotides at the end of a double-stranded DNA molecule are also referred to as "overhangs," e.g., as "5'-overhang" or as "3'-overhang," depending on whether the unpaired nucleotide(s) form(s) the 5' or the 5' end of the respective DNA strand. Double-stranded DNA molecule ends ending with unpaired nucleotide(s) are also referred to as sticky ends, as they can "stick to" other double-stranded DNA molecule ends comprising complementary unpaired nucleotide(s). A nuclease protein typically comprises a "binding domain" that mediates the interaction of the protein with the nucleic acid substrate, and also, in some cases, specifically binds to a target site, and a "cleavage domain" that catalyzes the cleavage of the phosphodiester bond within the nucleic acid backbone. In some embodiments a nuclease protein can bind and cleave a nucleic acid molecule in a monomeric form, while, in other embodiments, a nuclease protein has to dimerize or multimerize in order to cleave a target nucleic acid molecule. Binding domains and cleavage domains of naturally occurring nucleases, as well as modular binding domains and cleavage domains that can be fused to create nucleases binding specific target sites, are well known to those of skill in the art. For example, the binding domain of RNA-programmable nucleases (e.g., Cas9), or a Cas9 protein having an inactive DNA cleavage domain, can be used as a binding domain (e.g., that binds a gRNA to direct binding to a target site) to specifically bind a desired target site, and fused or conjugated to a cleavage domain, for example, the cleavage domain of FokI, to create an engineered nuclease cleaving the target site. In some embodiments, Cas9 fusion proteins provided herein comprise the cleavage domain of FokI, and are therefore referred to as "fCas9" proteins. In some embodiments, the cleavage domain of FokI, e.g., in a fCas9 protein corresponds to, or comprises in part or whole, the amino acid sequence (or variants thereof) set forth as SEQ ID NO:6, below. In some embodiments, variants or homologues of the FokI cleavage domain include any variant or homologue capable of dimerizing (e.g., as part of fCas9 fusion protein) with another FokI cleavage domain at a target site in a target nucleic acid, thereby resulting in cleavage of the target nucleic acid. In some embodiments, variants of the FokI cleavage domain (e.g., variants of SEQ ID NO:6) are provided which are at least about 70% identical, at least about 80% identical, at least about 90% identical, at least about 95% identical, at least about 98% identical, at least about 99% identical, at least about 99.5% identical, or at least about 99.9% to SEQ ID NO:6. In some embodiments, variants of the FokI cleavage domain (e.g., variants of SEQ ID NO:6) are provided having an amino acid sequence which is shorter, or longer than SEQ ID NO:6, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids or more.

Cleavage Domain of FokI:

```
                                            (SEQ ID NO: 6)
GSQLVKSELEEKKSELRHKLKYVPHEYIELIEIARNSTQDRILEMKVMEF

FMKVYGYRGKHLGGSRKPDGAIYTVGSPIDYGVIVDTKAYSGGYNLPIGQ

ADEMQRYVEENQTRNKHINPNEWWKVYPSSVTEFKFLFVSGHFKGNYKAQ

LTRLNHITNCNGAVLSVEELLIGGEMIKAGTLTLEEVRRKFNNGEINF
```

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, gRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadeno sine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term "pharmaceutical composition," as used herein, refers to a composition that can be administrated to a subject in the context of treatment and/or prevention of a disease or disorder. In some embodiments, a pharmaceutical composition comprises an active ingredient, e.g., a nuclease or recombinase fused to a Cas9 protein, or fragment thereof (or a nucleic acid encoding a such a fusion), and optionally a pharmaceutically acceptable excipient. In some embodiments, a pharmaceutical composition comprises inventive Cas9 variant/fusion (e.g., fCas9) protein(s) and gRNA(s) suitable for targeting the Cas9 variant/fusion protein(s) to a target nucleic acid. In some embodiments, the target nucleic acid is a gene. In some embodiments, the target nucleic acid is an allele associated with a disease, whereby the allele is cleaved by the action of the Cas9 variant/fusion protein(s). In some embodiments, the allele is an allele of the CLTA gene, the EMX gene, the HBB gene, the VEGF gene, or the CCR5 gene. See e.g., the Examples; FIGS. 7, 8, 13, 14, 15, 17 and 19.

The term "proliferative disease," as used herein, refers to any disease in which cell or tissue homeostasis is disturbed in that a cell or cell population exhibits an abnormally elevated proliferation rate. Proliferative diseases include hyperproliferative diseases, such as pre-neoplastic hyperplastic conditions and neoplastic diseases. Neoplastic diseases are characterized by an abnormal proliferation of cells and include both benign and malignant neoplasias. Malignant neoplasia is also referred to as cancer. In some embodiments, the compositions and methods provided herein are useful for treating a proliferative disease. For example, in some embodiments, pharmaceutical compositions comprising Cas9 (e.g., fCas9) protein(s) and gRNA(s) suitable for targeting the Cas9 protein(s) to an VEGF allele, whereby the allele is inactivated by the action of the Cas9 protein(s). See, e.g., the Examples.

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. The term "fusion protein" as used herein refers to a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, *Molecular Cloning: A Laboratory Manual* ($4^{th}$ ed., Cold Spring Harbor Laboratory Press, Cold Spring Harbor, N.Y. (2012)), the entire contents of which are incorporated herein by reference.

The term "RNA-programmable nuclease," and "RNA-guided nuclease" are used interchangeably herein and refer to a nuclease that forms a complex with (e.g., binds or associates with) one or more RNA that is not a target for cleavage. In some embodiments, an RNA-programmable nuclease, when in a complex with an RNA, may be referred to as a nuclease: RNA complex. Typically, the bound RNA(s) is referred to as a guide RNA (gRNA). gRNAs can exist as a complex of two or more RNAs, or as a single RNA molecule. gRNAs that exist as a single RNA molecule may be referred to as single-guide RNAs (sgRNAs), though "gRNA" is used interchangeabley to refer to guide RNAs that exist as either single molecules or as a complex of two or more molecules. Typically, gRNAs that exist as single RNA species comprise two domains: (1) a domain that shares homology to a target nucleic acid (e.g., and directs binding of a Cas9 complex to the target); and (2) a domain that binds a Cas9 protein. In some embodiments, domain (2) corresponds to a sequence known as a tracrRNA, and comprises a stem-loop structure. For example, in some embodiments, domain (2) is homologous to a tracrRNA as depicted in FIG. 1E of Jinek et al., *Science* 337:816-821(2012), the entire contents of which is incorporated herein by reference. Other examples of gRNAs (e.g., those including domain 2) can be found in U.S. Provisional Patent Application, U.S. Ser. No. 61/874,682, filed Sep. 6, 2013, entitled "Switchable Cas9 Nucleases And Uses Thereof;" U.S. Provisional Patent Application, U.S. Ser. No. 61/874,746, filed Sep. 6, 2013, entitled "Delivery System For Functional Nucleases;" PCT Application WO 2013/176722, filed Mar. 15, 2013, entitled "Methods and Compositions for RNA-Directed Target DNA Modification and for RNA-Directed Modulation of Transcription;" and PCT Application WO 2013/142578, filed Mar. 20, 2013, entitled "RNA-Directed DNA Cleavage by the Cas9-crRNA Complex;" the entire contents of each are hereby incorporated by reference in their entirety. Still other examples of gRNAs and gRNA structure are provided herein. See e.g., the Examples. In some embodiments, a gRNA comprises two or more of domains (1) and (2), and may be referred to as an "extended gRNA." For example, an extended gRNA will e.g., bind two or more Cas9 proteins and bind a target nucleic acid at two or more distinct regions, as described herein. The gRNA comprises a nucleotide sequence that complements a target site, which mediates binding of the nuclease/RNA complex to said target site, providing the sequence specificity of the nuclease:RNA complex. In some embodiments, the RNA-programmable nuclease is the (CRISPR-associated system) Cas9 endonuclease, for example Cas9 (Csn1) from *Streptococcus pyogenes* (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. Science 337:816-821 (2012), the entire contents of each of which are incorporated herein by reference.

Because RNA-programmable nucleases (e.g., Cas9) use RNA:DNA hybridization to determine target DNA cleavage sites, these proteins are able to cleave, in principle, any sequence specified by the guide RNA. Methods of using RNA-programmable nucleases, such as Cas9, for site-specific cleavage (e.g., to modify a genome) are known in the art (see e.g., Cong, L. et al. Multiplex genome engineering using CRISPR/Cas systems. *Science* 339, 819-823 (2013); Mali, P. et al. RNA-guided human genome engineering via Cas9. *Science* 339, 823-826 (2013); Hwang, W. Y. et al. Efficient genome editing in zebrafish using a CRISPR-Cas system. *Nature biotechnology* 31, 227-229 (2013); Jinek, M. et al. RNA-programmed genome editing in human cells. *eLife* 2, e00471 (2013); Dicarlo, J. E. et al. Genome engineering in *Saccharomyces cerevisiae* using CRISPR-Cas systems. *Nucleic acids research* (2013); Jiang, W. et al. RNA-guided editing of bacterial genomes using CRISPR-Cas systems. *Nature biotechnology* 31, 233-239 (2013); the entire contents of each of which are incorporated herein by reference).

The term "recombinase," as used herein, refers to a site-specific enzyme that mediates the recombination of DNA between recombinase recognition sequences, which results in the excision, integration, inversion, or exchange (e.g., translocation) of DNA fragments between the recombinase recognition sequences. Recombinases can be classified into two distinct families: serine recombinases (e.g., resolvases and invertases) and tyrosine recombinases (e.g., integrases). Examples of serine recombinases include, without limitation, Hin, Gin, Tn3, β-six, CinH, ParA, γδ, Bxb1, φC31, TP901, TG1, φBT1, R4, φRV1, φFC1, MR11, A118, U153, and gp29. Examples of tyrosine recombinases include, without limitation, Cre, FLP, R, Lambda, HK101, HK022, and pSAM2. The serine and tyrosine recombinase names stem from the conserved nucleophilic amino acid residue that the recombinase uses to attack the DNA and which becomes covalently linked to the DNA during strand exchange. Recombinases have numerous applications, including the creation of gene knockouts/knock-ins and gene therapy applications. See, e.g., Brown et al., "Serine recombinases as tools for genome engineering." *Methods.* 2011; 53(4):372-9; Hirano et al., "Site-specific recombinases as tools for heterologous gene integration." *Appl. Microbiol. Biotechnol.* 2011; 92(2):227-39; Chavez and Calos, "Therapeutic applications of the ΦC31 integrase system." *Curr. Gene Ther.* 2011; 11(5):375-81; Turan and Bode, "Site-specific recombinases: from tag-and-target- to tag-and-exchange-based genomic modifications." *FASEB J.* 2011; 25(12):4088-107; Venken and Bellen, "Genome-wide manipulations of *Drosophila melanogaster* with transposons, Flp recombinase, and ΦC31 integrase." *Methods Mol. Biol.* 2012; 859:203-28; Murphy, "Phage recombinases and their applications." *Adv. Virus Res.* 2012; 83:367-414; Zhang et al., "Conditional gene manipulation: Cre-ating a new biological era." *J. Zhejiang Univ. Sci. B.* 2012; 13(7):511-24; Karpenshif and Bernstein, "From yeast to mammals: recent advances in genetic control of homologous recombination." *DNA Repair (Amst).* 2012; 1; 11(10): 781-8; the entire contents of each are hereby incorporated by reference in their entirety. The recombinases provided herein are not meant to be exclusive examples of recombinases that can be used in embodiments of the invention. The methods and compositions of the invention can be expanded by mining databases for new orthogonal recombinases or designing synthetic recombinases with defined DNA specificities (See, e.g., Groth et al., "Phage integrases: biology and applications." *J. Mol. Biol.* 2004; 335, 667-678; Gordley et al., "Synthesis of programmable integrases." *Proc. Natl. Acad. Sci. USA.* 2009; 106, 5053-5058; the entire contents of each are hereby incorporated by reference in their entirety). Other examples of recombinases that are useful in the methods and compositions described herein are known to those of skill in the art, and any new recombinase that is discovered or generated is expected to be able to be used in the different embodiments of the invention. In some embodiments, the catalytic domains of a recombinase are fused to a nuclease-inactivated RNA-programmable nuclease (e.g., dCas9, or a fragment thereof), such that the recombinase domain does not comprise a nucleic acid binding domain or is unable to bind to a target nucleic acid (e.g., the recombinase domain is engineered such that it does not have specific DNA binding activity). Recombinases lacking DNA binding activity and methods for engineering such are known, and include those described by Klippel et al., "Isolation and characterisation of unusual gin mutants." *EMBO J.* 1988; 7: 3983-3989: Burke et al., "Activating mutations of Tn3 resolvase marking interfaces important in recombination catalysis and its regulation. *Mol Microbiol.* 2004; 51: 937-948; Olorunniji et al., "Synapsis and catalysis by activated Tn3 resolvase mutants." *Nucleic Acids Res.* 2008; 36: 7181-7191; Rowland et al., "Regulatory mutations in Sin recombinase support a structure-based model of the synaptosome." *Mol Microbiol.* 2009; 74: 282-298; Akopian et al., "Chimeric recombinases with designed DNA sequence recognition." *Proc Natl Acad Sci USA.* 2003; 100: 8688-8691; Gordley et al., "Evolution of programmable zinc finger-recombinases with activity in human cells. *J Mol Biol.* 2007; 367: 802-813; Gordley et al., "Synthesis of programmable integrases." *Proc Natl Acad Sci USA.* 2009; 106: 5053-5058; Arnold et al., "Mutants of Tn3 resolvase which do not require accessory binding sites for recombination activity." *EMBO J.* 1999; 18: 1407-1414; Gaj et al., "Structure-guided reprogramming of serine recombinase DNA sequence specificity." *Proc Natl Acad Sci USA*. 2011; 108(2):498-503; and Proudfoot et al., "Zinc finger recombinases with adaptable DNA sequence specificity." *PLoS One*. 2011; 6(4): e19537; the entire contents of each are hereby incorporated by reference. For example, serine recombinases of the resolvase-invertase group, e.g., Tn3 and γδ resolvases and the Hin and Gin invertases, have modular structures with autonomous catalytic and DNA-binding domains (See, e.g., Grindley et al., "Mechanism of site-specific recombination." *Ann Rev Biochem*. 2006; 75: 567-605, the entire contents of which are incorporated by reference). The catalytic domains of these recombinases are thus amenable to being recombined with nuclease-inactivated RNA-programmable nucleases (e.g., dCas9, or a fragment thereof) as described herein, e.g., following the isolation of 'activated' recombinase mutants which do not require any accessory factors (e.g., DNA binding activities) (See, e.g., Klippel et al., "Isolation and characterisation of unusual gin mutants." *EMBO J*. 1988; 7: 3983-3989: Burke et al., "Activating mutations of Tn3 resolvase marking interfaces important in recombination catalysis and its regulation. *Mol Microbiol*. 2004; 51: 937-948; Olorunniji et al., "Synapsis and catalysis by activated Tn3 resolvase mutants." *Nucleic Acids Res*. 2008; 36: 7181-7191; Rowland et al., "Regulatory mutations in Sin recombinase support a structure-based model of the synaptosome." *Mol Microbiol*. 2009; 74: 282-298; Akopian et al., "Chimeric recombinases with designed DNA sequence recognition." *Proc Natl Acad Sci USA*. 2003; 100: 8688-8691). Additionally, many other natural serine recombinases having an N-terminal catalytic domain and a C-terminal DNA binding domain are known (e.g., phiC31 integrase, TnpX transposase, IS607 transposase), and their catalytic domains can be co-opted to engineer programmable site-specific recombinases as described herein (See, e.g., Smith et al., "Diversity in the serine recombinases." *Mol Microbiol*. 2002; 44: 299-307, the entire contents of which are incorporated by reference). Similarly, the core catalytic domains of tyrosine recombinases (e.g., Cre, λ integrase) are known, and can be similarly co-opted to engineer programmable site-specific recombinases as described herein (See, e.g., Guo et al., "Structure of Cre recombinase complexed with DNA in a site-specific recombination synapse." *Nature*. 1997; 389:40-46; Hartung et al., "Cre mutants with altered DNA binding properties." *J Biol Chem* 1998; 273:22884-22891; Shaikh et al., "Chimeras of the Flp and Cre recombinases: Tests of the mode of cleavage by Flp and Cre. *J Mol Biol*. 2000; 302:27-48; Rongrong et al., "Effect of deletion mutation on the recombination activity of Cre recombinase." *Acta Biochim Pol*. 2005; 52:541-544; Kilbride et al., "Determinants of product topology in a hybrid Cre-Tn3 resolvase site-specific recombination system." *J Mol Biol*. 2006; 355:185-195; Warren et al., "A chimeric cre recombinase with regulated directionality." *Proc Natl Acad Sci USA*. 2008 105:18278-18283; Van Duyne, "Teaching Cre to follow directions." *Proc Natl Acad Sci USA*. 2009 Jan. 6; 106(1):4-5; Numrych et al., "A comparison of the effects of single-base and triple-base changes in the integrase arm-type binding sites on the site-specific recombination of bacteriophage λ." *Nucleic Acids Res*. 1990; 18:3953-3959; Tirumalai et al., "The recognition of core-type DNA sites by λ integrase." *J Mol Biol*. 1998; 279:513-527; Aihara et al., "A conformational switch controls the DNA cleavage activity of λ integrase." *Mol Cell*. 2003; 12:187-198; Biswas et al., "A structural basis for allosteric control of DNA recombination by λ integrase." *Nature*. 2005; 435:1059-1066; and Warren et al., "Mutations in the amino-terminal domain of λ-integrase have differential effects on integrative and excisive recombination." *Mol Microbiol*. 2005; 55:1104-1112; the entire contents of each are incorporated by reference).

The term "recombine," or "recombination," in the context of a nucleic acid modification (e.g., a genomic modification), is used to refer to the process by which two or more nucleic acid molecules, or two or more regions of a single nucleic acid molecule, are modified by the action of a recombinase protein (e.g., an inventive recombinase fusion protein provided herein). Recombination can result in, inter alia, the insertion, inversion, excision or translocation of nucleic acids, e.g., in or between one or more nucleic acid molecules.

The term "subject," as used herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development.

The terms "target nucleic acid," and "target genome," as used herein in the context of nucleases, refer to a nucleic acid molecule or a genome, respectively, that comprises at least one target site of a given nuclease. In the context of fusions comprising a (nuclease-inactivated) RNA-programmable nuclease and a recombinase domain, a "target nucleic acid" and a "target genome" refers to one or more nucleic acid molecule(s), or a genome, respectively, that comprises at least one target site. In some embodiments, the target nucleic acid(s) comprises at least two, at least three, or at least four target sites. In some embodiments, the target nucleic acid(s) comprise four target sites.

The term "target site" refers to a sequence within a nucleic acid molecule that is either (1) bound and cleaved by a nuclease (e.g., Cas9 fusion proteins provided herein), or (2) bound and recombined (e.g., at or nearby the target site) by a recombinase (e.g., a dCas9-recombinase fusion protein provided herein). A target site may be single-stranded or double-stranded. In the context of RNA-guided (e.g., RNA-programmable) nucleases (e.g., a protein dimer comprising a Cas9 gRNA binding domain and an active Cas9 DNA cleavage domain or other nuclease domain such as FokI), a target site typically comprises a nucleotide sequence that is complementary to the gRNA(s) of the RNA-programmable nuclease, and a protospacer adjacent motif (PAM) at the 3' end adjacent to the gRNA-complementary sequence(s). In some embodiments, such as those involving fCas9, a target site can encompass the particular sequences to which fCas9 monomers bind, and/or the intervening sequence between the bound monomers that are cleaved by the dimerized FokI domains (See e.g., the Examples; and FIGS. 1A, 6D). In the context of fusions between RNA-guided (e.g., RNA-programmable, nuclease-inactivated) nucleases and a recombinase (e.g., a catalytic domain of a recombinase), a target site typically comprises a nucleotide sequence that is complementary to the gRNA of the RNA-programmable nuclease domain, and a protospacer adjacent motif (PAM) at the 3' end adjacent to the gRNA-complementary sequence. For example, in some embodiments, four recombinase monomers are coordinated to recombine a target nucleic acid(s), each monomer being fused to a (nuclease-inactivated) Cas9 protein guided by a gRNA. In such an example, each Cas9 domain is guided by a distinct gRNA to bind a target nucleic acid(s), thus the target nucleic acid comprises four target sites, each site targeted by a separate dCas9-recombinase fusion (thereby coordinating four recombinase monomers which recombine the target nucleic acid(s)). For the RNA-guided nuclease Cas9 (or gRNA-binding domain thereof) and inventive fusions of Cas9, the target site may be, in some embodiments, 17-20 base pairs plus a 3 base pair PAM (e.g., NNN, wherein N independently represents any nucleotide). Typically, the first nucleotide of a PAM can be any nucleotide, while the two downstream nucleotides are specified depending on the specific RNA-guided nuclease. Exemplary target sites (e.g., comprising a PAM) for RNA-guided nucleases, such as Cas9, are known to those of skill in the art and include, without limitation, NNG, NGN, NAG, and NGG, wherein N independently represents any nucleotide. In addition, Cas9 nucleases from different species (e.g., *S. thermophilus* instead of *S. pyogenes*) recognizes a PAM that comprises the sequence NGGNG. Additional PAM sequences are known, including, but not limited to, NNAGAAW and NAAR (see, e.g., Esvelt and Wang, Molecular Systems Biology, 9:641 (2013), the entire contents of which are incorporated herein by reference). In some aspects, the target site of an RNA-guided nuclease, such as, e.g., Cas9, may comprise the structure $[N_Z]$-[PAM], where each N is, independently, any nucleotide, and z is an integer between 1 and 50, inclusive. In some embodiments, z is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50. In some embodiments, z is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, z is 20. In some embodiments, "target site" may also refer to a sequence within a nucleic acid molecule that is bound but not cleaved by a nuclease. For example, certain embodiments described herein provide proteins comprising an inactive (or inactivated) Cas9 DNA cleavage domain. Such proteins (e.g., when also including a Cas9 RNA binding domain) are able to bind the target site specified by the gRNA; however, because the DNA cleavage site is inactivated, the target site is not cleaved by the particular protein. However, such proteins as described herein are typically conjugated, fused, or bound to another protein (e.g., a nuclease) or molecule that mediates cleavage of the nucleic acid molecule. In other embodiments, such proteins are conjugated, fused, or bound to a recombinase (or a catalytic domain of a recombinase), which mediates recombination of the target nucleic acid. In some embodiments, the sequence actually cleaved or recombined will depend on the protein (e.g., nuclease or recombinase) or molecule that mediates cleavage or recombination of the nucleic acid molecule, and in some cases, for example, will relate to the proximity or distance from which the inactivated Cas9 protein(s) is/are bound.

In the context of inventive proteins that dimerize (or multimerize), for example, dimers of a protein comprising a nuclease-inactivated Cas9 (or a Cas9 RNA binding domain) and a DNA cleavage domain (e.g., FokI cleavage domain or an active Cas9 cleavage domain), or fusions between a nuclease-inactivated Cas9 (or a Cas9 gRNA binding domain) and a recombinase (or catalytic domain of a recombinase), a target site typically comprises a left-half site (bound by one protein), a right-half site (bound by the second protein), and a spacer sequence between the half sites in which the cut or recombination is made. In some embodiments, either the left-half site or the right half-site (and not the spacer sequence) is cut or recombined. In other embodiments, the spacer sequence is cut or recombined. This structure ([left-half site]-[spacer sequence]-[right-half site]) is referred to herein as an LSR structure. In some embodiments, the left-half site and/or the right-half site correspond to an RNA-guided target site (e.g., a Cas9 target site). In some embodiments, either or both half-sites are shorter or longer than e.g., a typical region targeted by Cas9, for example shorter or longer than 20 nucleotides. In some embodiments, the left and right half sites comprise different nucleic acid sequences. In some embodiments involving inventive nucleases, the target site is a sequence comprising three (3) RNA-guided nuclease target site sequences, for example, three sequences corresponding to Cas9 target site sequences (See, e.g., FIG. 2C), in which the first and second, and second and third Cas9 target site sequences are separated by a spacer sequence. In some embodiments, the spacer sequence is at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 60, at least 70, at least 80, at least 90, at least 100, at least 125, at least 150, at least 175, at least 200, or at least 250 bp long. In some embodiments, the spacer sequence is between approximately 15 bp and approximately 25 bp long. In some embodiments, the spacer sequence is approximately 15 bp long. In some embodiments, the spacer sequence is approximately 25 bp long.

The term "Transcriptional Activator-Like Effector," (TALE) as used herein, refers to bacterial proteins comprising a DNA binding domain, which contains a highly conserved 33-34 amino acid sequence comprising a highly variable two-amino acid motif (Repeat Variable Diresidue, RVD). The RVD motif determines binding specificity to a nucleic acid sequence and can be engineered according to methods known to those of skill in the art to specifically bind a desired DNA sequence (see, e.g., Miller, Jeffrey; et. al. (February 2011). "A TALE nuclease architecture for efficient genome editing". *Nature Biotechnology* 29 (2): 143-8; Zhang, Feng; et. al. (February 2011). "Efficient construction of sequence-specific TAL effectors for modulating mammalian transcription" *Nature Biotechnology* 29 (2): 149-53; Geiβler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". *PLoS ONE* 6 (5): e19509; Boch, Jens (February 2011). "TALEs of genome targeting". *Nature Biotechnology* 29 (2): 135-6; Boch, Jens; et. al. (December 2009). "Breaking the Code of DNA Binding Specificity of TAL-Type III Effectors". *Science* 326 (5959): 1509-12; and Moscou, Matthew J.; Adam J. Bogdanove (December 2009). "A Simple Cipher Governs DNA Recognition by TAL Effectors" *Science* 326 (5959): 1501; the entire contents of each of which are incorporated herein by reference). The simple relationship between amino acid sequence and DNA recognition has allowed for the engineering of specific DNA binding domains by selecting a combination of repeat segments containing the appropriate RVDs.

The term "Transcriptional Activator-Like Element Nuclease," (TALEN) as used herein, refers to an artificial nuclease comprising a transcriptional activator-like effector DNA binding domain to a DNA cleavage domain, for example, a FokI domain. A number of modular assembly schemes for generating engineered TALE constructs have been reported (see e.g., Zhang, Feng; et. al. (February 2011). "Efficient construction of sequence-specific TAL effectors for modulating mammalian transcription". *Nature Biotech-*

*nology* 29 (2): 149-53; Geißler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". *PLoS ONE* 6 (5): e19509; Cermak, T.; Doyle, E. L.; Christian, M.; Wang, L.; Zhang, Y.; Schmidt, C.; Baller, J. A.; Somia, N. V. et al. (2011). "Efficient design and assembly of custom TALEN and other TAL effector-based constructs for DNA targeting". *Nucleic Acids Research*; Morbitzer, R.; Elsaesser, J.; Hausner, J.; Lahaye, T. (2011). "Assembly of custom TALE-type DNA binding domains by modular cloning". *Nucleic Acids Research*; Li, T.; Huang, S.; Zhao, X.; Wright, D. A.; Carpenter, S.; Spalding, M. H.; Weeks, D. P.; Yang, B. (2011). "Modularly assembled designer TAL effector nucleases for targeted gene knockout and gene replacement in eukaryotes". *Nucleic Acids Research*.; Weber, E.; Gruetzner, R.; Werner, S.; Engler, C.; Marillonnet, S. (2011). Bendahmane, Mohammed. ed. "Assembly of Designer TAL Effectors by Golden Gate Cloning". *PLoS ONE* 6 (5): e19722; the entire contents of each of which are incorporated herein by reference).

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

The term "vector" refers to a polynucleotide comprising one or more recombinant polynucleotides of the present invention, e.g., those encoding a Cas9 protein (or fusion thereof) and/or gRNA provided herein. Vectors include, but are not limited to, plasmids, viral vectors, cosmids, artificial chromosomes, and phagemids. The vector is able to replicate in a host cell and is further characterized by one or more endonuclease restriction sites at which the vector may be cut and into which a desired nucleic acid sequence may be inserted. Vectors may contain one or more marker sequences suitable for use in the identification and/or selection of cells which have or have not been transformed or genomically modified with the vector. Markers include, for example, genes encoding proteins which increase or decrease either resistance or sensitivity to antibiotics (e.g., kanamycin, ampicillin) or other compounds, genes which encode enzymes whose activities are detectable by standard assays known in the art (e.g., β-galactosidase, alkaline phosphatase, or luciferase), and genes which visibly affect the phenotype of transformed or transfected cells, hosts, colonies, or plaques. Any vector suitable for the transformation of a host cell (e.g., *E. coli*, mammalian cells such as CHO cell, insect cells, etc.) as embraced by the present invention, for example, vectors belonging to the pUC series, pGEM series, pET series, pBAD series, pTET series, or pGEX series. In some embodiments, the vector is suitable for transforming a host cell for recombinant protein production. Methods for selecting and engineering vectors and host cells for expressing proteins (e.g., those provided herein), transforming cells, and expressing/purifying recombinant proteins are well known in the art, and are provided by, for example, Green and Sambrook, *Molecular Cloning: A Laboratory Manual* (4th ed., Cold Spring Harbor Laboratory Press, Cold Spring Harbor, N.Y. (2012)).

The term "zinc finger," as used herein, refers to a small nucleic acid-binding protein structural motif characterized by a fold and the coordination of one or more zinc ions that stabilize the fold. Zinc fingers encompass a wide variety of differing protein structures (see, e.g., Klug A, Rhodes D (1987). "Zinc fingers: a novel protein fold for nucleic acid recognition". *Cold Spring Harb. Symp. Quant. Biol.* 52: 473-82, the entire contents of which are incorporated herein by reference). Zinc fingers can be designed to bind a specific sequence of nucleotides, and zinc finger arrays comprising fusions of a series of zinc fingers, can be designed to bind virtually any desired target sequence. Such zinc finger arrays can form a binding domain of a protein, for example, of a nuclease, e.g., if conjugated to a nucleic acid cleavage domain. Different types of zinc finger motifs are known to those of skill in the art, including, but not limited to, $Cys_2His_2$, Gag knuckle, Treble clef, Zinc ribbon, $Zn_2/Cys_6$, and TAZ2 domain-like motifs (see, e.g., Krishna S S, Majumdar I, Grishin N V (January 2003). "Structural classification of zinc fingers: survey and summary". *Nucleic Acids Res.* 31 (2): 532-50). Typically, a single zinc finger motif binds 3 or 4 nucleotides of a nucleic acid molecule. Accordingly, a zinc finger domain comprising 2 zinc finger motifs may bind 6-8 nucleotides, a zinc finger domain comprising 3 zinc finger motifs may bind 9-12 nucleotides, a zinc finger domain comprising 4 zinc finger motifs may bind 12-16 nucleotides, and so forth. Any suitable protein engineering technique can be employed to alter the DNA-binding specificity of zinc fingers and/or design novel zinc finger fusions to bind virtually any desired target sequence from 3-30 nucleotides in length (see, e.g., Pabo C O, Peisach E, Grant R A (2001). "Design and selection of novel cys2His2 Zinc finger proteins". *Annual Review of Biochemistry* 70: 313-340; Jamieson A C, Miller J C, Pabo C O (2003). "Drug discovery with engineered zinc-finger proteins". *Nature Reviews Drug Discovery* 2 (5): 361-368; and Liu Q, Segal D J, Ghiara J B, Barbas C F (May 1997). "Design of polydactyl zinc-finger proteins for unique addressing within complex genomes". *Proc. Natl. Acad. Sci. U.S.A.* 94 (11); the entire contents of each of which are incorporated herein by reference). Fusions between engineered zinc finger arrays and protein domains that cleave a nucleic acid can be used to generate a "zinc finger nuclease." A zinc finger nuclease typically comprises a zinc finger domain that binds a specific target site within a nucleic acid molecule, and a nucleic acid cleavage domain that cuts the nucleic acid molecule within or in proximity to the target site bound by the binding domain. Typical engineered zinc finger nucleases comprise a binding domain having between 3 and 6 individual zinc finger motifs and binding target sites ranging from 9 base pairs to 18 base pairs in length. Longer target sites are particularly attractive in situations where it is desired to bind and cleave a target site that is unique in a given genome.

The term "zinc finger nuclease," as used herein, refers to a nuclease comprising a nucleic acid cleavage domain conjugated to a binding domain that comprises a zinc finger array. In some embodiments, the cleavage domain is the cleavage domain of the type II restriction endonuclease FokI. Zinc finger nucleases can be designed to target virtually any desired sequence in a given nucleic acid molecule for cleavage, and the possibility to design zinc finger binding domains to bind unique sites in the context of complex genomes allows for targeted cleavage of a single genomic site in living cells, for example, to achieve a targeted genomic alteration of therapeutic value. Targeting a double-strand break to a desired genomic locus can be used to introduce frame-shift mutations into the coding sequence of a gene due to the error-prone nature of the non-homologous DNA repair pathway. Zinc finger nucleases can be generated to target a site of interest by methods well known to those of skill in the art. For example, zinc finger binding domains with a desired specificity can be designed by combining individual zinc finger motifs of known specificity. The structure of the zinc finger protein Zif268 bound to DNA has informed much of the work in this field and the concept of obtaining zinc fingers for each of the 64 possible base pair triplets and then mixing and matching these modular zinc fingers to design proteins with any desired sequence specificity has been described (Pavletich N P, Pabo C O (May 1991). "Zinc finger-DNA recognition: crystal structure of a Zif268-DNA complex at 2.1 Å". *Science* 252 (5007): 809-17, the entire contents of which are incorporated herein). In some embodiments, separate zinc fingers that each recognizes a 3 base pair DNA sequence are combined to generate 3-, 4-, 5-, or 6-finger arrays that recognize target sites ranging from 9 base pairs to 18 base pairs in length. In some embodiments, longer arrays are contemplated. In other embodiments, 2-finger modules recognizing 6-8 nucleotides are combined to generate 4-, 6-, or 8-zinc finger arrays. In some embodiments, bacterial or phage display is employed to develop a zinc finger domain that recognizes a desired nucleic acid sequence, for example, a desired nuclease target site of 3-30 bp in length. Zinc finger nucleases, in some embodiments, comprise a zinc finger binding domain and a cleavage domain fused or otherwise conjugated to each other via a linker, for example, a polypeptide linker. The length of the linker determines the distance of the cut from the nucleic acid sequence bound by the zinc finger domain. If a shorter linker is used, the cleavage domain will cut the nucleic acid closer to the bound nucleic acid sequence, while a longer linker will result in a greater distance between the cut and the bound nucleic acid sequence. In some embodiments, the cleavage domain of a zinc finger nuclease has to dimerize in order to cut a bound nucleic acid. In some such embodiments, the dimer is a heterodimer of two monomers, each of which comprise a different zinc finger binding domain. For example, in some embodiments, the dimer may comprise one monomer comprising zinc finger domain A conjugated to a FokI cleavage domain, and one monomer comprising zinc finger domain B conjugated to a FokI cleavage domain. In this non-limiting example, zinc finger domain A binds a nucleic acid sequence on one side of the target site, zinc finger domain B binds a nucleic acid sequence on the other side of the target site, and the dimerize FokI domain cuts the nucleic acid in between the zinc finger domain binding sites.

DETAILED DESCRIPTION OF CERTAIN EMBODIMENTS OF THE INVENTION

Site-specific nucleases and site-specific recombinases are powerful tools for targeted genome modification in vitro and in vivo. It has been reported that nuclease cleavage in living cells triggers a DNA repair mechanism that frequently results in a modification of the cleaved and repaired genomic sequence, for example, via homologous recombination. Accordingly, the targeted cleavage of a specific unique sequence within a genome opens up new avenues for gene targeting and gene modification in living cells, including cells that are hard to manipulate with conventional gene targeting methods, such as many human somatic or embryonic stem cells. Another approach utilizes site-specific recombinases, which possess all the functionality required to bring about efficient, precise integration, deletion, inversion, or translocation of specified DNA segments.

Nuclease-mediated modification of disease-related sequences, e.g., the CCR-5 allele in HIV/AIDS patients, or of genes necessary for tumor neovascularization, can be used in the clinical context, and two site specific nucleases are currently in clinical trials (Perez, E. E. et al., "Establishment of HIV-1 resistance in CD4+ T cells by genome editing using zinc-finger nucleases." *Nature biotechnology*. 26, 808-816 (2008); ClinicalTrials.gov identifiers: NCT00842634, NCT01044654, NCT01252641, NCT01082926). Accordingly, nearly any genetic disease can be treated using site-specific nucleases and/or recombinases and include, for example, diseases associated with triplet expansion (e.g., Huntington's disease, myotonic dystrophy, spinocerebellar ataxias, etc.), cystic fibrosis (by targeting the CFTR gene), hematological disease (e.g., hemoglobinopathies), cancer, autoimmune diseases, and viral infections. Other diseases that can be treated using the inventive compositions and/or methods provided herein include, but are not limited to, achondroplasia, achromatopsia, acid maltase deficiency, adenosine deaminase deficiency, adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the 6th codon of beta-globin (HbC), hemophilia, Hurler Syndrome, hypophosphatasia, Klinefleter syndrome, Krabbes Disease, Langer-Giedion Syndrome, leukocyte adhesion deficiency (LAD), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis *imperfecta, porphyria*, Prader-Willi syndrome, progeria, Proteus syndrome, retinoblastoma, Rett syndrome, Rubinstein-Taybi syndrome, Sanfilippo syndrome, severe combined immuno-deficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, and X-linked lymphoproliferative syndrome (XLP).

One aspect of site-specific genomic modification is the possibility of off-target nuclease or recombinase effects, e.g., the cleavage or recombination of genomic sequences that differ from the intended target sequence by one or more nucleotides. Undesired side effects of off-target cleavage/recombination range from insertion into unwanted loci during a gene targeting event to severe complications in a clinical scenario. Off-target cleavage or recombination of sequences encoding essential gene functions or tumor suppressor genes by an endonuclease or recombinase administered to a subject may result in disease or even death of the subject. Accordingly, it is desirable to employ new strategies in designing nucleases and recombinases having the greatest chance of minimizing off-target effects.

The methods and compositions of the present disclosure represent, in some aspects, an improvement over previous methods and compositions providing nucleases (and methods of their use) and recombinases (and methods of their use) engineered to have improved specificity for their intended targets. For example, nucleases and recombinases known in the art, both naturally occurring and those engineered, typically have a target (e.g., DNA) binding domain that recognizes a particular sequence. Additionally, known nucleases and recombinases may comprise a DNA binding domain and a catalytic domain in a single protein capable of inducing cleavage or recombination, and as such the chance for off-target effects are increased as cleavage or recombination likely occurs upon off-target binding of the nuclease or recombinase, respectively. Aspects of the present invention relate to the recognition that increasing the number of sequences (e.g., having a nuclease bind at more than one site at a desired target), and/or splitting the activities (e.g., target binding and target cleaving) of a nuclease between two or more proteins, will increase the specificity of a nuclease and thereby decrease the likelihood of off-target effects. Other aspects of the present invention relate to the recognition that fusions between the catalytic domain of recombinases (or recombinases having inactive DNA binding domains) and nuclease-inactivated RNA-programmable nucleases allow for the targeted recombination of DNA at any location.

In the context of site-specific nucleases, the strategies, methods, compositions, and systems provided herein can be utilized to improve the specificity of any site-specific nuclease, for example, variants of the Cas9 endonuclease, Zinc Finger Nucleases (ZFNs) and Transcription Activator-Like Effector Nucleases (TALENs). Suitable nucleases for modification as described herein will be apparent to those of skill in the art based on this disclosure.

In certain embodiments, the strategies, methods, compositions, and systems provided herein are utilized to improve the specificity of the RNA-guided (e.g., RNA-programmable) endonuclease Cas9. Whereas typical endonucleases recognize and cleave a single target sequence, Cas9 endonuclease uses RNA:DNA hybridization to determine target DNA cleavage sites, enabling a single monomeric protein to cleave, in principle, any sequence specified by the guide RNA (gRNA). While Cas9:guide RNA complexes have been successfully used to modify both cells (Cong, L. et al. Multiplex genome engineering using CRISPR/Cas systems. *Science.* 339, 819-823 (2013); Mali, P. et al. RNA-guided human genome engineering via Cas9. *Science.* 339, 823-826 (2013); Jinek, M. et al. RNA-programmed genome editing in human cells. *eLife* 2, e00471 (2013)) and organisms (Hwang, W. Y. et al. Efficient genome editing in zebrafish using a CRISPR-Cas system. *Nature Biotechnology.* 31, 227-229 (2013)), a study using Cas9:guide RNA complexes to modify zebrafish embryos observed toxicity (e.g., off-target effects) at a rate similar to that of ZFNs and TALENs (Hwang, W. Y. et al. *Nature Biotechnology.* 31, 227-229 (2013)). Further, while recently engineered variants of Cas9 that cleave only one DNA strand ("nickases") enable double-stranded breaks to be specified by two distinct gRNA sequences (Cho, S. W. et al. Analysis of off-target effects of CRISPR/Cas-derived RNA-guided endonucleases and nickases. *Genome Res.* 24, 132-141 (2013); Ran, F. A. et al. Double Nicking by RNA-Guided CRISPR Cas9 for Enhanced Genome Editing Specificity. *Cell* 154, 1380-1389 (2013); Mali, P. et al. CAS9 transcriptional activators for target specificity screening and paired nickases for cooperative genome engineering. *Nat. Biotechnol.* 31, 833-838 (2013)), these variants still suffer from off-target cleavage activity (Ran, F. A. et al. Double Nicking by RNA-Guided CRISPR Cas9 for Enhanced Genome Editing Specificity. *Cell* 154, 1380-1389 (2013); Fu, Y., et al., Improving CRISPR-Cas nuclease specificity using truncated guide RNAs. *Nat. Biotechnol.* (2014)) arising from the ability of each monomeric nickase to remain active when individually bound to DNA (Cong, L. et al. Multiplex Genome Engineering Using CRISPR/Cas Systems. *Science* 339, 819-823 (2013); Jinek, M. et al. *Science* 337, 816-821 (2012); Gasiunas, G., et al., Cas9-crRNA ribonucleoprotein complex mediates specific DNA cleavage for adaptive immunity in bacteria. *Proc. Natl. Acad. Sci.* 109, E2579-E2586 (2012). Accordingly, aspects of the present disclosure aim at reducing the chances for Cas9 off-target effects using novel engineered Cas9 variants. In one example, a Cas9 variant (e.g., fCas9) is provided which has improved specificity as compared to the Cas9 nickases or wild type Cas9, exhibiting, e.g., >10-fold, >50-fold, >100-fold, >140-fold, >200-fold, or more, higher specificity than wild type Cas9 (see e.g., the Examples).

Other aspects of the present disclosure provide strategies, methods, compositions, and systems utilizing inventive RNA-guided (e.g., RNA-programmable) Cas9-recombinase fusion proteins. Whereas typical recombinases recognize and recombine distinct target sequences, the Cas9-recombinase fusions provided herein use RNA:DNA hybridization to determine target DNA recombination sites, enabling the fusion proteins to recombine, in principle, any region specified by the gRNA(s).

While of particular relevance to DNA and DNA-cleaving nucleases and/or recombinases, the inventive concepts, methods, strategies and systems provided herein are not limited in this respect, but can be applied to any nucleic acid:nuclease or nucleic acid:recombinase system.

Nucleases

Figure 20:
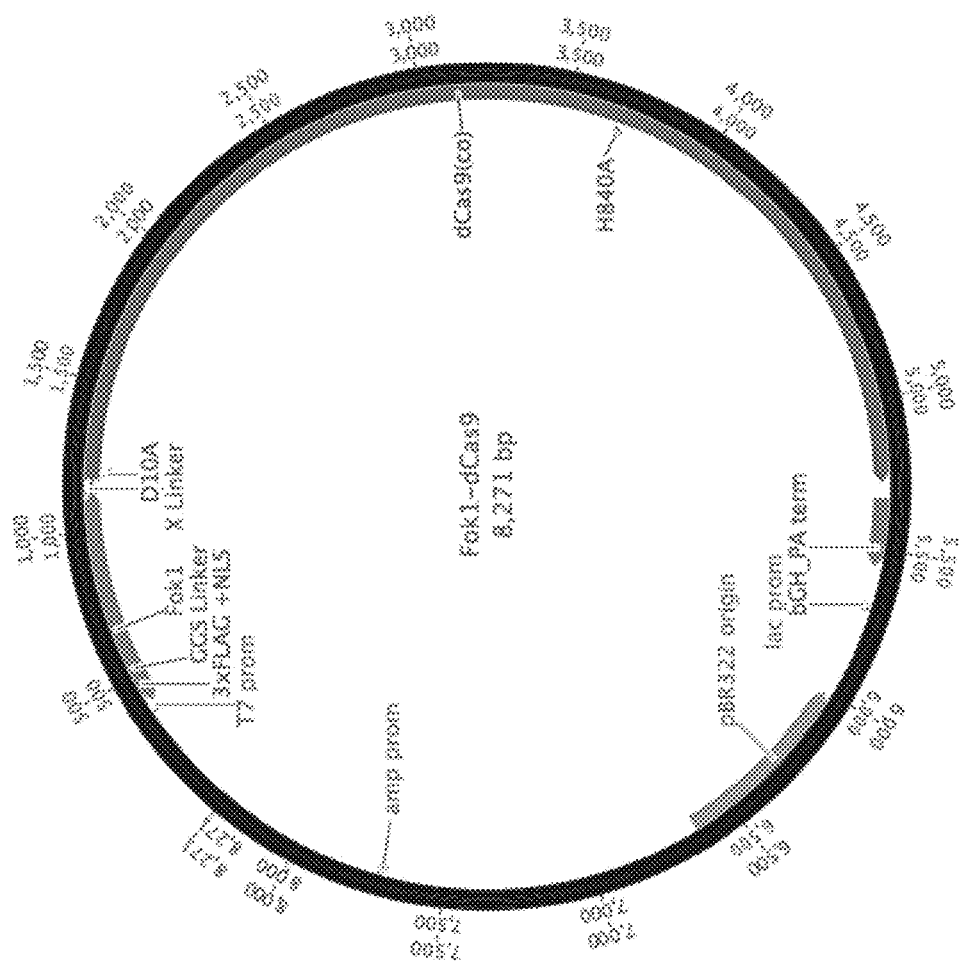
FIG. 20 depicts a vector map detailing an exemplary plasmid containing a Fok1-dCas9 (fCas9) construct.

Some aspects of this disclosure provide site-specific nucleases with enhanced specificity that are designed using the methods and strategies described herein. Some embodiments of this disclosure provide nucleic acids encoding such nucleases. Some embodiments of this disclosure provide expression constructs comprising such encoding nucleic acids (See, e.g., FIG. 20). For example, in some embodiments an isolated nuclease is provided that has been engineered to cleave a desired target site within a genome. In some embodiments, the isolated nuclease is a variant of an RNA-programmable nuclease, such as a Cas9 nuclease.

In one embodiment, fusion proteins are provided comprising two domains: (i) an RNA-programmable nuclease (e.g., Cas9 protein, or fragment thereof) domain fused or linked to (ii) a nuclease domain. For example, in some aspects, the Cas9 protein (e.g., the Cas9 domain of the fusion protein) comprises a nuclease-inactivated Cas9 (e.g., a Cas9 lacking DNA cleavage activity; "dCas9") that retains RNA (gRNA) binding activity and is thus able to bind a target site complementary to a gRNA. In some aspects, the nuclease fused to the nuclease-inactivated Cas9 domain is any nuclease requiring dimerization (e.g., the coming together of two monomers of the nuclease) in order to cleave a target nucleic acid (e.g., DNA). In some embodiments, the nuclease fused to the nuclease-inactivated Cas9 is a monomer of the FokI DNA cleavage domain, e.g., thereby producing the Cas9 variant referred to as fCas9. The FokI DNA cleavage domain is known, and in some aspects corresponds to amino acids 388-583 of FokI (NCBI accession number J04623). In some embodiments, the FokI DNA cleavage domain corresponds to amino acids 300-583, 320-583, 340-583, or 360-583 of FokI. See also Wah et al., "Structure of FokI has implications for DNA cleavage" *Proc. Natl. Acad. Sci. USA.* 1998; 1; 95(18): 10564-9; Li et al., "TAL nucleases (TALNs): hybrid proteins composed of TAL effectors and FokI DNA-cleavage domain" *Nucleic Acids Res.* 2011; 39(1):359-72; Kim et al., "Hybrid restriction enzymes: zinc finger fusions to Fok I cleavage domain" *Proc. Natl Acad. Sci. USA*. 1996; 93:1156-1160; the entire contents of each are herein incorporated by reference). In some embodiments, the FokI DNA cleavage domain corresponds to, or comprises in part or whole, the amino acid sequence set forth as SEQ ID NO:6. In some embodiments, the FokI DNA cleavage domain is a variant of FokI (e.g., a variant of SEQ ID NO:6), as described herein.

In some embodiments, a dimer of the fusion protein is provided, e.g., dimers of fCas9. For example, in some embodiments, the fusion protein forms a dimer with itself to mediate cleavage of the target nucleic acid. In some embodiments, the fusion proteins, or dimers thereof, are associated with one or more gRNAs. In some aspects, because the dimer contains two fusion proteins, each having a Cas9 domain having gRNA binding activity, a target nucleic acid is targeted using two distinct gRNA sequences that complement two distinct regions of the nucleic acid target. See, e.g., FIGS. 1A, 6D. Thus, in this example, cleavage of the target nucleic acid does not occur until both fusion proteins bind the target nucleic acid (e.g., as specified by the gRNA:target nucleic acid base pairing), and the nuclease domains dimerize (e.g., the FokI DNA cleavage domains; as a result of their proximity based on the binding of the Cas9:gRNA domains of the fusion proteins) and cleave the target nucleic acid, e.g., in the region between the bound Cas9 fusion proteins (the "spacer sequence"). This is exemplified by the schematics shown in FIGS. 1A and 6D. This approach represents a notable improvement over wild type Cas9 and other Cas9 variants, such as the nickases (Ran et al. Double Nicking by RNA-Guided CRISPR Cas9 for Enhanced Genome Editing Specificity. *Cell* 154, 1380-1389 (2013); Mali et al. CAS9 transcriptional activators for target specificity screening and paired nickases for cooperative genome engineering. *Nat. Biotechnol.* 31, 833-838 (2013)), which do not require the dimerization of nuclease domains to cleave a nucleic acid. These nickase variants, as described in the Examples, can induce cleaving, or nicking upon binding of a single nickase to a nucleic acid, which can occur at on- and off-target sites, and nicking is known to induce mutagenesis. An exemplary nucleotide encoding a Cas9 nickase (SEQ ID NO:7) and an exemplary amino acid sequence of Cas9 nickase (SEQ ID NO:8) are provided below. As the variants provided herein require the binding of two Cas9 variants in proximity to one another to induce target nucleic acid cleavage, the chances of inducing off-target cleavage is reduced. See, e.g., the Examples. For example, in some embodiments, a Cas9 variant fused to a nuclease domain (e.g., fCas9) has an on-target: off-target modification ratio that is at least 2-fold, at least 5-fold, at least 10-fold, at least 20-fold, at least 30-fold, at least 40-fold, at least 50-fold, at least 60-fold, at least 70-fold, at least 80-fold, at least 90-fold, at least 100-fold, at least 110-fold, at least 120-fold, at least 130-fold, at least 140-fold, at least 150-fold, at least 175-fold, at least 200-fold, at least 250-fold, or more higher than the on-target:off-target modification ratio of a wild type Cas9 or other Cas9 variant (e.g., nickase). In some embodiments, a Cas9 variant fused to a nuclease domain (e.g., fCas9) has an on-target:off-target modification ratio that is between about 60- to 180-fold, between about 80- to 160-fold, between about 100- to 150-fold, or between about 120- to 140-fold higher than the on-target:off-target modification ratio of a wild type Cas9 or other Cas9 variant. Methods for determining on-target:off-target modification ratios are known, and include those described in the Examples. In certain embodiments, the on-target:off-target modification ratios are determined by measuring the number or amount of modifications of known Cas9 off-target sites in certain genes. For example, the Cas9 off-target sites of the CLTA, EMX, and VEGF genes are known, and modifications at these sites can be measured and compared between test proteins and controls. The target site and its corresponding known off-target sites (see, e.g., Table 5 for CLTA, EMX, and VEGF off-target sites) are amplified from genomic DNA isolated from cells (e.g., HEK293) treated with a particular Cas9 protein or variant. The modifications are then analyzed by high-throughput sequencing. Sequences containing insertions or deletions of two or more base pairs in potential genomic off-target sites and present in significantly greater numbers (P value <0.005, Fisher's exact test) in the target gRNA-treated samples versus the control gRNA-treated samples are considered Cas9 nuclease-induced genome modifications.

Cas9 Nickase (Nucleotide Sequence):

```
                                              (SEQ ID NO: 7)
ATGGACTATAAGGACCACGACGGAGACTACAAGGATCATGATATTGATTA

CAAAGACGATGACGATAAGATGGCCCCAAAGAAGAAGCGGAAGGTCGGTA

TCCACGGAGTCCCAGCAGCCGATAAAAAGTATTCTATTGGTTTAGCTATC

GGCACTAATTCCGTTGGATGGGCTGTCATAACCGATGAATACAAAGTACC

TTCAAAGAAATTTAAGGTGTTGGGGAACACAGACCGTCATTCGATTAAAA

AGAATCTTATCGGTGCCCTCCTATTCGATAGTGGCGAAACGGCAGAGGCG

ACTCGCCTGAAACGAACCGCTCGGAGAAGGTATACACGTCGCAAGAACCG

AATATGTTACTTACAAGAAATTTTTAGCAATGAGATGGCCAAAGTTGACG

ATTCTTTCTTTCACCGTTTGGAAGAGTCCTTCCTTGTCGAAGAGGACAAG

AAACATGAACGGCACCCCATCTTTGGAAACATAGTAGATGAGGTGGCATA

TCATGAAAAGTACCCAACGATTTATCACCTCAGAAAAAAGCTAGTTGACT

CAACTGATAAAGCGGACCTGAGGTTAATCTACTTGGCTCTTGCCCATATG

ATAAAGTTCCGTGGGCACTTTCTCATTGAGGGTGATCTAAATCCGGACAA

CTCGGATGTCGACAAACTGTTCATCCAGTTAGTACAAACCTATAATCAGT

TGTTTGAAGAGAACCCTATAAATGCAAGTGGCGTGGATGCGAAGGCTATT

CTTAGCGCCCGCCTCTCTAAATCCCGACGGCTAGAAAACCTGATCGCACA

ATTACCCGGAGAGAAGAAAAATGGGTTGTTCGGTAACCTTATAGCGCTCT

CACTAGGCCTGACACCAAATTTTAAGTCGAACTTCGACTTAGCTGAAGAT

GCCAAATTGCAGCTTAGTAAGGACACGTACGATGACGATCTCGACAATCT

ACTGGCACAAATTGGAGATCAGTATGCGGACTTATTTTTGGCTGCCAAAA

ACCTTAGCGATGCAATCCTCCTATCTGACATACTGAGAGTTAATACTGAG

ATTACCAAGGCGCCGTTATCCGCTTCAATGATCAAAAGGTACGATGAACA

TCACCAAGACTTGACACTTCTCAAGGCCCTAGTCCGTCAGCAACTGCCTG

AGAAATATAAGGAAATATTCTTTGATCAGTCGAAAAACGGGTACGCAGGT

TATATTGACGGCGGAGCGAGTCAAGAGGAATTCTACAAGTTTATCAAACC

CATATTAGAGAAGATGGATGGGACGGAAGAGTTGCTTGTAAAACTCAATC

GCGAAGATCTACTGCGAAAGCAGCGGACTTTCGACAACGGTAGCATTCCA

CATCAAATCCACTTAGGCGAATTGCATGCTATACTTAGAAGGCAGGAGGA

TTTTTATCCGTTCCTCAAAGACAATCGTGAAAAGATTGAGAAAATCCTAA

CCTTTCGCATACCTTACTATGTGGGACCCCTGGCCCGAGGGAACTCTCGG
```

```
TTCGCATGGATGACAAGAAAGTCCGAAGAAACGATTACTCCATGGAATTT
TGAGGAAGTTGTCGATAAAGGTGCGTCAGCTCAATCGTTCATCGAGAGGA
TGACCAACTTTGACAAGAATTTACCGAACGAAAAAGTATTGCCTAAGCAC
AGTTTACTTTACGAGTATTTCACAGTGTACAATGAACTCACGAAAGTTAA
GTATGTCACTGAGGGCATGCGTAAACCCGCCTTTCTAAGCGGAGAACAGA
AGAAAGCAATAGTAGATCTGTTATTCAAGACCAACCGCAAAGTGACAGTT
AAGCAATTGAAAGAGGACTACTTTAAGAAAATTGAATGCTTCGATTCTGT
CGAGATCTCCGGGGTAGAAGATCGATTTAATGCGTCACTTGGTACGTATC
ATGACCTCCTAAAGATAATTAAAGATAAGGACTTCCTGGATAACGAAGAG
AATGAAGATATCTTAGAAGATATAGTGTTGACTCTTACCCTCTTTGAAGA
TCGGGAAATGATTGAGGAAAGACTAAAAACATACGCTCACCTGTTCGACG
ATAAGGTTATGAAACAGTTAAAGAGGCGTCGCTATACGGGCTGGGGACGA
TTGTCGCGGAAACTTATCAACGGGATAAGAGACAAGCAAAGTGGTAAAAC
TATTCTCGATTTTCTAAAGAGCGACGGCTTCGCCAATAGGAACTTTATGC
AGCTGATCCATGATGACTCTTTAACCTTCAAAGAGGATATACAAAAGGCA
CAGGTTTCCGGACAAGGGGACTCATTGCACGAACATATTGCGAATCTTGC
TGGTTCGCCAGCCATCAAAAAGGGCATACTCCAGACAGTCAAAGTAGTGG
ATGAGCTAGTTAAGGTCATGGGACGTCACAAACCGGAAAACATTGTAATC
GAGATGGCACGCGAAAATCAAACGACTCAGAAGGGGCAAAAAAACAGTCG
AGAGCGGATGAAGAGAATAGAAGAGGGTATTAAAGAACTGGGCAGCCAGA
TCTTAAAGGAGCATCCTGTGGAAAATACCCAATTGCAGAACGAGAAACTT
TACCTCTATTACCTACAAAATGGAAGGGACATGTATGTTGATCAGGAACT
GGACATAAACCGTTTATCTGATTACGACGTCGATCACATTGTACCCCAAT
CCTTTTTGAAGGACGATTCAATCGACAATAAAGTGCTTACACGCTCGGAT
AAGAACCGAGGGAAAAGTGACAATGTTCCAAGCGAGGAAGTCGTAAAGAA
AATGAAGAACTATTGGCGGCAGCTCCTAAATGCGAAACTGATAACGCAAA
GAAAGTTCGATAACTTAACTAAAGCTGAGAGGGGTGGCTTGTCTGAACTT
GACAAGGCCGGATTTATTAAACGTCAGCTCGTGGAAACCCGCCAAATCAC
AAAGCATGTTGCACAGATACTAGATTCCCGAATGAATACGAAATACGACG
AGAACGATAAGCTGATTCGGGAAGTCAAAGTAATCACTTTAAAGTCAAAA
TTGGTGTCGGACTTCAGAAAGGATTTTCAATTCTATAAAGTTAGGGAGAT
AAATAACTACCACCATGCGCACGACGCTTATCTTAATGCCGTCGTAGGGA
CCGCACTCATTAAGAAATACCCGAAGCTAGAAAGTGAGTTTGTGTATGGT
GATTACAAAGTTTATGACGTCCGTAAGATGATCGCGAAAAGCGAACAGGA
GATAGGCAAGGCTACAGCCAAATACTTCTTTTATTCTAACATTATGAATT
TCTTTAAGACGGAAATCACTCTGGCAAACGGAGAGATACGCAACGACCT
TTAATTGAAACCAATGGGGAGACAGGTGAAATCGTATGGGATAAGGGCCG
GGACTTCGCGACGGTGAGAAAAGTTTTGTCCATGCCCCAAGTCAACATAG
TAAAGAAAACTGAGGTGCAGACCGGAGGGTTTTCAAAGGAATCGATTCTT
CCAAAAAGGAATAGTGATAAGCTCATCGCTCGTAAAAAGGACTGGGACCC
GAAAAAGTACGGTGGCTTCGATAGCCCTACAGTTGCCTATTCTGTCCTAG
TAGTGGCAAAAGTTGAGAAGGGAAAATCCAAGAAACTGAAGTCAGTCAAA
GAATTATTGGGGATAACGATTATGGAGCGCTCGTCTTTTGAAAAGAACCC
CATCGACTTCCTTGAGGCGAAAGGTTACAAGGAAGTAAAAAAGGATCTCA
TAATTAAACTACCAAAGTATAGTCTGTTTGAGTTAGAAAATGGCCGAAAA
CGGATGTTGGCTAGCGCCGGAGAGCTTCAAAAGGGGAACGAACTCGCACT
ACCGTCTAAATACGTGAATTTCCTGTATTTAGCGTCCCATTACGAGAAGT
TGAAAGGTTCACCTGAAGATAACGAACAGAAGCAACTTTTTGTTGAGCAG
CACAAACATTATCTCGACGAAATCATAGAGCAAATTTCGGAATTCAGTAA
GAGAGTCATCCTAGCTGATGCCAATCTGGACAAAGTATTAAGCGCATACA
ACAAGCACAGGGATAAACCCATACGTGAGCAGGCGGAAAATATTATCCAT
TTGTTTACTCTTACCAACCTCGGCGCTCCAGCCGCATTCAAGTATTTTGA
CACAACGATAGATCGCAAACGATACACTTCTACCAAGGAGGTGCTAGACG
CGACACTGATTCACCAATCCATCACGGGATTATATGAAACTCGGATAGAT
TTGTCACAGCTTGGGGGTGAC
```

Cas9 Nickase (D10A)(Amino Acid Sequence):

(SEQ ID NO: 8)
MDKKYSIGLAIGTNSVGWAVITDEYKVPSKKFKVLGNTDRHSIKKNLIGA
LLFDSGETAEATRLKRTARRRYTRRKNRICYLQEIFSNEMAKVDDSFFHR
LEESFLVEEDKKHERHPIFGNIVDEVAYHEKYPTIYHLRKKLVDSTDKAD
LRLIYLALAHMIKFRGHFLIEGDLNPDNSDVDKLFIQLVQTYNQLFEENP
INASGVDAKAILSARLSKSRRLENLIAQLPGEKKNGLFGNLIALSLGLTP
NFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEI
FFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVD
LLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQ
LKRRRYTGWGRLSRKLINGIRDKQSGKTILDFLKSDGFANRNFMQLIHDD
SLTFKEDIQKAQVSGQGDSLHEHIANLAGSPAIKKGILQTVKVVDELVKV
MGRHKPENIVIEMARENQTTQKGQKNSRERMKRIEEGIKELGSQILKEHP
VENTQLQNEKLYLYYLQNGRDMYVDQELDINRLSDYDVDHIVPQSFLKDD
SIDNKVLTRSDKNRGKSDNVPSEEVVKKMKNYWRQLLNAKLITQRKFDNL
TKAERGGLSELDKAGFIKRQLVETRQITKHVAQILDSRMNTKYDENDKLI
REVKVITLKSKLVSDFRKDFQFYKVREINNYHHAHDAYLNAVVGTALIKK
YPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEV
QTGGFSKESILPKRNSDKLIARKKDWDPKKYGGFDSPTVAYSVLVVAKVE

-continued
KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD

Figure 9:
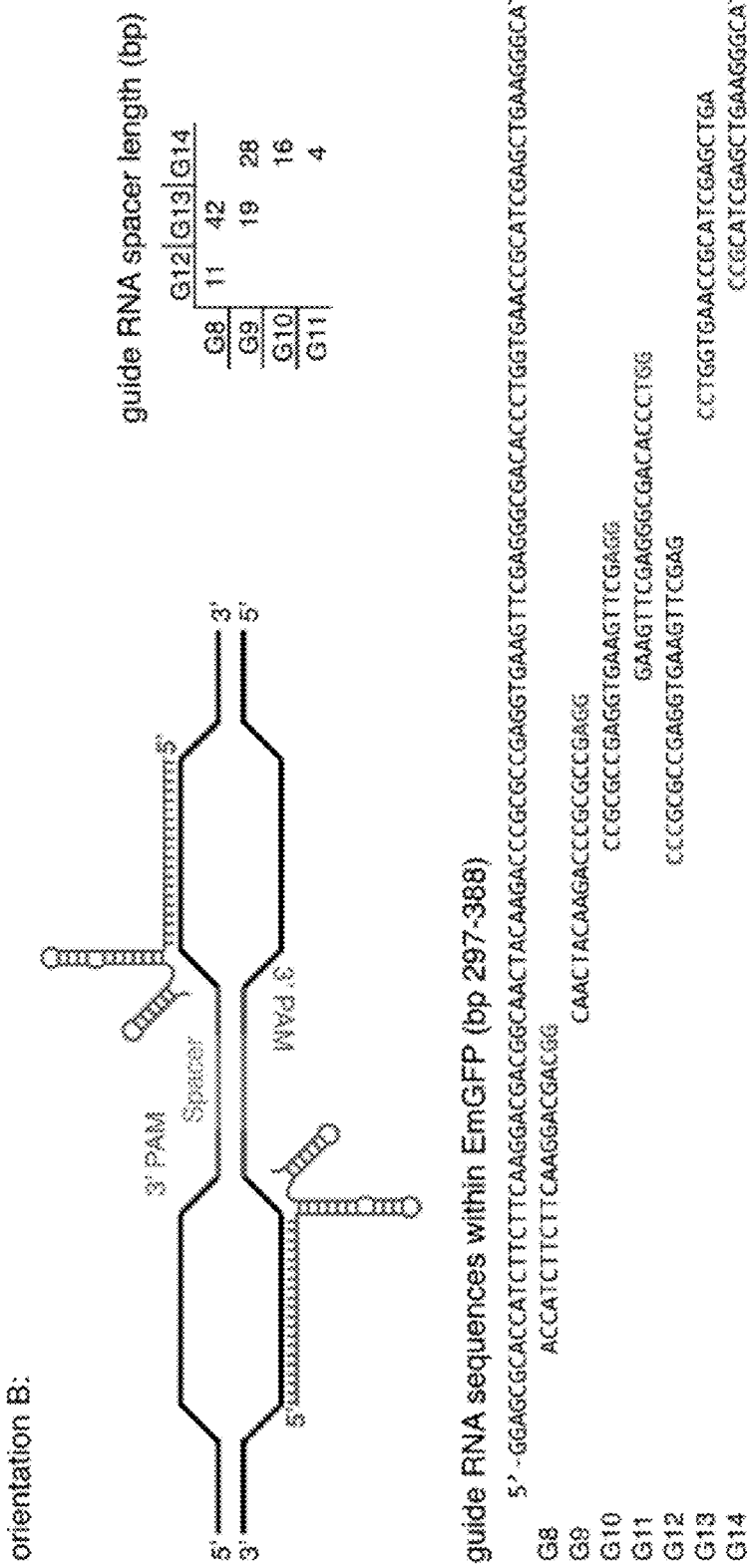
FIG. 9 shows the target DNA sequences in a genomic GFP gene. Seven gRNA target sites were chosen to test FokI-dCas9 candidate activity in an orientation in which the PAM is adjacent to the cleaved spacer sequence (orientation B). Together, these seven gRNAs enabled testing of FokI-dCas9 fusion variants across six spacer lengths ranging from 4 to 42 bp. The sequences shown are identified as follows: "EmGFP (bp 297-388)" corresponds to SEQ ID NO:212; "G8" corresponds to SEQ ID NO:213; "G9" corresponds to SEQ ID NO:214; "G10" corresponds to SEQ ID NO:215; "G11" corresponds to SEQ ID NO:216; "G12" corresponds to SEQ ID NO:217; "G13" corresponds to SEQ ID NO:218; and "G14" corresponds to SEQ ID NO:219.

In some embodiments, the gRNAs which bind the Cas9 variants (e.g., fCas9) can be oriented in one of two ways, with respect to the spacer sequence, deemed the "A" and "B" orientations. In orientation A, the region of the gRNAs that bind the PAM motifs is distal to the spacer sequence with the 5' ends of the gRNAs adjacent to the spacer sequence (FIG. 6C); whereas in orientation B, the region of the gRNAs that bind the PAM motifs is adjacent to the spacer sequence (FIG. 9). In some embodiments, the gRNAs are engineered or selected to bind (e.g., as part of a complex with a Cas9 variant, such as fCas9) to a target nucleic acid in the A or B orientation. In some embodiments, the gRNAs are engineered or selected to bind (e.g., as part of a complex with a Cas9 variant such as fCas9) to a target nucleic acid in the A orientation. In some embodiments, the gRNAs are engineered or selected to bind (e.g., as part of a complex with a Cas9 variant, such as fCas9) to a target nucleic acid in the B orientation.

In some embodiments, the domains of the fusion protein are linked via a linker e.g., as described herein. In certain embodiments, the linker is a peptide linker. In other embodiments, the linker is a non-peptidic linker. In some embodiments, a functional domain is linked via a peptide linker (e.g., fused) or a non-peptidic linker to an inventive fusion protein. In some embodiments, the functional domain is a nuclear localization signal (NLS) domain. An NLS domain comprises an amino acid sequence that "tags" or signals a protein for import into the cell nucleus by nuclear transport. Typically, this signal consists of one or more short sequences of positively charged lysines or arginines exposed on the protein surface. NLS sequences are well known in the art (See e.g., Lange et al., "Classical nuclear localization signals: definition, function, and interaction with importin alpha." *J Biol Chem.* 2007 Feb. 23; 282(8):5101-5; the entire contents of which is hereby incorporated by reference), and include, for example those described in the Examples section. In some embodiments, the NLS sequence comprises, in part or in whole, the amino acid sequence MAPKKKRKVGIHRGVP (SEQ ID NO:318). The domains (e.g., two or more of a gRNA binding domain (dCas9 domain), a catalytic nuclease domain, and a NLS domain) associated via a linker can be linked in any orientation or order. For example, in some embodiments, any domain can be at the N-terminus, the C-terminus, or in between the domains at the N- and C-termini of the fusion protein. In some embodiments, the orientation or order of the domains in an inventive fusion protein are as provided in FIG. 6B. In some embodiments, wherein the fusion protein comprises three domains (e.g., a gRNA binding domain (e.g., dCas9 domain), a nuclease domain (e.g., FokI), and an NLS domain), each domain is connected via a linker, as provided herein. In some embodiments, the domains are not connected via a linker. In some embodiments, one or more of the domains is/are connected via a linker.

In some embodiments, an inventive fusion protein (e.g., fCas9) comprising three domains (e.g., a gRNA binding domain (e.g., dCas9 domain), a nuclease domain (e.g., FokI), and an NLS domain) is encoded by a nucleotide sequence (or fragment or variant thereof) set forth as SEQ ID NO:9, SEQ ID NO:10, SEQ ID NO:11, SEQ ID NO:12, or SEQ ID NO:319, as shown below.

fCas9 (e.g., dCas9-NLS-GGS3linker-FokI):

(SEQ ID NO: 9)
ATGGATAAAAAGTATTCTATTGGTTTAGCTATCGGCACTAATTCCGTTGG

ATGGGCTGTCATAACCGATGAATACAAAGTACCTTCAAAGAAATTTAAGG

TGTTGGGGAACACAGACCGTCATTCGATTAAAAAGAATCTTATCGGTGCC

CTCCTATTCGATAGTGGCGAAACGGCAGAGGCGACTCGCCTGAAACGAAC

CGCTCGGAGAAGGTATACACGTCGCAAGAACCGAATATGTTACTTACAAG

AAATTTTTAGCAATGAGATGGCCAAAGTTGACGATTCTTTCTTTCACCGT

TTGGAAGAGTCCTTCCTTGTCGAAGAGGACAAGAAACATGAACGGCACCC

CATCTTTGGAAACATAGTAGATGAGGTGGCATATCATGAAAAGTACCCAA

CGATTTATCACCTCAGAAAAAAGCTAGTTGACTCAACTGATAAAGCGGAC

CTGAGGTTAATCTACTTGGCTCTTGCCCATATGATAAAGTTCCGTGGGCA

CTTTCTCATTGAGGGTGATCTAAATCCGGACAACTCGGATGTCGACAAAC

TGTTCATCCAGTTAGTACAAACCTATAATCAGTTGTTTGAAGAGAACCCT

ATAAATGCAAGTGGCGTGGATGCGAAGGCTATTCTTAGCGCCCGCCTCTC

TAAATCCCGACGGCTAGAAAACCTGATCGCACAATTACCCGGAGAGAAGA

AAAATGGGTTGTTCGGTAACCTTATAGCGCTCTCACTAGGCCTGACACCA

AATTTTAAGTCGAACTTCGACTTAGCTGAAGATGCCAAATTGCAGCTTAG

TAAGGACACGTACGATGACGATCTCGACAATCTACTGGCACAAATTGGAG

ATCAGTATGCGGACTTATTTTTGGCTGCCAAAAACCTTAGCGATGCAATC

CTCCTATCTGACATACTGAGAGTTAATACTGAGATTACCAAGGCGCCGTT

ATCCGCTTCAATGATCAAAAGGTACGATGAACATCACCAAGACTTGACAC

TTCTCAAGGCCCTAGTCCGTCAGCAACTGCCTGAGAAATATAAGGAAATA

TTCTTTGATCAGTCGAAAAACGGGTACGCAGGTTATATTGACGGCGGAGC

GAGTCAAGAGGAATTCTACAAGTTTATCAAACCCATATTAGAGAAGATGG

ATGGGACGGAAGAGTTGCTTGTAAAACTCAATCGCGAAGATCTACTGCGA

AAGCAGCGGACTTTCGACAACGGTAGCATTCCACATCAAATCCACTTAGG

CGAATTGCATGCTATACTTAGAAGGCAGGAGGATTTTTATCCGTTCCTCA

AAGACAATCGTGAAAAGATTGAGAAAATCCTAACCTTTCGCATACCTTAC

TATGTGGGACCCCTGGCCCGAGGGAACTCTCGGTTCGCATGGATGACAAG

AAAGTCCGAAGAAACGATTACTCCATGGAATTTTGAGGAAGTTGTCGATA

AAGGTGCGTCAGCTCAATCGTTCATCGAGAGGATGACCAACTTTGACAAG

AATTTACCGAACGAAAAAGTATTGCCTAAGCACAGTTTACTTTACGAGTA

TTTCACAGTGTACAATGAACTCACGAAAGTTAAGTATGTCACTGAGGGCA

TGCGTAAACCCGCCTTTCTAAGCGGAGAACAGAAGAAAGCAATAGTAGAT

CTGTTATTCAAGACCAACCGCAAAGTGACAGTTAAGCAATTGAAAGAGGA

CTACTTTAAGAAAATTGAATGCTTCGATTCTGTCGAGATCTCCGGGGTAG

AAGATCGATTTAATGCGTCACTTGGTACGTATCATGACCTCCTAAAGATA

ATTAAAGATAAGGACTTCCTGGATAACGAAGAGAATGAAGATATCTTAGA

```
AGATATAGTGTTGACTCTTACCCTCTTTGAAGATCGGGAAATGATTGAGG
AAAGACTAAAAACATACGCTCACCTGTTCGACGATAAGGTTATGAAACAG
TTAAAGAGGCGTCGCTATACGGGCTGGGGACGATTGTCGCGGAAACTTAT
CAACGGGATAAGAGACAAGCAAAGTGGTAAAACTATTCTCGATTTTCTAA
AGAGCGACGGCTTCGCCAATAGGAACTTTATGCAGCTGATCCATGATGAC
TCTTTAACCTTCAAAGAGGATATACAAAAGGCACAGGTTTCCGGACAAGG
GGACTCATTGCACGAACATATTGCGAATCTTGCTGGTTCGCCAGCCATCA
AAAAGGGCATACTCCAGACAGTCAAAGTAGTGGATGAGCTAGTTAAGGTC
ATGGGACGTCACAAACCGGAAAACATTGTAATCGAGATGGCACGCGAAAA
TCAAACGACTCAGAAGGGGCAAAAAAACAGTCGAGAGCGGATGAAGAGAA
TAGAAGAGGGTATTAAAGAACTGGGCAGCCAGATCTTAAAGGAGCATCCT
GTGGAAAATACCCAATTGCAGAACGAGAAACTTTACCTCTATTACCTACA
AAATGGAAGGGACATGTATGTTGATCAGGAACTGGACATAAACCGTTTAT
CTGATTACGACGTCGATGCCATTGTACCCCAATCCTTTTTGAAGGACGAT
TCAATCGACAATAAAGTGCTTACACGCTCGGATAAGAACCGAGGGAAAAG
TGACAATGTTCCAAGCGAGGAAGTCGTAAAGAAAATGAAGAACTATTGGC
GGCAGCTCCTAAATGCGAAACTGATAACGCAAAGAAAGTTCGATAACTTA
ACTAAAGCTGAGAGGGGTGGCTTGTCTGAACTTGACAAGGCCGGATTTAT
TAAACGTCAGCTCGTGGAAACCCGCCAAATCACAAAGCATGTTCACAGA
TACTAGATTCCCGAATGAATACGAAATACGACGAGAACGATAAGCTGATT
CGGGAAGTCAAAGTAATCACTTTAAAGTCAAAATTGGTGTCGGACTTCAG
AAAGGATTTTCAATTCTATAAAGTTAGGGAGATAAATAACTACCACCATG
CGCACGACGCTTATCTTAATGCCGTCGTAGGGACCGCACTCATTAAGAAA
TACCCGAAGCTAGAAAGTGAGTTTGTGTATGGTGATTACAAAGTTTATGA
CGTCCGTAAGATGATCGCGAAAAGCGAACAGGAGATAGGCAAGGCTACAG
CCAAATACTTCTTTTATTCTAACATTATGAATTTCTTTAAGACGGAAATC
ACTCTGGCAAACGGAGAGATACGCAAACGACCTTTAATTGAAACCAATGG
GGAGACAGGTGAAATCGTATGGGATAAGGGCCGGGACTTCGCGACGGTGA
GAAAAGTTTTGTCCATGCCCCAAGTCAACATAGTAAAGAAAACTGAGGTG
CAGACCGGAGGGTTTTCAAAGGAATCGATTCTTCCAAAAAGGAATAGTGA
TAAGCTCATCGCTCGTAAAAAGGACTGGGACCCGAAAAAGTACGGTGGCT
TCGATAGCCCTACAGTTGCCTATTCTGTCCTAGTAGTGGCAAAAGTTGAG
AAGGGAAAATCCAAGAAACTGAAGTCAGTCAAAGAATTATTGGGGATAAC
GATTATGGAGCGCTCGTCTTTTGAAAAGAACCCCATCGACTTCCTTGAGG
CGAAAGGTTACAAGGAAGTAAAAAAGGATCTCATAATTAAACTACCAAAG
TATAGTCTGTTTGAGTTAGAAAATGGCCGAAAACGGATGTTGGCTAGCGC
CGGAGAGCTTCAAAAGGGGAACGAACTCGCACTACCGTCTAAATACGTGA
ATTTCCTGTATTTAGCGTCCCATTACGAGAAGTTGAAAGGTTCACCTGAA
GATAACGAACAGAAGCAACTTTTTGTTGAGCAGCACAAACATTATCTCGA
CGAAATCATAGAGCAAATTTCGGAATTCAGTAAGAGAGTCATCCTAGCTG
ATGCCAATCTGGACAAAGTATTAAGCGCATACAACAAGCACAGGGATAAA
CCCATACGTGAGCAGGCGGAAAATATTATCCATTTGTTTACTCTTACCAA
CCTCGGCGCTCCAGCCGCATTCAAGTATTTTGACACAACGATAGATCGCA
AACGATACACTTCTACCAAGGAGGTGCTAGACGCGACACTGATTCACCAA
TCCATCACGGGATTATATGAAACTCGGATAGATTTGTCACAGCTTGGGGG
TGACGGATCCCCCAAGAAGAAGAGGAAAGTCTCGAGCGACTACAAAGACC
ATGACGGTGATTATAAAGATCATGACATCGATTACAAGGATGACGATGAC
AAGGCTGCAGGATCAGGTGGAAGTGGCGGCAGCGGAGGTTCTGGATCCCA
ACTAGTCAAAAGTGAACTGGAGGAGAAGAAATCTGAACTTCGTCATAAAT
TGAAATATGTGCCTCATGAATATATTGAATTAATTGAAATTGCCAGAAAT
TCCACTCAGGATAGAATTCTTGAAATGAAGGTAATGGAATTTTTTATGAA
AGTTTATGGATATAGAGGTAAACATTTGGGTGGATCAAGGAAACCGGACG
GAGCAATTTATACTGTCGGATCTCCTATTGATTACGGTGTGATCGTGGAT
ACTAAAGCTTATAGCGGAGGTTATAATCTGCCAATTGGCCAAGCAGATGA
AATGCAACGATATGTCGAAGAAATCAAACACGAAACAAACATATCAACC
CTAATGAATGGTGGAAAGTCTATCCATCTTCTGTAACGGAATTTAAGTTT
TTATTTGTGAGTGGTCACTTTAAAGGAAACTACAAAGCTCAGCTTACACG
ATTAAATCATATCACTAATTGTAATGGAGCTGTTCTTAGTGTAGAAGAGC
TTTTAATTGGTGGAGAAATGATTAAAGCCGGCACATTAACCTTAGAGGAA
GTCAGACGGAAATTTAATAACGGCAGATAAACTTT
``` fCas9 (e.g., NLS-dCas9-GGS3linker-FokI):

(SEQ ID NO: 10)
```
ATGGACTACAAAGACCATGACGGTGATTATAAAGATCATGACATCGATTA
CAAGGATGACGATGACAAGATGGCCCCCAAGAAGAAGAGGAAGGTGGGCA
TTCACCGCGGGGTACCTATGGATAAAAAGTATTCTATTGGTTTAGCTATC
GGCACTAATTCCGTTGGATGGGCTGTCATAACCGATGAATACAAAGTACC
TTCAAAGAAATTTAAGGTGTTGGGGAACACAGACCGTCATTCGATTAAAA
AGAATCTTATCGGTGCCCTCCTATTCGATAGTGGCGAAACGGCAGAGGCG
ACTCGCCTGAAACGAACCGCTCGGAGAAGGTATACACGTCGCAAGAACCG
AATATGTTACTTACAAGAAATTTTTAGCAATGAGATGGCCAAAGTTGACG
ATTCTTTCTTTCACCGTTTGGAAGAGTCCTTCCTTGTCGAAGAGGACAAG
AAACATGAACGGCACCCCATCTTTGGAAACATAGTAGATGAGGTGGCATA
TCATGAAAGTACCCAACGATTTATCACCTCAGAAAAAGCTAGTTGACT
CAACTGATAAAGCGGACCTGAGGTTAATCTACTTGGCTCTTGCCCATATG
ATAAAGTTCCGTGGGCACTTTCTCATTGAGGGTGATCTAAATCCGGACAA
CTCGGATGTCGACAAACTGTTCATCCAGTTAGTACAAACCTATAATCAGT
TGTTTGAAGAACCCTATAAATGCAAGTGGCGTGGATGCGAAGGCTATT
CTTAGCGCCCGCCTCTCTAAATCCCGACGGCTAGAAAACCTGATCGCACA
ATTACCCGGAGAAGAAAAATGGGTTGTTCGGTAACCTTATAGCGCTCT
CACTAGGCCTGACACCAAATTTTAAGTCGAACTTCGACTTAGCTGAAGAT
GCCAAATTGCAGCTTAGTAAGGACACGTACGATGACGATCTCGACAATCT
```

```
ACTGGCACAAATTGGAGATCAGTATGCGGACTTATTTTTGGCTGCCAAAA
ACCTTAGCGATGCAATCCTCCTATCTGACATACTGAGAGTTAATACTGAG
ATTACCAAGGCGCCGTTATCCGCTTCAATGATCAAAAGGTACGATGAACA
TCACCAAGACTTGACACTTCTCAAGGCCCTAGTCCGTCAGCAACTGCCTG
AGAAATATAAGGAAATATTCTTTGATCAGTCGAAAAACGGGTACGCAGGT
TATATTGACGGCGGAGCGAGTCAAGAGGAATTCTACAAGTTTATCAAACC
CATATTAGAGAAGATGGATGGGACGGAAGAGTTGCTTGTAAAACTCAATC
GCGAAGATCTACTGCGAAAGCAGCGGACTTTCGACAACGGTAGCATTCCA
CATCAAATCCACTTAGGCGAATTGCATGCTATACTTAGAAGGCAGGAGGA
TTTTTATCCGTTCCTCAAAGACAATCGTGAAAAGATTGAGAAAATCCTAA
CCTTTCGCATACCTTACTATGTGGGACCCCTGGCCCGAGGGAACTCTCGG
TTCGCATGGATGACAAGAAAGTCCGAAGAAACGATTACTCCATGGAATTT
TGAGGAAGTTGTCGATAAAGGTGCGTCAGCTCAATCGTTCATCGAGAGGA
TGACCAACTTTGACAAGAATTTACCGAACGAAAAAGTATTGCCTAAGCAC
AGTTTACTTTACGAGTATTTCACAGTGTACAATGAACTCACGAAAGTTAA
GTATGTCACTGAGGGCATGCGTAAACCCGCCTTTCTAAGCGGAGAACAGA
AGAAAGCAATAGTAGATCTGTTATTCAAGACCAACCGCAAAGTGACAGTT
AAGCAATTGAAAGAGGACTACTTTAAGAAAATTGAATGCTTCGATTCTGT
CGAGATCTCCGGGGTAGAAGATCGATTTAATGCGTCACTTGGTACGTATC
ATGACCTCCTAAAGATAATTAAAGATAAGGACTTCCTGGATAACGAAGAG
AATGAAGATATCTTAGAAGATATAGTGTTGACTCTTACCCTCTTTGAAGA
TCGGAAATGATTGAGGAAAGACTAAAAACATACGCTCACCTGTTCGACG
ATAAGGTTATGAAACAGTTAAAGAGGCGTCGCTATACGGGCTGGGGACGA
TTGTCGCGGAAACTTATCAACGGGATAAGAGACAAGCAAAGTGGTAAAAC
TATTCTCGATTTTCTAAAGAGCGACGGCTTCGCCAATAGGAACTTTATGC
AGCTGATCCATGATGACTCTTTAACCTTCAAAGAGGATATACAAAAGGCA
CAGGTTTCCGGACAAGGGGACTCATTGCACGAACATATTGCGAATCTTGC
TGGTTCGCCAGCCATCAAAAAGGGCATACTCCAGACAGTCAAAGTAGTGG
ATGAGCTAGTTAAGGTCATGGGACGTCACAAACCGGAAAACATTGTAATC
GAGATGGCACGCGAAAATCAAACGACTCAGAAGGGGCAAAAAAACAGTCG
AGAGCGGATGAAGAGAATAGAAGAGGGTATTAAAGAACTGGGCAGCCAGA
TCTTAAAGGAGCATCCTGTGGAAAATACCCAATTGCAGAACGAGAAACTT
TACCTCTATTACCTACAAAATGGAAGGGACATGTATGTTGATCAGGAACT
GGACATAAACCGTTTATCTGATTACGACGTCGATGCCATTGTACCCCAAT
CCTTTTTGAAGGACGATTCAATCGACAATAAAGTGCTTACACGCTCGGAT
AAGAACCGAGGGAAAGTGACAATGTTCCAAGCGAGGAAGTCGTAAAGAA
AATGAAGAACTATTGGCGGCAGCTCCTAAATGCGAAACTGATAACGCAAA
GAAAGTTCGATAACTTAACTAAAGCTGAGAGGGGTGGCTTGTCTGAACTT
GACAAGGCCGGATTTATTAAACGTCAGCTCGTGGAAACCCGCCAAATCAC
AAAGCATGTTGCACAGATACTAGATTCCCGAATGAATACGAAATACGACG
AGAACGATAAGCTGATTCGGGAAGTCAAAGTAATCACTTTAAAGTCAAAA
TTGGTGTCGGACTTCAGAAAGGATTTTCAATTCTATAAAGTTAGGGAGAT
AAATAACTACCACCATGCGCACGACGCTTATCTTAATGCCGTCGTAGGGA
CCGCACTCATTAAGAAATACCCGAAGCTAGAAAGTGAGTTTGTGTATGGT
GATTACAAAGTTTATGACGTCCGTAAGATGATCGCGAAAAGCGAACAGGA
GATAGGCAAGGCTACAGCCAAATACTTCTTTTATTCTAACATTATGAATT
TCTTTAAGACGGAAATCACTCTGGCAAACGGAGAGATACGCAAACGACCT
TTAATTGAAACCAATGGGGAGACAGGTGAAATCGTATGGGATAAGGGCCG
GGACTTCGCGACGGTGAGAAAAGTTTTGTCCATGCCCCAAGTCAACATAG
TAAAGAAAACTGAGGTGCAGACCGGAGGGTTTTCAAAGGAATCGATTCTT
CCAAAAAGGAATAGTGATAAGCTCATCGCTCGTAAAAAGGACTGGGACCC
GAAAAAGTACGGTGGCTTCGATAGCCCTACAGTTGCCTATTCTGTCCTAG
TAGTGGCAAAAGTTGAGAAGGGAAAATCCAAGAAACTGAAGTCAGTCAAA
GAATTATTGGGGATAACGATTATGGAGCGCTCGTCTTTTGAAAAGAACCC
CATCGACTTCCTTGAGGCGAAAGGTTACAAGGAAGTAAAAAAGGATCTCA
TAATTAAACTACCAAAGTATAGTCTGTTTGAGTTAGAAAATGGCCGAAAA
CGGATGTTGGCTAGCGCCGGAGAGCTTCAAAAGGGGAACGAACTCGCACT
ACCGTCTAAATACGTGAATTTCCTGTATTTAGCGTCCCATTACGAGAAGT
TGAAAGGTTCACCTGAAGATAACGAACAGAAGCAACTTTTTGTTGAGCAG
CACAAACATTATCTCGACGAAATCATAGAGCAAATTTCGGAATTCAGTAA
GAGAGTCATCCTAGCTGATGCCAATCTGGACAAAGTATTAAGCGCATACA
ACAAGCACAGGGATAAACCCATACGTGAGCAGGCGGAAAATATTATCCAT
TTGTTTACTCTTACCAACCTCGGCGCTCCAGCCGCATTCAAGTATTTTGA
CACAACGATAGATCGCAAACGATACACTTCTACCAAGGAGGTGCTAGACG
CGACACTGATTCACCAATCCATCACGGGATTATATGAAACTCGGATAGAT
TTGTCACAGCTTGGGGGTGACTCAGGTGGAAGTGGCGGCAGCGGAGGTTC
TGGATCCCAACTAGTCAAAAGTGAACTGGAGGAGAAGAAATCTGAACTTC
GTCATAAATTGAAATATGTGCCTCATGAATATATTGAATTAATTGAAATT
GCCAGAAATTCCACTCAGGATAGAATTCTTGAAATGAAGGTAATGGAATT
TTTTATGAAAGTTTATGGATATAGAGGTAAACATTTGGGTGGATCAAGGA
AACCGGACGGAGCAATTTATACTGTCGGATCCCTATTGATTACGGTGTG
ATCGTGGATACTAAAGCTTATAGCGGAGGTTATAATCTGCCAATTGGCCA
AGCAGATGAAATGCAACGATATGTCGAAGAAATCAAACACGAAACAAAC
ATATCAACCCTAATGAATGGTGGAAAGTCTATCCATCTTCTGTAACGGAA
TTTAAGTTTTTATTTGTGAGTGGTCACTTTAAAGGAAACTACAAAGCTCA
GCTTACACGATTAAATCATATCACTAATTGTAATGGAGCTGTTCTTAGTG
TAGAAGAGCTTTTAATTGGTGGAGAAATGATTAAAGCCGGCACATTAACC
TTAGAGGAAGTCAGACGGAAATTTAATAACGGCGAGATAAACTTT
``` fCas9 (e.g., FokI-GGS3linker-dCas9-NLS):

(SEQ ID NO: 11)
```
ATGGGATCCCAACTAGTCAAAAGTGAACTGGAGGAGAAGAAATCTGAACT
TCGTCATAAATTGAAATATGTGCCTCATGAATATATTGAATTAATTGAAA
TTGCCAGAAATTCCACTCAGGATAGAATTCTTGAAATGAAGGTAATGGAA
TTTTTTATGAAAGTTTATGGATATAGAGGTAAACATTTGGGTGGATCAAG
GAAACCGGACGGAGCAATTTATACTGTCGGATCTCCTATTGATTACGGTG
TGATCGTGGATACTAAAGCTTATAGCGGAGGTTATAATCTGCCAATTGGC
CAAGCAGATGAAATGCAACGATATGTCGAAGAAAATCAAACACGAAACAA
ACATATCAACCCTAATGAATGGTGGAAAGTCTATCCATCTTCTGTAACGG
AATTTAAGTTTTTATTTGTGAGTGGTCACTTTAAAGGAAACTACAAAGCT
CAGCTTACACGATTAAATCATATCACTAATTGTAATGGAGCTGTTCTTAG
TGTAGAAGAGCTTTTAATTGGTGGAGAAATGATTAAAGCCGGCACATTAA
CCTTAGAGGAAGTCAGACGGAAATTTAATAACGGCGAGATAAACTTTGGC
GGTAGTGGGGGATCTGGGGGAAGTATGGATAAAAAGTATTCTATTGGTTT
AGCTATCGGCACTAATTCCGTTGGATGGGCTGTCATAACCGATGAATACA
AAGTACCTTCAAAGAAATTTAAGGTGTTGGGGAACACAGACCGTCATTCG
ATTAAAAAGAATCTTATCGGTGCCCTCCTATTCGATAGTGGCGAAACGGC
AGAGGCGACTCGCCTGAAACGAACCGCTCGGAGAAGGTATACACGTCGCA
AGAACCGAATATGTTACTTACAAGAAATTTTTAGCAATGAGATGGCCAAA
GTTGACGATTCTTTCTTTCACCGTTTGGAAGAGTCCTTCCTTGTCGAAGA
GGACAAGAAACATGAACGGCACCCCATCTTTGGAAACATAGTAGATGAGG
TGGCATATCATGAAAAGTACCCAACGATTTATCACCTCAGAAAAAGCTA
GTTGACTCAACTGATAAAGCGGACCTGAGGTTAATCTACTTGGCTCTTGC
CCATATGATAAAGTTCCGTGGGCACTTTCTCATTGAGGGTGATCTAAATC
CGGACAACTCGGATGTCGACAAACTGTTCATCCAGTTAGTACAAACCTAT
AATCAGTTGTTTGAAGAGAACCCTATAAATGCAAGTGGCGTGGATGCGAA
GGCTATTCTTAGCGCCCGCCTCTCTAAATCCCGACGGCTAGAAAACCTGA
TCGCACAATTACCCGGAGAGAAGAAAAATGGGTTGTTCGGTAACCTTATA
GCGCTCTCACTAGGCCTGACACCAAATTTTAAGTCGAACTTCGACTTAGC
TGAAGATGCCAAATTGCAGCTTAGTAAGGACACGTACGATGACGATCTCG
ACAATCTACTGGCACAAATTGGAGATCAGTATGCGGACTTATTTTTGGCT
GCCAAAAACCTTAGCGATGCAATCCTCCTATCTGACATACTGAGAGTTAA
TACTGAGATTACCAAGGCGCCGTTATCCGCTTCAATGATCAAAAGGTACG
ATGAACATCACCAAGACTTGACACTTCTCAAGGCCCTAGTCCGTCAGCAA
CTGCCTGAGAAATATAAGGAAATATTCTTTGATCAGTCGAAAAACGGGTA
CGCAGGTTATATTGACGGCGGAGCGAGTCAAGAGGAATTCTACAAGTTTA
TCAAACCCATATTAGAGAAGATGGATGGGACGGAAGAGTTGCTTGTAAAA
CTCAATCGCGAAGATCTACTGCGAAAGCAGCGGACTTTCGACAACGGTAG
CATTCCACATCAAATCCACTTAGGCGAATTGCATGCTATACTTAGAAGGC
AGGAGGATTTTTATCCGTTCCTCAAAGACAATCGTGAAAAGATTGAGAAA
ATCCTAACCTTTCGCATACCTTACTATGTGGGACCCCTGGCCCGAGGGAA
CTCTCGGTTCGCATGGATGACAAGAAAGTCCGAAGAAACGATTACTCCAT
GGAATTTTGAGGAAGTTGTCGATAAAGGTGCGTCAGCTCAATCGTTCATC
GAGAGGATGACCAACTTTGACAAGAATTTACCGAACGAAAAAGTATTGCC
TAAGCACAGTTTACTTTACGAGTATTTCACAGTGTACAATGAACTCACGA
AAGTTAAGTATGTCACTGAGGGCATGCGTAAACCCGCCTTTCTAAGCGGA
GAACAGAAGAAAGCAATAGTAGATCTGTTATTCAAGACCAACCGCAAAGT
GACAGTTAAGCAATTGAAAGAGGACTACTTTAAGAAAATTGAATGCTTCG
ATTCTGTCGAGATCTCCGGGGTAGAAGATCGATTTAATGCGTCACTTGGT
ACGTATCATGACCTCCTAAAGATAATTAAAGATAAGGACTTCCTGGATAA
CGAAGAGAATGAAGATATCTTAGAAGATATAGTGTTGACTCTTACCCTCT
TTGAAGATCGGGAAATGATTGAGGAAAGACTAAAAACATACGCTCACCTG
TTCGACGATAAGGTTATGAAACAGTTAAAGAGGCGTCGCTATACGGGCTG
GGGACGATTGTCGCGGAAACTTATCAACGGGATAAGAGACAAGCAAAGTG
GTAAAACTATTCTCGATTTTCTAAAGAGCGACGGCTTCGCCAATAGGAAC
TTTATGCAGCTGATCCATGATGACTCTTTAACCTTCAAAGAGGATATACA
AAAGGCACAGGTTTCCGGACAAGGGGACTCATTGCACGAACATATTGCGA
ATCTTGCTGGTTCGCCAGCCATCAAAAAGGGCATACTCCAGACAGTCAAA
GTAGTGGATGAGCTAGTTAAGGTCATGGGACGTCACAAACCGGAAAACAT
TGTAATCGAGATGGCACGCGAAAATCAAACGACTCAGAAGGGGCAAAAAA
ACAGTCGAGAGCGGATGAAGAGAATAGAAGAGGGTATTAAAGAACTGGGC
AGCCAGATCTTAAAGGAGCATCCTGTGGAAAATACCCAATTGCAGAACGA
GAAACTTTACCTCTATTACCTACAAAATGGAAGGGACATGTATGTTGATC
AGGAACTGGACATAAACCGTTTATCTGATTACGACGTCGATGCCATTGTA
CCCCAATCCTTTTTGAAGGACGATTCAATCGACAATAAAGTGCTTACACG
CTCGGATAAGAACCGAGGGAAAAGTGACAATGTTCCAAGCGAGGAAGTCG
TAAAGAAAATGAAGAACTATTGGCGGCAGCTCCTAAATGCGAAACTGATA
ACGCAAAGAAAGTTCGATAACTTAACTAAAGCTGAGAGGGGTGGCTTGTC
TGAACTTGACAAGGCCGGATTTATTAAACGTCAGCTCGTGGAAACCCGCC
AAATCACAAAGCATGTTGCACAGATACTAGATTCCCGAATGAATACGAAA
TACGACGAGAACGATAAGCTGATTCGGGAAGTCAAAGTAATCACTTTAAA
GTCAAAATTGGTGTCGGACTTCAGAAAGGATTTTCAATTCTATAAAGTTA
GGGAGATAAATAACTACCACCATGCGCACGACGCTTATCTTAATGCCGTC
GTAGGGACCGCACTCATTAAGAAATACCCGAAGCTAGAAAGTGAGTTTGT
GTATGGTGATTACAAAGTTTATGACGTCCGTAAGATGATCGCGAAAAGCG
AACAGGAGATAGGCAAGGCTACAGCCAAATACTTCTTTTATTCTAACATT
ATGAATTTCTTTAAGACGGAAATCACTCTGGCAAACGGAGAGATACGCAA
ACGACCTTTAATTGAAACCAATGGGGAGACAGGTGAAATCGTATGGGATA
AGGGCCGGGACTTCGCGACGGTGAGAAAAGTTTTGTCCATGCCCCAAGTC
AACATAGTAAAGAAAACTGAGGTGCAGACCGGAGGGTTTTCAAAGGAATC
```

GATTCTTCCAAAAAGGAATAGTGATAAGCTCATCGCTCGTAAAAAGGACT

GGGACCCGAAAAAGTACGGTGGCTTCGATAGCCCTACAGTTGCCTATTCT

GTCCTAGTAGTGGCAAAAGTTGAGAAGGGAAAATCCAAGAAACTGAAGTC

AGTCAAAGAATTATTGGGGATAACGATTATGGAGCGCTCGTCTTTTGAAA

AGAACCCCATCGACTTCCTTGAGGCGAAAGGTTACAAGGAAGTAAAAAAG

GATCTCATAATTAAACTACCAAAGTATAGTCTGTTTGAGTTAGAAAATGG

CCGAAAACGGATGTTGGCTAGCGCCGGAGAGCTTCAAAAGGGGAACGAAC

TCGCACTACCGTCTAAATACGTGAATTTCCTGTATTTAGCGTCCCATTAC

GAGAAGTTGAAAGGTTCACCTGAAGATAACGAACAGAAGCAACTTTTTGT

TGAGCAGCACAAACATTATCTCGACGAAATCATAGAGCAAATTTCGGAAT

TCAGTAAGAGAGTCATCCTAGCTGATGCCAATCTGGACAAAGTATTAAGC

GCATACAACAAGCACAGGGATAAACCCATACGTGAGCAGGCGGAAAATAT

TATCCATTTGTTTACTCTTACCAACCTCGGCGCTCCAGCCGCATTCAAGT

ATTTTGACACAACGATAGATCGCAAACGATACACTTCTACCAAGGAGGTG

CTAGACGCGACACTGATTCACCAATCCATCACGGGATTATATGAAACTCG

GATAGATTTGTCACAGCTTGGGGGTGACGGATCCCCCAAGAAGAAGAGGA

AAGTCTCGAGCGACTACAAAGACCATGACGGTGATTATAAAGATCATGAC

ATCGATTACAAGGATGACGATGACAAGGCTGCAGGA fCas9 (e.g., NLS-FokI-GGS3linker-dCas9):

(SEQ ID NO: 12)
ATGGACTACAAAGACCATGACGGTGATTATAAAGATCATGACATCGATTA

CAAGGATGACGATGACAAGATGGCCCCCAAGAAGAAGAGGAAGGTGGGCA

TTCACCGCGGGGTACCTGGAGGTTCTATGGGATCCCAACTAGTCAAAAGT

GAACTGGAGGAGAAGAAATCTGAACTTCGTCATAAATTGAAATATGTGCC

TCATGAATATATTGAATTAATTGAAATTGCCAGAAATTCCACTCAGGATA

GAATTCTTGAAATGAAGGTAATGGAATTTTTTATGAAAGTTTATGGATAT

AGAGGTAAACATTTGGGTGGATCAAGGAAACCGGACGGAGCAATTTATAC

TGTCGGATCTCCTATTGATTACGGTGTGATCGTGGATACTAAAGCTTATA

GCGGAGGTTATAATCTGCCAATTGGCCAAGCAGATGAAATGCAACGATAT

GTCGAAGAAATCAAACACGAAACAAACATATCAACCCTAATGAATGGTG

GAAAGTCTATCCATCTTCTGTAACGGAATTTAAGTTTTTATTTGTGAGTG

GTCACTTTAAAGGAAACTACAAAGCTCAGCTTACACGATTAAATCATATC

ACTAATTGTAATGGAGCTGTTCTTAGTGTAGAAGAGCTTTTAATTGGTGG

AGAAATGATTAAAGCCGGCACATTAACCTTAGAGGAAGTCAGACGGAAAT

TTAATAACGGCGAGATAAACTTTGGCGGTAGTGGGGGATCTGGGGGAAGT

ATGGATAAAAAGTATTCTATTGGTTTAGCTATCGGCACTAATTCCGTTGG

ATGGGCTGTCATAACCGATGAATACAAAGTACCTTCAAAGAAATTTAAGG

TGTTGGGGAACACAGACCGTCATTCGATTAAAAAGAATCTTATCGGTGCC

CTCCTATTCGATAGTGGCGAAACGGCAGAGGCGACTCGCCTGAAACGAAC

CGCTCGGAGAAGGTATACACGTCGCAAGAACCGAATATGTTACTTACAAG

AAATTTTTAGCAATGAGATGGCCAAAGTTGACGATTCTTTCTTTCACCGT

TTGGAAGAGTCCTTCCTTGTCGAAGAGGACAAGAAACATGAACGGCACCC

CATCTTTGGAAACATAGTAGATGAGGTGGCATATCATGAAAAGTACCCAA

CGATTTATCACCTCAGAAAAAAGCTAGTTGACTCAACTGATAAAGCGGAC

CTGAGGTTAATCTACTTGGCTCTTGCCCATATGATAAAGTTCCGTGGGCA

CTTTCTCATTGAGGGTGATCTAAATCCGGACAACTCGGATGTCGACAAAC

TGTTCATCCAGTTAGTACAAACCTATAATCAGTTGTTTGAAGAGAACCCT

ATAAATGCAAGTGGCGTGGATGCGAAGGCTATTCTTAGCGCCCGCCTCTC

TAAATCCCGACGGCTAGAAAACCTGATCGCACAATTACCCGGAGAGAAGA

AAAATGGGTTGTTCGGTAACCTTATAGCGCTCTCACTAGGCCTGACACCA

AATTTTAAGTCGAACTTCGACTTAGCTGAAGATGCCAAATTGCAGCTTAG

TAAGGACACGTACGATGACGATCTCGACAATCTACTGGCACAAATTGGAG

ATCAGTATGCGGACTTATTTTTGGCTGCCAAAAACCTTAGCGATGCAATC

CTCCTATCTGACATACTGAGAGTTAATACTGAGATTACCAAGGCGCCGTT

ATCCGCTTCAATGATCAAAAGGTACGATGAACATCACCAAGACTTGACAC

TTCTCAAGGCCCTAGTCCGTCAGCAACTGCCTGAGAAATATAAGGAAATA

TTCTTTGATCAGTCGAAAAACGGGTACGCAGGTTATATTGACGGCGGAGC

GAGTCAAGAGGAATTCTACAAGTTTATCAAACCCATATTAGAGAAGATGG

ATGGGACGGAAGAGTTGCTTGTAAAACTCAATCGCGAAGATCTACTGCGA

AAGCAGCGGACTTTCGACAACGGTAGCATTCCACATCAAATCCACTTAGG

CGAATTGCATGCTATACTTAGAAGGCAGGAGGATTTTTATCCGTTCCTCA

AAGACAATCGTGAAAAGATTGAGAAAATCCTAACCTTTCGCATACCTTAC

TATGTGGGACCCCTGGCCCGAGGGAACTCTCGGTTCGCATGGATGACAAG

AAAGTCCGAAGAAACGATTACTCCATGGAATTTTGAGGAAGTTGTCGATA

AAGGTGCGTCAGCTCAATCGTTCATCGAGAGGATGACCAACTTTGACAAG

AATTTACCGAACGAAAAAGTATTGCCTAAGCACAGTTTACTTTACGAGTA

TTTCACAGTGTACAATGAACTCACGAAAGTTAAGTATGTCACTGAGGGCA

TGCGTAAACCCGCCTTTCTAAGCGGAGAACAGAAGAAAGCAATAGTAGAT

CTGTTATTCAAGACCAACCGCAAAGTGACAGTTAAGCAATTGAAAGAGGA

CTACTTTAAGAAAATTGAATGCTTCGATTCTGTCGAGATCTCCGGGGTAG

AAGATCGATTTAATGCGTCACTTGGTACGTATCATGACCTCCTAAAGATA

ATTAAAGATAAGGACTTCCTGGATAACGAAGAGAATGAAGATATCTTAGA

AGATATAGTGTTGACTCTTACCCTCTTTGAAGATCGGGAAATGATTGAGG

AAAGACTAAAAACATACGCTCACCTGTTCGACGATAAGGTTATGAAACAG

TTAAAGAGGCGTCGCTATACGGGCTGGGACGATTGTCGCGGAAACTTAT

CAACGGGATAAGAGACAAGCAAAGTGGTAAAACTATTCTCGATTTTCTAA

AGAGCGACGGCTTCGCCAATAGGAACTTTATGCAGCTGATCCATGATGAC

TCTTTAACCTTCAAAGAGGATATACAAAAGGCACAGGTTTCCGGACAAGG

GGACTCATTGCACGAACATATTGCGAATCTTGCTGGTTCGCCAGCCATCA

AAAAGGGCATACTCCAGACAGTCAAAGTAGTGGATGAGCTAGTTAAGGTC

ATGGGACGTCACAAACCGGAAAACATTGTAATCGAGATGGCACGCGAAAA

-continued

TCAAACGACTCAGAAGGGGCAAAAAAACAGTCGAGAGCGGATGAAGAGAA
TAGAAGAGGGTATTAAAGAACTGGGCAGCCAGATCTTAAAGGAGCATCCT
GTGGAAAATACCCAATTGCAGAACGAGAAACTTTACCTCTATTACCTACA
AAATGGAAGGGACATGTATGTTGATCAGGAACTGGACATAAACCGTTTAT
CTGATTACGACGTCGATGCCATTGTACCCCAATCCTTTTTGAAGGACGAT
TCAATCGACAATAAAGTGCTTACACGCTCGGATAAGAACCGAGGGAAAAG
TGACAATGTTCCAAGCGAGGAAGTCGTAAAGAAAATGAAGAACTATTGGC
GGCAGCTCCTAAATGCGAAACTGATAACGCAAAGAAAGTTCGATAACTTA
ACTAAAGCTGAGAGGGGTGGCTTGTCTGAACTTGACAAGGCCGGATTTAT
TAAACGTCAGCTCGTGGAAACCCGCCAAATCACAAAGCATGTTGCACAGA
TACTAGATTCCCGAATGAATACGAAATACGACGAGAACGATAAGCTGATT
CGGGAAGTCAAAGTAATCACTTTAAAGTCAAAATTGGTGTCGGACTTCAG
AAAGGATTTTCAATTCTATAAAGTTAGGGAGATAAATAACTACCACCATG
CGCACGACGCTTATCTTAATGCCGTCGTAGGGACCGCACTCATTAAGAAA
TACCCGAAGCTAGAAAGTGAGTTTGTGTATGGTGATTACAAAGTTTATGA
CGTCCGTAAGATGATCGCGAAAAGCGAACAGGAGATAGGCAAGGCTACAG
CCAAATACTTCTTTTATTCTAACATTATGAATTTCTTTAAGACGGAAATC
ACTCTGGCAAACGGAGAGATACGCAAACGACCTTTAATTGAAACCAATGG
GGAGACAGGTGAAATCGTATGGGATAAGGGCCGGGACTTCGCGACGGTGA
GAAAAGTTTTGTCCATGCCCCAAGTCAACATAGTAAAGAAAACTGAGGTG
CAGACCGGAGGGTTTTCAAAGGAATCGATTCTTCCAAAAAGGAATAGTGA
TAAGCTCATCGCTCGTAAAAAGGACTGGGACCCGAAAAAGTACGGTGGCT
TCGATAGCCCTACAGTTGCCTATTCTGTCCTAGTAGTGGCAAAAGTTGAG
AAGGGAAAATCCAAGAAACTGAAGTCAGTCAAAGAATTATTGGGGATAAC
GATTATGGAGCGCTCGTCTTTTGAAAAGAACCCCATCGACTTCCTTGAGG
CGAAAGGTTACAAGGAAGTAAAAAAGGATCTCATAATTAAACTACCAAAG
TATAGTCTGTTTGAGTTAGAAAATGGCCGAAAACGGATGTTGGCTAGCGC
CGGAGAGCTTCAAAAGGGGAACGAACTCGCACTACCGTCTAAATACGTGA
ATTTCCTGTATTTAGCGTCCCATTACGAGAAGTTGAAAGGTTCACCTGAA
GATAACGAACAGAAGCAACTTTTTGTTGAGCAGCACAAACATTATCTCGA
CGAAATCATAGAGCAAATTTCGGAATTCAGTAAGAGAGTCATCCTAGCTG
ATGCCAATCTGGACAAAGTATTAAGCGCATACAACAAGCACAGGGATAAA
CCCATACGTGAGCAGGCGGAAAATATTATCCATTTGTTTACTCTTACCAA
CCTCGGCGCTCCAGCCGCATTCAAGTATTTTGACACAACGATAGATCGCA
AACGATACACTTCTACCAAGGAGGTGCTAGACGCGACACTGATTCACCAA
TCCATCACGGGATTATATGAAACTCGGATAGATTTGTCACAGCTTGGGGG
TGAC fCas9:

(SEQ ID NO: 319)
ATGGACTACAAAGACCATGACGGTGATTATAAAGATCATGACATCGATTA
CAAGGATGACGATGACAAGATGGCCCCCAAGAAGAAGAGGAAGGTGGGCA
TTCACCGCGGGGTACCTGGAGGTTCTGGATCCCAACTAGTCAAAAGTGAA
CTGGAGGAGAAGAAATCTGAACTTCGTCATAAATTGAAATATGTGCCTCA
TGAATATATTGAATTAATTGAAATTGCCAGAAATTCCACTCAGGATAGAA
TTCTTGAAATGAAGGTAATGGAATTTTTTATGAAAGTTTATGGATATAGA
GGTAAACATTTGGGTGGATCAAGGAAACCGGACGGAGCAATTTATACTGT
CGGATCTCCTATTGATTACGGTGTGATCGTGGATACTAAAGCTTATAGCG
GAGGTTATAATCTGCCAATTGGCCAAGCAGATGAAATGCAACGATATGTC
GAAGAAAATCAAACACGAAACAAACATATCAACCCTAATGAATGGTGGAA
AGTCTATCCATCTTCTGTAACGGAATTTAAGTTTTTATTTGTGAGTGGTC
ACTTTAAAGGAAACTACAAAGCTCAGCTTACACGATTAAATCATATCACT
AATTGTAATGGAGCTGTTCTTAGTGTAGAAGAGCTTTTAATTGGTGGAGA
AATGATTAAAGCCGGCACATTAACCTTAGAGGAAGTCAGACGGAAATTTA
ATAACGGCGAGATAAACTTTAGCGGCAGCGAGACTCCCGGGACCTCAGAG
TCCGCCACACCCGAAAGTGATAAAAGTATTCTATTGGTTTAGCTATCGG
CACTAATTCCGTTGGATGGGCTGTCATAACCGATGAATACAAAGTACCTT
CAAAGAAATTTAAGGTGTTGGGAACACAGACCGTCATTCGATTAAAAAG
AATCTTATCGGTGCCCTCCTATTCGATAGTGGCGAAACGGCAGAGGCGAC
TCGCCTGAAACGAACCGCTCGGAGAAGGTATACACGTCGCAAGAACCGAA
TATGTTACTTACAAGAAATTTTTAGCAATGAGATGGCCAAAGTTGACGAT
TCTTTCTTTCACCGTTTGGAAGAGTCCTTCCTTGTCGAAGAGGACAAGAA
ACATGAACGGCACCCCATCTTTGGAAACATAGTAGATGAGGTGGCATATC
ATGAAAAGTACCCAACGATTTATCACCTCAGAAAAAAGCTAGTTGACTCA
ACTGATAAAGCGGACCTGAGGTTAATCTACTTGGCTCTTGCCCATATGAT
AAAGTTCCGTGGGCACTTTCTCATTGAGGGTGATCTAAATCCGGACAACT
CGGATGTCGACAAACTGTTCATCCAGTTAGTACAAACCTATAATCAGTTG
TTTGAAGAACCCTATAAATGCAAGTGGCGTGGATGCGAAGGCTATTCT
TAGCGCCCGCCTCTCTAAATCCCGACGGCTAGAAAACCTGATCGCACAAT
TACCCGGAGAGAAGAAAATGGGTTGTTCGGTAACCTTATAGCGCTCTCA
CTAGGCCTGACACCAAATTTTAAGTCGAACTTCGACTTAGCTGAAGATGC
CAAATTGCAGCTTAGTAAGGACACGTACGATGACGATCTCGACAATCTAC
TGGCACAAATTGGAGATCAGTATGCGGACTTATTTTTGGCTGCCAAAAAC
CTTAGCGATGCAATCCTCCTATCTGACATACTGAGAGTTAATACTGAGAT
TACCAAGGCGCCGTTATCCGCTTCAATGATCAAAAGGTACGATGAACATC
ACCAAGACTTGACACTTCTCAAGGCCCTAGTCCGTCAGCAACTGCCTGAG
AAATATAAGGAAATATCTTTGATCAGTCGAAAAACGGGTACGCAGGTTA
TATTGACGGCGGAGCGAGTCAAGAGGAATTCTACAAGTTTATCAAACCCA
TATTAGAGAAGATGGATGGGACGGAAGAGTTGCTTGTAAAACTCAATCGC

```
GAAGATCTACTGCGAAAGCAGCGGACTTTCGACAACGGTAGCATTCCACA
TCAAATCCACTTAGGCGAATTGCATGCTATACTTAGAAGGCAGGAGGATT
TTTATCCGTTCCTCAAAGACAATCGTGAAAAGATTGAGAAAATCCTAACC
TTTCGCATACCTTACTATGTGGGACCCCTGGCCCGAGGGAACTCTCGGTT
CGCATGGATGACAAGAAAGTCCGAAGAAACGATTACTCCATGGAATTTTG
AGGAAGTTGTCGATAAAGGTGCGTCAGCTCAATCGTTCATCGAGAGGATG
ACCAACTTTGACAAGAATTTACCGAACGAAAAGTATTGCCTAAGCACAG
TTTACTTTACGAGTATTTCACAGTGTACAATGAACTCACGAAAGTTAAGT
ATGTCACTGAGGGCATGCGTAAACCCGCCTTTCTAAGCGGAGAACAGAAG
AAAGCAATAGTAGATCTGTTATTCAAGACCAACCGCAAAGTGACAGTTAA
GCAATTGAAAGAGGACTACTTTAAGAAAATTGAATGCTTCGATTCTGTCG
AGATCTCCGGGGTAGAAGATCGATTTAATGCGTCACTTGGTACGTATCAT
GACCTCCTAAAGATAATTAAAGATAAGGACTTCCTGGATAACGAAGAGAA
TGAAGATATCTTAGAAGATATAGTGTTGACTCTTACCCTCTTTGAAGATC
GGGAAATGATTGAGGAAAGACTAAAAACATACGCTCACCTGTTCGACGAT
AAGGTTATGAAACAGTTAAAGAGGCGTCGCTATACGGGCTGGGGACGATT
GTCGCGGAAACTTATCAACGGGATAAGAGACAAGCAAAGTGGTAAAACTA
TTCTCGATTTTCTAAAGAGCGACGGCTTCGCCAATAGGAACTTTATGCAG
CTGATCCATGATGACTCTTTAACCTTCAAAGAGGATATACAAAAGGCACA
GGTTTCCGGACAAGGGGACTCATTGCACGAACATATTGCGAATCTTGCTG
GTTCGCCAGCCATCAAAAAGGGCATACTCCAGACAGTCAAAGTAGTGGAT
GAGCTAGTTAAGGTCATGGGACGTCACAAACCGGAAAACATTGTAATCGA
GATGGCACGCGAAAATCAAACGACTCAGAAGGGGCAAAAAAACAGTCGAG
AGCGGATGAAGAGAATAGAAGAGGGTATTAAAGAACTGGGCAGCCAGATC
TTAAAGGAGCATCCTGTGGAAAATACCCAATTGCAGAACGAGAAACTTTA
CCTCTATTACCTACAAAATGGAAGGGACATGTATGTTGATCAGGAACTGG
ACATAAACCGTTTATCTGATTACGACGTCGATGCCATTGTACCCCAATCC
TTTTTGAAGGACGATTCAATCGACAATAAAGTGCTTACACGCTCGGATAA
GAACCGAGGGAAAAGTGACAATGTTCCAAGCGAGGAAGTCGTAAAGAAAA
TGAAGAACTATTGGCGGCAGCTCCTAAATGCGAAACTGATAACGCAAAGA
AAGTTCGATAACTTAACTAAAGCTGAGAGGGGTGGCTTGTCTGAACTTGA
CAAGGCCGGATTTATTAAACGTCAGCTCGTGGAAACCCGCCAAATCACAA
AGCATGTTGCACAGATACTAGATTCCCGAATGAATACGAAATACGACGAG
AACGATAAGCTGATTCGGGAAGTCAAAGTAATCACTTTAAAGTCAAAATT
GGTGTCGGACTTCAGAAAGGATTTTCAATTCTATAAAGTTAGGGAGATAA
ATAACTACCACCATGCGCACGACGCTTATCTTAATGCCGTCGTAGGGACC
GCACTCATTAAGAAATACCCGAAGCTAGAAAGTGAGTTTGTGTATGGTGA
TTACAAAGTTTATGACGTCCGTAAGATGATCGCGAAAAGCGAACAGGAGA
TAGGCAAGGCTACAGCCAAATACTTCTTTTATTCTAACATTATGAATTTC
TTTAAGACGGAAATCACTCTGGCAAACGGAGAGATACGCAAACGACCTTT
AATTGAAACCAATGGGGAGACAGGTGAAATCGTATGGGATAAGGGCCGGG
ACTTCGCGACGGTGAGAAAAGTTTTGTCCATGCCCCAAGTCAACATAGTA
AAGAAAACTGAGGTGCAGACCGGAGGGTTTTCAAAGGAATCGATTCTTCC
AAAAAGGAATAGTGATAAGCTCATCGCTCGTAAAAAGGACTGGGACCCGA
AAAAGTACGGTGGCTTCGATAGCCCTACAGTTGCCTATTCTGTCCTAGTA
GTGGCAAAAGTTGAGAAGGGAAAATCCAAGAAACTGAAGTCAGTCAAAGA
ATTATTGGGGATAACGATTATGGAGCGCTCGTCTTTTGAAAAGAACCCCA
TCGACTTCCTTGAGGCGAAAGGTTACAAGGAAGTAAAAAAGGATCTCATA
ATTAAACTACCAAAGTATAGTCTGTTTGAGTTAGAAAATGGCCGAAAACG
GATGTTGGCTAGCGCCGGAGAGCTTCAAAAGGGGAACGAACTCGCACTAC
CGTCTAAATACGTGAATTTCCTGTATTTAGCGTCCCATTACGAGAAGTTG
AAAGGTTCACCTGAAGATAACGAACAGAAGCAACTTTTTGTTGAGCAGCA
CAAACATTATCTCGACGAAATCATAGAGCAAATTTCGGAATTCAGTAAGA
GAGTCATCCTAGCTGATGCCAATCTGGACAAAGTATTAAGCGCATACAAC
AAGCACAGGGATAAACCCATACGTGAGCAGGCGGAAAATATTATCCATTT
GTTTACTCTTACCAACCTCGGCGCTCCAGCCGCATTCAAGTATTTTGACA
CAACGATAGATCGCAAACGATACACTTCTACCAAGGAGGTGCTAGACGCG
ACACTGATTCACCAATCCATCACGGGATTATATGAAACTCGGATAGATTT
GTCACAGCTTGGGGGTGAC
```

In some embodiments, an inventive fusion protein (e.g., fCas9) corresponds to or is encoded by a homologue of any one of SEQ ID NO:9-12 or SEQ ID NO:319.

In some embodiments, an inventive fusion protein (e.g., fCas9) comprises, in part of in whole, one or more of the amino acid sequences set forth as SEQ ID NO:5, SEQ ID NO:320, SEQ ID NO:6, SEQ ID NO:16, SEQ ID NO:318, and SEQ ID NO:321, as provided herein and shown below. The various domains corresponding to SEQ ID NO:5, SEQ ID NO:320, SEQ ID NO:6, SEQ ID NO:16, SEQ ID NO:318, and SEQ ID NO:321 may be arranged in any order with respect to each other. For example, in some embodiments, a dCas9 domain (e.g., SEQ ID NO:5 or SEQ ID NO:320) is at the amino or carboxy terminus, or is somewhere in between the amino and carboxy termini. Similarly, each of the other domains corresponding to SEQ ID NO:6, SEQ ID NO:16, SEQ ID NO:318, and SEQ ID NO:321 may be at the amino or carboxy terminus, or somewhere in between the amino and carboxy termini of an inventive fusion protein (e.g., fCas9). Examples of inventive fusion proteins having various domain arrangements include the inventive fusion proteins corresponding to SEQ ID NOs:9-12 and SEQ ID NO:319. In some embodiments, an inventive fusion protein comprises additional or other domains, such as other linkers, other NLS domains, other nuclease domains, or other Cas9 domains, which may be in addition to or substituted for any of the domains as provided herein.

FokI Cleavage Domain:

(SEQ ID NO: 6)
GSQLVKSELEEKKSELRHKLKYVPHEYIELIEIARNSTQDRILEMKVMEF
FMKVYGYRGKHLGGSRKPDGAIYTVGSPIDYGVIVDTKAYSGGYNLPIGQ

-continued dCas9:

(SEQ ID NO: 320)
DKKYSIGLAIGTNSVGWAVITDEYKVPSKKFKVLGNTDRHSIKKNLIGAL

LFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPI

NASGVDAKAILSARLSKSRRLENLIAQLPGEKKNGLFGNLIALSLGLTPN

FKSNFDLAEDAKLQLSKDTYDDDLDNLLAQIGDQYADLFLAAKNLSDAIL

LSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYY

VGPLARGNSRFAWMTRKSEETITPWNFEEVVDKGASAQSFIERMTNFDKN

LPNEKVLPKHSLLYEYFTVYNELTKVKYVTEGMRKPAFLSGEQKKAIVDL

LFKTNRKVTVKQLKEDYFKKIECFDSVEISGVEDRFNASLGTYHDLLKII

KDKDFLDNEENEDILEDIVLTLTLFEDREMIEERLKTYAHLFDDKVMKQL

KRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDAIVPQSFLKDDS

IDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEK

GKSKKLKSVKELLGITIMERSSFEKNPIDFLEAKGYKEVKKDLIIKLPKY

SLFELENGRKRMLASAGELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKRYTSTKEVLDATLIHQS

ITGLYETRIDLSQLGGD

3×FLAG TAG:

MDYKDHDGDYKDHDIDYKDDDDK    (SEQ ID NO: 321)

NLS Domain:

MAPKKKRKVGIHRGVP    (SEQ ID NO: 318)

XTEN Linker:

SGSETPGTSESATPES    (SEQ ID NO: 16)

In some embodiments, the fusion proteins forming the dimer are coordinated through the action of a single extended gRNA (e.g., as opposed to two separate gRNAs, each binding a monomer of the fusion protein dimer). Thus, in some aspects, the single extended gRNA contains at least two portions, separated by a linker sequence, that complement the target nucleic acid (e.g., bind the target nucleic acid at two distinct sites), and the gRNA is able to bind at least two fusion proteins, as described herein. This is exemplified by the schematic shown in FIG. 1B. In some embodiments, the linker sequence separating the two portions in the extended gRNA has complementarity with the target sequence. In some embodiments, the extended gRNA is at least 50, at least 60, at least 70, at least 80, at least 90, at least 100, at least 125, at least 150, at least 175, at least 200, at least 250, at least 300, at least 350, at least 400, at least 500, at least 600, at least 700, at least 800, at least 900, or at least 1000 or more nucleotides in length. Whether the fusion proteins are coordinated through separate or a single gRNA, to form dimers that can cleave a target nucleic acid, it is expected that the specificity of such cleavage is enhanced (e.g., reduced or no off-target cleavage) as compared to nucleases having a single target nucleic acid binding site. Methods for determining the specificity of a nuclease are known (see e.g., published PCT Application, WO 2013/066438; pending provisional application U.S. 61/864,289; and Pattanayak, V., Ramirez, C. L., Joung, J. K. & Liu, D. R. Revealing off-target cleavage specificities of zinc-finger nucleases by in vitro selection. *Nature Methods* 8, 765-770 (2011), the entire contents of each of which are incorporated herein by reference).

Figure 4:
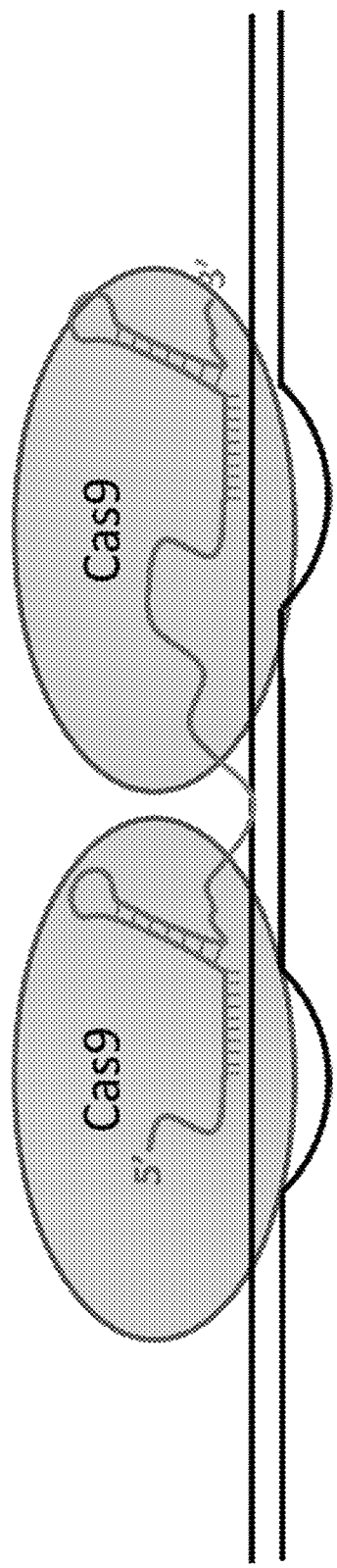
FIG. 4 shows how two Cas9 proteins can be coordinated through the action of a single extended RNA containing two distinct gRNA motifs. Each gRNA targeting region is shortened, such that a single Cas9:gRNA unit cannot bind efficiently by itself. The normal 20 nt targeting sequence has been altered so that some portion (e.g., the 5' initial 10 nt) has been changed to some non-specific linker sequence, such as AAAAAAAAAA (SEQ ID NO:13), with only 10 nt of the gRNA remaining to direct target binding (alternatively this 5' 10 nt is truncated entirely). This "low-affinity" gRNA unit exists as part of a tandem gRNA construct with a second, distinct low-affinity gRNA unit downstream, separated by a linker sequence. In some embodiments, there are more than two low-affinity gRNA units (e.g., at least 3, at least 4, at least 5, etc.). In some embodiments, the linker comprises a target nucleic acid complementary sequence (e.g., as depicted by the linker region contacting the DNA target).

According to another embodiment, dimers of Cas9 protein are provided. In some embodiments, the dimers are coordinated through the action of a single extended gRNA that comprises at least two portions that complement the target nucleic acid. In some embodiments, the portions complementary to the target nucleic acid comprise no more than 25, no more than 24, no more than 23, no more than 22, no more than 21, no more than 20, no more than 19, no more than 18, no more than 17, no more than 16, no more than 15, no more than 14, no more than 13, no more than 12, no more than 11, no more than 10, no more than 9, no more than 8, no more than 7, no more than 6, or no more than 5 nucleotides that complement the target nucleic acid. In some embodiments, the portions complementary to the target nucleic acid comprise 5-30, 5-25, or 5-20 nucleotides. In some embodiments, the portions complementary to the target nucleic acid comprise 15-25, 19-21, or 20 nucleotides. In some embodiments, the portions comprise the same number of nucleotides that complement the target nucleic acid. In some embodiments, the portions comprise different numbers of nucleotides that complement the target nucleic acid. For example, in some embodiments, the extended gRNA comprises two portions that complement (e.g., and hybridize to) the target nucleic acid, each portion comprising 5-19, 10-15, or 10 nucleotides that complement the target nucleic acid. Without wishing to be bound by any particular theory, having the portions comprise fewer than approximately 20 nucleotides typical of gRNAs (e.g., having the portions comprise approximately 5-19, 10-15, or 10 complementary nucleotides), ensures that a single Cas9:gRNA unit cannot bind efficiently by itself. Thus the cooperative binding between Cas9 proteins coordinated by such an extended gRNA improves the specificity and cleavage of intended target nucleic acids. In some embodiments, the linker sequence separating the two portions of the extended gRNA has complementarity with the target sequence. For example, in some embodiments, the linker sequence has at least 5, at least 6, at least 7, at least 8, at least 9, at least 10, at least 11, at least 12, at least 13, at least 14, at least 15, at least 20, at least 25, at least 30, at least 40, or at least 50 nucleotides that complement the target nucleic acid. Without wishing to be bound by any particular theory, it is believed that having an extended gRNA that comprises multiple binding sites (e.g., multiple low-affinity binding sites), including those that are bound by a Cas9 protein as well as those in the linker sequence, provides for increased specificity by promoting cooperative binding. Certain aspects of this embodiment are shown in FIG. 4. In some embodiments, any of the Cas9 proteins described herein may be coordinated through a single extended gRNA.

In another embodiment, proteins comprising a fragment of an RNA-programmable nuclease (e.g., Cas9) are provided. For example, in some embodiments, a protein comprising the gRNA binding domain of Cas9 is provided. In some embodiments, the protein comprising the gRNA binding domain of Cas9 does not comprise a DNA cleavage domain (referred to herein as the "A-half" of Cas9). In other embodiments, proteins comprising the DNA cleavage domain(s) (e.g., the HNH, RuvC1 subdomains) of Cas9 are provided. In some embodiments, the "DNA cleavage domain" refers collectively to the portions of Cas9 required for double-stranded DNA cleavage (e.g., the HNH, RuvC1 subdomains). In some embodiments, the protein comprising the DNA cleavage domain of Cas9 does not comprise a gRNA binding domain (referred to herein as the "B-half" of Cas9). In some embodiments, dimers are provided that comprise (i) a protein comprising the gRNA binding domain of Cas9 (e.g., the A-half), and (ii) a protein comprising the DNA cleavage domain of Cas9 (e.g., the B-half). In some embodiments, the dimer is bound by a gRNA. For example, such dimers are expected to recapitulate the binding and cleaving activities of a full length Cas9 protein. In some embodiments, such dimers are referred to herein as "dimeric split Cas9." Using a dimeric split Cas9 to cleave a target nucleic acid is expected to provide for increased specificity as compared to a single full length Cas9 protein because both halves of the protein must be co-localized to associate and re-fold into a nuclease-active state. This strategy is shown in the schematic of FIG. 2A.

In some embodiments, fusion proteins comprising two domains are provided: (i) a protein capable of specifically binding a target nucleic acid (e.g., a nuclease-inactivated RNA programmable nuclease, such as a nuclease-inactivated Cas9, as described herein) fused or linked to (ii) a fragment of an RNA-programmable nuclease (e.g., the A- or B-half of Cas9, as described herein). In some embodiments, domain (i) of the aforementioned fusion protein comprises a DNA binding domain, for example, a DNA binding domain of a zinc finger or TALE protein. In some embodiments, the fusion protein comprises (i) a nuclease-inactivated Cas9, and (ii) a gRNA binding domain of Cas9 (e.g., Cas9 A-half). In some embodiments, domain (ii) of the fusion protein does not include a DNA cleavage domain. In other embodiments, the fusion protein comprises (i) a nuclease-inactivated Cas9, and (ii) a DNA cleavage domain (e.g., Cas9 B-half). In some embodiments, domain (ii) of the fusion protein does not include a gRNA binding domain.

Figure 2B:
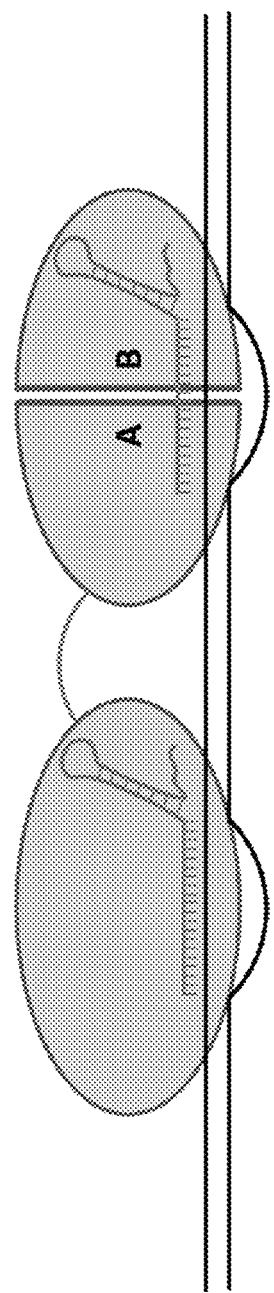

In some embodiments, dimers are provided that comprise two proteins: (i) a fusion protein comprising a nuclease-inactivated Cas9 and a gRNA binding domain of Cas9 (e.g., nuclease-inactivated Cas9 fused to Cas9 A-half), and (ii) a protein comprising the DNA cleavage domain of Cas9 (e.g., Cas9 B-half). In other embodiments, the dimer comprises (i) a fusion protein comprising a nuclease-inactivated Cas9 and a DNA cleavage domain of Cas9 (e.g., nuclease-inactivated Cas9 fused to Cas9 B-half), and (ii) a protein comprising the gRNA binding domain of Cas9 (e.g., Cas9 A-half). In some embodiments, the protein dimers include one or more gRNAs. For example, in some embodiments, the dimers include two gRNAs: one bound by the nuclease-inactivated Cas9 domain of the fusion protein; the other bound by the A-half domain (e.g., either the A-half of the fusion protein, or the A-half of the dimer not part of the fusion protein). Such a dimer (e.g., associated with two gRNAs having sequences binding separate regions of a target nucleic acid) is expected to have improved specificity compared to e.g., a Cas9 protein having a single gRNA. This strategy is shown in FIG. 2B.

Figure 2C:
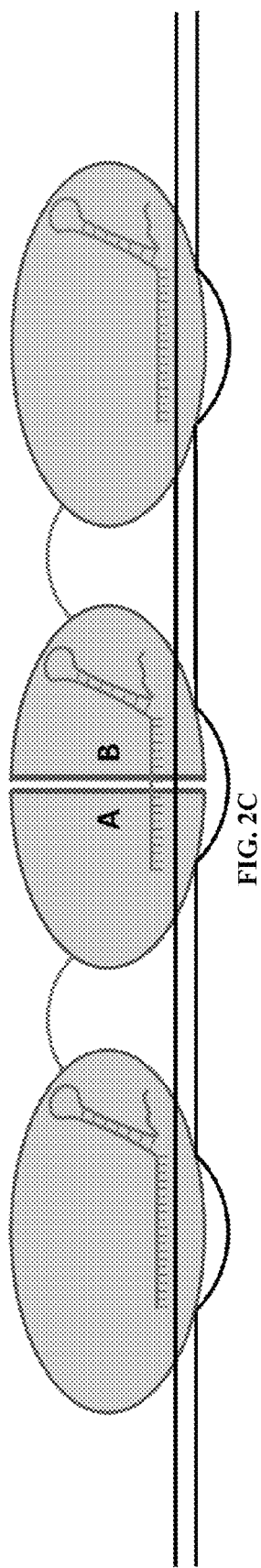
Figure 3:
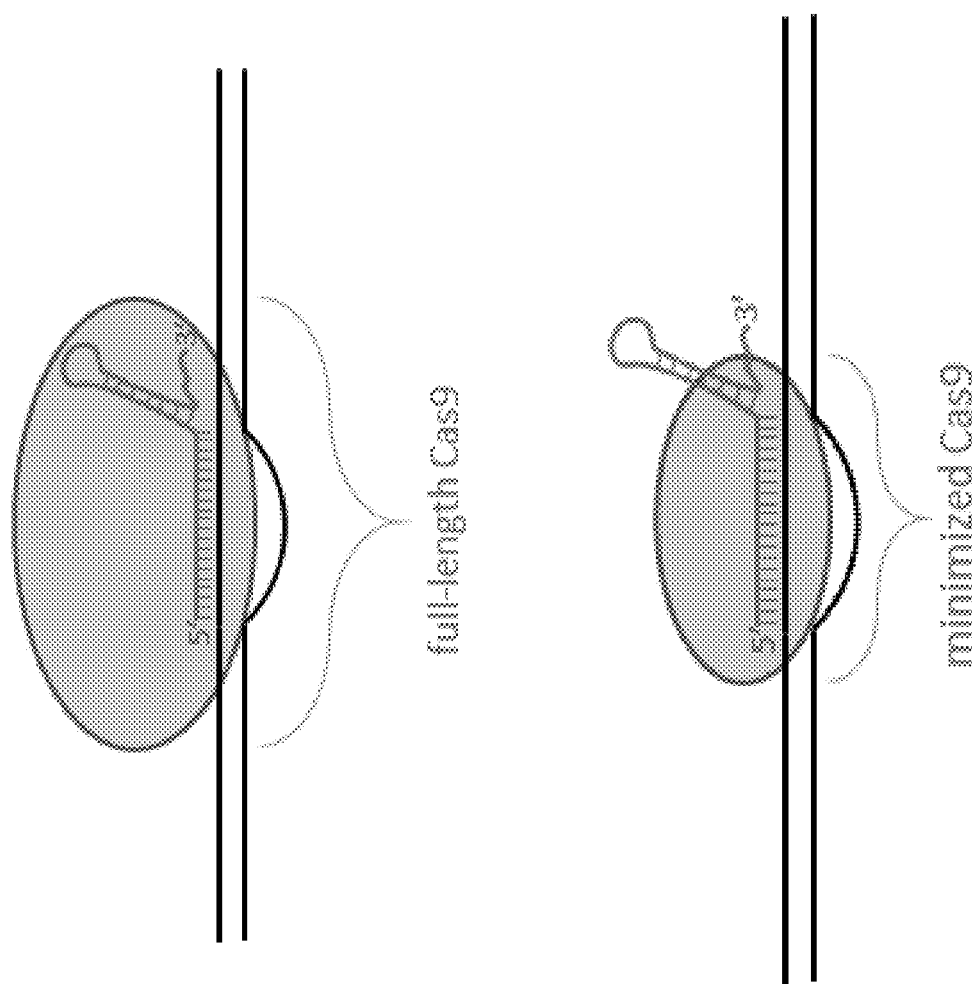
FIG. 3 shows schematically a minimal Cas9 protein that comprises the essential domains for Cas9 activity. Full-length Cas9 is a 4.1 kb gene which results in a protein of >150 kDa. Specific deletions and/or truncations decrease the size of Cas9 without affecting its activity (e.g., gRNA binding and DNA cleavage activity). The minimized Cas9 protein increases the efficacy of, for example, delivery to cells using viral vectors such as AAV (accommodating sequences ~<4700 bp) or lentivirus (accommodating sequences ~<9 kb), or when pursuing multiplexed gRNA/Cas9 approaches.

In some embodiments, a protein dimer is provided that comprises two fusion proteins: (i) a fusion protein comprising a nuclease-inactivated Cas9 and a gRNA binding domain of Cas9 (e.g., a nuclease-inactivated Cas9 fused to a Cas9 A-half), and (ii) a fusion protein comprising a nuclease-inactivated Cas9 and a DNA cleavage domain (e.g., a nuclease-inactivated Cas9 fused to a Cas9 B-half). In some embodiments, the dimer is associated with (e.g., binds) one or more distinct gRNAs. For example, in some embodiments, the dimer is associated with two or three gRNAs. In some embodiments, the dimer is associated with three gRNAs. For example, upon binding of one nuclease-inactivated Cas9: gRNA to a region of a nucleic acid target, and binding of the other nuclease-inactivated Cas9:gRNA to a second region of the nucleic acid target, the split Cas9 halves (e.g., A-half and B-half of the fusion proteins) can dimerize and bind a third gRNA complementary to a third region of the nucleic acid target, to become a fully active Cas9 nuclease, which can cleave dsDNA. This strategy is illustrated in FIG. 2C.

According to another aspect of the invention, minimized Cas9 proteins are provided. By "minimized," it is meant that the Cas9 protein comprises amino acid deletions and/or truncations, as compared to the wild type protein, but retains gRNA binding activity, DNA cleavage activity, or both. Any of the embodiments herein describing Cas9 proteins (e.g., split Cas9 proteins, Cas9 A-half, Cas9 B-half, nuclease-inactivated Cas9 fusion proteins, etc.) can utilize a minimized Cas9 protein. In some embodiments, minimized Cas9 proteins comprising N-terminal deletions and/or truncations are provided. In some embodiments, minimized Cas9 proteins comprising C-terminal deletions and/or truncations are provided. In some embodiments, minimized Cas9 proteins are provided that comprise N- and/or C-terminal deletions and/or truncations. In some embodiments, the minimized Cas9 protein retains both gRNA binding and DNA cleavage activities. In some embodiments, the minimized Cas9 protein comprises an N-terminal truncation that removes at least 5, at least 10, at least 15, at least 20, at least 25, at least 40, at least 40, at least 50, at least 75, at least 100, at least 150, at least 200, at least 250, at least 300, at least 350, at least 400, at least 450, or at least 500 amino acids. In some embodiments, the minimized Cas9 protein comprises a C-terminal truncation that removes at least 5, at least 10, at least 15, at least 20, at least 25, at least 40, at least 40, at least 50, at least 75, at least 100, at least 150, at least 200, at least 250, at least 300, at least 350, at least 400, at least 450, or at least 500 amino acids. In some embodiments, deletions are made within Cas9, for example in regions not affecting gRNA binding and/or DNA cleavage. In some embodiments, the minimized Cas9 protein is associated with one or more gRNAs. In certain embodiments, the minimized Cas9 protein is associated with one gRNA.

Recombinases

Some aspects of this disclosure provide RNA-guided recombinase fusion proteins that are designed using the methods and strategies described herein. Some embodiments of this disclosure provide nucleic acids encoding such recombinases. Some embodiments of this disclosure provide expression constructs comprising such encoding nucleic acids. For example, in some embodiments an isolated recombinase is provided that has been engineered to recombine a desired target site (e.g., a site targeted by one or more gRNAs bound to one or more of the engineered recombinases) within a genome, e.g., with another site in the genome or with an exogenous nucleic acid. In some embodiments, the isolated recombinase comprises a variant of an RNA-programmable nuclease, such as a Cas9 nuclease. In some embodiments, the Cas9 variant is a nuclease-inactivated Cas9 (e.g., dCas9). In some embodiments, dCas9 is encoded by a nucleotide sequence comprising in part or in whole, SEQ ID NO:5 or SEQ ID NO:320. In some embodiments, dCas9 is encoded by a nucleotide sequence comprising a variant of SEQ ID NO:5 or SEQ ID NO:320.

In one embodiment, an RNA-guided recombinase fusion protein is provided. Typically, the fusion protein comprises two or more domains. In some embodiments, the fusion protein comprises two domains. In some embodiments, one of the two or more domains is a nuclease-inactivated Cas9 (or fragment thereof, e.g., Cas9 A-half), for example, those described herein (e.g., dCas9). The Cas9 domain of the recombinase fusion protein is capable of binding one or more gRNAs, and thereby directs or targets the recombinase fusion protein(s) to a target nucleic acid, e.g., as described herein. Another domain of the two or more domains is a recombinase, or a fragment thereof, e.g., a catalytic domain of a recombinase. By "catalytic domain of a recombinase," it is meant that a fusion protein includes a domain comprising an amino acid sequence of (e.g., derived from) a recombinase, such that the domain is sufficient to induce recombination when contacted with a target nucleic acid (either alone or with additional factors including other recombinase catalytic domains which may or may not form part of the fusion protein). In some embodiments, a catalytic domain of a recombinase excludes a DNA binding domain of the recombinase. In some embodiments, the catalytic domain of a recombinase includes part or all of a recombinase, e.g., the catalytic domain may include a recombinase domain and a DNA binding domain, or parts thereof, or the catalytic domain may include a recombinase domain and a DNA binding domain that is mutated or truncated to abolish DNA binding activity. Recombinases and catalytic domains of recombinases are known to those of skill in the art, and include, for example, those described herein. In some embodiments, the catalytic domain is derived from any recombinase. In some embodiments, the recombinase catalytic domain is a catalytic domain of a Tn3 resolvase, a Hin recombinase, or a Gin recombinase. In some embodiments, the catalytic domain comprises a Tn3 resolvase (e.g., Stark Tn3 recombinase) that is encoded by a nucleotide sequence comprising, in part or in whole, SEQ ID NO:322, as provided below. In some embodiments, a Tn3 catalytic domain is encoded by a variant of SEQ ID NO:322. In some embodiments, a Tn3 catalytic domain is encoded by a polynucleotide (or a variant thereof) that encodes the polypeptide corresponding to SEQ ID NO:325. In some embodiments, the catalytic domain comprises a Hin recombinase that is encoded by a nucleotide sequence comprising, in part or in whole, SEQ ID NO:323, as provided below. In some embodiments, a Hin catalytic domain is encoded by a variant of SEQ ID NO:323. In some embodiments, a Hin catalytic domain is encoded by a polynucleotide (or a variant thereof) that encodes the polypeptide corresponding to SEQ ID NO:326. In some embodiments, the catalytic domain comprises a Gin recombinase (e.g., Gin beta recombinase) that is encoded by a nucleotide sequence comprising, in part or in whole, SEQ ID NO:324, as provided below. In some embodiments, a Gin catalytic domain is encoded by a variant of SEQ ID NO:324. In some embodiments, a Gin catalytic domain is encoded by a polynucleotide (or a variant thereof) that encodes the polypeptide corresponding to SEQ ID NO:327. Stark Tn3 Recombinase (Nucleotide: SEQ ID NO:322; Amino Acid: SEQ ID NO:325):

```
                                         (SEQ ID NO: 322)
ATGGCCCTGTTTGGCTACGCACGCGTGTCTACCAGTCAACAGTCACTCGA
TTTGCAAGTGAGGGCTCTTAAAGATGCCGGAGTGAAGGCAAACAGAATTT
TTACTGATAAGGCCAGCGGAAGCAGCACAGACAGAGAGGGGCTGGATCTC
CTGAGAATGAAGGTAAAGGAGGGTGATGTGATCTTGGTCAAAAAATTGGA
TCGACTGGGGAGAGACACAGCTGATATGCTTCAGCTTATTAAAGAGTTTG
ACGCTCAGGGTGTTGCCGTGAGGTTTATCGATGACGGCATCTCAACCGAC
TCCTACATTGGTCTTATGTTTGTGACAATTTTGTCCGCTGTGGCTCAGGC
TGAGCGGAGAAGGATTCTCGAAAGGACGAATGAGGGACGGCAAGCAGCTA
AGTTGAAAGGTATCAAATTTGGCAGACGAAGG (SEQ ID NO: 325)
MALFGYARVSTSQQSLDLQVRALKDAGVKANRIFTDKASGSSTDREGLDL
LRMKVKEGDVILVKKLDRLGRDTADMLQLIKEFDAQGVAVRFIDDGISTD
SYIGLMFVTILSAVAQAERRRILERTNEGRQAAKLKGIKFGRRR
```

Hin Recombinase (Nucleotide: SEQ ID NO:323; Amino Acid: SEQ ID NO:326):

```
                                         (SEQ ID NO: 323)
ATGGCAACCATTGGCTACATAAGGGTGTCTACCATCGACCAAAATATCGA
CCTGCAGCGCAACGCTCTGACATCCGCCAACTGCGATCGGATCTTCGAGG
ATAGGATCAGTGGCAAGATCGCCAACCGGCCCGGTCTGAAGCGGGCTCTG
AAGTACGTGAATAAGGGCGATACTCTGGTTGTGTGGAAGTTGGATCGCTT
GGGTAGATCAGTGAAGAATCTCGTAGCCCTGATAAGCGAGCTGCACGAGA
GGGGTGCACATTTCCATTCTCTGACCGATTCCATCGATACGTCTAGCGCC
ATGGGCCGATTCTTCTTTTACGTCATGTCCGCCCTCGCTGAAATGGAGCG
CGAACTTATTGTTGAACGGACTTTGGCTGGACTGGCAGCGGCTAGAGCAC
AGGGCCGACTTGGA (SEQ ID NO: 326)
MATIGYIRVSTIDQNIDLQRNALTSANCDRIFEDRISGKIANRPGLKRAL
KYVNKGDTLVVWKLDRLGRSVKNLVALISELHERGAHFHSLTDSIDTSSA
MGRFFFYVMSALAEMERELIVERTLAGLAAARAQGRLG
```

Gin Beta Recombinase (Nucleotide: SEQ ID NO:324; Amino Acid: SEQ ID NO:327):

```
                                         (SEQ ID NO: 324)
ATGCTCATTGGCTATGTAAGGGTCAGCACCAATGACCAAAACACAGACTT
GCAACGCAATGCTTTGGTTTGCGCCGGATGTGAACAGATATTTGAAGATA
AACTGAGCGGCACTCGGACAGACAGACCTGGGCTTAAGAGAGCACTGAAA
AGACTGCAGAAGGGGGACACCCTGGTCGTCTGGAAACTGGATCGCCTCGG
ACGCAGCATGAAACATCTGATTAGCCTGGTTGGTGAGCTTAGGGAGAGAG
GAATCAACTTCAGAAGCCTGACCGACTCCATCGACACCAGTAGCCCCATG
GGACGATTCTTCTTCTATGTGATGGGAGCACTTGCTGAGATGGAAAGAGA
GCTTATTATCGAAAGAACTATGGCTGGTATCGCTGCTGCCCGGAACAAAG
GCAGACGGTTCGGCAGACCGCCGAAGAGCGGC (SEQ ID NO: 327)
MLIGYVRVSTNDQNTDLQRNALVCAGCEQIFEDKLSGTRTDRPGLKRALK
RLQKGDTLVVWKLDRLGRSMKHLISLVGELRERGINFRSLTDSIDTSSPM
GRFFFYVMGALAEMERELIIERTMAGIAAARNKGRRFGRPPKSG
```

In some embodiments, the recombinase catalytic domain is fused to the N-terminus, the C-terminus, or somewhere in between the N- and C-termini of a Cas9 protein (e.g., sCas9). In some embodiments, the fusion protein further comprises a nuclear localization signal (NLS; e.g., any of those provided herein). For example, in some embodiments, the general architecture of exemplary RNA-guided recombinase fusion proteins (e.g., Cas9-recombinase fusions) comprise one of the following structures:
[NH$_2$]-[Cas9]-[recombinase]-[COOH],
[NH2]-[recombinase]-[Cas9],
[NH$_2$]-[NLS]-[Cas9]-[recombinase]-[COOH],

[NH₂]-[NLS]-[recombinase]-[Cas9]-[COOH],
[NH₂]-[Cas9]-[NLS]-[recombinase]-[COOH],
[NH₂]-[recombinase]-[NLS]-[Cas9]-[COOH],
[NH₂]-[Cas9]-[recombinase]-[NLS]-[COOH], or
[NH₂]-[recombinase]-[Cas9]-[NLS]-[COOH]
wherein NLS is a nuclear localization signal, NH₂ is the N-terminus of the fusion protein, and COOH is the C-terminus of the fusion protein. In some embodiments, a linker is inserted between the Cas9 domain and the recombinase domain, e.g., any linker provided herein. Additional features, such as sequence tags (e.g., any of those provided herein), may also be present.

Pharmaceutical Compositions

In some embodiments, any of the nucleases (e.g., fusion proteins comprising nucleases or nuclease domains) and recombinases (e.g., fusion proteins comprising recombinases or recombinase catalytic domains) described herein are provided as part of a pharmaceutical composition. For example, some embodiments provide pharmaceutical compositions comprising a nuclease and/or recombinase as provided herein, or a nucleic acid encoding such a nuclease and/or recombinase, and a pharmaceutically acceptable excipient. Pharmaceutical compositions may optionally comprise one or more additional therapeutically active substances.

In some embodiments, compositions provided herein are administered to a subject, for example, to a human subject, in order to effect a targeted genomic modification within the subject. In some embodiments, cells are obtained from the subject and are contacted with a nuclease and/or recombinase ex vivo. In some embodiments, cells removed from a subject and contacted ex vivo with an inventive nuclease and/or recombinase are re-introduced into the subject, optionally after the desired genomic modification has been effected or detected in the cells. Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, domesticated animals, pets, and commercially relevant mammals such as cattle, pigs, horses, sheep, cats, dogs, mice, and/or rats; and/or birds, including commercially relevant birds such as chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient, and then, if necessary and/or desirable, shaping and/or packaging the product into a desired single- or multi-dose unit.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21ˢᵗ Edition, A. R. Gennaro (Lippincott, Williams & Wilkins, Baltimore, Md., 2006; incorporated in its entirety herein by reference) discloses various excipients used in formulating pharmaceutical compositions and known techniques for the preparation thereof. See also PCT application PCT/US2010/055131, incorporated in its entirety herein by reference, for additional suitable methods, reagents, excipients and solvents for producing pharmaceutical compositions comprising a nuclease. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this disclosure.

In some embodiments, compositions in accordance with the present invention may be used for treatment of any of a variety of diseases, disorders, and/or conditions, including but not limited to one or more of the following: autoimmune disorders (e.g. diabetes, lupus, multiple sclerosis, psoriasis, rheumatoid arthritis); inflammatory disorders (e.g. arthritis, pelvic inflammatory disease); infectious diseases (e.g. viral infections (e.g., HIV, HCV, RSV), bacterial infections, fungal infections, sepsis); neurological disorders (e.g. Alzheimer's disease, Huntington's disease; autism; Duchenne muscular dystrophy); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); etc.

Methods for Site-Specific Nucleic Acid Cleavage

In another embodiment of this disclosure, methods for site-specific nucleic acid (e.g., DNA) cleavage are provided. In some embodiments, the methods comprise contacting a DNA with any of the Cas9:gRNA complexes described herein. For example, in some embodiments, the method comprises contacting a DNA with a fusion protein (e.g., fCas9) that comprises two domains: (i) a nuclease-inactivated Cas9 (dCas9); and (ii) a nuclease (e.g., a FokI DNA cleavage domain), wherein the wherein the inactive Cas9 domain binds a gRNA that hybridizes to a region of the DNA. In some embodiments, the method further comprises contacting the DNA with a second fusion protein described herein (e.g., fCas9), wherein the nuclease-inactivated Cas9 (dCas9) domain of the second fusion protein binds a second gRNA that hybridizes to a second region of DNA, wherein the binding of the fusion proteins results in the dimerization of the nuclease domains of the fusion proteins, such that the DNA is cleaved in a region between the bound fusion proteins. See e.g., FIGS. 1A, 6D. In some embodiments, the gRNAs bound to each fusion protein hybridize to the same strand of the DNA, or they hybridize to opposing strands of the DNA. In some embodiments, the gRNAs hybridize to regions of the DNA that are no more than 10, no more than 15, no more than 20, no more than 25, no more than 30, no more than 40, 50, no more than 60, no more than 70, no more than 80, no more than 90, or no more than 100 base pairs apart. The region between the bound Cas9:gRNA complexes may be referred to as the "spacer sequence," which is typically where the target nucleic acid is cleaved. See, e.g., FIGS. 6C-D. In some embodiments, the spacer sequence is at least 5, at least 10, at least 15, at least 20, at least 25, at least 30 at least 35, at least 40, at least 45, at least 50, at least 60, at least 70, at least 80, at least 90, or at least 100 base pairs in length. In some embodiments, the spacer sequence is between about 5 and about 50 base pairs, about 10 and about 40, or about 15 and about 30 base pairs in length. In some embodiments, the spacer sequence is about 15 to about 25 base pairs in length. In some embodiments, the spacer sequence is about 15, about 20, or about 25 base pairs in length. In some embodiments, the Cas9:gRNA complexes are bound in the A orientation, as described herein. In some embodiments, the Cas9:gRNA complexes are bound in the B orientation, as described herein. In some embodiments, the method has an on-target:off-target modification ratio that is at least 2-fold, at least 5-fold, at least 10-fold, at least 20-fold, at least 30-fold, at least 40-fold, at least 50-fold, at least 60-fold, at least 70-fold, at least 80-fold, at least 90-fold, at least 100-fold, at least 110-fold, at least 120-fold, at least 130-fold, at least 140-fold, at least 150-fold, at least 175-fold, at least 200-fold, or at least 250-fold or more higher than the on-target:off-target modification ratio of methods utilizing a wild type Cas9 or other Cas9 variant. In some embodiments, the method has an on-target:off-target modification ratio that is between about 60- to about 180-fold, between about 80- to about 160-fold, between about 100- to about 150-fold, or between about 120- to about 140-fold higher than the on-target:off-target modification ratio of methods utilizing a wild type Cas9 or other Cas9 variant. Methods for determining on-target:off-target modification ratios are known, and include those described in the Examples. In some embodiments, the fusion proteins are coordinated or associated through a single gRNA, e.g., as described herein.

In some embodiments, the method comprises contacting a nucleic acid with a dimer of Cas9 proteins (or fragments thereof) coordinated with (e.g., bound by) a single gRNA as described herein. In some embodiments, the single gRNA comprises at least two portions that hybridize to the nucleic acid. In some embodiments, the portions comprise at least 5, at least 10, at least 15, or at least 19 complementary nucleotides. In some embodiments, the portions comprise fewer than 20 complementary nucleotides. In some embodiments, a linker sequence separates the portions, wherein the linker sequence also comprises nucleotides complementary to the target nucleic acid (e.g., but are not bound by a Cas9 protein). In some embodiments, the linker sequence does not hybridize to the target nucleic acid.

In some embodiments, the methods comprise contacting a DNA with a protein dimer of fusion proteins described herein, wherein the fusion proteins are bound by one or more gRNAs. For example, in some embodiments, one fusion protein of the dimer comprises a gRNA binding domain of Cas9 (e.g., Cas9 A-half), wherein the protein does not comprise a DNA cleavage domain (e.g., Cas9 B-half); and the other fusion protein of the dimer comprises a DNA cleavage domain of Cas9 (e.g., Cas9 B-half), wherein the protein does not comprise a gRNA binding domain (e.g., Cas9 A-half). Thus, in some embodiments, the binding of a gRNA (e.g., that hybridizes to a target nucleic acid) to one or both of the monomers of the dimer co-localizes the dimer to the target nucleic acid, allowing the dimer to re-fold into a nuclease-active state and cleave the target nucleic acid.

In some embodiments, the method comprises contacting a nucleic acid with protein dimers comprising two proteins: (i) a fusion protein comprising a nuclease-inactivated Cas9 and a gRNA binding domain of Cas9 (e.g., nuclease-inactivated Cas9 fused to Cas9 A-half), and (ii) a protein comprising the DNA cleavage domain of Cas9 (e.g., Cas9 B-half). In other embodiments, the dimer comprises (i) a fusion protein comprising a nuclease-inactivated Cas9 and a DNA cleavage domain of Cas9 (e.g., nuclease-inactivated Cas9 fused to Cas9 B-half), and (ii) a protein comprising the gRNA binding domain of Cas9 (e.g., Cas9 A-half). In some embodiments, the protein dimers are associated with one or more gRNAs. For example, in some embodiments, the dimers are associated with two gRNAs: one bound by the nuclease-inactivated Cas9 domain of the fusion protein; the other bound by the A-half domain (e.g., either the A-half of the fusion protein, or the A-half of the dimer not part of the fusion protein). In some embodiments, the protein dimer comprises (i) a fusion protein comprising a nuclease-inactivated Cas9 and a gRNA binding domain of Cas9 (e.g., a nuclease-inactivated Cas9 fused to a Cas9 A-half), and (ii) a fusion protein comprising a nuclease-inactivated Cas9 and a DNA cleavage domain (e.g., a nuclease-inactivated Cas9 fused to a Cas9 B-half). In some embodiments, the dimer is associated with one or more distinct gRNAs. For example, in some embodiments, the dimer is associated with two or three gRNAs. In some embodiments, the dimer is associated with three gRNAs. For example, upon binding of one nuclease-inactivated Cas9:gRNA to a region of a nucleic acid target, and binding of the other nuclease-inactivated Cas9:gRNA to a second region of the nucleic acid target, the split Cas9 halves (e.g., A-half and B-half of the fusion proteins) dimerize and bind a third gRNA complementary to a third region of the nucleic acid target, to become a fully active Cas9 nuclease leading to cleave of the target DNA.

In some embodiments, a method for site-specific cleavage of a nucleic acid comprises contacting a nucleic acid (e.g., DNA) with a minimized Cas9 protein (e.g., as described herein) associated with a gRNA.

In some embodiments, any of the methods provided herein can be performed on DNA in a cell, for example a bacterium, a yeast cell, or a mammalian cell. In some embodiments, the DNA contacted by any Cas9 protein provided herein is in a eukaryotic cell. In some embodiments, the methods can be performed on a cell or tissue in vitro or ex vivo. In some embodiments, the eukaryotic cell is in an individual, such as a patient or research animal. In some embodiments, the individual is a human.

Methods for Site-Specific Recombination

Figure 5A:
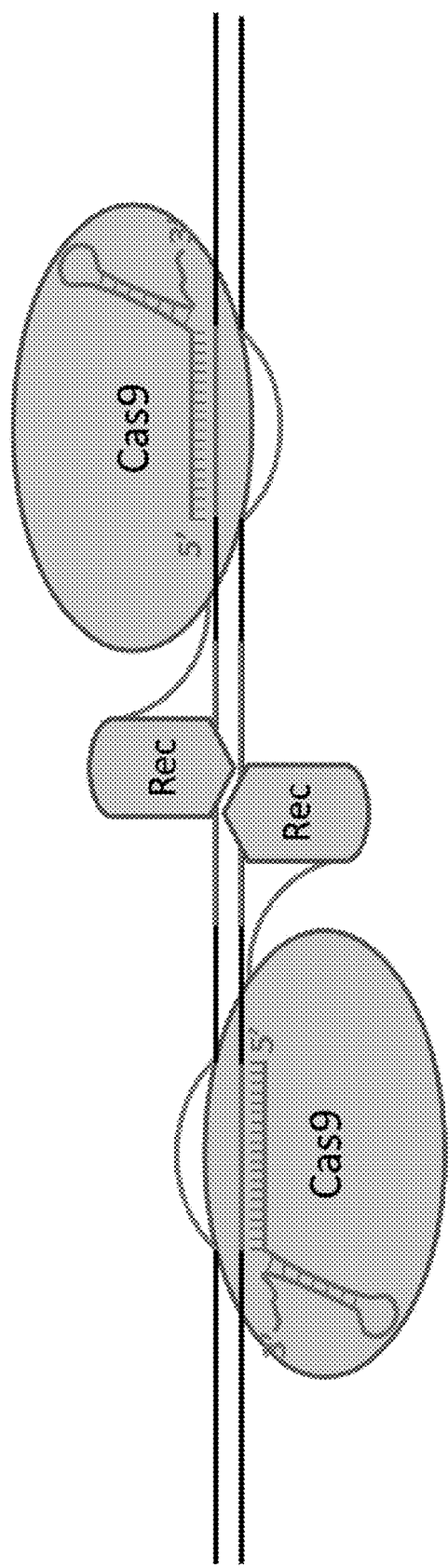
FIG. 5 shows schematically, how Cas9-recombinase fusions can be coordinated through gRNAs to bind and recombine target DNAs at desired sequences (sites). (A, B) Nuclease-inactivated Cas9 (dCas9) protein is fused to a monomer of a recombinase domain (Rec). Site-specific recombination is achieved through dimerization (A) of the recombinase catalytic domain monomers at the target site, and then tetramerization (B) of two dimers assembled on separate Cas9-recombination sites. The fusion to dCas9:gRNA complexes determines the sequence identity of the flanking target sites while the recombinase catalytic domain determines the identity of the core sequence (the sequence between the two dCas9-binding sites). (B) Recombination proceeds through strand cleavage, exchange, and re-ligation within the dCas9-recombinase tetramer complex.
Figure 5B:
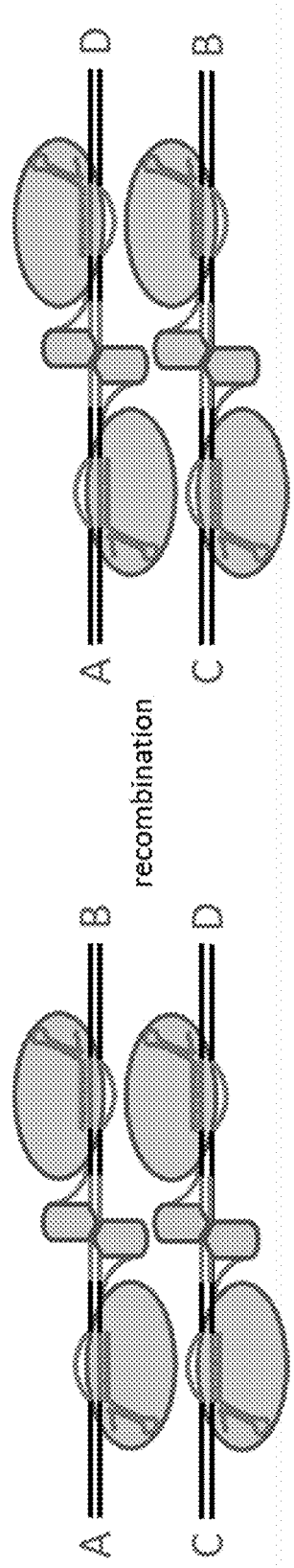

In another embodiment of this disclosure, methods for site-specific nucleic acid (e.g., DNA) recombination are provided. In some embodiments, the methods are useful for inducing recombination of or between two or more regions of two or more nucleic acid (e.g., DNA) molecules. In other embodiments, the methods are useful for inducing recombination of or between two or more regions in a single nucleic acid molecule (e.g., DNA). In some embodiments, the recombination of one or more target nucleic acid molecules requires the formation of a tetrameric complex at the target site. Typically, the tetramer comprises four (4) inventive RNA-guided recombinase fusion proteins (e.g., a complex of any four inventive recombinase fusion protein provided herein). In some embodiments, each recombinase fusion protein of the tetramer targets a particular DNA sequence via a distinct gRNA bound to each recombinase fusion protein (See, e.g., FIG. 5).

In some embodiments, the method for site-specific recombination between two DNA molecules comprises (a) contacting a first DNA with a first RNA-guided recombinase fusion protein, wherein the nuclease-inactivated Cas9 domain binds a first gRNA that hybridizes to a region of the first DNA; (b) contacting the first DNA with a second RNA-guided recombinase fusion protein, wherein the nuclease-inactivated Cas9 domain of the second fusion protein binds a second gRNA that hybridizes to a second region of the first DNA; (c) contacting a second DNA with a third RNA-guided recombinase fusion protein, wherein the nuclease-inactivated Cas9 domain of the third fusion protein binds a third gRNA that hybridizes to a region of the second DNA; and (d) contacting the second DNA with a fourth RNA-guided recombinase fusion protein, wherein the nuclease-inactivated Cas9 domain of the fourth fusion protein binds a fourth gRNA that hybridizes to a second region of the second DNA. The binding of the fusion proteins in steps (a)-(d) results in the tetramerization of the recombinase catalytic domains of the fusion proteins, such that the DNAs are recombined. In some embodiments, the gRNAs of steps (a) and (b) hybridize to opposing strands of the first DNA, and the gRNAs of steps (c) and (d) hybridize to opposing strands of the second DNA. In some embodiments, the target sites of the gRNAs of steps (a)-(d) are spaced to allow for tetramerization of the recombinase catalytic domains. For example, in some embodiments, the target sites of the gRNAs of steps (a)-(d) are no more than 10, no more 15, no more than 20, no more than 25, no more than 30, no more than 40, no more than 50, no more than 60, no more than 70, no more than 80, no more than 90, or no more than 100 base pairs apart. In some embodiments, the two regions of the two DNA molecules being recombined share homology, such that the regions being recombined are at least 80%, at least 90%, at least 95%, at least 98%, or are 100% homologous.

In another embodiment, methods for site-specific recombination between two regions of a single DNA molecule are provided. In some embodiments, the methods comprise (a) contacting a DNA with a first RNA-guided recombinase fusion protein, wherein the nuclease-inactivated Cas9 domain binds a first gRNA that hybridizes to a region of the DNA; (b) contacting the DNA with a second RNA-guided recombinase fusion protein, wherein the nuclease-inactivated Cas9 domain of the second fusion protein binds a second gRNA that hybridizes to a second region of the DNA; (c) contacting the DNA with a third RNA-guided recombinase fusion protein, wherein the nuclease-inactivated Cas9 domain of the third fusion protein binds a third gRNA that hybridizes to a third region of the DNA; and (d) contacting the DNA with a fourth RNA-guided recombinase fusion protein, wherein the nuclease-inactivated Cas9 domain of the fourth fusion protein binds a fourth gRNA that hybridizes to a fourth region of the DNA. The binding of the fusion proteins in steps (a)-(d) results in the tetramerization of the recombinase catalytic domains of the fusion proteins, such that the DNA is recombined. In some embodiments, two of the gRNAs of steps (a)-(d) hybridize to the same strand of the DNA, and the other two gRNAs of steps (a)-(d) hybridize to the opposing strand of the DNA. In some embodiments, the gRNAs of steps (a) and (b) hybridize to regions of the DNA that are no more 10, no more than 15, no more than 20, no more than 25, no more than 30, no more than 40, no more than 50, no more than 60, no more than 70, no more than 80, no more than 90, or no more than 100 base pairs apart, and the gRNAs of steps (c) and (d) hybridize to regions of the DNA that are no more than 10, no more 15, no more than 20, no more than 25, no more than 30, no more than 40, no more than 50, no more than 60, no more than 70, no more than 80, no more than 90, or no more than 100 base pairs apart. In some embodiments, the two regions of the DNA molecule being recombined share homology, such that the regions being recombined are at least 80%, at least 90%, at least 95%, at least 98%, or are 100% homologous.

In some embodiments, any of the inventive methods for site-specific recombination are amenable for inducing recombination, such that the recombination results in excision (e.g., a segment of DNA is excised from a target DNA molecule), insertion (e.g., a segment of DNA is inserted into a target DNA molecule), inversion (e.g., a segment of DNA is inverted in a target DNA molecule), or translocation (e.g., the exchange of DNA segments between one or more target DNA molecule(s)). In some embodiments, the particular recombination event (e.g., excision, insertion, inversion, translocation, etc.) depends, inter alia, on the orientation (e.g., with respect to the target DNA molecule(s)) of the bound RNA-guided recombinase fusion protein(s). In some embodiments, the orientation, or direction, in which a RNA-guided recombinase fusion protein binds a target nucleic acid can be controlled, e.g., by the particular sequence of the gRNA bound to the RNA-guided recombinase fusion protein(s). Methods for controlling or directing a particular recombination event are known in the art, and include, for example, those described by Turan and Bode, "Site-specific recombinases: from tag-and-target- to tag-and-exchange-based genomic modifications." *FASEB J.* 2011; December; 25(12):4088-107, the entire contents of which are hereby incorporated by reference.

In some embodiments, any of the methods for site-specific recombination can be performed in vivo or in vitro. In some embodiments, any of the methods for site-specific recombination are performed in a cell (e.g., recombine genomic DNA in a cell). The cell can be prokaryotic or eukaryotic. The cell, such as a eukaryotic cell, can be in an individual, such as a subject, as described herein (e.g., a human subject). The methods described herein are useful for the genetic modification of cells in vitro and in vivo, for example, in the context of the generation of transgenic cells, cell lines, or animals, or in the alteration of genomic sequence, e.g., the correction of a genetic defect, in a cell in or obtained from a subject. In some embodiments, a cell obtained from a subject and modified according to the methods provided herein, is re-introduced into a subject (e.g., the same subject), e.g., to treat a disease, or for the production of genetically modified organisms in agriculture or biological research.

In applications in which it is desirable to recombine two or more nucleic acids so as to insert a nucleic acid sequence into a target nucleic acid, a nucleic acid comprising a donor sequence to be inserted is also provided, e.g., to a cell. By a "donor sequence" it is meant a nucleic acid sequence to be inserted at the target site induced by one or more RNA-guided recombinase fusion protein(s). In some embodiments, e.g., in the context of genomic modifications, the donor sequence will share homology to a genomic sequence at the target site, e.g., 1%, 2%, 3%, 4%, 5%, 10%, 20%, 30%, 40%, 50%, 60%, 70%, 80%, 85%, 90%, 95%, or 100% homology with the nucleotide sequences flanking the target site, e.g., within about 100 bases or less of the target site, e.g. within about 90 bases, within about 80 bases, within about 70 bases, within about 60 bases, within about 50 bases, within about 40 bases, within about 30 bases, within about 15 bases, within about 10 bases, within about 5 bases, or immediately flanking the target site. In some embodiments, the donor sequence does not share any homology with the target nucleic acid, e.g., does not share homology to a genomic sequence at the target site. Donor sequences can be of any length, e.g., 10 nucleotides or more, 50 nucleotides or more, 100 nucleotides or more, 250 nucleotides or more, 500 nucleotides or more, 1000 nucleotides or more, 5000 nucleotides or more, 10000 nucleotides or more, 100000 nucleotides or more, etc.

Typically, the donor sequence is not identical to the target sequence that it replaces or is inserted into. In some embodiments, the donor sequence contains at least one or more single base changes, insertions, deletions, inversions or rearrangements with respect to the target sequence (e.g., target genomic sequence). In some embodiments, donor sequences also comprise a vector backbone containing sequences that are not homologous to the DNA region of interest and that are not intended for insertion into the DNA region of interest.

The donor sequence may comprise certain sequence differences as compared to the target (e.g., genomic) sequence, for example restriction sites, nucleotide polymorphisms, selectable markers (e.g., drug resistance genes, fluorescent proteins, enzymes etc.), which can be used to assess for successful insertion of the donor sequence at the target site or in some cases may be used for other purposes (e.g., to signify expression at the targeted genomic locus). In some embodiments, if located in a coding region, such nucleotide sequence differences will not change the amino acid sequence, or will make silent amino acid changes (e.g., changes which do not affect the structure or function of the protein). In some embodiments, these sequences differences may include flanking recombination sequences such as FLPs, loxP sequences, or the like, that can be activated at a later time for removal of e.g., a marker sequence.

The donor sequence may be provided to the cell as single-stranded DNA, single-stranded RNA, double-stranded DNA, or double-stranded RNA. It may be introduced into a cell in linear or circular form. If introduced in linear form, the ends of the donor sequence may be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, e.g., Chang et al., *Proc. Natl. Acad Sci USA*. 1987; 84:4959-4963; Nehls et al., *Science*. 1996; 272:886-889. In some embodiments, a donor sequence can be introduced into a cell as part of a vector molecule having additional sequences such as, for example, replication origins, promoters and genes encoding antibiotic resistance. In some embodiments, donor sequences can be introduced as naked nucleic acid, as nucleic acid complexed with an agent such as a liposome or poloxamer, or can be delivered by viruses (e.g., adenovirus, AAV, etc.).

Polynucleotides, Vectors, Cells, Kits

In another embodiment of this disclosure, polynucleotides encoding one or more of the inventive proteins and/or gRNAs are provided. For example, polynucleotides encoding any of the proteins described herein are provided, e.g., for recombinant expression and purification of isolated nucleases and recombinases, e.g., comprising Cas9 variants. In some embodiments, an isolated polynucleotide comprises one or more sequences encoding a Cas9 half site (e.g., A-half and/or B-half). In some embodiments, an isolated polynucleotide comprises one or more sequences encoding a Cas9 fusion protein, for example, any of the Cas9 fusion proteins described herein (e.g., those comprising a nuclease-inactivated Cas9). In some embodiments, an isolated polynucleotides comprises one or more sequences encoding a gRNA, alone or in combination with a sequence encoding any of the proteins described herein.

In some embodiments, vectors encoding any of the proteins described herein are provided, e.g., for recombinant expression and purification of Cas9 proteins, and/or fusions comprising Cas9 proteins (e.g., variants). In some embodiments, the vector comprises or is engineered to include an isolated polynucleotide, e.g., those described herein. In some embodiments, the vector comprises one or more sequences encoding a Cas9 protein (as described herein), a gRNA, or combinations thereof, as described herein. Typically, the vector comprises a sequence encoding an inventive protein operably linked to a promoter, such that the fusion protein is expressed in a host cell.

In some embodiments, cells are provided, e.g., for recombinant expression and purification of any of the Cas9 proteins provided herein. The cells include any cell suitable for recombinant protein expression, for example, cells comprising a genetic construct expressing or capable of expressing an inventive protein (e.g., cells that have been transformed with one or more vectors described herein, or cells having genomic modifications, for example, those that express a protein provided herein from an allele that has been incorporated in the cell's genome). Methods for transforming cells, genetically modifying cells, and expressing genes and proteins in such cells are well known in the art, and include those provided by, for example, Green and Sambrook, *Molecular Cloning: A Laboratory Manual* (4$^{th}$ ed., Cold Spring Harbor Laboratory Press, Cold Spring Harbor, N.Y. (2012)) and Friedman and Rossi, *Gene Transfer: Delivery and Expression of DNA and RNA, A Laboratory Manual* (1$^{st}$ ed., Cold Spring Harbor Laboratory Press, Cold Spring Harbor, N.Y. (2006)).

Some aspects of this disclosure provide kits comprising a Cas9 variant and/or nuclease and/or recombinase, as provided herein. In some embodiments, the kit comprises a polynucleotide encoding an inventive Cas9 variant, nuclease, and/or recombinase, e.g., as provided herein. In some embodiments, the kit comprises a vector for recombinant protein expression, wherein the vector comprises a polynucleotide encoding any of the proteins provided herein. In some embodiments, the kit comprises a cell (e.g., any cell suitable for expressing Cas9 proteins or fusions comprising Cas9 proteins, such as bacterial, yeast, or mammalian cells) that comprises a genetic construct for expressing any of the proteins provided herein. In some embodiments, any of the kits provided herein further comprise one or more gRNAs and/or vectors for expressing one or more gRNAs. In some embodiments, the kit comprises an excipient and instructions for contacting the nuclease and/or recombinase with the excipient to generate a composition suitable for contacting a nucleic acid with the nuclease and/or recombinase such that hybridization to and cleavage and/or recombination of a target nucleic acid occurs. In some embodiments, the composition is suitable for delivering a Cas9 protein to a cell. In some embodiments, the composition is suitable for delivering a Cas9 protein to a subject. In some embodiments, the excipient is a pharmaceutically acceptable excipient.

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLES

Example 1

Fusion of Inactivated Cas9 to FokI Nuclease Improves Genome Modification Specificity Methods:
Oligonucleotides and PCR All oligonucleotides were purchased from Integrated DNA Technologies (IDT). Oligonucleotide sequences are listed in Table 1. PCR was performed with 0.4 µL of 2 U/µL Phusion Hot Start Flex DNA polymerase (NEB) in 50 μL with 1×HF Buffer, 0.2 mM dNTP mix (0.2 mM dATP, 0.2 mM dCTP, 0.2 mM dGTP, 0.2 mM dTTP) (NEB), 0.5 μM of each primer and a program of: 98° C., 1 min; 35 cycles of [98° C., 15 s; 65° C., 15 s; 72° C., 30 s] unless otherwise noted.

Construction of FokI-dCas9, Cas9 Nickase and gRNA Expression Plasmids

The human codon-optimized *streptococcus pyogenes* Cas9 nuclease with NLS and 3×FLAG tag (Addgene plasmid 43861)[2] was used as the wild-type Cas9 expression plasmid. PCR (72° C., 3 min) products of wild-type Cas9 expression plasmid as template with Cas9_Exp primers listed in Table 1 below were assembled with Gibson Assembly Cloning Kit (New England Biolabs) to construct Cas9 and FokI-dCas9 variants. Expression plasmids encoding a single gRNA construct (gRNA G1 through G13) were cloned as previously described. Briefly, gRNA oligonucleotides listed in Table 1 containing the 20-bp protospacer target sequence were annealed and the resulting 4-bp overhangs were ligated into BsmBI-digested gRNA expression plasmid. gRNA expression plasmids encoding expression of two separate gRNA constructs from separate promoters on a single plasmid were cloned in a two-step process. First, one gRNA (gRNA E1, V1, C1, C3, H1, G1, G2 or G3) was cloned as above and used as template for PCR (72° C., 3 min) with PCR_Pla-fwd and PCR_Pla-rev primers, 1 μl DpnI (NEB) was added, and the reaction was incubated at 37° C. for 30 min and then subjected to QIAquick PCR Purification Kit (Qiagen) for the "1$^{st}$ gRNA+vector DNA". PCR (72° C., 3 min) of 100 pg of BsmBI-digested gRNA expression plasmid as template with PCR_gRNA-fwd1, PCR_gRNA-rev1, PCR_gRNA-rev2 and appropriate PCR_gRNA primer listed in Table 1 was DpnI treated and purified as above for the "2$^{nd}$ gRNA insert DNA". ~200 ng of "1$^{st}$ gRNA+vector DNA" and ~200 ng of "2$^{nd}$ gRNA insert DNA" were blunt-end ligated in 1× T4 DNA Ligase Buffer, 1 μl of T4 DNA Ligase (400 U/μl, NEB) in a total volume of 20 μl at room temperature (~21° C.) for 15 min. For all cloning, 1 μl of ligation or assembly reaction was transformed into Mach1 chemically competent cells (Life Technologies).

TABLE 1

| Oligonucleotides. '/5Phos/' indicates 5' phosphorylated oligonucleotides. | |
|---|---|
| dCas9-NLS-FokI primers: | |
| Cas9_Exp_CNF_Fok1 + Plas-Fwd | CGGCGAGATAAACTTTTAA TGACCGGTCATCATCACCA (SEQ ID NO: 26) |
| Cas9_Exp_CNF_Cas9coD10-Rev | CCAACGGAATTAGTGCCGATAGCTAAACCAATAGAATACTTTTTATC (SEQ ID NO: 27) |
| Cas9_Exp_CNF_Cas9coD10-Fwd | GATAAAAAGTATTCTATTGGTTTAGCTATCGGCACTAATTCCGTTGG (SEQ ID NO: 28) |
| Cas9_Exp_CNF_Cas9coH850-Rev | TTCAAAAAGGATTGGGGTACAATGGCATCGACGTCGTAATCAGATAAAC (SEQ ID NO: 29) |
| Cas9_Exp_CNF_Cas9coH850-Fwd | GTTTATCTGATTACGACGTCGATGCCATTGTACCCCAATCCTTTTTGAA (SEQ ID NO: 30) |
| Cas9_Exp_CNF_(Cas9)NLS + GGS-Fok-Rev | TTGGGATCCAGAACCTCCTCCTGCAGCCTTGTCATCG (SEQ ID NO: 31) |
| Cas9_Exp_CNF_(Cas9)NLS + GGS3-Fok-Rev | TTGGGATCCAGAACCTCC GCTGCCGCCACTTCCACCTGA TCCTGCAGCCTTGTCATCG (SEQ ID NO: 32) |
| Cas9_Exp_CNF_(Cas9)NLS + GGS-Fok-Fwd | CGATGACAAGGCTGCAGGAGGAGGTTCTGGATCCCAA (SEQ ID NO: 33) |
| Cas9_Exp_CNF_(Cas9)NLS + GGS3-Fok-Fwd | CGATGACAAGGCTGCAGGA TCAGGTGGAAGTGGCGGCAGC GGAGGTTCTGGATCCCAA (SEQ ID NO: 34) |
| Cas9_Exp_CNF_Fok1 + Plas-Rev | TGGTGATGATGACCGGTCA TTAAAAGTTTATCTCGCCG (SEQ ID NO: 35) |
| NLS-dCas9-FokI primers: | |
| Cas9_Exp_NCF_Fok1 + Plas-Fwd | CGGCGAGATAAACTTTTAA TGACCGGTCATCATCACCA (SEQ ID NO: 36) |
| Cas9_Exp_NCF_PlasS + FLAG (NLS-Fok1-Rev | TAGGGAGAGCCGCCACCATGGACTACAAAGACCATGACGG (SEQ ID NO: 37) |
| Cas9_Exp_NCF_NLS + Cas9coD10-Rev | TAAACCAATAGAATACTTTTTATC CATAGGTACCCCGCGGTGAATG (SEQ ID NO: 38) |
| Cas9_Exp_NCF_Cas9coD10-Fwd | GATAAAAAGTATTCTATTGGTTTAGCTATCGGCACTAATTCCGTTGG (SEQ ID NO: 39) |
| Cas9_Exp_NCF_Cas9coH850-Rev | TTCAAAAAGGATTGGGGTACAATGGCATCGACGTCGTAATCAGATAAAC (SEQ ID NO: 40) |
| Cas9_Exp_NCF_Cas9coH850-Fwd | GTTTATCTGATTACGACGTCGATGCCATTGTACCCCAATCCTTTTTGAA (SEQ ID NO: 41) |

TABLE 1-continued

Oligonucleotides. '/5Phos/' indicates 5' phosphorylated oligonucleotides.

| | |
|---|---|
| Cas9_Exp_NCF_Cas9End + GGS-Fok-Rev | TTGGGATCCAGAACCTCCGTCACCCCCAAGCTGTG (SEQ ID NO: 42) |
| Cas9_Exp_NCF_Cas9End + GGS3-Fok-Rev | TTGGGATCCAGAACCTCC GCTGCCGCCACTTCCACCTGA GTCACCCCCAAGCTGTG (SEQ ID NO: 43) |
| Cas9_Exp_NCF_Cas9End + GGS-Fok-Fwd | CACAGCTTGGGGGTGACGGAGGTTCTGGATCCCAA (SEQ ID NO: 44) |
| Cas9_Exp_NCF_Cas9End + GGS3-Fok-Fwd | CACAGCTTGGGGGTGAC TCAGGTGGAAGTGGCGGCAGC GGAGGTTCTGGATCCCAA (SEQ ID NO: 45) |
| Cas9_Exp_NCF_Fok1 + Plas-Rev | TGGTGATGATGACCGGTCA TTAAAAGTTTATCTCGCCG (SEQ ID NO: 46) |
| FokI-dCas9-NLS primers: | |
| Cas9_Exp_FCN_PlasS + Fok-Fwd | TAGGGAGAGCCGCCACCATGGGATCCCAACTAGTCAAAAG (SEQ ID NO: 47) |
| Cas9_Exp_FCN_Fok1GGS + Cas-Rev | ACCAATAGAATACTTTTTATCCATGCTGCCACCAAAGTTTATCTC (SEQ ID NO: 48) |
| Cas9_Exp_FCN_Fok1GGS3 + Cas-Rev | ACCAATAGAATACTTTTTATCCATGCTGCCGCCACTTCCACCTG (SEQ ID NO: 49) |
| Cas9_Exp_FCN_Cas9coD10-Fwd | GATAAAAAGTATTCTATTGGTTTAGCTATCGGCACTAATTCCGTTGG (SEQ ID NO: 50) |
| Cas9_Exp_FCN_Cas9coH850-Rev | CCAACGGAATTAGTGCCGATAGCTAAACCAATAGAATACTTTTTATC (SEQ ID NO: 51) |
| Cas9_Exp_FCN_Cas9coH850-Fwd | GTTTATCTGATTACGACGTCGATGCCATTGTACCCCAATCCTTTTTGAA (SEQ ID NO: 52) |
| Cas9_Exp_FCN_Cas9End + PlasmidEn-Rev | TGGTGATGATGACCGGTCA GTCACCCCCAAGCTGTG (SEQ ID NO: 53) |
| Cas9_Exp_FCN_Cas9End + PlasmidEn-Fwd | CACAGCTTGGGGGTGAC TGACCGGTCATCATCACCA (SEQ ID NO: 54) |
| Cas9_Exp_FCN_PlasS + Fok-Rev | CTTTTGACTAGTTGGGATCCCATGGTGGCGGCTCTCCCTA (SEQ ID NO: 55) |
| gRNA_G1-top | ACACCCCTCGAACTTCACCTCGGCGG (SEQ ID NO: 56) |
| gRNA_G2-top | ACACCGTCGCCCTCGAACTTCACCTG (SEQ ID NO: 57) |
| gRNA_G3-top | ACACCCAGCTCGATGCGGTTCACCAG (SEQ ID NO: 58) |
| gRNA_G4-top | ACACCGGTGAACCGCATCGAGCTGAG (SEQ ID NO: 59) |
| gRNA_G5-top | ACACCGCTGAAGGGCATCGACTTCAG (SEQ ID NO: 60) |
| gRNA_G6-top | ACACCGGCATCGACTTCAAGGAGGAG (SEQ ID NO: 61) |
| gRNA_G7-top | ACACCCAAGGAGGACGGCAACATCCG (SEQ ID NO: 62) |
| gRNA_G8-top | ACACCACCATCTTCTTCAAGGACGAG (SEQ ID NO: 63) |
| gRNA_G9-top | ACACCCAACTACAAGACCCGCGCCGG (SEQ ID NO: 64) |
| gRNA_G10-top | ACACCCCGCGCCGAGGTGAAGTTCG (SEQ ID NO: 65) |
| gRNA_G11-top | ACACCGAAGTTCGAGGGCGACACCCG (SEQ ID NO: 66) |
| gRNA_G12-top | ACACCTTCGAACTTCACCTCGGCGCG (SEQ ID NO: 67) |
| gRNA_G13-top | ACACCTCAGCTCGATGCGGTTCACCG (SEQ ID NO: 68) |
| gRNA_G14-top | ACACCCGATGCCCTTCAGCTCGATGG (SEQ ID NO: 69) |
| gRNA_G1-bottom | AAAACCGCCGAGGTGAAGTTCGAGGG (SEQ ID NO: 70) |
| gRNA_G2-bottom | AAAACAGGTGAAGTTCGAGGGCGACG (SEQ ID NO: 71) |
| gRNA_G3-bottom | AAAACTGGTGAACCGCATCGAGCTGG (SEQ ID NO: 72) |

TABLE 1-continued

Oligonucleotides. '/5Phos/' indicates 5' phosphorylated oligonucleotides.

| | |
|---|---|
| gRNA_G4-bottom | AAAACTCAGCTCGATGCGGTTCACCG (SEQ ID NO: 73) |
| gRNA_G5-bottom | AAAACTGAAGTCGATGCCCTTCAGCG (SEQ ID NO: 74) |
| gRNA_G6-bottom | AAAACTCCTCCTTGAAGTCGATGCCG (SEQ ID NO: 75) |
| gRNA_G7-bottom | AAAACGGATGTTGCCGTCCTCCTTGG (SEQ ID NO: 76) |
| gRNA_G8-bottom | AAAACTCGTCCTTGAAGAAGATGGTG (SEQ ID NO: 77) |
| gRNA_G9-bottom | AAAACCGGCGCGGGTCTTGTAGTTGG (SEQ ID NO: 78) |
| gRNA_G10-bottom | AAAACCGAACTTCACCTCGGCGCGGG (SEQ ID NO: 79) |
| gRNA_G11-bottom | AAAACGGGTGTCGCCCTCGAACTTCG (SEQ ID NO: 80) |
| gRNA_G12-bottom | AAAACGCGCCGAGGTGAAGTTCGAAG (SEQ ID NO: 81) |
| gRNA_G13-bottom | AAAACGGTGAACCGCATCGAGCTGAG (SEQ ID NO: 82) |
| gRNA_G14-bottom | AAAACCATCGAGCTGAAGGGCATCGG (SEQ ID NO: 83) |
| gRNA_C1-top | ACACCTGGCCTGCTTGCTAGACTTGG (SEQ ID NO: 84) |
| gRNA_C3-top | ACACCGCAGATGTAGTGTTTCCACAG (SEQ ID NO: 85) |
| gRNA_H1-top | ACACCCTTGCCCCACAGGGCAGTAAG (SEQ ID NO: 86) |
| gRNA_E1-top | ACACCGAGTCCGAGCAGAAGAAGAAG (SEQ ID NO: 87) |
| gRNA_V1-top | ACACCGGGTGGGGGGAGTTTGCTCCG (SEQ ID NO: 88) |
| gRNA_C1-bottom | AAAACCAAGTCTAGCAAGCAGGCCAG (SEQ ID NO: 89) |
| gRNA_C3-bottom | AAAACTGTGGAAACACTACATCTGCG (SEQ ID NO: 90) |
| gRNA_H1-bottom | AAAACTTCTTCTTCTGCTCGGACTCG (SEQ ID NO: 91) |
| gRNA_E1-bottom | AAAACTTACTGCCCTGTGGGGCAAGG (SEQ ID NO: 92) |
| gRNA_V1-bottom | AAAACGGAGCAAACTCCCCCCACCCG (SEQ ID NO: 93) |
| PCR_Pla-fwd | AGG AAA GAA CAT GTG AGC AAA AG (SEQ ID NO: 94) |
| PCR_Pla-rev | CAGCGAGTCAGTGAGCGA (SEQ ID NO: 95) |
| PCR_gRNA-fwd1 | CTGTACAAAAAAGCAGGCTTTA (SEQ ID NO: 96) |
| PCR_gRNA-rev1 | AACGTAGGTCTCTACCGCTGTACAAAAAAGCAGGCTTTA (SEQ ID NO: 97) |
| PCR_gRNA-rev2 | AAAAAAAGCACCGACTCGGTGCCACTTTTTCAAGTTGATAACGGACTAGCC<br>TTATTTTAACTTGCTATTTCTAGCTCTAAAAC (SEQ ID NO: 98) |
| PCR_gRNA_G1 | TTGCTATTTCTAGCTCTAAAACCGCCGAGGTGAAGTTCGAGGGGTGTTTCG<br>TCCTTTCCA (SEQ ID NO: 99) |
| PCR_gRNA_G2 | TTGCTATTTCTAGCTCTAAAACAGGTGAAGTTCGAGGGCGACGGTGTTTCG<br>TCCTTTCCA (SEQ ID NO: 100) |
| PCR_gRNA_G3 | TTGCTATTTCTAGCTCTAAAACTGGTGAACCGCATCGAGCTGGGTGTTTCGT<br>CCTTTCCA (SEQ ID NO: 101) |
| PCR_gRNA_G4 | TTGCTATTTCTAGCTCTAAAACTCAGCTCGATGCGGTTCACCGGTGTTTCGT<br>CCTTTCCA (SEQ ID NO: 102) |
| PCR_gRNA_G5 | TTGCTATTTCTAGCTCTAAAACTGAAGTCGATGCCCTTCAGCGGTGTTTCGT<br>CCTTTCCA (SEQ ID NO: 103) |
| PCR_gRNA_G6 | TTGCTATTTCTAGCTCTAAAACTCCTCCTTGAAGTCGATGCCGGTGTTTCGT<br>CCTTTCCA (SEQ ID NO: 104) |
| PCR_gRNA_G7 | TTGCTATTTCTAGCTCTAAAACGGATGTTGCCGTCCTCCTTGGGTGTTTCGT<br>CCTTTCCA (SEQ ID NO: 105) |
| PCR_gRNA_C2 | TTGCTATTTCTAGCTCTAAAACGCTTGAGGGAGATGAGGACTGGTGTTTCG<br>TCCTTTCCA (SEQ ID NO: 106) |

TABLE 1-continued

Oligonucleotides. '/5Phos/' indicates 5' phosphorylated oligonucleotides.

| | |
|---|---|
| PCR_gRNA_C4 | TTGCTATTTCTAGCTCTAAAACATGACTGTGAAGAGCTTCACGGTGTTTCGTCCTTTCCA (SEQ ID NO: 107) |
| PCR_gRNA_E2 | TTGCTATTTCTAGCTCTAAAACGAGGACAAAGTACAAACGGCGGTGTTTCGTCCTTTCCA (SEQ ID NO: 108) |
| PCR_gRNA_E3 | TTGCTATTTCTAGCTCTAAAACGAACCGGAGGACAAAGTACAGGTGTTTCGTCCTTTCCA (SEQ ID NO: 109) |
| PCR_gRNA_H2 | TTGCTATTTCTAGCTCTAAAACCACCACCAACTTCATCCACGGGTGTTTCGTCCTTTCCA (SEQ ID NO: 110) |
| PCR_gRNA_H3 | TTGCTATTTCTAGCTCTAAAACGGGCCTCACCACCAACTTCAGGTGTTTCGTCCTTTCCA (SEQ ID NO: 111) |
| PCR_gRNA_H4 | TTGCTATTTCTAGCTCTAAAACGCCCAGGGCCTCACCACCAAGGTGTTTCGTCCTTTCCA (SEQ ID NO: 112) |
| PCR_gRNA_H5 | TTGCTATTTCTAGCTCTAAAACACCTGCCCAGGGCCTCACCAGGTGTTTCGTCCTTTCCA (SEQ ID NO: 113) |
| PCR_gRNA_H6 | TTGCTATTTCTAGCTCTAAAACTGATACCAACCTGCCCAGGGGTGTTTCGTCCTTTCCA (SEQ ID NO: 114) |
| PCR_gRNA_H7 | TTGCTATTTCTAGCTCTAAAACTAAACCTGTCTTGTAACCTTGGTGTTTCGTCCTTTCCA (SEQ ID NO: 115) |
| PCR_gRNA_V2 | TTGCTATTTCTAGCTCTAAAACGCTCTGGCTAAAGAGGGAATGGTGTTTCGTCCTTTCCA (SEQ ID NO: 116) |
| PCR_gRNA_V3 | TTGCTATTTCTAGCTCTAAAACCGGCTCTGGCTAAAGAGGGAGGTGTTTCGTCCTTTCCA (SEQ ID NO: 117) |
| PCR_gRNA_V4 | TTGCTATTTCTAGCTCTAAAACTCTGCACACCCCGGCTCTGGGGTGTTTCGTCCTTTCCA (SEQ ID NO: 118) |
| Survey_GFP-fwd | TACGGCAAGCTGACCCTGAA (SEQ ID NO: 119) |
| Survey_GFP-rev | GTCCATGCCGAGAGTGATCC (SEQ ID NO: 120) |
| Survye_CLTA-fwd | GCCAGGGGCTGTTATCTTGG (SEQ ID NO: 121) |
| Survye_CLTA-rev | ATGCACAGAAGCACAGGTTGA (SEQ ID NO: 122) |
| Survey_EMX-fwd | CTGTGTCCTCTTCCTGCCCT (SEQ ID NO: 123) |
| Survey_EMX-rev | CTCTCCGAGGAGAAGGCCAA (SEQ ID NO: 124) |
| Survey_HBB-fwd | GGTAGACCACCAGCAGCCTA (SEQ ID NO: 125) |
| Survey_HBB-rev | CAGTGCCAGAAGAGCCAAGG (SEQ ID NO: 126) |
| Survey_VEGF-fwd | CCACACAGCTTCCCGTTCTC (SEQ ID NO: 127) |
| Survey_VEGF-rev | GAGAGCCGTTCCCTCTTTGC (SEQ ID NO: 128) |
| HTS_EXM_ON-fwd | CCTCCCCATTGGCCTGCTTC (SEQ ID NO: 129) |
| HTS_EXM_Off1-fwd | TCGTCCTGCTCTCACTTAGAC (SEQ ID NO: 130) |
| HTS_EXM_Off2-fwd | TTTTGTGGCTTGGCCCCAGT (SEQ ID NO: 131) |
| HTS_EXM_Off3-fwd | TGCAGTCTCATGACTTGGCCT (SEQ ID NO: 132) |
| HTS_EXM_Off4-fwd | TTCTGAGGGCTGCTACCTGT (SEQ ID NO: 133) |
| HTS_VEFG_ON-fwd | ACATGAAGCAACTCCAGTCCCA (SEQ ID NO: 134) |
| HTS_EXM_Off1-fwd | AGCAGACCCACTGAGTCAACTG (SEQ ID NO: 135) |
| HTS_EXM_Off2-fwd | CCCGCCACAGTCGTGTCAT (SEQ ID NO: 136) |
| HTS_EXM_Off3-fwd | CGCCCCGGTACAAGGTGA (SEQ ID NO: 137) |
| HTS_EXM_Off4-fwd | GTACCGTACATTGTAGGATGTTT (SEQ ID NO: 138) |
| HTS_CLTA2_ON-fwd | CCTCATCTCCCTCAAGCAGGC (SEQ ID NO: 139) |

TABLE 1-continued

Oligonucleotides. '/5Phos/' indicates 5' phosphorylated oligonucleotides.

| | |
|---|---|
| HTS_CLTA2_Off1-fwd | ATTCTGCTCTTGAGGTTATTTGT (SEQ ID NO: 140) |
| HTS_CLTA2_Off2-fwd | CACCTCTGCCTCAAGAGCAGAAAA (SEQ ID NO: 141) |
| HTS_CLTA2_Off3-fwd | TGTGTGTGTGTGTGTAGGACT (SEQ ID NO: 142) |
| HTS_EXM_ON-rev | TCATCTGTGCCCCTCCCTCC (SEQ ID NO: 143) |
| HTS_EXM_Off-rev | CGAGAAGGAGGTGCAGGAG (SEQ ID NO: 144) |
| HTS_EXM_Off-rev | CGGGAGCTGTTCAGAGGCTG (SEQ ID NO: 145) |
| HTS_EXM_Off-rev | CTCACCTGGGCGAGAAAGGT (SEQ ID NO: 146) |
| HTS_EXM_Off-rev | AAAACTCAAAGAAATGCCCAATCA (SEQ ID NO: 147) |
| HTS_VEFG_ON-rev | AGACGCTGCTCGCTCCATTC (SEQ ID NO: 148) |
| HTS_EXM_Off1-rev | ACAGGCATGAATCACTGCACCT (SEQ ID NO: 149) |
| HTS_EXM_Off2-rev | GCGGCAACTTCAGACAACCGA (SEQ ID NO: 150) |
| HTS_EXM_Off3-rev | GACCCAGGGGCACCAGTT (SEQ ID NO: 151) |
| HTS_EXM_Off4-rev | CTGCCTTCATTGCTTAAAAGTGGAT (SEQ ID NO: 152) |
| HTS_CLTA2_ON-rev | ACAGTTGAAGGAAGGAAACATGC (SEQ ID NO: 153) |
| HTS_CLTA2_Off1-rev | GCTGCATTTGCCCATTTCCA (SEQ ID NO: 154) |
| HTS_CLTA2_Off2-rev | GTTGGGGGAGGAGGAGCTTAT (SEQ ID NO: 155) |
| HTS_CLTA2_Off3-rev | CTAAGAGCTATAAGGGCAAATGACT (SEQ ID NO: 156) |

Modification of Genomic GFP

HEK293-GFP stable cells (GenTarget) were used as a cell line constitutively expressing an Emerald GFP gene (GFP) integrated on the genome. Cells were maintained in Dulbecco's modified Eagle medium (DMEM, Life Technologies) supplemented with 10% (vol/vol) fetal bovine serum (FBS, Life Technologies) and penicillin/streptomycin (1×, Amresco). $5 \times 10^4$ HEK293-GFP cells were plated on 48-well collagen coated Biocoat plates (Becton Dickinson). One day following plating, cells at ~75% confluence were transfected with Lipofecatmine 2000 (Life Technologies) according to the manufacturer's protocol. Briefly, 1.5 μL of Lipofecatmine 2000 was used to transfect 950 ng of total plasmid (Cas9 expression plasmid plus gRNA expression plasmids). 700 ng of Cas9 expression plasmid, 125 ng of one gRNA expression plasmid and 125 ng of the paired gRNA expression plasmid with the pairs of targeted gRNAs listed in FIG. 6D and FIG. 9A. Separate wells were transfected with 1 μg of a near-infrared iRFP670 (Addgene plasmid 45457)[32] as a transfection control. 3.5 days following transfection, cells were trypsinized and resuspended in DMEM supplemented with 10% FBS and analyzed on a C6 flow cytometer (Accuri) with a 488 nm laser excitation and 520 nm filter with a 20 nm band pass. For each sample, transfections and flow cytometry measurements were performed once.

T7 Endonuclease I Surveyor Assays of Genomic Modifications

HEK293-GFP stable cells were transfected with Cas9 expression and gRNA expression plasmids as described above. A single plasmid encoding two separate gRNAs was transfected. For experiments titrating the total amount of expression plasmids (Cas9 expression+gRNA expression plasmid), 700/250, 350/125, 175/62.5, 88/31 ng of Cas9 expression plasmid/ng of gRNA expression plasmid were combined with inert carrier plasmid, pUC19 (NEB), as necessary to reach a total of 950 ng transfected plasmid DNA.

Genomic DNA was isolated from cells 2 days after transfection using a genomic DNA isolation kit, DNAdvance Kit (Agencourt). Briefly, cells in a 48-well plate were incubated with 40 μL of tryspin for 5 min at 37° C. 160 uL of DNAdvance lysis solution was added and the solution incubated for 2 hr at 55° C. and the subsequent steps in the Agencourt DNAdvance kit protocol were followed. 40 ng of isolated genomic DNA was used as template to PCR amplify the targeted genomic loci with flanking Survey primer pairs specified in Table 1. PCR products were purified with a QIAquick PCR Purification Kit (Qiagen) and quantified with Quant-iT™ PicoGreen® dsDNA Kit (Life Technologies). 250 ng of purified PCR DNA was combined with 2 μL of NEBuffer 2 (NEB) in a total volume of 19 μL and denatured then re-annealed with thermocycling at 95° C. for 5 min, 95 to 85° C. at 2° C./s; 85 to 20° C. at 0.2° C./s. The re-annealed DNA was incubated with 1 μl of T7 Endonuclease I (10 U/μl, NEB) at 37° C. for 15 min. 10 μL of 50% glycerol was added to the T7 Endonuclease reaction and 12 μL was analyzed on a 5% TBE 18-well Criterion PAGE gel (Bio-Rad) electrophoresed for 30 min at 150 V, then stained with 1×SYBR Gold (Life Technologies) for 30 min. Cas9-induced cleavage bands and the uncleaved band were visualized on an AlphaImager HP (Alpha Innotech) and quantified using ImageJ software.[33] The peak intensities of the cleaved bands were divided by the total intensity of all bands (uncleaved+cleaved bands) to determine the fraction cleaved which was used to estimate gene modification levels as previously described.[28] For each sample, transfections and subsequent modification measurements were performed in triplicate on different days.

High-Throughput Sequencing of Genomic Modifications

HEK293-GFP stable cells were transfected with Cas9 expression and gRNA expression plasmids, 700 ng of Cas9 expression plasmid plus 250 ng of a single plasmid expression a pair of gRNAs were transfected (high levels) and for just Cas9 nuclease, 88 ng of Cas9 expression plasmid plus 31 ng of a single plasmid expression a pair of gRNAs were transfected (low levels). Genomic DNA was isolated as above and pooled from three biological replicates. 150 ng or 600 ng of pooled genomic DNA was used as template to amplify by PCR the on-target and off-target genomic sites with flanking HTS primer pairs specified in Table 1. Relative amounts of crude PCR products were quantified by gel electrophoresis and samples treated with different gRNA pairs or Cas9 nuclease types were separately pooled in equimolar concentrations before purification with the QIAquick PCR Purification Kit (Qiagen). ~500 ng of pooled DNA was run a 5% TBE 18-well Criterion PAGE gel (BioRad) for 30 min at 200 V and DNAs of length ~125 bp to ~300 bp were isolated and purified by QIAquick PCR Purification Kit (Qiagen). Purified DNA was PCR amplified with primers containing sequencing adaptors, purified and sequenced on a MiSeq high-throughput DNA sequencer (Illumina) as described previously.[1]

Data Analysis

Illumina sequencing reads were filtered and parsed with scripts written in Unix Bash. All scripts were written in bash.

The Patmatch program[38] was used to search the human genome (GRCh37/hg19 build) for pattern sequences corresponding to Cas9 binding sites (CCN N$^{20}$ spacer N$^{20}$NGG for Orientation A and N$^{20}$NGG spacer CCN N$^{20}$ for Orientation B). The steps for the identification of ingels in sequences of genomic sites can be found below:

1) Sequence reads were initially filtered removing reads of less than 50 bases and removing reads with greater than 10% of the Illumina base scores not being B-J:

Example SeqA-1$^{st}$read:

(SEQ ID NO: 157)
TTCTGAGGGCTGCTACCTGTACATCTGCACAAGATTGCCTTTACTCCAT

GCCTTTCTTCTTCTGCTCTAACTCTGACAATCTGTCTTGCCATGCCATAA

GCCCCTATTCTTTCTGTAACCCCAAGATGGTATAAAAGCATCAATGATTG

GGC

Example SeqA-2$^{st}$read:

(SEQ ID NO: 158)
AAAACTCAAAGAAATGCCCAATCATTGATGCTTTTATACCATCTTGGG

GTTACAGAAAGAATAGGGGCTTATGGCATGGCAAGACAGATTGTCAGAGT

TAGAGCAGAAGAAGAAAGGCATGGAGTAAAGGCAATCTTGTGCAGATGTA

CAGGTAA

2) Find the first 20 bases four bases from the start of the reverse complement of SeqA-2$^{nd}$read in SeqA-1$^{st}$read allowing for 1 mismatch:

Reverse complement of SeqA-2$^{nd}$read:

(SEQ ID NO: 159)
TTACCTGTACATCTGCACAAGATTGCCTTTACTCCATGCCTTTCTTCT

TCTGCTCTAACTCTGACAATCTGTCTTGCCATGCCATAAGCCCCTATTCT

TTCTGTAACCCCAAGATGGTATAAAAGCATCAATGATTGGGCATTTCTTT

GAGTTTT

Position in SeqA-1$^{st}$read (SEQ ID NO: 160)
TTCTGAGGGCTGCTACCTGTACATCTGCACAAGATTGCCTTTACTCCATG

CCTTTCTTCTTCTGCTCTAACTCTGACAATCTGTCTTGCCATGCCATAAG

CCCCTATTCTTTCTGTAACCCCAAGATGGTATAAAAGCATCAATGATTGG

GC

3) Align and then combine sequences, removing any sequence with greater than 5% mismatches in the simple base pair alignment:

Combination of SeqA-1$^{st}$read and SeqA-2$^{nd}$read:

(SEQ ID NO: 161)
TTCTGAGGGCTGCTACCTGTACATCTGCACAAGATTGCCTTTACTCC

ATGCCTTTCTTCTTCTGCTCTAACTCTGACAATCTGTCTTGCCATGCCAT

AAGCCCCTATTCTTTCTGTAACCCCAAGATGGTATAAAAGCATCAATGAT

TGGGCATTTCTTTGAGTTTT

4) To identify the target site the flanking genomic sequences were searched for with the Patmatch program[38] allowing for varying amounts of bases from 1 to 300 between the flanking genomic sequences (Table 2):

TABLE 2

Patmatch Sequences

| Target Site | Downstream genomic sequence | Upstream genomic sequence |
|---|---|---|
| EMX_On | GGCCTGCTTCGTGGCAATGC (SEQ ID NO: 162) | ACCTGGGCCAGGGAGGGAGG (SEQ ID NO: 163) |
| EMX_Off1 | CTCACTTAGACTTTCTCTCC (SEQ ID NO: 164) | CTCGGAGTCTAGCTCCTGCA (SEQ ID NO: 165) |
| EMX_Off2 | TGGCCCCAGTCTCTCTTCTA (SEQ ID NO: 166) | CAGCCTCTGAACAGCTCCCG (SEQ ID NO: 167) |
| EMX_Off3 | TGACTTGGCCTTTGTAGGAA (SEQ ID NO: 168) | GAGGCTACTGAAACATAAGT (SEQ ID NO: 169) |
| EMX_Off4 | TGCTACCTGTACATCTGCAC (SEQ ID NO: 170) | CATCAATGATTGGGCATTTC (SEQ ID NO: 171) |

TABLE 2-continued

Patmatch Sequences

| Target Site | Downstream genomic sequence | Upstream genomic sequence |
|---|---|---|
| VEG_On | ACTCCAGTCCCAAATATGTA (SEQ ID NO: 172) | ACTAGGGGCGCTCGGCCAC (SEQ ID NO: 173) |
| VEG_Off1 | CTGAGTCAACTGTAAGCATT (SEQ ID NO: 174) | GGCCAGGTGCAGTGATTCAT (SEQ ID NO: 175) |
| VEG_Off2 | TCGTGTCATCTTGTTTGTGC (SEQ ID NO: 176) | GGCAGAGCCCAGCGGACACT (SEQ ID NO: 177) |
| VEG_Off3 | CAAGGTGAGCCTGGGTCTGT (SEQ ID NO: 178) | ATCACTGCCCAAGAAGTGCA (SEQ ID NO: 179) |
| VEG_Off4 | TTGTAGGATGTTTAGCAGCA (SEQ ID NO: 180) | ACTTGCTCTCTTTAGAGAAC (SEQ ID NO: 181) |
| CLT2_On | CTCAAGCAGGCCCCGCTGGT (SEQ ID NO: 182) | TTTTGGACCAAACCTTTTG (SEQ ID NO: 183) |
| CLT2_Off1 | TGAGGTTATTTGTCCATTGT (SEQ ID NO: 184) | TAAGGGGAGTATTTACACCA (SEQ ID NO: 185) |
| CLT2_Off2 | TCAAGAGCAGAAAATGTGAC (SEQ ID NO: 186) | CTTGCAGGGACCTTCTGATT (SEQ ID NO: 187) |
| CLT2_Off3 | TGTGTGTAGGACTAAACTCT (SEQ ID NO: 188) | GATAGCAGTATGACCTTGGG (SEQ ID NO: 189) |

Any target site sequences corresponding to the same size as the reference genomic site in the human genome (GRCh37/hg19 build) were considered unmodified and any sequences not the reference size were considered potential insertions or deletions. Sequences not the reference size were aligned with ClustalW[39] to the reference genomic site. Aligned sequences with more than one insertion or one deletion in the DNA spacer sequence in or between the two half-site sequences were considered indels. Since high-throughput sequencing can result in insertions or deletions of one base pairs (misphasing) at a low but relevant rates—indels of two bp are more likely to arise from Cas9 induced modifications.

Sample sizes for sequencing experiments were maximized (within practical experimental considerations) to ensure greatest power to detect effects. Statistical analyses for Cas9-modified genomic sites in Table 3 were performed as previously described[34] with multiple comparison correction using the Bonferroni method.

Table 3, referred to in the Results below, shows (A) results from sequencing CLTA on-target and previously reported genomic off-target sites amplified from 150 ng genomic DNA isolated from human cells treated with a plasmid expressing either wild-type Cas9, Cas9 nickase, or fCas9 and a single plasmid expressing two gRNAs targeting the CLTA on-target site (gRNA C3 and gRNA C4). As a negative control, transfection and sequencing were performed as above, but using two gRNAs targeting the GFP gene on-target site (gRNA G1, G2 or G3 and gRNA G4, G5, G6 or G7. Indels: the number of observed sequences containing insertions or deletions consistent with any of the three Cas9 nuclease-induced cleavage. Total: total number of sequence counts while only the first 10,000 sequences were analyzed for the on-target site sequences. Modified: number of indels divided by total number of sequences as percentages. Upper limits of potential modification were calculated for sites with no observed indels by assuming there is less than one indel then dividing by the total sequence count to arrive at an upper limit modification percentage, or taking the theoretical limit of detection (1/49,500), whichever value was larger. P-values: For wild-type Cas9 nuclease, Cas9 nickase or fCas9 nuclease, P-values were calculated as previously reported[18] using a two-sided Fisher's exact test between each sample treated with two gRNAs targeting the CLTA on-target site and the control sample treated with two gRNAs targeting the GFP on-target site. P-values of <0.0045 were considered significant and shown based on conservative multiple comparison correction using the Bonferroni method. On:off specificity is the ratio of on-target to off-target genomic modification frequency for each site. (B) Shows experimental and analytic methods as in (A) applied to EMX target sites using a single plasmid expressing two gRNAs targeting the EMX on-target site (gRNA E1 and gRNA E2). (C) shows experimental and analytic methods as in (A) applied to VEGF target sites using a single plasmid expressing two gRNAs targeting the VEGF on-target site (gRNA V1 and gRNA v2). (D) shows experimental and analytic methods as in (A) applied to VEGF on-target and VEGF off-target site 1 amplified from 600 ng genomic DNA to increase detection sensitivity to 1/198,000.

TABLE 3

Cellular modification induced by wild-type Cas9, Cas9 nickase, and fCas9 at on-target and off-target genomic sites.

(A)

| Nuclease type: | wt Cas9 | wt Cas9 | Cas9 nickase | fCas9 | wt Cas9 | Cas9 nickase | fCas9 |
|---|---|---|---|---|---|---|---|
| gRNA pair target: | CLTA | CLTA | CLTA | CLTA | GFP | GFP | GFP |

TABLE 3-continued

Cellular modification induced by wild-type Cas9, Cas9 nickase, and fCas9 at on-target and off-target genomic sites.

| Total expression plasmids (ng): | 1000 | 125 | 1000 | 1000 | 1000 | 1000 | 1000 |
|---|---|---|---|---|---|---|---|
| CLTA Sites | | | | | | | |
| CLT2_On | | | | | | | |
| Indels | 3528 | 1423 | 3400 | 575 | 3 | 13 | 5 |
| Total | 10000 | 10000 | 10000 | 10000 | 10000 | 10000 | 10000 |
| Modified (%) | 35.280 | 14.230 | 34.000 | 5.750 | 0.030 | 0.130 | 0.050 |
| P-value | <1.0E−300 | <1.0E−300 | <1.0E−300 | 1.4E−163 | | | |
| On:off specificity | 1 | 1 | | 1 | | | |
| CLT2_Off1 | | | | | | | |
| Indels | 316 | 44 | 2 | 2 | 1 | 3 | 3 |
| Total | 60620 | 64755 | 71537 | 63079 | 93883 | 91306 | 82055 |
| Modified (%) | 0.521 | 0.068 | 0.003 | 0.003 | <0.002 | 0.003 | 0.004 |
| P-value | 1.3E−126 | 2.1E−16 | | | | | |
| On:off specificity | 68 | 209 | | >2850 | | | |
| CLT2_Off2 | | | | | | | |
| Indels | 11 | 5 | 3 | 1 | 1 | 1 | 2 |
| Total | 72596 | 51093 | 59632 | 35541 | 69114 | 64412 | 39978 |
| Modified (%) | 0.015 | 0.010 | 0.005 | 0.003 | <0.002 | <0.002 | 0.005 |
| P-value | 6.5E−03 | | | | | | |
| On:off specificity | 2328 | 1454 | | >2850 | | | |
| CLT2_Off3 | | | | | | | |
| Indels | 11 | 10 | 0 | 0 | 1 | 1 | 1 |
| Total | 52382 | 44212 | 54072 | 48668 | 55670 | 58707 | 54341 |
| Modified (%) | 0.021 | 0.023 | <0.002 | <0.002 | <0.002 | <0.002 | <0.002 |
| P-value | 2.7E−03 | 3.5E−03 | | | | | |
| On:off specificity | 1680 | 629 | | >2850 | | | |

(B)

| Nuclease type: | wt Cas9 | wt Cas9 | Cas9 nickase | fCas9 | wt Cas9 | Cas9 nickase | fCas9 |
|---|---|---|---|---|---|---|---|
| gRNA pair: | EMX | EMX | EMX | EMX | GFP | GFP | GFP |
| Total expression plasmids (ng): | 1000 | 125 | 1000 | 1000 | 1000 | 1000 | 1000 |
| EMX Site | | | | | | | |
| EMX_On | | | | | | | |
| Indels | 5111 | 2683 | 2267 | 522 | 0 | 0 | 2 |
| Total | 10000 | 10000 | 10000 | 10000 | 10000 | 10000 | 10000 |
| Modified (%) | 51.110 | 26.830 | 22.670 | 5.220 | <0.002 | <0.002 | 0.020 |
| P-value | <1.0E−300 | <1.0E−300 | <1.0E−300 | 1.0E−154 | | | |
| On:off specificity | 1 | 1 | 1 | 1 | | | |
| EMX_Off1 | | | | | | | |
| Indels | 386 | 122 | 7 | 1 | 4 | 9 | 7 |
| Total | 109787 | 83420 | 124564 | 88424 | 102817 | 90020 | 96526 |
| Modified (%) | 0.352 | 0.146 | 0.006 | <0.002 | 0.004 | 0.010 | 0.007 |
| P-value | 1.3E−103 | 2.8E−37 | | | | | |
| On:off specificity | 145 | 183 | >11222 | >2584 | | | |
| EMX_Off2 | | | | | | | |
| Indels | 74 | 58 | 3 | 6 | 3 | 0 | 4 |
| Total | 98568 | 94108 | 105747 | 78871 | 81717 | 79469 | 79193 |
| Modified (%) | 0.075 | 0.062 | 0.003 | 0.008 | 0.004 | <0.002 | 0.005 |
| P-value | 3.2E−16 | 1.4E−12 | | | | | |
| On:off specificity | 681 | 435 | >11222 | >2584 | | | |
| EMX_Off3 | | | | | | | |
| Indels | 736 | 178 | 20 | 14 | 12 | 11 | 17 |
| Total | 72888 | 65139 | 82348 | 59593 | 74341 | 73408 | 75080 |
| Modified (%) | 1.010 | 0.273 | 0.024 | 0.023 | 0.016 | 0.015 | 0.023 |
| P-value | 2.5E−202 | 3.1E−44 | | | | | |
| On:off specificity | 51 | 98 | >11222 | >2584 | | | |
| EMX_Off4 | | | | | | | |
| Indels | 4149 | 620 | 3 | 3 | 6 | 7 | 5 |
| Total | 107537 | 91695 | 91368 | 91605 | 111736 | 119643 | 128088 |

TABLE 3-continued

Cellular modification induced by wild-type Cas9, Cas9 nickase, and fCas9 at on-target and off-target genomic sites.

| | | | | | | | |
|---|---|---|---|---|---|---|---|
| Modified (%) | 3.858 | 0.676 | 0.003 | 0.003 | 0.005 | 0.006 | 0.004 |
| P-value | <1.0E−300 | 1.9E−202 | | | | | |
| On:off specificity | 13 | 40 | >11222 | >2584 | | | |

(C)

| Nuclease type: | wt Cas9 | wt Cas9 | Cas9 nickase | fCas9 | wt Cas9 | Cas9 nickase | fCas9 |
|---|---|---|---|---|---|---|---|
| gRNA pair: | VEGF | VEGF | VEGF | VEGF | GFP | GFP | GFP |
| Total expression plasmids (ng): | 1000 | 125 | 1000 | 1000 | 1000 | 1000 | 1000 |

VEGF Sites

VEG_On

| | | | | | | | |
|---|---|---|---|---|---|---|---|
| Indels | 5253 | 2454 | 1230 | 1041 | 8 | 0 | 1 |
| Total | 10000 | 10000 | 10000 | 10000 | 10000 | 10000 | 10000 |
| Modified (%) | 52.530 | 24.540 | 12.300 | 10.410 | 0.080 | <0.002 | 0.010 |
| P-value | <1.0E−300 | <1.0E−300 | <1.0E−300 | 6.6E−286 | | | |
| On:off specificity | 1 | 1 | 1 | 1 | | | |

VEG_Off1

| | | | | | | | |
|---|---|---|---|---|---|---|---|
| Indels | 2950 | 603 | 22 | 0 | 0 | 4 | 1 |
| Total | 82198 | 71163 | 90434 | 77557 | 74765 | 79738 | 74109 |
| Modified (%) | 3.589 | 0.847 | 0.024 | <0.002 | <0.002 | 0.005 | <0.002 |
| P-value | <1.0E−300 | 3.2E−188 | 2.5E−06 | | | | |
| On:off specificity | 15 | 29 | 506 | >5150 | | | |

VEG_Off2

| | | | | | | | |
|---|---|---|---|---|---|---|---|
| Indels | 863 | 72 | 3 | 3 | 0 | 2 | 1 |
| Total | 102501 | 49836 | 119702 | 65107 | 54247 | 65753 | 61556 |
| Modified (%) | 0.842 | 0.144 | 0.003 | 0.005 | <0.002 | 0.003 | <0.002 |
| P-value | 3.5E−159 | 9.6E−24 | | | | | |
| On:off specificity | 62 | 170 | >6090 | >5150 | | | |

VEG_Off3

| | | | | | | | |
|---|---|---|---|---|---|---|---|
| Indels | 260 | 33 | 3 | 2 | 3 | 1 | 0 |
| Total | 91277 | 83124 | 90063 | 84385 | 62126 | 68165 | 69811 |
| Modified (%) | 0.285 | 0.040 | 0.003 | 0.002 | 0.005 | <0.002 | <0.002 |
| P-value | 6.8E−54 | 1.0E−05 | | | | | |
| On:off specificity | 184 | 618 | >6090 | >5150 | | | |

VEG_Off4

| | | | | | | | |
|---|---|---|---|---|---|---|---|
| Indels | 1305 | 149 | 3 | 2 | 3 | 2 | 4 |
| Total | 59827 | 41203 | 65964 | 57828 | 60906 | 61219 | 62162 |
| Modified (%) | 2.181 | 0.362 | 0.005 | 0.003 | 0.005 | 0.003 | 0.006 |
| P-value | <1.0E−300 | 2.7E−54 | | | | | |
| On:off specificity | 24 | 68 | >6090 | >5150 | | | |

(D)

| Nuclease type: | Cas9 nickase | fCas9 | Cas9 nickase | fCas9 |
|---|---|---|---|---|
| gRNA pair: | VEGF | VEGF | GFP | GFP |
| Total expression plasmids (ng): | 1000 | 1000 | 1000 | 1000 |

VEGF Sites

VEG_On

| | | | | |
|---|---|---|---|---|
| Indels | 2717 | 2122 | 10 | 13 |
| Total | 10000 | 10000 | 10000 | 10000 |
| Modified (%) | 27.170 | 21.220 | 0.100 | 0.130 |
| P-value | <1.0E−300 | <1.0E−300 | | |
| On:off specificity | 1 | 1 | | |

VEG_Off1

| | | | | |
|---|---|---|---|---|
| Indels | 67 | 30 | 3 | 2 |
| Total | 302573 | 233567 | 204454 | 190240 |
| Modified (%) | 0.022 | 0.013 | | |
| P-value | 5.9E−12 | 2.5E−06 | | |
| On:off specificity | 1227 | 1652 | | |

Results

Recently engineered variants of Cas9 that cleave only one DNA strand ("nickases") enable double-stranded breaks to be specified by two distinct gRNA sequences,[5-7] but still suffer from off-target cleavage activity[6,8] arising from the ability of each monomeric nickase to remain active when individually bound to DNA.[9-11] In contrast, the development of a FokI nuclease fusion to a catalytically dead Cas9 that requires simultaneous DNA binding and association of two FokI-dCas9 monomers to cleave DNA is described here. Off-target DNA cleavage of the engineered FokI-dCas9 (fCas9) is further reduced by the requirement that only sites flanked by two gRNAs ~15 or 25 base pairs apart are cleaved, a much more stringent spacing requirement than nickases. In human cells, fCas9 modified target DNA sites with efficiency comparable to that of nickases, and with >140-fold higher specificity than wild-type Cas9. Target sites that conform to the substrate requirements of fCas9 are abundant in the human genome, occurring on average once every 34 bp.

In cells, Cas9:gRNA-induced double strand breaks can result in functional gene knockout through non-homologous end joining (NHEJ) or alteration of a target locus to virtually any sequence through homology-directed repair (HDR) with an exogenous DNA template.[9,15,16] Cas9 is an especially convenient genome editing platform,[17] as a genome editing agent for each new target site of interest can be accessed by simply generating the corresponding gRNA. This approach has been widely used to create targeted knockouts and gene insertions in cells and model organisms, and has also been recognized for its potential therapeutic relevance.

While Cas9:gRNA systems provide an unprecedented level of programmability and ease of use, studies[1-5] have reported the ability of Cas9 to cleave off-target genomic sites, resulting in modification of unintended loci that can limit the usefulness and safety of Cas9 as a research tool and as a potential therapeutic. It was hypothesized that engineering Cas9 variants to cleave DNA only when two simultaneous, adjacent Cas9:DNA binding events take place could substantially improve genome editing specificity since the likelihood of two adjacent off-target binding events is much smaller than the likelihood of a single off-target binding event (approximately $1/n^2$ vs. $1/n$). Such an approach is distinct from the recent development of mutant Cas9 proteins that cleave only a single strand of dsDNA, such as nickases. Nickases can be used to nick opposite strands of two nearby target sites, generating what is effectively a double strand break, and paired Cas9 nickases can effect substantial on-target DNA modification with reduced off-target modification.[5,6,8] Because each of the component Cas9 nickases remains catalytically active[9-11] and single-stranded DNA cleavage events are weakly mutagenic,[18,19] nickases can induce genomic modification even when acting as monomers.[5,7,16] Indeed, Cas9 nickases have been previously reported to induce off-target modifications in cells.[6,8] Moreover, since paired Cas9 nickases can efficiently induce dsDNA cleavage-derived modification events when bound up to ~100 bp apart,[6] the statistical number of potential off-target sites for paired nickases is larger than that of a more spatially constrained dimeric Cas9 cleavage system.

Figure 6A:
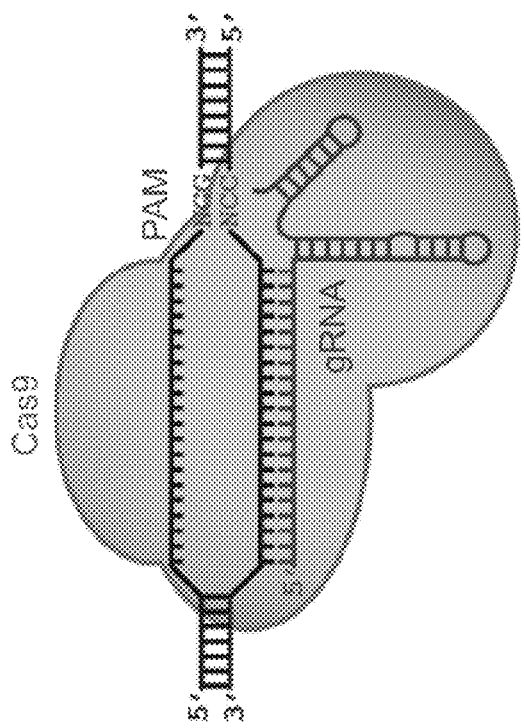
FIG. 6 shows architectures of Cas9 and FokI-dCas9 fusion variants. (A) Cas9 protein in complex with a guide RNA (gRNA) binds to target DNA. The *S. pyogenes* Cas9 protein recognizes the PAM sequence NGG, initiating unwinding of dsDNA and gRNA:DNA base pairing. (B) FokI-dCas9 fusion architectures tested. Four distinct configurations of NLS, FokI nuclease, and dCas9 were assembled. Seventeen (17) protein linker variants were also tested. (C) gRNA target sites tested within GFP. Seven gRNA target sites were chosen to test FokI-dCas9 activity in an orientation in which the PAM is distal from the cleaved spacer sequence (orientation A). Together, these seven gRNAs enabled testing of FokI-dCas9 fusion variants across spacer lengths ranging from 5 to 43 bp. See FIG. 9 for guide RNAs used to test orientation B, in which the PAM is adjacent to the spacer sequence. (D) Monomers of FokI nuclease fused to dCas9 bind to separate sites within the target locus. Only adjacently bound FokI-dCas9 monomers can assemble a catalytically active FokI nuclease dimer, triggering dsDNA cleavage. The sequences shown in (C) are identified as follows: "EmGFP (bp 326-415)" corresponds to SEQ ID NO:204; "G1" corresponds to SEQ ID NO:205; "G2" corresponds to SEQ ID NO:206; "G3" corresponds to SEQ ID NO:207; "G4" corresponds to SEQ ID NO:208; "G5" corresponds to SEQ ID NO:209; "G6" corresponds to SEQ ID NO:210; and "G7" corresponds to SEQ ID NO:211.
FIG. 6C), each gRNA individually, or no gRNAs. The Indel modification percentage is shown below each lane for samples with modification above the detection limit (~2%). (C-G) show graphs depicting Indel modification efficiency for (C) two pairs of gRNAs spaced 14 or 25 bp apart targeting the GFP site, (D) one pair of gRNAs spaced 19 bp apart targeting the CLTA site, (E) one pair of gRNAs spaced 23 bp apart targeting the EMX site, (F) one pair of gRNAs spaced 16 bp apart targeting the HBB site, and (G) two pairs of gRNAs spaced 14 or 16 bp apart targeting the VEGF site. Error bars reflect standard error of the mean from three biological replicates performed on different days.
Figure 6B:
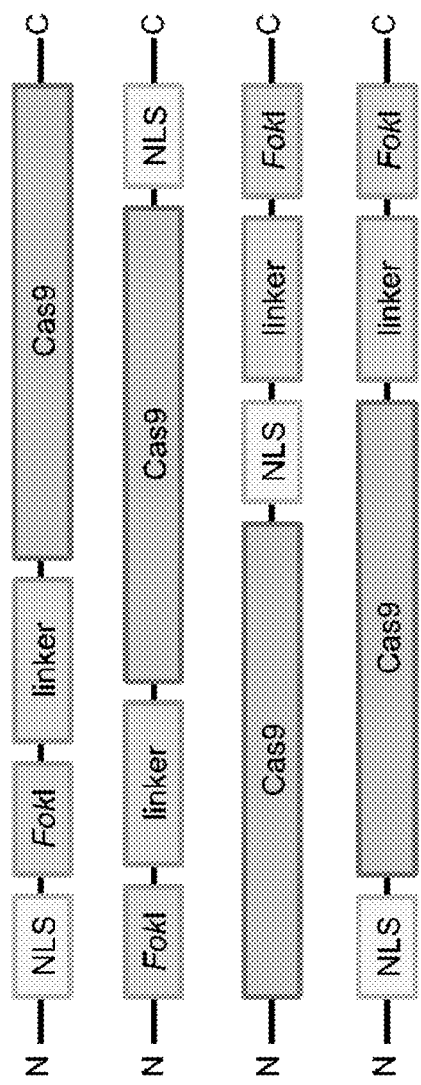
Figure 6C:
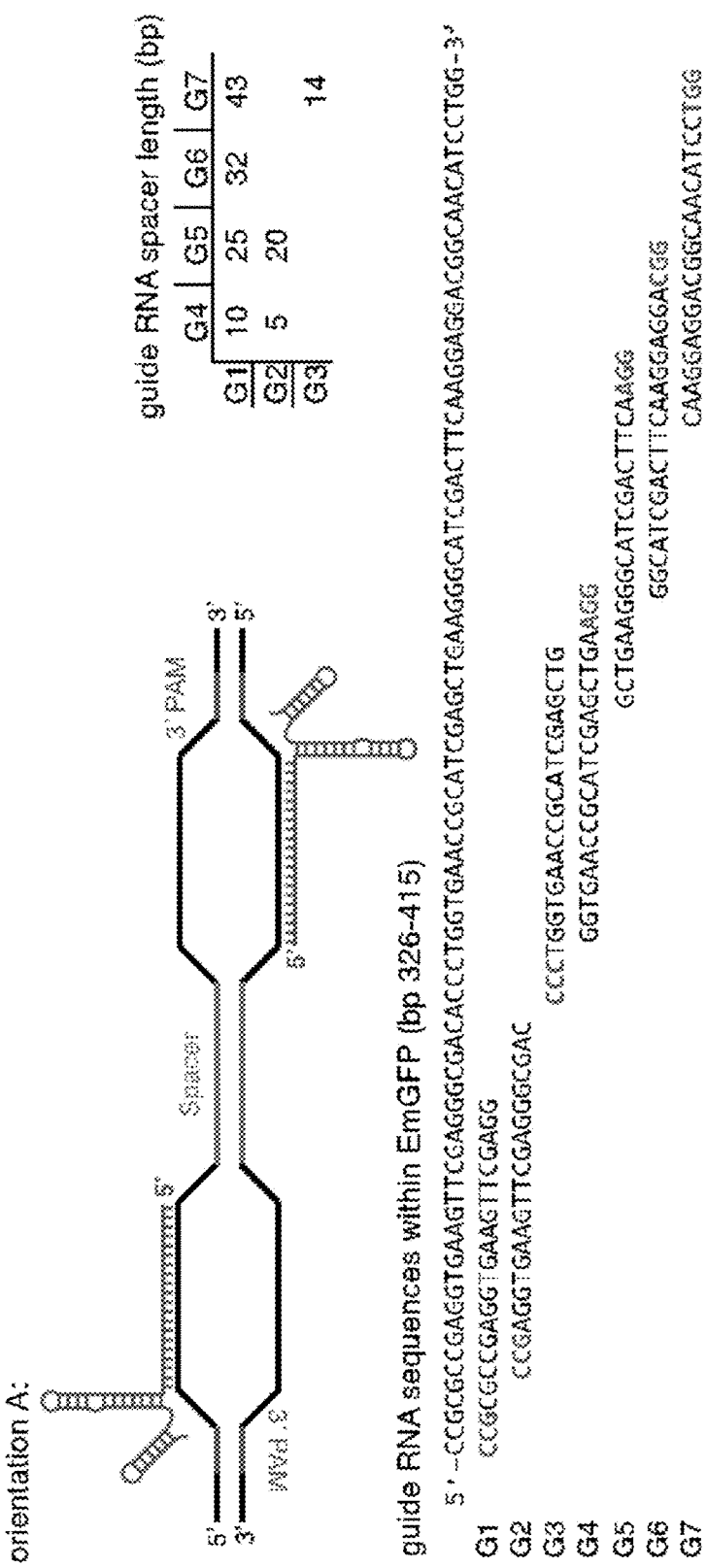
Figure 6D:
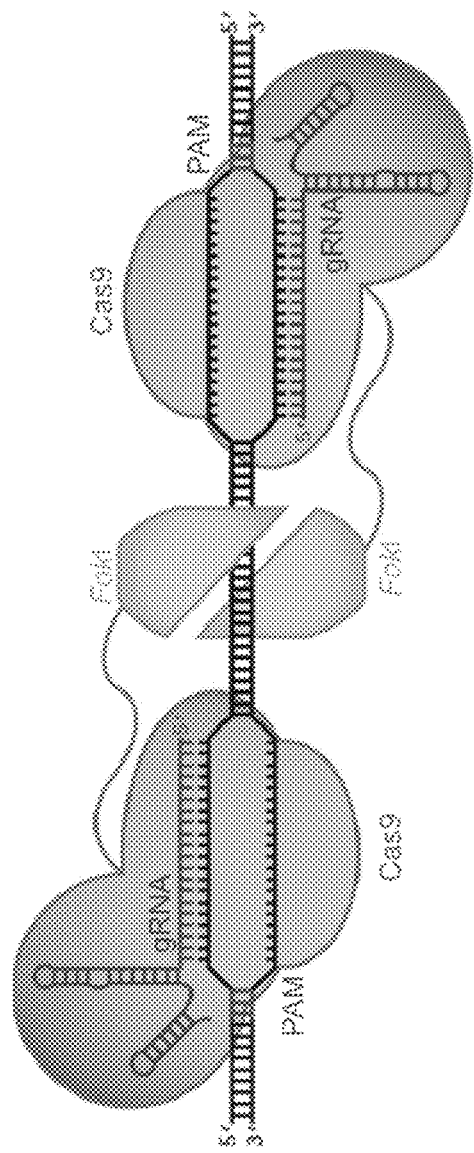

To further improve the specificity of the Cas9:gRNA system, an obligate dimeric Cas9 system is provided herein. In this example, fusing the FokI restriction endonuclease cleavage domain to a catalytically dead Cas9 (dCas9) created an obligate dimeric Cas9 that would cleave DNA only when two distinct FokI-dCas9:gRNA complexes bind to adjacent sites ("half-sites") with particular spacing constraints (FIG. 6D). In contrast with Cas9 nickases, in which single-stranded DNA cleavage by monomers takes place independently, the DNA cleavage of FokI-dCas9 requires simultaneous binding of two distinct FokI-dCas9 monomers because monomeric FokI nuclease domains are not catalytically competent.[21] This approach increased the specificity of DNA cleavage relative to wild-type Cas9 by doubling the number of specified target bases contributed by both monomers of the FokI-dCas9 dimer, and offered improved specificity compared to nickases due to inactivity of monomeric FokI-dCas9:gRNA complexes, and the more stringent spatial requirements for assembly of a FokI-dCas9 dimer.

While fusions of Cas9 to short functional peptide tags have been described to enable gRNA-programmed transcriptional regulation,[22] it is believed that no fusions of Cas9 with active enzyme domains have been previously reported. Therefore a wide variety of FokI-dCas9 fusion proteins were constructed and characterized with distinct configurations of a FokI nuclease domain, dCas9 containing inactivating mutations D10A and H840A, and a nuclear localization sequence (NLS). FokI was fused to either the N- or C-terminus of dCas9, and varied the location of the NLS to be at either terminus or between the two domains (FIG. 6B). The length of the linker sequence was varied as either one or three repeats of Gly-Gly-Ser (GGS) between the FokI and dCas9 domains. Since previously developed dimeric nuclease systems are sensitive to the length of the spacer sequence between half-sites,[23,24] a wide range of spacer sequence lengths was tested between two gRNA binding sites within a test target gene, Emerald GFP (referred to hereafter as GFP) (FIG. 6C and FIG. 9). Two sets of gRNA binding-site pairs with different orientations were chosen within GFP. One set placed the pair of NGG PAM sequences distal from the spacer sequence, with the 5' end of the gRNA adjacent to the spacer (orientation A) (FIG. 6C), while the other placed the PAM sequences immediately adjacent to the spacer (orientation B) (FIG. 9). In total, seven pairs of gRNAs were suitable for orientation A, and nine were suitable for orientation B. By pairwise combination of the gRNA targets, eight spacer lengths were tested in both dimer orientations, ranging from 5 to 43 bp in orientation A, and 4 to 42 bp in orientation B. In total, DNA constructs corresponding to 104 pairs of FokI-dCas9:gRNA complexes were generated and tested, exploring four fusion architectures, 17 protein linker variants (described below), both gRNA orientations and 13 spacer lengths between half-sites.

Figures 10A, 10B:
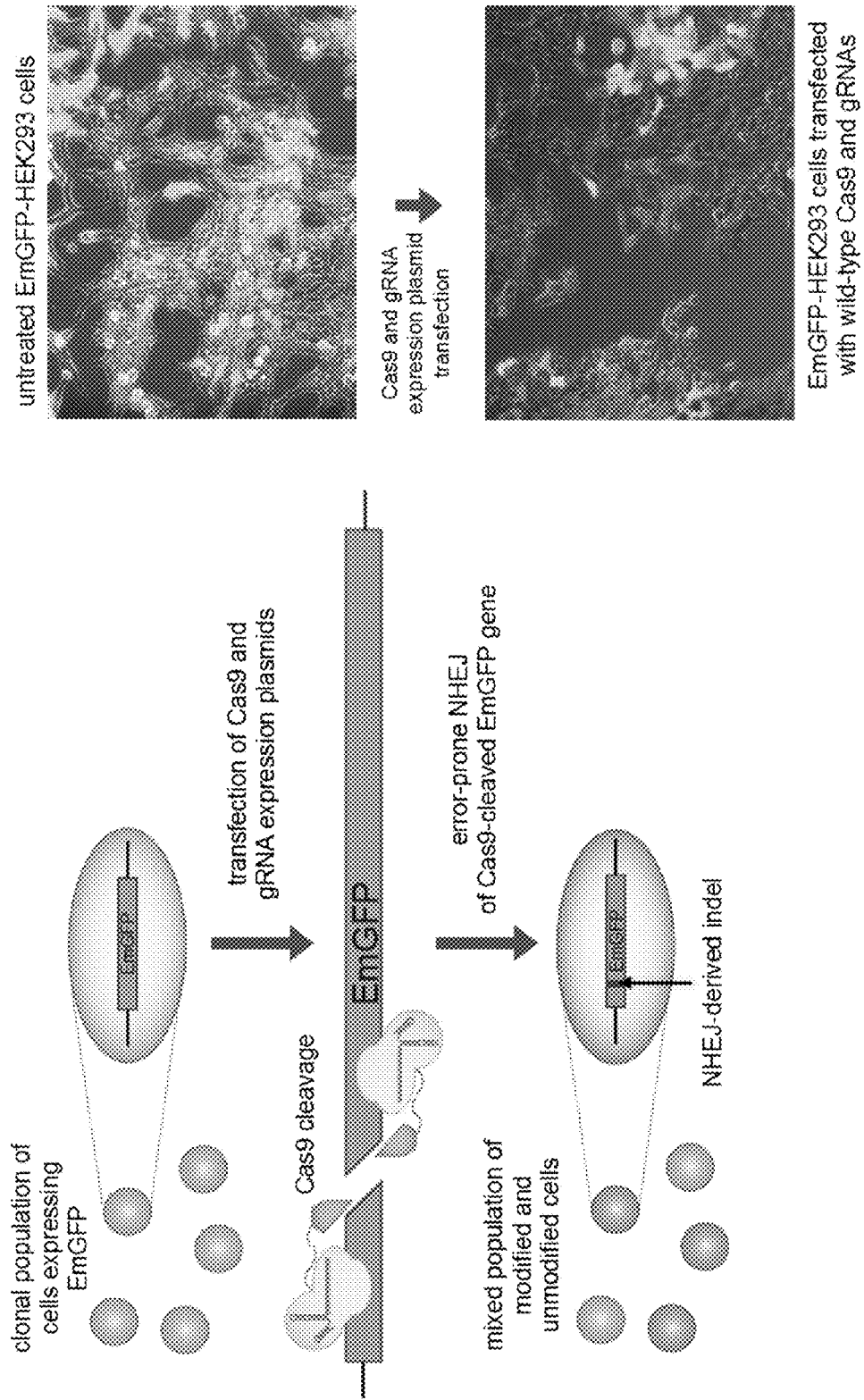
FIG. 10 shows a GFP disruption assay for measuring genomic DNA-modification activity. (A) depicts schematically a HEK293-derived cell line constitutively expressing a genomically integrated EmGFP gene used to test the activity of candidate FokI-dCas9 fusion constructs. Co-transfection of these cells with appropriate nuclease and gRNA expression plasmids leads to dsDNA cleavage within the EmGFP coding sequence, stimulating error-prone NHEJ and generating indels that can disrupt the expression of GFP, leading to loss of cellular fluorescence. The fraction of cells displaying a loss of GFP fluorescence is then quantitated by flow cytometry. (B) shows typical epifluorescence microscopy images at 200× magnification of EmGFP-HEK293 cells before and after co-transfection with wild-type Cas9 and gRNA expression plasmids.

To assay the activities of these candidate FokI-dCas9:gRNA pairs, a previously described flow cytometry-based fluorescence assay[2,8] in which DNA cleavage and NHEJ of a stably integrated constitutively expressed GFP gene in HEK293 cells leads to loss of cellular fluorescence was used (FIG. 10). For comparison, the initial set of FokI-dCas9 variants were assayed side-by-side with the corresponding Cas9 nickases and wild-type Cas9 in the same expression plasmid across both gRNA spacer orientation sets A and B. Cas9 protein variants and gRNA were generated in cells by transient co-transfection of the corresponding Cas9 protein expression plasmids together with the appropriate pair of gRNA expression plasmids. The FokI-dCas9 variants, nickases, and wild-type Cas9 all targeted identical DNA sites using identical gRNAs.

Figure 11A:
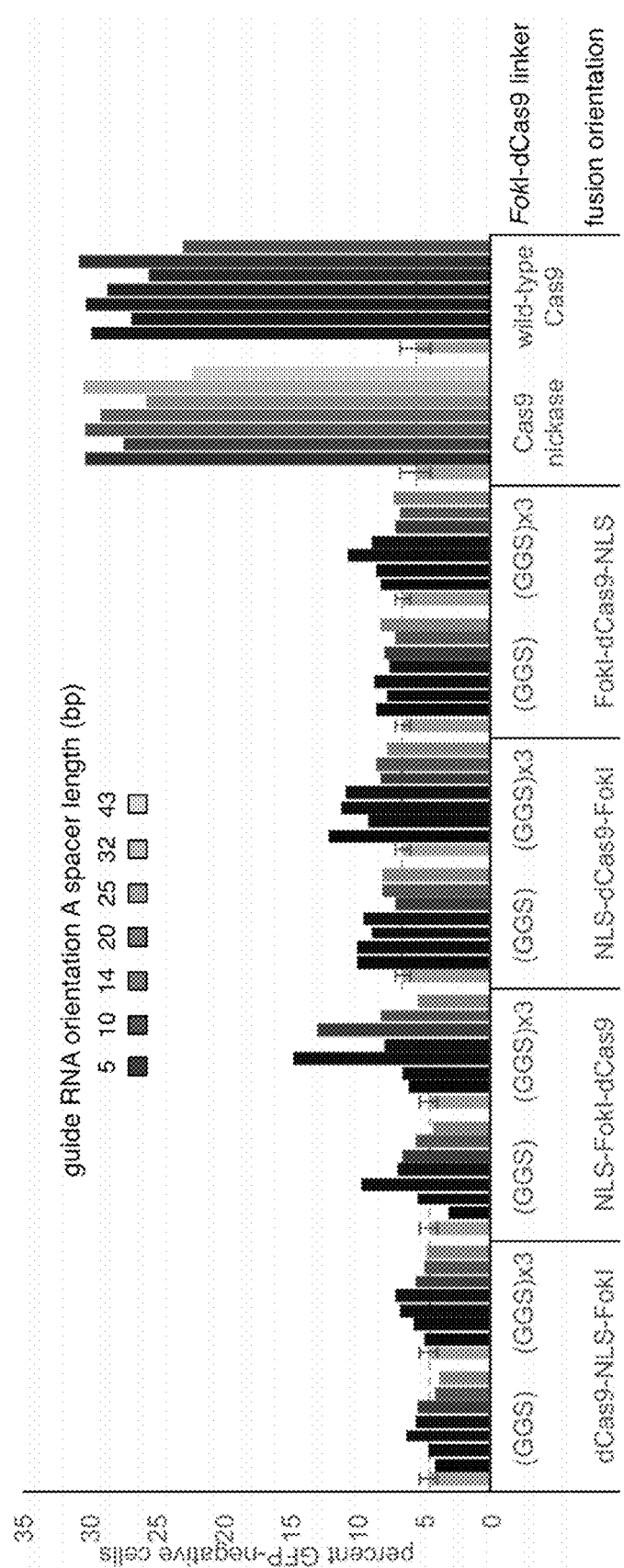
FIG. 11 shows a graph depicting the activities of FokI-dCas9 fusion candidates combined with gRNA pairs of different orientations and varying spacer lengths. The fusion architectures described in FIG. 6B were tested for functionality by flow cytometry using the GFP loss-of-function reporter across all (A) orientation A gRNA spacers and (B) orientation B gRNA spacers (FIG. 6C and FIG. 9). All FokI-dCas9 fusion data shown are the results of single trials. Wild-type Cas9 and Cas9 nickase data are the average of two replicates, while the 'no treatment' negative control data is the average of 6 replicates, with error bars representing one standard deviation. The grey dotted line across the Y-axis corresponds to the average of the 'no treatment' controls performed on the same day. The sequence shown as "(GGS)×3" corresponds to SEQ ID NO:14.
Figure 11B:
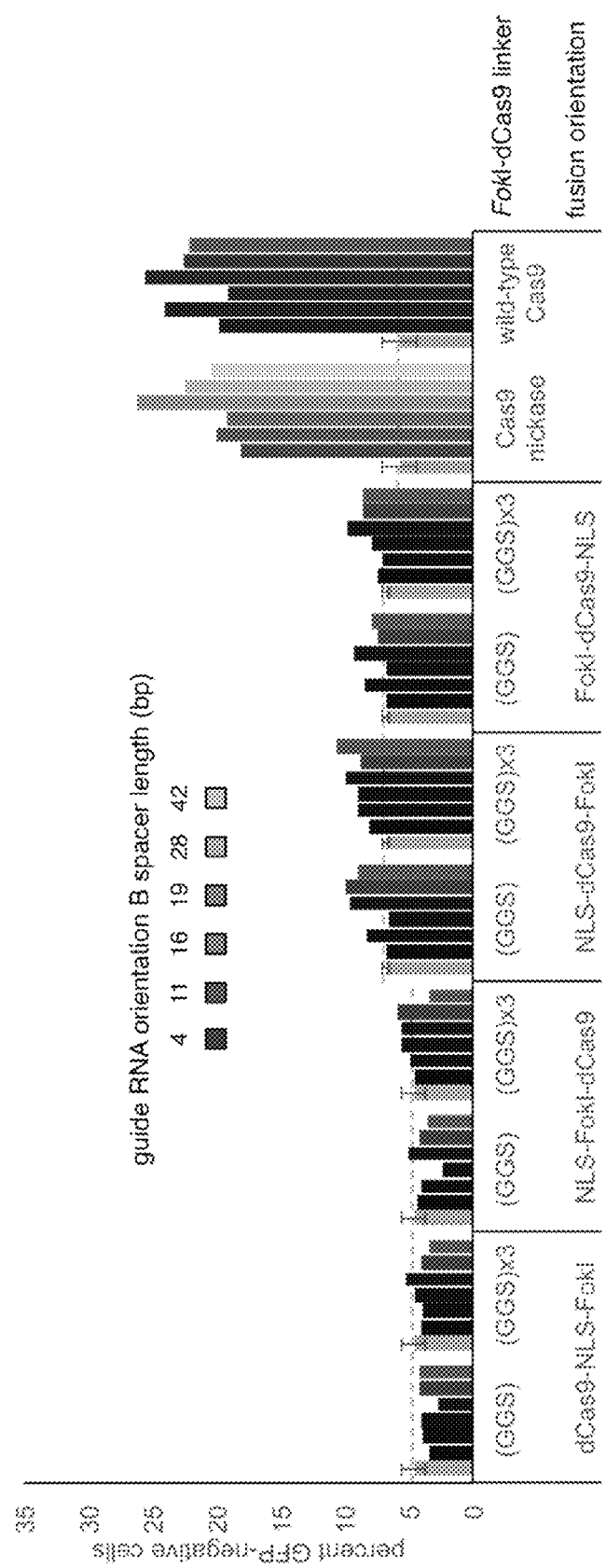

Most of the initial FokI-dCas9 fusion variants were inactive or very weakly active (FIG. 11). The NLS-FokI-dCas9 architecture (listed from N to C terminus), however, resulted in a 10% increase of GFP-negative cells above corresponding the no-gRNA control when used in orientation A, with PAMs distal from the spacer (FIG. 11A). In contrast, NLS-FokI-dCas9 activity was undetectable when used on gRNA pairs with PAMs adjacent to the spacer (FIG. 11B). Examination of the recently reported Cas9 structures[25,26] reveals that the Cas9 N-terminus protrudes from the RuvCI domain, which contacts the 5' end of the gRNA:DNA duplex. Without wishing to be bound by any particular theory, it is speculated that this arrangement places an N-terminally fused FokI distal from the PAM, resulting in a preference for gRNA pairs with PAMs distal from the cleaved spacer (FIG. 6D). While other FokI-dCas9 fusion pairings and the other gRNA orientation in some cases showed modest activity (FIG. 11), NLS-FokI-dCas9 with gRNAs in orientation A were chosen for further development.

Figure 12B:
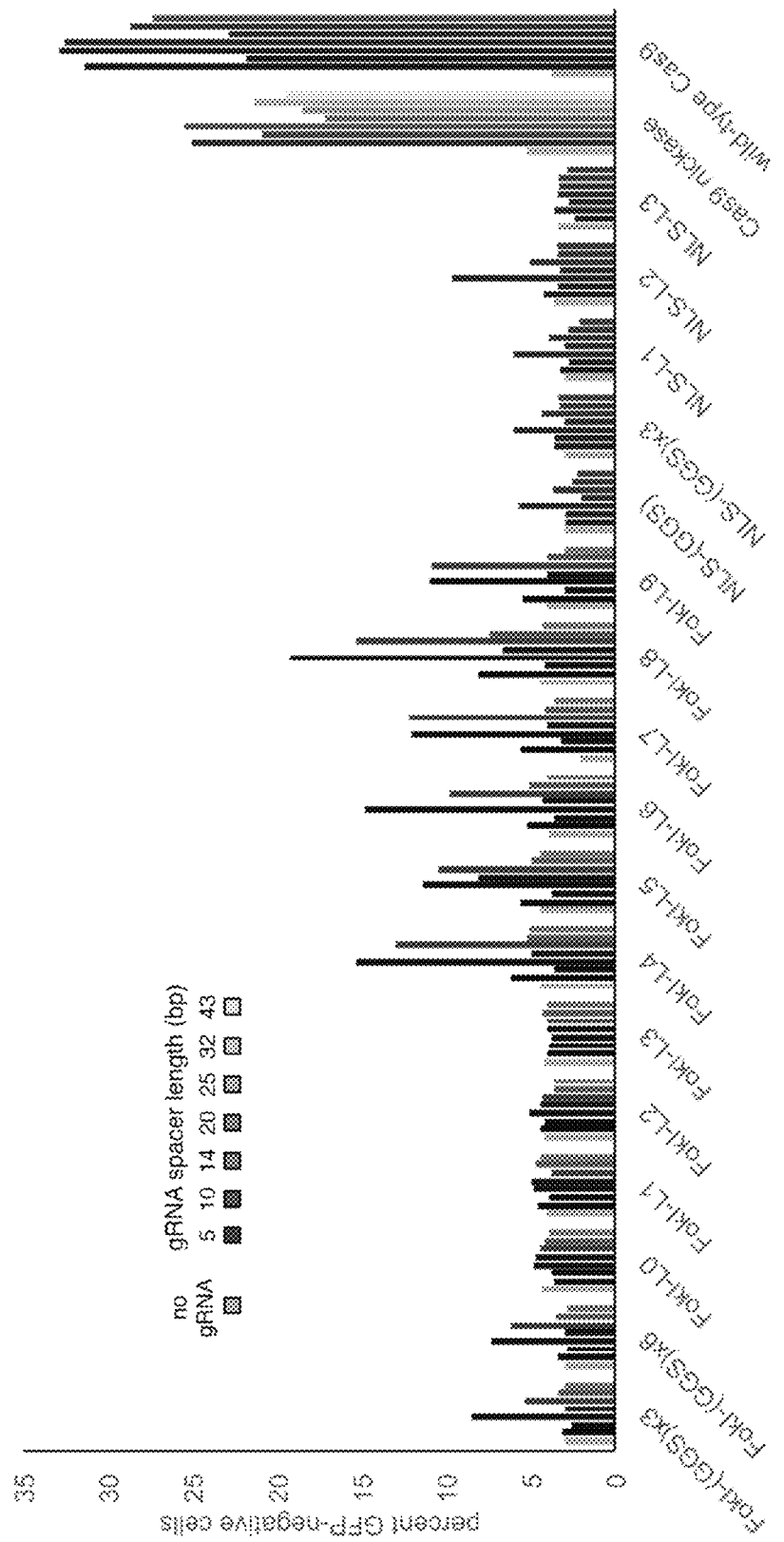
FIG. 12 shows the optimization of protein linkers in NLS-FokI-dCas9. (A) shows a table of all linker variants tested. Wild-type Cas9 and Cas9 nickase were included for comparison. The initial active construct NLS-FokI-dCas9 with a (GGS)$_3$ (SEQ ID NO:14) linker between FokI and dCas9 was tested across a range of alternate linkers. The final choice of linkers for fCas9 is highlighted. (B) shows a graph depicting the activity of FokI-dCas9 fusions with linker variants. Each variant was tested across a range of spacer lengths from 5 to 43 bp using gRNA pair orientation A. A control lacking gRNA ("no gRNA") was included for each separate fusion construct. NLS-FokI-dCas9 variant L8 showed the best activity, approaching the activity of Cas9 nickase. Variants L4 through L9 show peak activity with 14- and 25-bp spacer lengths, suggesting two optimal spacer lengths roughly one helical turn of dsDNA apart. The sequences shown in (A) are identified as follows: GGSGGSGGS corresponds to SEQ ID NO:14; GGSGGSGGSGGSGGSGGS corresponds to SEQ ID NO:15; MKIIEQLPSA corresponds to SEQ ID NO:22; VRHKLKRVGS corresponds to SEQ ID NO:23; VPFLLEPDNINGKTC corresponds to SEQ ID NO:19; GHGTGSTGSGSS corresponds to SEQ ID NO:24; MSRPDPA corresponds to SEQ ID NO:25; GSAGSAAGSGEF corresponds to SEQ ID NO:20; SGSETPGTSESA corresponds to SEQ ID NO:17; SGSETPGTSESATPES corresponds to SEQ ID NO:16; SGSETPGTSESATPEGGSGGS corresponds to SEQ ID NO:18; GGSM corresponds to SEQ ID NO:301; and SIVAQLSRPDPA corresponds to SEQ ID NO:21.

Next the protein linkers between the NLS and FokI domain, and between the FokI domain and dCas9 in the NLS-FokI-dCas9 architecture were optimized. 17 linkers with a wide range of amino acid compositions, predicted flexibilities, and lengths varying from 9 to 21 residues were tested (FIG. 12A). Between the FokI domain and dCas9 a flexible 18-residue linker, $(GGS)_6$ (SEQ ID NO:15), and a 16-residue "XTEN" linker (FokI-L8 in FIG. 12A) were identified based on a previously reported engineered protein with an open, extended conformation,[27] as supporting the highest levels of genomic GFP modification FIG. 12B).

The XTEN protein was originally designed to extend the serum half-life of translationally fused biologic drugs by increasing their hydrodynamic radius, acting as protein-based functional analog to chemical PEGylation.[35] Possessing a chemically stable, non-cationic, and non-hydrophobic primary sequence, and an extended conformation, it is hypothesized that a portion of XTEN could function as a stable, inert linker sequence for fusion proteins. The sequence of the XTEN protein tag from E-XTEN was analyzed, and repeating motifs within the amino acid sequence were aligned. The sequence used in the FokI-dCas9 fusion construct FokI-L8 (FIG. 12A) was derived from the consensus sequence of a common E-XTEN motif, and a 16 amino acid sequence was chosen from within this motif to test as a FokI-dCas9 linker.

Many of the FokI-dCas9 linkers tested including the optimal XTEN linker resulted in nucleases with a marked preference for spacer lengths of ~15 and ~25 bp between half-sites, with all other spacer lengths, including 20 bp, showing substantially lower activity (FIG. 12B). This pattern of linker preference is consistent with a model in which the FokI-dCas9 fusions must bind to opposite faces of the DNA double helix to cleave DNA, with optimal binding taking place ~1.5 or 2.5 helical turns apart. The variation of NLS-FokI linkers did not strongly affect nuclease performance, especially when combined with the XTEN FokI-dCas9 linker (FIG. 12B).

In addition to assaying linkers between the FokI domain and dCas9 in the NLS-FokI-dCas9 architecture, four linker variants between the N-terminal NLS and the FokI domain were also tested (FIG. 12A). Although a NLS-GSAG-SAAGSGEF (SEQ ID NO:20)-FokI-dCas9 linker exhibited nearly 2-fold better GFP gene modification than the other NLS-FokI linkers tested when a simple GGS linker was used between the FokI and dCas9 domains (FIG. 12B), the GSAG-SAAGSGEF (SEQ ID NO:20) linker did not perform substantially better when combined with the XTEN linker between the FokI and dCas9 domains.

Figure 7A:
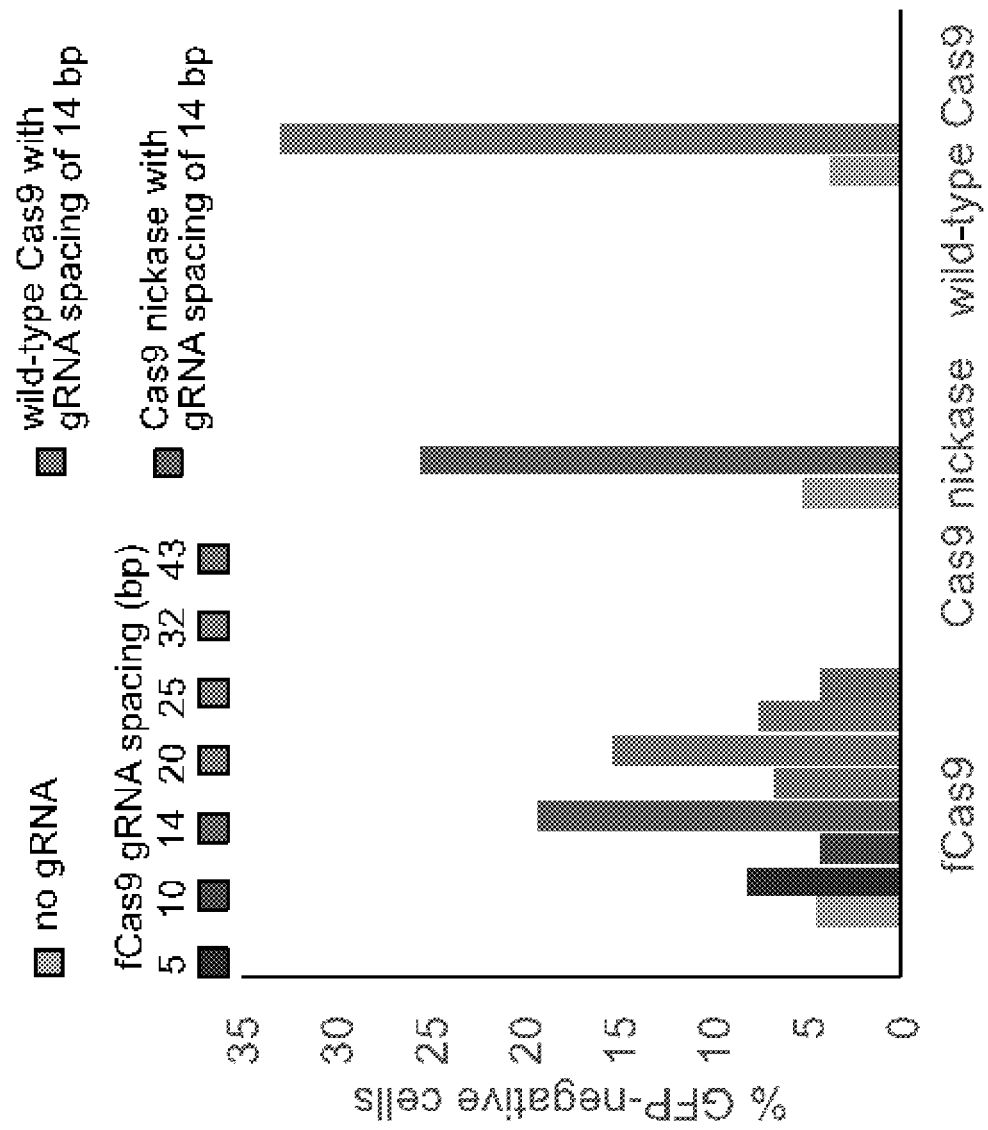
FIG. 7 shows genomic DNA modification by fCas9, Cas9 nickase, and wild-type Cas9. (A) shows a graph depicting GFP disruption activity of fCas9, Cas9 nickase, or wild-type Cas9 with either no gRNA, or gRNA pairs of variable spacer length targeting the GFP gene in orientation A. (B) is an image of a gel showing Indel modification efficiency from PAGE analysis of a Surveyor cleavage assay of renatured target-site DNA amplified from cells treated with fCas9, Cas9 nickase, or wild-type Cas9 and two gRNAs spaced 14 bp apart targeting the GFP site (gRNAs G3 and G7.

The NLS-GGS-FokI-XTEN-dCas9 construct consistently exhibited the highest activity among the tested candidates, inducing loss of GFP in ~15% of cells, compared to ~20% and ~30% for Cas9 nickases and wild-type Cas9 nuclease, respectively (FIG. 7A). All subsequent experiments were performed using this construct, hereafter referred to as fCas9. To confirm the ability of fCas9 to efficiently modify genomic target sites, the T7 endonuclease I Surveyor assay[28] was used to measure the amount of mutation at each of seven target sites within the integrated GFP gene in HEK293 cells treated with fCas9, Cas9 nickase, or wild-type Cas9 and either two distinct gRNAs in orientation A or no gRNAs as a negative control. Consistent with the flow cytometry-based studies, fCas9 was able to modify the GFP target sites with optimal spacer lengths of ~15 or ~25 bp at a rate of ~20%, comparable to the efficiency of nickase-induced modification and approximately two-thirds that of wild-type Cas9 (FIGS. 7A-C).

Figure 13:
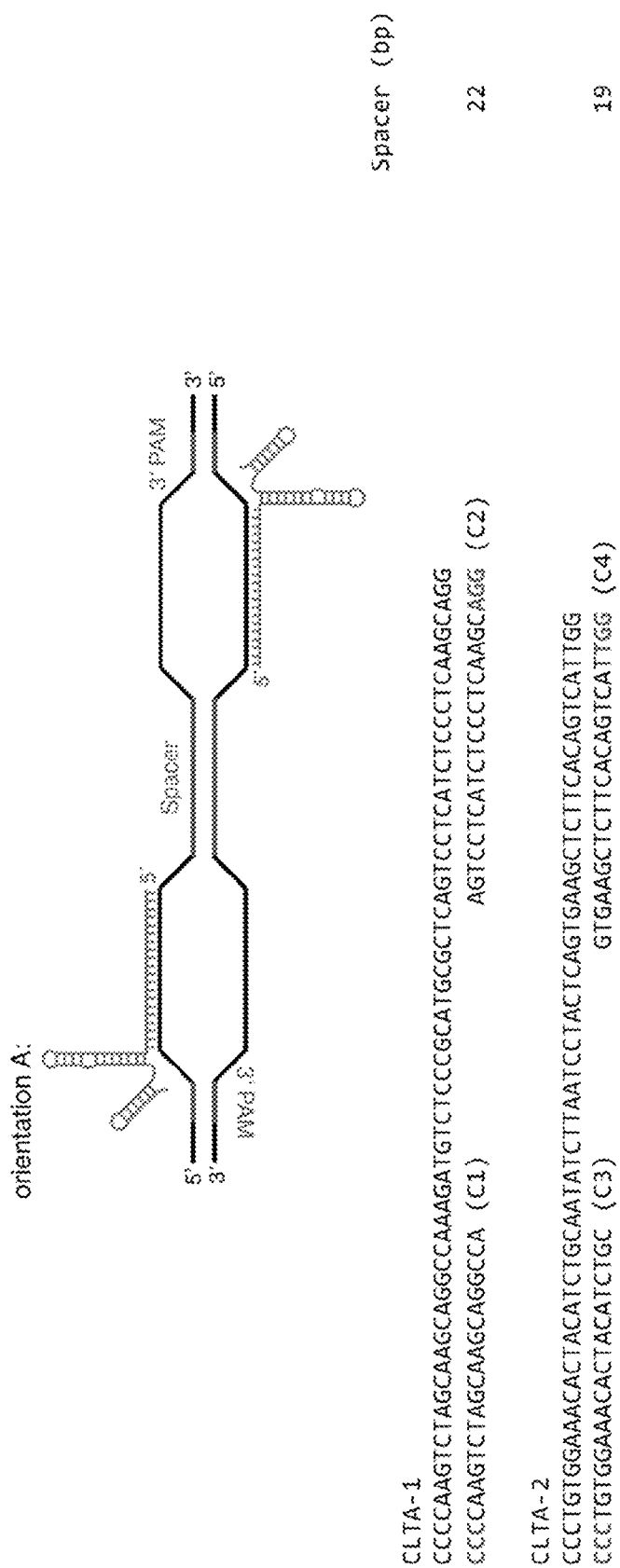
FIG. 13 shows target DNA sequences in endogenous human EMX, VEGF, CLTA, and HBB genes. The gRNA target sites tested within endogenous human EMX, VEGF, CLTA, and HBB genes are shown. Thirteen gRNA target sites were chosen to test the activity of the optimized fCas9 fusion in an orientation in which the PAM is distal from the cleaved spacer sequence (orientation A). Together, these 13 gRNAs enabled testing of fCas9 fusion variants across eight spacer lengths ranging from 5 to 47 bp. The sequences shown are identified as follows: "CLTA-1" corresponds to SEQ ID NO:220; "C1" corresponds to SEQ ID NO:221; "C2" corresponds to SEQ ID NO:222; "C3" corresponds to SEQ ID NO:224; "C4" corresponds to SEQ ID NO:225; "HBC" corresponds to SEQ ID NO:226; "H1" corresponds to SEQ ID NO:227; "H2" corresponds to SEQ ID NO:228; "H3" corresponds to SEQ ID NO:229; "H4" corresponds to SEQ ID NO:230; "H5" corresponds to SEQ ID NO:231; "H6" corresponds to SEQ ID NO:232; "H7" corresponds to SEQ ID NO:233; "EMX" corresponds to SEQ ID NO:234; "E1" corresponds to SEQ ID NO:235; "E2" corresponds to SEQ ID NO:236; "E3" corresponds to SEQ ID NO:237; "VEGF" corresponds to SEQ ID NO:238; "V1" corresponds to SEQ ID NO:239; "V2" corresponds to SEQ ID NO:240; "V3" corresponds to SEQ ID NO:241; and "V4" corresponds to SEQ ID NO:242.
Figures 14A, 14B:
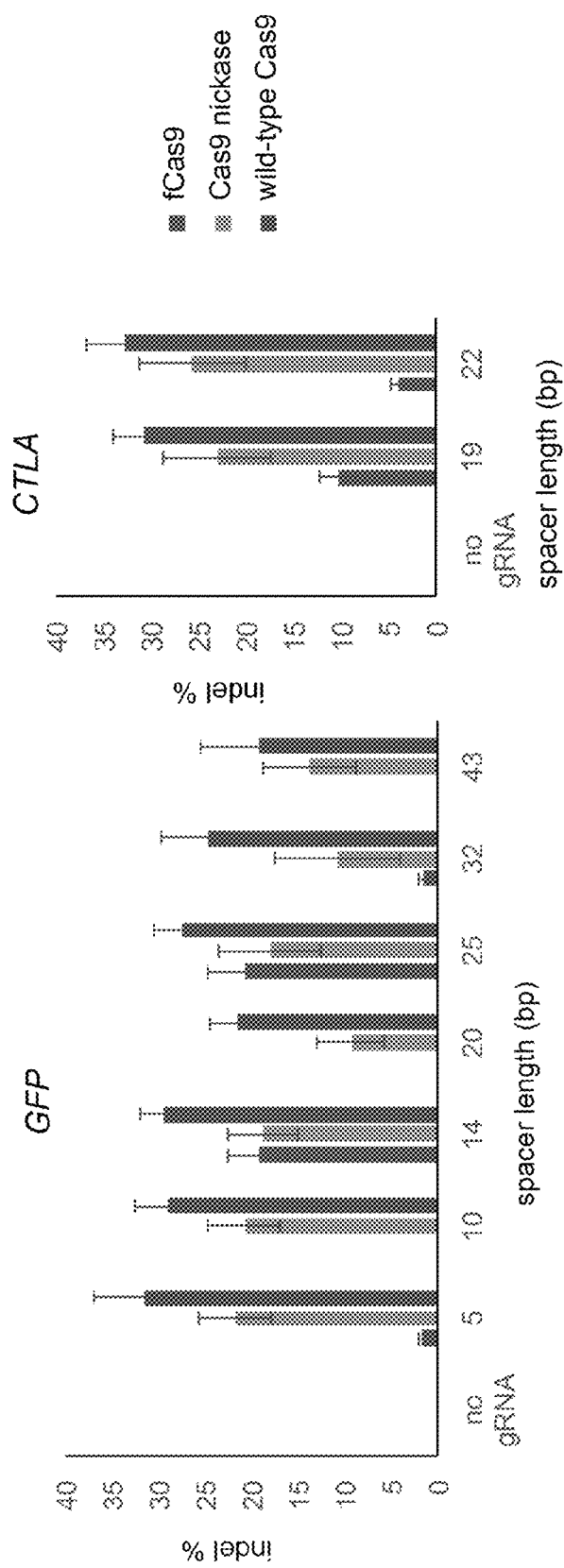
FIG. 14 shows graphs depicting spacer length preference of genomic DNA modification by fCas9, Cas9 nickase, and wild-type Cas9. Indel modification efficiency for (A) pairs of gRNAs targeting the GFP site, (B) pairs of gRNAs targeting the CLTA site, (C) pairs of gRNAs targeting the EMX site (D) pairs of gRNAs targeting the HBB site, and (E) pairs of gRNAs targeting the VEGF site. Error bars reflect standard error of the mean from three biological replicates performed on different days.
Figure 17:
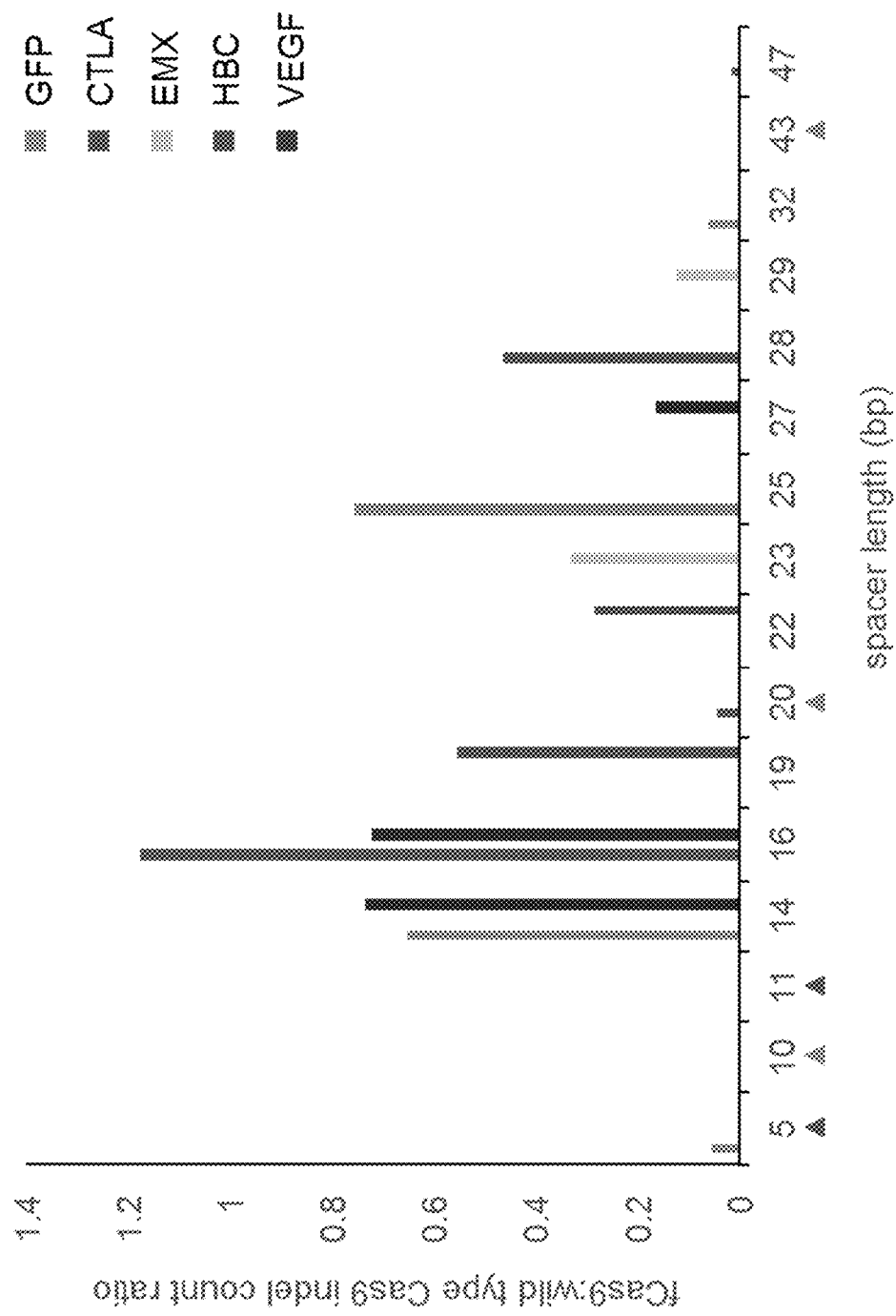
FIG. 17 shows a graph depicting how fCas9 indel frequency of genomic targets reflects gRNA pair spacer length preference. The graph shows the relationship between spacer length (number of by between two gRNAs) and the indel modification efficiency of fCas9 normalized to the indel modification efficiency of the same gRNAs co-expressed with wild-type Cas9 nuclease. Colored triangles below the X-axis denote spacer lengths that were tested but which yielded no detectable indels for the indicated target gene. These results suggest that fCas9 requires ~15 bp or ~25 bp between half-sites to efficiently cleave DNA.

Next the ability of the optimized fCas9 to modify four distinct endogenous genomic loci by Surveyor assay was evaluated. CLTA (two sites), EMX (two sites), HBB (six sites) VEGF (three sites), and were targeted with two gRNAs per site in orientation A spaced at various lengths (FIG. 13). Consistent with the results of the experiments targeting GFP, at appropriately spaced target half-sites fCas9 induced efficient modification of all four genes, ranging from 8% to 22% target chromosomal site modification (FIGS. 7D-G and FIG. 14). Among the gRNA spacer lengths resulting in the highest modification at each of the five genes targeted (including GFP), fCas9 induced on average 15.6% (±6.3% s.d.) modification, while Cas9 nickase and wild-type Cas9 induced on average 22.1% (±4.9% s.d.) and 30.4% (±3.1% s.d.) modification, respectively, from their optimal gRNA pairs for each gene. Because decreasing the amount of Cas9 expression plasmid and gRNA expression plasmid during transfection generally did not proportionally decrease genomic modification activity for Cas9 nickase and fCas9 (FIGS. 15A-C), expression was likely not limiting under the conditions tested.

Figure 8B:
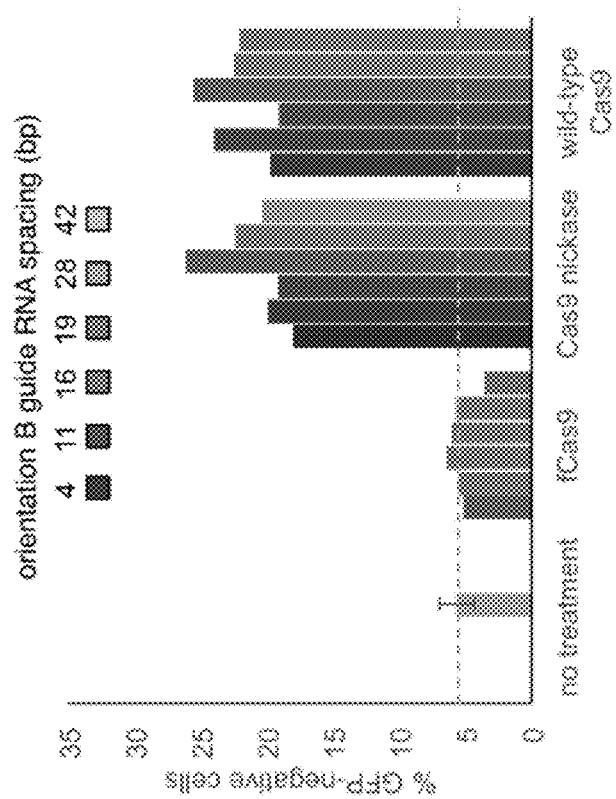
FIG. 8 shows the DNA modification specificity of fCas9, Cas9 nickase, and wild-type Cas9. (A) shows a graph depicting GFP gene disruption by wild-type Cas9, Cas9 nickase, and fCas9 using gRNA pairs in orientation A. High activity of fCas9 requires spacer lengths of ~15 and 25 bp, roughly one DNA helical turn apart. (B) shows a graph depicting GFP gene disruption using gRNA pairs in orientation B. Cas9 nickase, but not fCas9, accepts either orientation of gRNA pairs. (C) shows a graph depicting GFP gene disruption by fCas9, but not Cas9 nickase or wild-type Cas9, which depends on the presence of two gRNAs. Four single gRNAs were tested along with three gRNA pairs of varying spacer length. In the presence of gRNA pairs in orientation A with spacer lengths of 14 or 25 bp (gRNAs 1+5, and gRNAs 3+7, respectively), fCas9 is active, but not when a gRNA pair with a 10-bp spacer (gRNAs 1+4) is used. In (A-C), "no treatment" refers to cells receiving no plasmid DNA. (D-F) show graphs depicting the indel mutation frequency from high-throughput DNA sequencing of amplified genomic on-target sites and off-target sites from human cells treated with fCas9, Cas9 nickase, or wild-type Cas9 and (D) two gRNAs spaced 19 bp apart targeting the CLTA site (gRNAs C1 and C2), (E) two gRNAs spaced 23 bp apart targeting the EMX site (gRNAs E1 and E2), or (F, G) two gRNAs spaced 14 bp apart targeting the VEGF site (gRNAs V1 and V2). (G) shows a graph depicting two in-depth trials to measure genome modification at VEGF off-target site 1. Trial 1 used 150 ng of genomic input DNA and >8×10$^5$ sequence reads for each sample; trial 2 used 600 ng of genomic input DNA and >23×10$^5$ sequence reads for each sample. In (D-G), all significant (P value <0.005 Fisher's Exact Test) indel frequencies are shown. P values are listed in Table 3. For (D-F) each on- and off-target sample was sequenced once with >10,000 sequences analyzed per on-target sample and an average of 76,260 sequences analyzed per off-target sample (Table 3). The sequences shown in (C) are identified as follows, from top to bottom: the sequence found at the top of FIG. 8C corresponds to SEQ ID NO:204; "G1" corresponds to SEQ ID NO:205; "G3" corresponds to SEQ ID NO:207; "G5" corresponds to SEQ ID NO:209; "G7" corresponds to SEQ ID NO:211; "G1+4" corresponds to SEQ ID NO:205 and SEQ ID NO:208; "G1+5" corresponds to SEQ ID NO:205 and SEQ ID NO:209; "G3+7" corresponds to SEQ ID NO:207 and SEQ ID NO:211.
Figure 8A:
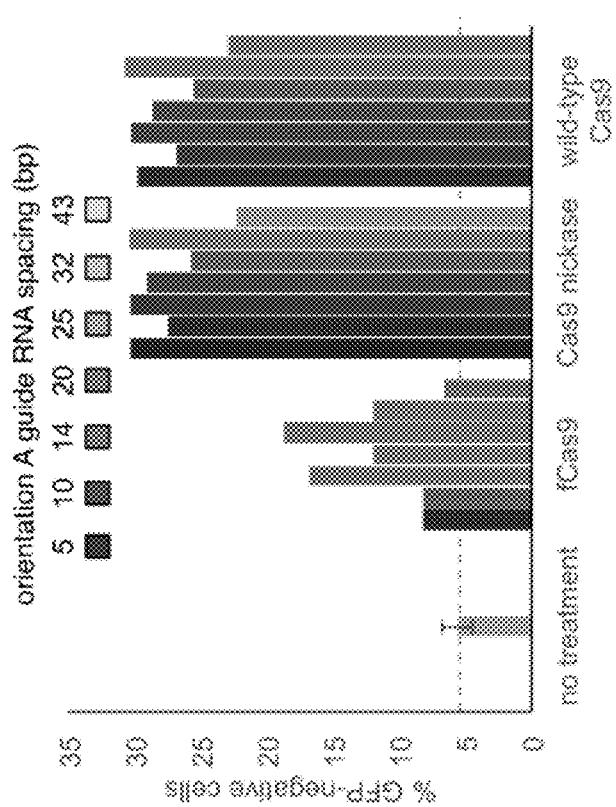

As the gRNA requirements of fCas9 potentially restricts the number of potential off-target substrates of fCas9, the effect of guide RNA orientation on the ability of fCas9, Cas9 nickase, and wild-type Cas9 to cleave target GFP sequences were compared. Consistent with previous reports,[5,6,17] Cas9 nickase efficiently cleaved targets when guide RNAs were bound either in orientation A or orientation B, similar to wild-type Cas9 (FIG. 8A, B). In contrast, fCas9 only cleaved the GFP target when guide RNAs were aligned in orientation A (FIG. 8A). This orientation requirement further limits opportunities for undesired off-target DNA cleavage.

Figure 7B:
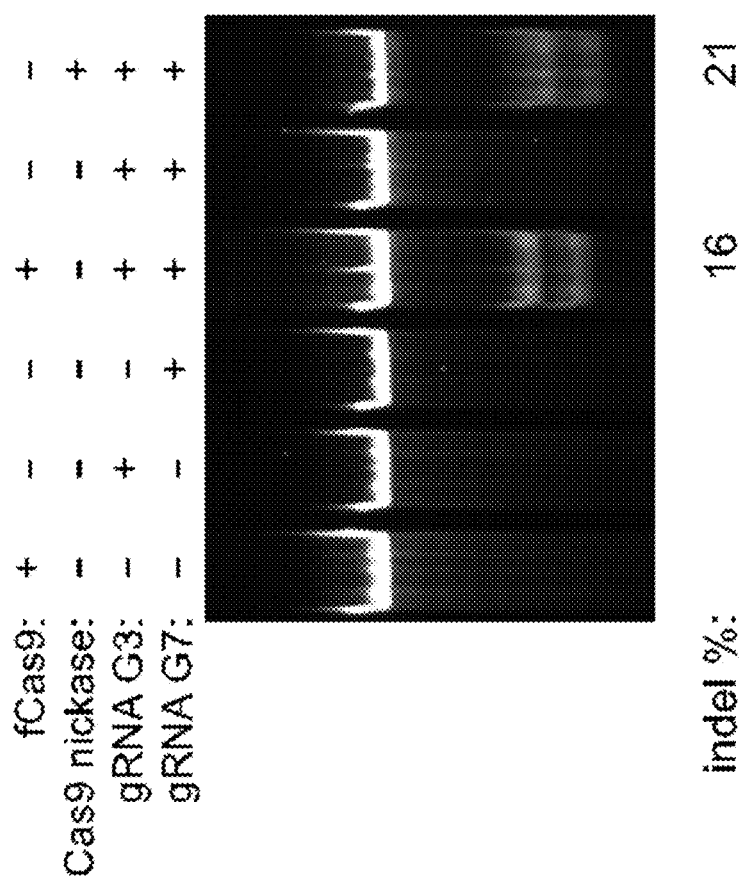
Figures 7C, 7D, 7E:
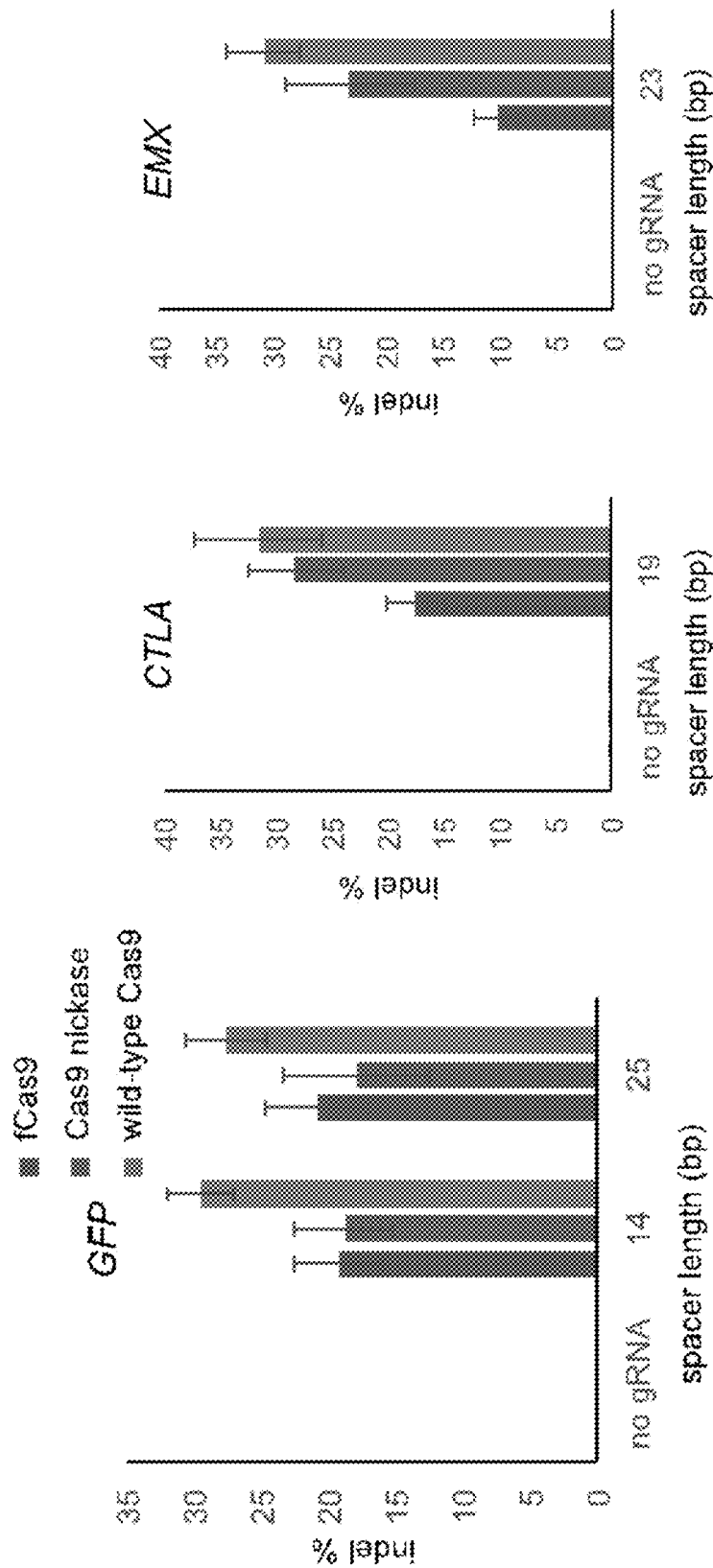
Figures 7F, 7G:
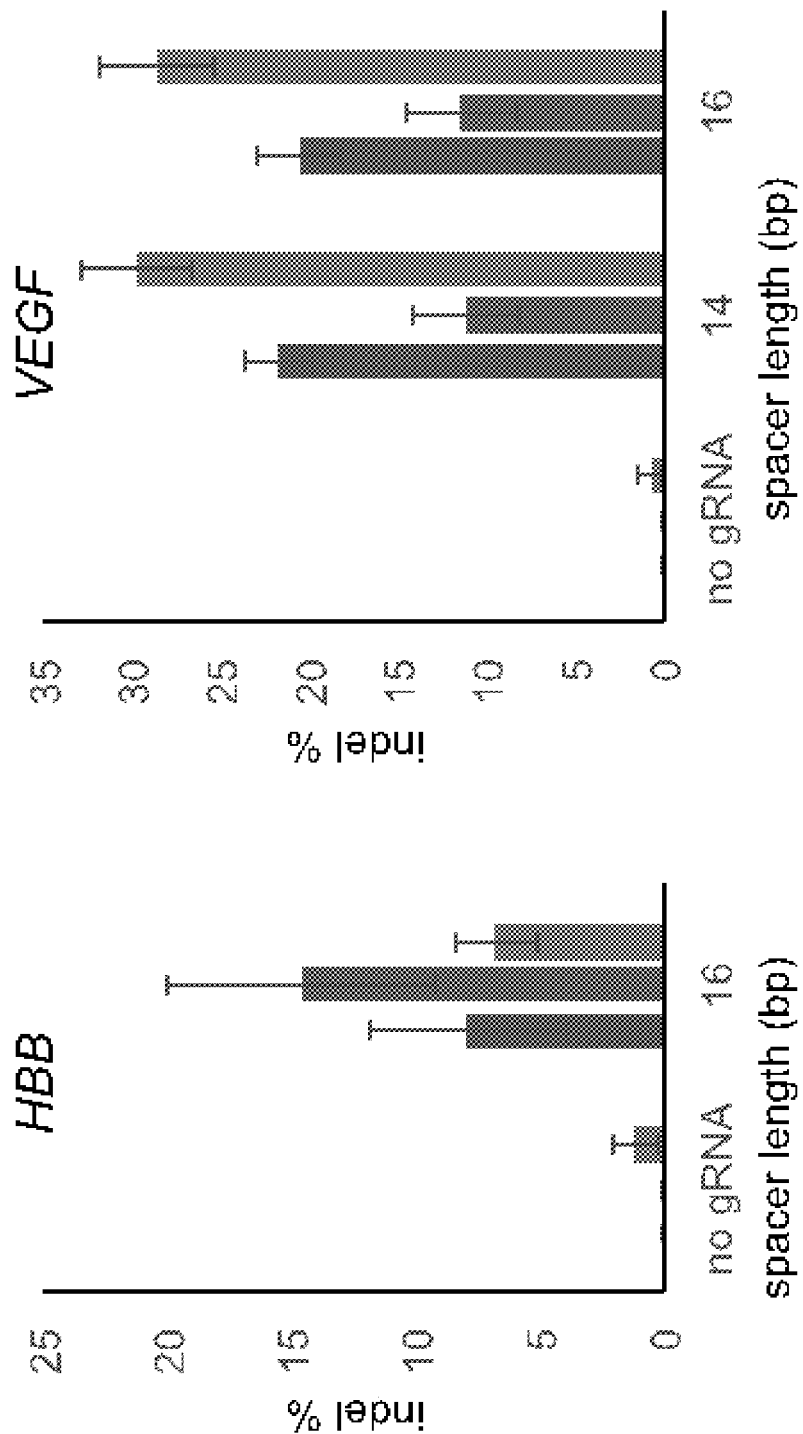
Figure 8C:
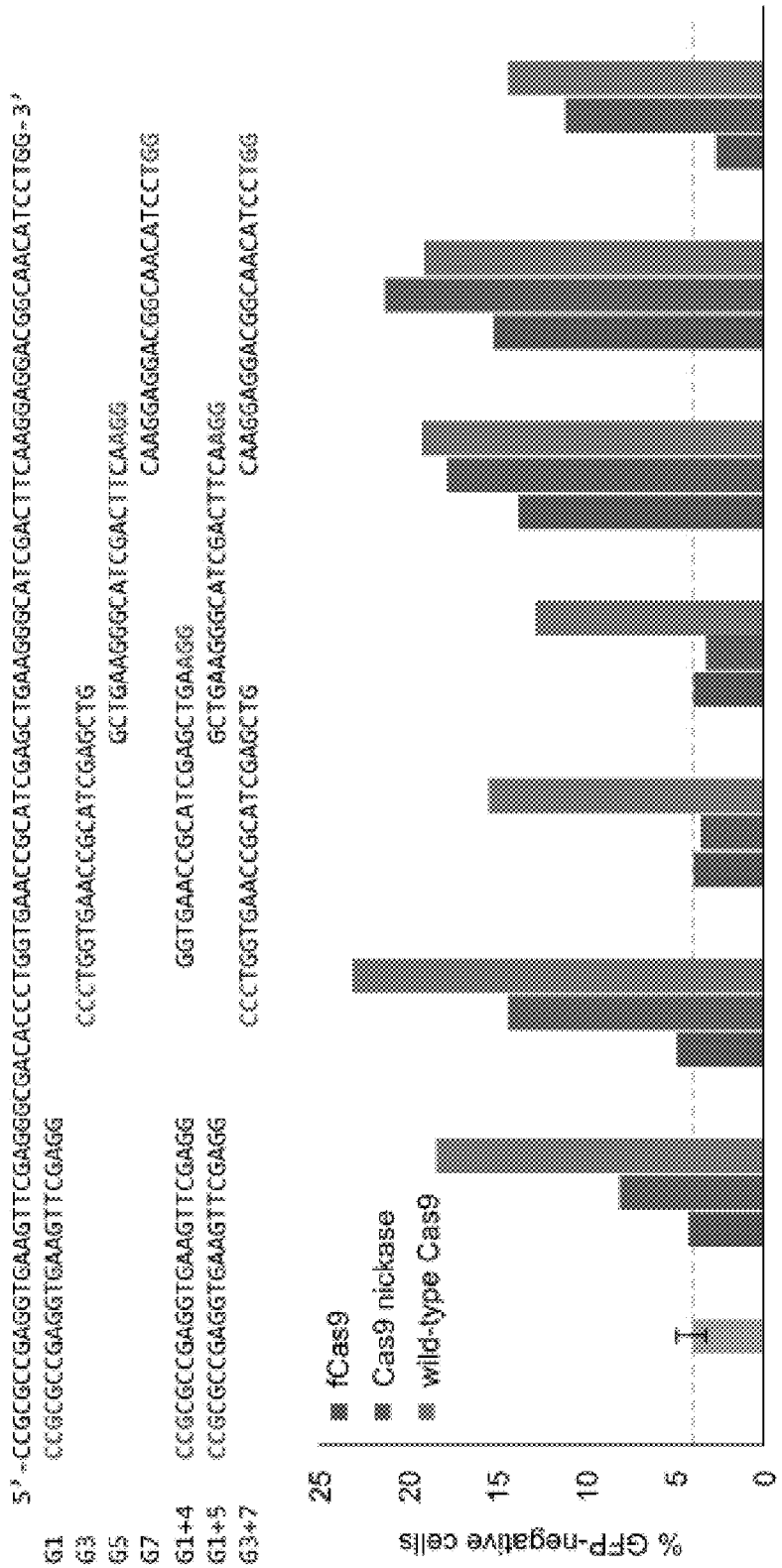

Importantly, no modification was observed by GFP disruption or Surveyor assay when any of four single gRNAs were expressed individually with fCas9, as expected since two simultaneous binding events are required for FokI activity (FIG. 7B and FIG. 8C). In contrast, GFP disruption resulted from expression of any single gRNA with wild-type Cas9 (as expected) and, for two single gRNAs, with Cas9 nickase (FIG. 8C). Surprisingly, Surveyor assay revealed that although GFP was heavily modified by wild-type Cas9 with single gRNAs, neither fCas9 nor Cas9 nickase showed detectable modification (<~2%) in cells treated with single gRNAs (FIG. 16A). High-throughput sequencing to detect indels at the GFP target site in cells treated with a single gRNA and fCas9, Cas9 nickase, or wild-type Cas9 revealed the expected substantial level of modification by wild-type Cas9 (3-7% of sequence reads). Modification by fCas9 in the presence of any of the four single gRNAs was not detected above background (<~0.03% modification), consistent with the requirement of fCas9 to engage two gRNAs in order to cleave DNA. In contrast, Cas9 nickases in the presence of single gRNAs resulted in modification levels ranging from 0.05% to 0.16% at the target site (FIG. 16B). The detection of bona fide indels at target sites following Cas9 nickase treatment with single gRNAs confirms the mutagenic potential of genomic DNA nicking, consistent with previous reports.[5,7,18,19]

The observed rate of nickase-induced DNA modification, however, did not account for the much higher GFP disruption signal in the flow cytometry assay (FIG. 8C). Since the gRNAs that induced GFP signal loss with Cas9 nickase (gRNAs G1 and G3) both target the non-template strand of the GFP gene, and since targeting the non-template strand with dCas9 in the coding region of a gene is known to mediate efficient transcriptional repression,[29] it is speculated that Cas9 nickase combined with the G1 or G3 single guide RNAs induced substantial transcriptional repression, in addition to a low level of genome modification. The same effect was not seen for fCas9, suggesting that fCas9 may be more easily displaced from DNA by transcriptional machinery. Taken together, these results indicate that fCas9 can modify genomic DNA efficiently and in a manner that requires simultaneous engagement of two guide RNAs targeting adjacent sites, unlike the ability of wild-type Cas9 and Cas9 nickase to cleave DNA when bound to a single guide RNA.

The above results collectively reveal much more stringent spacer, gRNA orientation, and guide RNA pairing requirements for fCas9 compared with Cas9 nickase. In contrast with fCas9 (FIG. 17), Cas9 nickase cleaved sites across all spacers assayed (5- to 47-bp in orientation A and 4 to 42 bp in orientation B in this work) (FIG. 8A, B). These observations are consistent with previous reports of Cas9 nickases modifying sites targeted by gRNAs with spacer lengths up to 100 bp apart.[6] The more stringent spacer and gRNA orientation requirements of fCas9 compared with Cas9 nickase reduces the number of potential genomic off-target sites of the former by approximately 10-fold (Table 4). Although the more stringent spacer requirements of fCas9 also reduce the number of potential targetable sites, sequences that conform to the fCas9 spacer and dual PAM requirements exist in the human genome on average once every 34 bp ($9.2 \times 10^7$ sites in $3.1 \times 10^9$ bp) (Table 4). It is also anticipated that the growing number of Cas9 homologs with different PAM specificities[30] are amenable for use as described herein, and will further increase the number of targetable sites using the fCas9 approach.

In Table 4 (A) column 2 shows the number of sites in the human genome with paired gRNA binding sites in orientation A allowing for a spacer length from ~8 bp to 25 bp (column 1) between the two gRNA binding sites. gRNA binding sites in orientation A have the NGG PAM sequences distal from the spacer sequence ($CCNN_{20}$-spacer-$N_{20}NGG$). Column 3 shows the number of sites in the human genome with paired gRNA binding sites in orientation B allowing for a spacer length from 4 to 25 bp (column 1) between the two gRNA binding sites. gRNA binding sites in orientation B have the NGG PAM sequences adjacent to the spacer sequence ($N_{20}NGG$ spacer $CCNN_{20}$). NC indicates the number of sites in the human genome was not calculated. Negative spacer lengths refer to target gRNA binding sites that overlap by the indicated number of base pairs. Table 4 (B) shows the sum of the number of paired gRNA binding sites in orientation A with spacer lengths of 13 to 19 bp, or 22 to 29 bp, the spacer preference of fCas9 (FIG. 16). Sum of the number of paired gRNA binding sites with spacer lengths of –8 bp to 100 bp in orientation A, or 4 to 42 bp in orientation B, the spacer preference of Cas9 nickases (4 to 42 bp in orientation B is based on FIGS. 8B, C, and –8 bp to 100 bp in orientation A is based on previous reports[36,37]).

TABLE 4

Paired gRNA target site abundances for fCas9 and Cas9 nickase in the human genome.

(A)

| Spacer length (b) | Number of paired gRNA sites in orientation A | Number of paired gRNA sites in orientation B |
|---|---|---|
| −8 | 6874293 | NC |
| −7 | 6785996 | NC |
| −6 | 6984064 | NC |
| −5 | 7023260 | NC |
| −4 | 6487302 | NC |
| −3 | 6401348 | NC |
| −2 | 6981383 | NC |
| −1 | 7230098 | NC |
| 0 | 7055143 | NC |
| 1 | 6598582 | NC |
| 2 | 6877046 | NC |
| 3 | 6971447 | NC |
| 4 | 6505614 | 5542549 |
| 5 | 6098107 | 5663458 |
| 6 | 6254974 | 6819289 |
| 7 | 6680118 | 6061225 |
| 8 | 7687598 | 5702252 |
| 9 | 6755736 | 7306646 |
| 10 | 6544849 | 6387485 |
| 11 | 6918186 | 6172852 |
| 12 | 6241723 | 5799496 |
| 13 | 6233385 | 7092283 |
| 14 | 6298717 | 7882433 |
| 15 | 6181422 | 7472725 |
| 16 | 6266909 | 6294684 |
| 17 | 6647352 | 6825904 |
| 18 | 6103603 | 6973590 |
| 19 | 5896092 | 6349456 |
| 20 | 6000683 | 5835825 |
| 21 | 5858015 | 6056352 |
| 22 | 6116108 | 6531913 |
| 23 | 5991254 | 6941816 |
| 24 | 6114969 | 6572849 |
| 25 | 6135119 | 5671641 |

(B)

| Cas9 variant | Preferred spacer lengths (bp) | Total sites |
|---|---|---|
| fCas9 | 13 to 19, or 22 to 29, in orientation A | 92354891 |
| Cas9 nickase | −8 to 100 in orientation A 4 to 42 in orientation B | 953048977 |

To evaluate the DNA cleavage specificity of fCas9, the modification of known Cas9 off-target sites of CLTA, EMX, and VEGF genomic target sites were measured.[1,2,6,8] The target site and its corresponding known off-target sites (Table 5) were amplified from genomic DNA isolated from HEK293 cells treated with fCas9, Cas9 nickase, or wild-type Cas9 and two gRNAs spaced 19 bp apart targeting the CLTA site, two gRNAs spaced 23 bp apart targeting the EMX site, two gRNAs spaced 14 bp apart targeting the VEGF site, or two gRNAs targeting an unrelated site (GFP) as a negative control. In total 11 off-target sites were analyzed by high-throughput sequencing.

The sensitivity of the high-throughput sequencing method for detecting genomic off-target cleavage is limited by the amount genomic DNA (gDNA) input into the PCR amplification of each genomic target site. A 1 ng sample of human gDNA represents only ~330 unique genomes, and thus only ~330 unique copies of each genomic site are present. PCR amplification for each genomic target was performed on a total of 150 ng of input gDNA, which provides amplicons derived from at most 50,000 unique gDNA copies. Therefore, the high-throughput sequencing assay cannot detect rare genome modification events that occur at a frequency of less than 1 in 50,000, or 0.002%.

TABLE 5

Known off-target substrates of Cas9 target sites in EMX, VEGF, and CLTA. List of genomic on-target and off-targets sites of the EMX, VEGF, and CLTA are shown with mutations from on-target in lower case and bold. PAMs are shown in upper case bold.

| | Genomic target site |
|---|---|
| EMX_On | GAGTCCGAGCAGAAGAAGAAGGG (SEQ ID NO: 190) |
| EMX_Off1 | GAGgCCGAGCAGAAGAAagACGG (SEQ ID NO: 191) |
| EMX_Off2 | GAGTCCtAGCAGgAGAAGAAGaG (SEQ ID NO: 192) |
| EMX_Off3 | GAGTCtaAGCAGAAGAAGAAGaG (SEQ ID NO: 193) |
| EMX_Off4 | GAGTtaGAGCAGAAGAAGAAAGG (SEQ ID NO: 194) |
| VEG_On | GGGTGGGGGGAGTTTGCTCCTGG (SEQ ID NO: 195) |
| VEG_Off1 | GGaTGGaGGGAGTTTGCTCCTGG (SEQ ID NO: 196) |
| VEG_Off2 | GGGaGGGtGGAGTTTGCTCCTGG (SEQ ID NO: 197) |
| VEG_Off3 | cGGgGGaGGGAGTTTGCTCCTGG (SEQ ID NO: 198) |
| VEG_Off4 | GGGgaGGGGaAGTTTGCTCCTGG (SEQ ID NO: 199) |
| CLT2_On | GCAGATGTAGTGTTTCCACAGGG (SEQ ID NO: 200) |
| CLT2_Off1 | aCaaATGTAGTaTTTCCACAGGG (SEQ ID NO: 201) |
| CLT2_Off2 | cCAGATGTAGTaTTcCCACAGGG (SEQ ID NO: 202) |
| CLT2_Off3 | ctAGATGaAGTGcTTCCACATGG (SEQ ID NO: 203) |

Figures 8D, 8E:
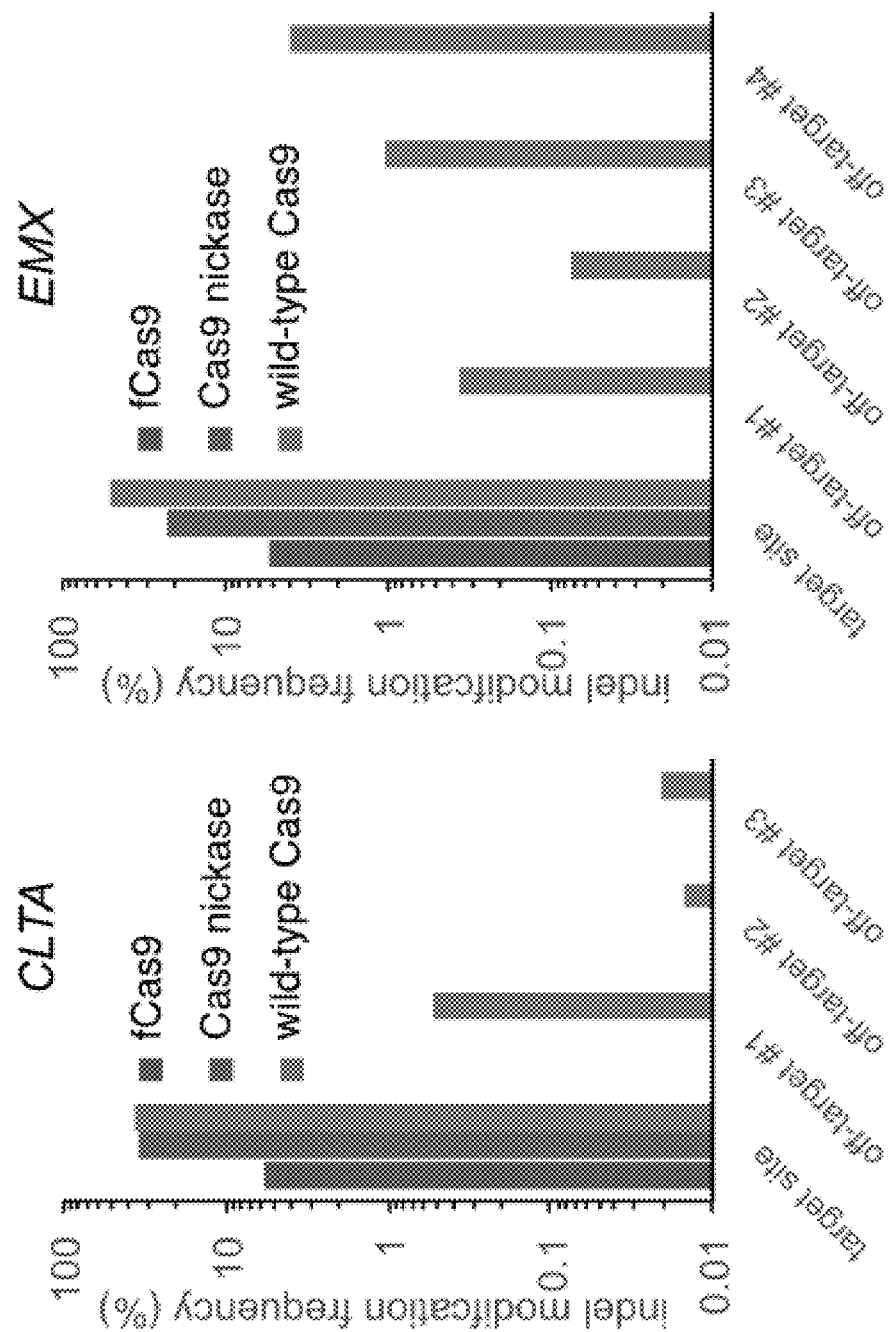
Figures 8F, 8G:
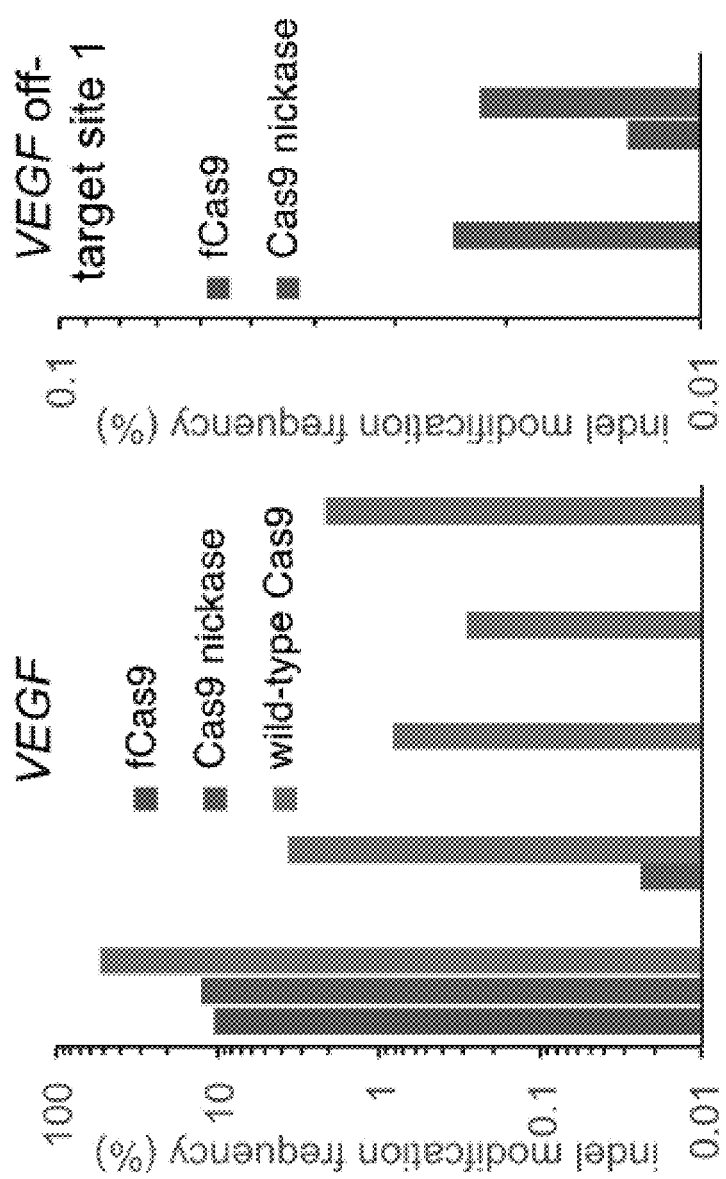

Sequences containing insertions or deletions of two or more base pairs in potential genomic off-target sites and present in significantly greater numbers (P value <0.005, Fisher's exact test) in the target gRNA-treated samples versus the control gRNA-treated samples were considered Cas9 nuclease-induced genome modifications. For 10 of the 11 off-target sites assayed, fCas9 did not result in any detectable genomic off-target modification within the sensitivity limit of the assay (<0.002%,), while demonstrating substantial on-target modification efficiencies of 5% to 10% (FIGS. 8D-F and Table 3). The detailed inspection of fCas9-modified VEGF on-target sequences (FIG. 18A) revealed a prevalence of deletions ranging from two to dozens of base pairs consistent with cleavage occurring in the DNA spacer between the two target binding sites, similar to the effects of FokI nuclease domains fused to zinc finger or TALE DNA-binding domains.[31]

In contrast, genomic off-target DNA cleavage was observed for wild-type Cas9 at all 11 sites assayed. Using the detection limit of the assay as an upper bound for off-target fCas9 activity, it was calculated that fCas9 has a much lower off-target modification rate than wild-type Cas9 nuclease. At the 11 off-target sites modified by wild-type Cas9 nuclease, fCas9 resulted in on-target:off-target modification ratios at least 140-fold higher than that of wild-type Cas9 (FIG. 8D-F).

Consistent with previous reports,[5,6,8] Cas9 nickase also induced substantially fewer off-target modification events (1/11 off-target sites modified at a detectable rate) compared to wild-type Cas9. An initial high-throughput sequencing assay revealed significant (P value <$10^{-3}$, Fisher's Exact Test) modification induced by Cas9 nickases in 0.024% of sequences at VEGF off-target site 1. This genomic off-target site was not modified by fCas9 despite similar VEGF on-target modification efficiencies of 12.3% for Cas9 nickase and 10.4% for fCas9 (FIG. 8F and Table 3C). Because Cas9 nickase-induced modification levels were within an order of magnitude of the limit of detection and fCas9 modification levels were undetected, the experiment was repeated with a larger input DNA samples and a greater number of sequence reads (150 versus 600 ng genomic DNA and >8×$10^5$ versus >23×$10^5$ reads for the initial and repeated experiments, respectively) to detect off-target cleavage at this site by Cas9 nickase or fCas9. From this deeper interrogation, it was observed that Cas9 nickase and fCas9 both significantly modify (P value <$10^{-5}$, Fisher's Exact Test) VEGF off-target site 1 (FIG. 8G, Table 3D, FIG. 18B). For both experiments interrogating the modification rates at VEGF off-target site 1, fCas9 exhibited a greater on-target:off-target DNA modification ratio than that of Cas9 nickase (>5,150 and 1,650 for fCas9, versus 510 and 1,230 for Cas9 nickase, FIG. 8G).

Figure 18C:
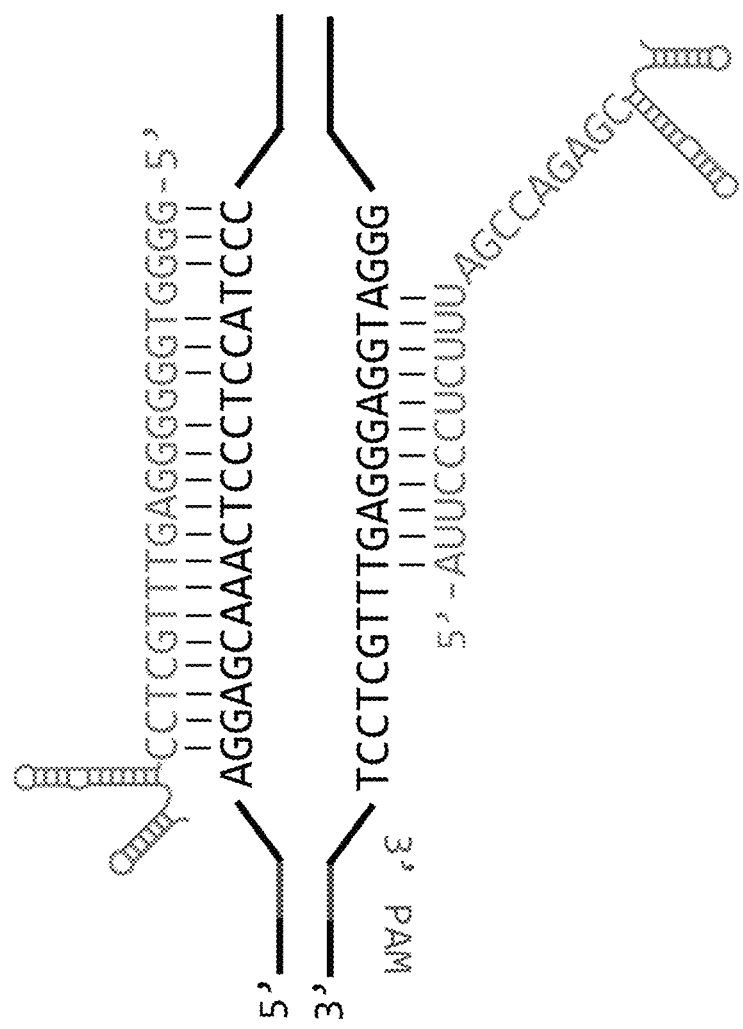
FIG. 18 shows modifications induced by Cas9 nuclease, Cas9 nickases, or fCas9 nucleases at endogenous loci. (A) shows examples of modified sequences at the VEGF on-target site with wild-type Cas9 nuclease, Cas9 nickases, or fCas9 nucleases and a single plasmid expressing two gRNAs targeting the VEGF on-target site (gRNA V1 and gRNA V2). For each example shown, the unmodified genomic site is the first sequence, followed by the top eight sequences containing deletions. The numbers before each sequence indicate sequencing counts. The gRNA target sites are bold and capitalized. (B) is an identical analysis as in (A) for VEGF off-target site 1VEG_Off1. (C) shows the potential binding mode of two gRNAs to VEGF off-target site 1. The top strand is bound in a canonical mode, while the bottom strand binds the second gRNA, gRNA V2, through gRNA:DNA base pairing that includes G:U base pairs. The sequences shown in (A) are identified, top to bottom, as follows: SEQ ID NO:243; SEQ ID NO:244; SEQ ID NO:245; SEQ ID NO:246; SEQ ID NO:247; SEQ ID NO:248; SEQ ID NO:249; SEQ ID NO:250; SEQ ID NO:251; SEQ ID NO:252; SEQ ID NO:253; SEQ ID NO:254; SEQ ID NO:255; SEQ ID NO:256; SEQ ID NO:257; SEQ ID NO:258; SEQ ID NO:259; SEQ ID NO:260; SEQ ID NO:261; SEQ ID NO:262; SEQ ID NO:263; SEQ ID NO:264; SEQ ID NO:265; SEQ ID NO:266; SEQ ID NO:267; SEQ ID NO:268; and SEQ ID NO:269. The sequences shown in (B) are identified, top to bottom, as follows: SEQ ID NO:270; SEQ ID NO:271; SEQ ID NO:272; SEQ ID NO:273; SEQ ID NO:274; SEQ ID NO:275; SEQ ID NO:276; SEQ ID NO:277; SEQ ID NO:278; SEQ ID NO:279; SEQ ID NO:280; SEQ ID NO:281; SEQ ID NO:282; SEQ ID NO:283; SEQ ID NO:284; SEQ ID NO:285; SEQ ID NO:286; SEQ ID NO:287; SEQ ID NO:288; SEQ ID NO:289; SEQ ID NO:290; SEQ ID NO:291; SEQ ID NO:292; SEQ ID NO:293; SEQ ID NO:294; SEQ ID NO:295; and SEQ ID NO:296. The sequences shown in (C) are identified, top to bottom, as follows: SEQ ID NO:297; SEQ ID NO:298; SEQ ID NO:299; and SEQ ID NO:300.

On either side of VEGF off-target site 1 there exist no other sites with six or fewer mutations from either of the two half-sites of the VEGF on-target sequence. The first 11 bases of one gRNA (V2) might hybridize to the single-stranded DNA freed by canonical Cas9:gRNA binding within VEGF off-target site 1 (FIG. 18C). Through this gRNA:DNA hybridization it is possible that a second Cas9 nickase or fCas9 could be recruited to modify this off-target site at a very low, but detectable level. Judicious gRNA pair design could eliminate this potential mode of off-target DNA cleavage, as VEGF off-target site 1 is highly unusual in its ability to form 11 consecutive potential base pairs with the second gRNA of a pair. In general, fCas9 was unable to modify the genomic off-target sites tested because of the absence of any adjacent second binding site required to dimerize and activate the FokI nuclease domain.

The optimized FokI-dCas9 fusion architecture developed in this work modified all five genomic loci targeted, demonstrating the generality of using fCas9 to induce genomic modification in human cells, although modification with fCas9 was somewhat less efficient than with wild-type Cas9. The use of fCas9 is straightforward, requiring only that PAM sequences be present with an appropriate spacing and orientation, and using the same gRNAs as wild-type Cas9 or Cas9 nickases. The observed low off-target:on-target modification ratios of fCas9, >140-fold lower than that of wild-type Cas9, likely arises from the distinct mode of action of dimeric FokI, in which DNA cleavage proceeds only if two DNA sites are occupied simultaneously by two FokI domains at a specified distance (here, ~15 bp or ~25 bp apart) and in a specific half-site orientation. The resulting unusually low off-target activity of fCas9 enable applications of Cas9:gRNA-based technologies that require a very high degree of target specificity, such as ex vivo or in vivo therapeutic modification of human cells.

References

1. Pattanayak, V. et al. High-throughput profiling of off-target DNA cleavage reveals RNA-programmed Cas9 nuclease specificity. *Nat. Biotechnol.* 31, 839-843 (2013).
2. Fu, Y. et al. High-frequency off-target mutagenesis induced by CRISPR-Cas nucleases in human cells. *Nat. Biotechnol.* 31, 822-826 (2013).
3. Hsu, P. D. et al. DNA targeting specificity of RNA-guided Cas9 nucleases. *Nat. Biotechnol.* 31, 827-832 (2013).
4. Cradick, T. J., Fine, E. J., Antico, C. J. & Bao, G. CRISPR/Cas9 systems targeting-globin and CCR5 genes have substantial off-target activity. *Nucleic Acids Res.* 41, 9584-9592 (2013).
5. Cho, S. W. et al. Analysis of off-target effects of CRISPR/Cas-derived RNA-guided endonucleases and nickases. *Genome Res.* 24, 132-141 (2013).
6. Ran, F. A. et al. Double Nicking by RNA-Guided CRISPR Cas9 for Enhanced Genome Editing Specificity. *Cell* 154, 1380-1389 (2013).
7. Mali, P. et al. CAS9 transcriptional activators for target specificity screening and paired nickases for cooperative genome engineering. *Nat. Biotechnol.* 31, 833-838 (2013).
8. Fu, Y., Sander, J. D., Reyon, D., Cascio, V. M. & Joung, J. K. Improving CRISPR-Cas nuclease specificity using truncated guide RNAs. *Nat. Biotechnol.* (2014). doi:10.1038/nbt.2808
9. Cong, L. et al. Multiplex Genome Engineering Using CRISPR/Cas Systems. *Science* 339, 819-823 (2013).
10. Jinek, M. et al. A Programmable Dual-RNA-Guided DNA Endonuclease in Adaptive Bacterial Immunity. *Science* 337, 816-821 (2012).
11. Gasiunas, G., Barrangou, R., Horvath, P. & Siksnys, V. Cas9-crRNA ribonucleoprotein complex mediates specific DNA cleavage for adaptive immunity in bacteria. *Proc. Natl. Acad. Sci.* 109, E2579-E2586 (2012).
12. Wang, T., Wei, J. J., Sabatini, D. M. & Lander, E. S. Genetic screens in human cells using the CRISPR-Cas9 system. *Science* 343, 80-84 (2014).
13. Shalem, O. et al. Genome-Scale CRISPR-Cas9 Knockout Screening in Human Cells. *Science* 343, 84-87 (2013).
14. Perez, E. E. et al. Establishment of HIV-1 resistance in CD4+ T cells by genome editing using zinc-finger nucleases. *Nat. Biotechnol.* 26, 808-816 (2008).
15. Jinek, M. et al. RNA-programmed genome editing in human cells. *eLife* 2, e00471-e00471 (2013).
16. Mali, P. et al. RNA-Guided Human Genome Engineering via Cas9. *Science* 339, 823-826 (2013).
17. Mali, P., Esvelt, K. M. & Church, G. M. Cas9 as a versatile tool for engineering biology. *Nat. Methods* 10, 957-963 (2013).
18. Ramirez, C. L. et al. Engineered zinc finger nickases induce homology-directed repair with reduced mutagenic effects. *Nucleic Acids Res.* 40, 5560-5568 (2012).
19. Wang, J. et al. Targeted gene addition to a predetermined site in the human genome using a ZFN-based nicking enzyme. *Genome Res.* 22, 1316-1326 (2012).
20. Gaj, T., Gersbach, C. A. & Barbas, C. F. ZFN, TALEN, and CRISPR/Cas-based methods for genome engineering. *Trends Biotechnol.* 31, 397-405 (2013).
21. Vanamee, É. S., Santagata, S. & Aggarwal, A. K. FokI requires two specific DNA sites for cleavage. *J. Mol. Biol.* 309, 69-78 (2001).
22. Maeder, M. L. et al. CRISPR RNA-guided activation of endogenous human genes. *Nat. Methods* 10, 977-979 (2013).
23. Pattanayak, V., Ramirez, C. L., Joung, J. K. & Liu, D. R. Revealing off-target cleavage specificities of zinc-finger nucleases by in vitro selection. *Nat. Methods* 8, 765-770 (2011).
24. Guilinger, J. P. et al. Broad specificity profiling of TALENs results in engineered nucleases with improved DNA-cleavage specificity. *Nat. Methods* (2014). doi:10.1038/nmeth.2845
25. Nishimasu, H. et al. Crystal Structure of Cas9 in Complex with Guide RNA and Target DNA. *Cell* (2014). doi: 10.1016/j.cell.2014.02.001
26. Jinek, M. et al. Structures of Cas9 Endonucleases Reveal RNA-Mediated Conformational Activation. *Science* (2014). doi:10.1126/science.1247997
27. Schellenberger, V. et al. A recombinant polypeptide extends the in vivo half-life of peptides and proteins in a tunable manner. *Nat. Biotechnol.* 27, 1186-1190 (2009).
28. Guschin, D. Y. et al. in *Eng. Zinc Finger Proteins* (Mackay, J. P. & Segal, D. J.) 649, 247-256 (Humana Press, 2010).
29. Qi, L. S. et al. Repurposing CRISPR as an RNA-guided platform for sequence-specific control of gene expression. *Cell* 152, 1173-1183 (2013).
30. Esvelt, K. M. et al. Orthogonal Cas9 proteins for RNA-guided gene regulation and editing. *Nat. Methods* 10, 1116-1121 (2013).
31. Kim, Y., Kweon, J. & Kim, J.-S. TALENs and ZFNs are associated with different mutation signatures. *Nat. Methods* 10, 185-185 (2013).
32. Shcherbakova, D. M. & Verkhusha, V. V. Near-infrared fluorescent proteins for multicolor in vivo imaging. *Nat. Methods* 10, 751-754 (2013).
33. Schneider, C. A., Rasband, W. S. & Eliceiri, K. W. NIH Image to ImageJ: 25 years of image analysis. *Nat. Methods* 9, 671-675 (2012).
34. Sander, J. D. et al. In silico abstraction of zinc finger nuclease cleavage profiles reveals an expanded landscape of off-target sites. *Nucleic Acids Res.* 41, e181-e181 (2013).
35. Schellenberger, V. et al. A recombinant polypeptide extends the in vivo half-life of peptides and proteins in a tunable manner. *Nat. Biotechnol.* 27, 1186-1190 (2009).
36. Mali, P. et al. CAS9 transcriptional activators for target specificity screening and paired nickases for cooperative genome engineering. *Nat. Biotechnol.* 31, 833-838 (2013).
37. Ran, F. A. et al. Double Nicking by RNA-Guided CRISPR Cas9 for Enhanced Genome Editing Specificity. *Cell* 154, 1380-1389 (2013).
38. Yan, T. et al. PatMatch: a program for finding patterns in peptide and nucleotide sequences. *Nucleic Acids Res.* 33, W262-W266 (2005).
39. Larkin, M. A. et al. Clustal W and Clustal X version 2.0. *Bioinformatics* 23, 2947-2948 (2007).

Example 2

Targetting CCR5 for Cas9 Variant-Mediated Inactivation

In addition to providing powerful research tools, site-specific nucleases also have potential as gene therapy agents, and site-specific zinc finger endonucleases have recently entered clinical trials: CCR5-2246, targeting a human CCR-5 allele as part of an anti-HIV therapeutic approach.

In a similar approach, the inventive Cas9 variants of the present disclosure may be used to inactivate CCR5, for example in autologous T cells obtained from a subject which, once modified by a Cas9 variant, are re-introduced into the subject for the treatment or prevention of HIV infection.

In this example, the CCR5 gene is targeted in T cells obtained from a subject. CCR5 protein is required for certain common types of HIV to bind to and enter T cells, thereby infecting them. T cells are one of the white blood cells used by the body to fight HIV.

Some people are born lacking CCR5 expression on their T cells and remain healthy and are resistant to infection with HIV. Others have low expression of CCR5 on their T cells, and their HIV disease is less severe and is slower to cause disease (AIDS).

In order to delete the CCR5 protein on the T cells, large numbers of T-cells are isolated from a subject. Cas9 variants (e.g., fCas9) and gRNA capable of inactivating CCR5 are then delivered to the isolated T cells using a viral vector, e.g., an adenoviral vector. Examples of suitable Cas9 variants include those inventive fusion proteins provided herein. Examples of suitable target sequences for gRNAs targetting the CCR5 allele include those described in FIG. 19, e.g., SEQ ID NOs:303-310 and 312-317. The viral vector(s) capable of expressing the Cas9 variant and gRNA is/are added to the isolated T cells to knock out the CCR5 protein. When the T cells are returned to subject, there is minimal adenovirus or Cas9 variant protein present. The removal of the CCR5 protein on the T cells subjects receive, however, is permanent. The cells are then reintroduced to the subject for the treatment or prevention of HIV/AIDS.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

What is claimed is:

1. A fusion protein comprising two domains:
   (i) a nuclease-inactivated Cas9 (dCas9) domain comprising an amino acid sequence that is at least 90% identical to the amino acid sequence of SEQ ID NO: 5, wherein the dCas9 comprises a D10A and/or a H840A mutation and lacks nuclease activity; and
   (ii) a nuclease domain that is at least 90% identical to SEQ ID NO: 6,
   wherein the two domains are separated by a peptide linker selected from the group consisting of (GGS)$_3$, (GGS)$_6$, SGSETPGTSESATPES (SEQ ID NO:16), SGSETPGTSESA (SEQ ID NO:17), SGSETPGTSESATPEGGSGGS (SEQ ID NO:18), VPFLLEPDNINGKTC (SEQ ID NO:19), GSAGSAAGSGEF (SEQ ID NO:20), SIVAQLSRPDPA (SEQ ID NO:21), MKIIEQLPSA (SEQ ID NO:22), VRHKLKRVGS (SEQ ID NO:23), GHGTGSTGSGSS (SEQ ID NO:24), MSRPDPA (SEQ ID NO:25), and GGSM (SEQ ID NO:301).

2. The fusion protein of claim 1, wherein the nuclease domain comprises a FokI DNA cleavage domain consisting essentially of amino acids 300-583, 320-583, 340-583, 360-583, or 388-583 of FokI (MFLSMVSKIRTFGWVQNPGKFENLKRVVQVFDRNSKVHNEVKNIKIPTLVKESKIQKELVA IMNQHDLIYTYKELVGTGTSIRSEAPCDAIIQATIADQGNKKGYIDNWSSDGFLRWAHALGF IEYINKSDSFVITDVGLAYSKSADGSAIEKEILIEAISSYPPAIRILTLLEDGQHLTKFDLGKNL GFSGESGFTSLPEGILLDTLANAMPKDKGEIRNNWEGSSDKYARMIGGWLDKLGLVKQGK KEFIIPTLGKPDNKEFISHAFKITGEGLKVLRRAKGSTKFTRVPKRVYWEMLATNLTDKEYV RTRRALILEILIKAGSLKIEQIQDNLKKLGFDEVIETIENDIKGLINTGIFIEIKGRFYQLKDHIL QFVIPNRGVTKQLVKSELEEKKSELRHKLKYVPHEYIELIEIARNSTQDRILEMKVMEFFMK VYGYRGKHLGGSRKPDGAIYTVGSPIDYGVIVDTKAYSGGYNLPIGQADEMQRYVEENQT RNKHINPNEWWKVYPSSVTEFKFLFVSGHFKGNYKAQLTRLNHITNCNGAVLSVEELLIGG EMIKAGTLTLEEVRRKFNNGEINF, SEQ ID NO: 328).

3. The fusion protein of claim 1, further comprising a nuclear localization signal (NLS) domain.

4. The fusion protein of claim 3, wherein the fusion protein comprises the structure [NLS domain]-GGS-[FokI DNA cleavage domain]-[peptide linker]-[dCas9 domain].

5. The fusion protein of claim 1, wherein the amino acid sequence of the peptide linker is selected from the group consisting of SGSETPGTSESATPES (SEQ ID NO:16), SGSETPGTSESA (SEQ ID NO:17), and SGSETPGTSESATPEGGSGGS (SEQ ID NO:18).

6. The fusion protein of claim 1, wherein the fusion protein is encoded by a nucleotide sequence set forth as SEQ ID NO:9, SEQ ID NO:10, SEQ ID NO:11, or SEQ ID NO:12.

7. A dimer of the fusion protein of claim 1.

8. The fusion protein of claim 1, wherein the nuclease-inactivated Cas9 domain is bound to a gRNA.

9. A kit comprising a fusion protein of claim 1.

10. The kit of claim 9, further comprising one or more gRNAs and/or vectors for expressing one or more gRNAs.

* * * * *